(12) United States Patent
Mett

(10) Patent No.: US 10,202,426 B2
(45) Date of Patent: Feb. 12, 2019

(54) FLAGELLIN COMPOSITIONS AND USES

(71) Applicant: Genome Protection, Inc., Buffalo, NY (US)

(72) Inventor: Vadim Mett, Buffalo, NY (US)

(73) Assignee: Genome Protection, Inc., Buffalo, NY (US)

( * ) Notice: Subject to any disclaimer, the term of this patent is extended or adjusted under 35 U.S.C. 154(b) by 0 days.

(21) Appl. No.: 15/329,870

(22) PCT Filed: Jul. 29, 2015

(86) PCT No.: PCT/US2015/042684
§ 371 (c)(1),
(2) Date: Oct. 9, 2017

(87) PCT Pub. No.: WO2016/019034
PCT Pub. Date: Feb. 4, 2016

(65) Prior Publication Data
US 2018/0251498 A1    Sep. 6, 2018

Related U.S. Application Data

(60) Provisional application No. 62/117,366, filed on Feb. 17, 2015, provisional application No. 62/110,744, filed on Feb. 2, 2015, provisional application No. 62/031,116, filed on Jul. 30, 2014.

(51) Int. Cl.
| | | |
|---|---|---|
| A61K 39/00 | (2006.01) | |
| A61K 39/02 | (2006.01) | |
| A61K 49/00 | (2006.01) | |
| C07K 14/195 | (2006.01) | |
| A61K 38/16 | (2006.01) | |
| A61K 39/39 | (2006.01) | |
| A61K 45/06 | (2006.01) | |

(52) U.S. Cl.
CPC .......... *C07K 14/195* (2013.01); *A61K 38/164* (2013.01); *A61K 39/0013* (2013.01); *A61K 39/02* (2013.01); *A61K 39/39* (2013.01); *A61K 45/06* (2013.01); *A61K 2039/55505* (2013.01); *A61K 2039/55516* (2013.01); *A61K 2039/55583* (2013.01); *A61K 2039/55594* (2013.01); *A61K 2039/57* (2013.01); *A61K 2039/575* (2013.01); *C07K 2319/00* (2013.01); *C07K 2319/21* (2013.01); *Y02A 50/388* (2018.01); *Y02A 50/39* (2018.01); *Y02A 50/466* (2018.01); *Y02A 50/484* (2018.01)

(58) Field of Classification Search
CPC ............................... A61K 39/00; A61K 39/02
USPC .................. 424/9.1, 9.2, 184.1, 185.1, 234.1
See application file for complete search history.

(56) References Cited

U.S. PATENT DOCUMENTS

| | | |
|---|---|---|
| 4,554,101 A | 11/1985 | Hopp |
| 5,399,494 A | 3/1995 | Kaper et al. |
| 5,693,476 A | 12/1997 | Scheller |
| 6,130,082 A | 10/2000 | Majarian et al. |
| 7,404,963 B2 | 7/2008 | Sotomayor et al. |
| 7,638,485 B2 | 12/2009 | Gudkov |
| 7,794,731 B2 | 9/2010 | Mizel et al. |
| 8,007,812 B2 | 8/2011 | Gudkov et al. |
| 8,106,005 B2 | 1/2012 | Gudkov |
| 8,287,882 B2 | 10/2012 | Gudkov et al. |
| 8,324,163 B2 | 12/2012 | Gudkov et al. |
| 8,580,321 B2 | 11/2013 | Gudkov et al. |
| 2002/0009747 A1 | 1/2002 | Miller et al. |
| 2003/0044429 A1 | 3/2003 | Aderem et al. |
| 2005/0147627 A1 | 7/2005 | Aderem et al. |
| 2005/0266391 A1 | 12/2005 | Bennett et al. |
| 2006/0275255 A1 | 12/2006 | Gudkov |
| 2007/0202551 A1 | 8/2007 | Gudkov |
| 2007/0269406 A1 | 11/2007 | Ichim |
| 2008/0124361 A1 | 5/2008 | Mizel et al. |
| 2008/0182797 A1 | 7/2008 | Nudler |
| 2009/0011982 A1 | 1/2009 | Gudkov et al. |
| 2009/0081157 A1 | 3/2009 | Kornbluth et al. |
| 2009/0123467 A1 | 5/2009 | Bedi et al. |
| 2009/0175880 A1 | 7/2009 | Keler et al. |
| 2009/0246303 A1 | 10/2009 | Gudkov et al. |
| 2010/0056454 A1 | 3/2010 | Gudkov |
| 2011/0319595 A1 | 12/2011 | Gudkov et al. |
| 2013/0004515 A1 | 1/2013 | Gudkov et al. |
| 2013/0324462 A1 | 12/2013 | Gudkov et al. |

FOREIGN PATENT DOCUMENTS

| | | |
|---|---|---|
| WO | 1992005816 | 4/1992 |
| WO | 1993018150 | 9/1993 |
| WO | 1999029312 | 6/1999 |
| WO | 2001040280 | 6/2001 |
| WO | 2001055210 | 8/2001 |
| WO | 2002044363 | 6/2002 |
| WO | 2003027251 | 4/2003 |
| WO | 2003028659 | 4/2003 |

(Continued)

OTHER PUBLICATIONS

Pashenkov et al. "Phase II trial of a toll-like receptor 9-activating oligonucleotide in patients with metastic melanoma" J Clin Oncol 24: 5716-5724 2006.

(Continued)

*Primary Examiner* — Rodney P Swartz

(74) *Attorney, Agent, or Firm* — Morgan, Lewis & Bockius LLP

(57) ABSTRACT

The present invention relates to compositions comprising improved flagellin derived constructs and methods of using the same in the treatment of various diseases.

20 Claims, 24 Drawing Sheets

Specification includes a Sequence Listing.

(56) References Cited

FOREIGN PATENT DOCUMENTS

| WO | 2004086039 | 10/2004 |
|---|---|---|
| WO | 2005056041 | 6/2005 |
| WO | 2005056042 | 6/2005 |
| WO | 2005056054 | 6/2005 |
| WO | 2005056055 | 6/2005 |
| WO | 2005057218 | 6/2005 |
| WO | 2006066214 | 6/2006 |
| WO | 2006069198 | 6/2006 |
| WO | 2007030581 | 3/2007 |
| WO | 2008157473 | 12/2008 |
| WO | 2009102818 | 8/2009 |
| WO | 2010040096 | 4/2010 |
| WO | 2010133885 | 11/2010 |
| WO | 2011027222 | 3/2011 |
| WO | 2011044246 | 4/2011 |

OTHER PUBLICATIONS

Patchen M. L. "Amifostine plus granulocyte colony-stimulating factor therapy enhances recovery from supralethal radiation exposures: preclinical experience in animals models" European Journal of Cancer 31A(1):S17-S21 (1995).
Rensing-Ehl et al., Local Fas/APO-1 )(CD95) Ligand-Mediated Tumor Cell Killing in vivo, Eur J Immunol, 1995, vol. 25, pp. 2253-2258.
Rhee et al. "Toll-like receptor 5 engagement modulates tumor development and growth in a mouse xenograft model of human colon cancer" Gastroenterology Aug. 2008; 135(2): 518-528.
Samatey F. A. et al. "Structure of the bacterial flagellar protofilament and implications for a switch for supercoiling" Nature 410:331-337 (2001).
Satyamitra M. et al. "In vivo postirradiation protection by a vitamin E analog a-TMG" Radiation Research 160 (6):655-661 (2003).
Schmidt et al. "Intratumoural injection of the toll-like receptor-2/6 agonist 'macrophage-activating lipopeptide-2' in patients with pancreatic carcinoma: a phase I/II trial" Brit J Cancer 97: 598-604 2007.
Sebastiani G. et. al. "Cloning and characterization of the murine Toll-like Receptor 5 (Tlr5) gene: sequence and mRNA expression studies in *Salmonella*-susceptible MOLF/Ei mice" Genomics 64(3):230-240 (2000).
Seed T. et al. "New strategies for the prevention of radiation injury: possible implications for countering radiation hazards of long-term space travel" Journal of Radiation Research 43:S239-S244 (2002).
Selander R. K. et al. "Molecular evolutionary genetics of the cattle-adapted serovar *Salmonella dublin*" Journal of Bacteriology 174(11):3587-3592 (1992).
Service R. F. "Tumor-Killer Made; How Does It Work?" Science 274:2009 (1996).
Sfondrini et al. "Antitumor Activity of the TLR-5 Ligand Flagellin in Mouse Models of Cancer" The Journal of Immunology 2006 176:6624-6630.
Smith K. D. et al. "Toll-like receptor 5 recognizes a conserved site on flagellin required for protofilament formation and bacterial motility" Nature Immunology 4(12)1247-1253 (2003).
Song et al. "Flagellin promotes the proliferation of gastric cancers via the Toll-like receptor 5" Int J Mol Med 28:115-119 2011.
Spadaro J. A. et al. "Radioprotectant combinations spare radiation-induced damage to the physis more than fractionation alone" Int. J. Radiat. Biol. 81(10):759-765 (2005) Abstract.
Sredni B. et al. "The immunomodulator AS101 administered orally as a chemoprotective and radioprotective agent" Int. J. Immunopharmacol. 14(4):613-619 (1992).
Streeter P. R. et al. "Activation of the G-CSF and Flt-3 receptors protects hematopoietic stem cells from lethal irradiation" Experimental Hematology 31(11):1119-1125 (2003).
Symon Z. et al. "Selective radioprotection of hepatocytes by systemic and portal vein infusions of amifostine in a rat liver tumor model" Int. J. Radiation Oncology Biol. Phys. 50(2):473-478 (2001).
Tallant T. et al. "Flagellin acting via TLR5 is the major activator of key signaling pathways leading to NF-KB and proinflammatory gene program activation in intestinal epithelial cells" BMC Microbiology 4(1):33 (2004).
Timmer et al. "Fas receptor-mediated apoptosis: a clinical application?" J Pathol 196: 125-134 2002.
Trauth et al. "Monoclonal antibody-mediated tumor regression by induction of apoptosis" Science 245: 301-305 1989.
Tsujimoto H. et al. "Flagellin enhances NK cell proliferation and activation directly and through dendritic cell-NK cell Interactions" Journal of Leukocyte Biology 78(4):888-897 (2005).
Vasquez R. J. et al. "Nanomolar concentrations of nocodazole alter microtubule dynamic instability in vivo and in vitro" Molecular Biology of the Cell 8(6):973-985 (1997).
Vijay-Kumar et al. "Flagellin Treatment Protects against Chemicals Bacteria Viruses and Radiation" The Journal of Immunology 2008 180:8280-8285.
Waddick K G. et al. "In vitro and in vivo antileukemic activity of B43-pokeweed antiviral protein against radiation-resistant human B-cell precursor leukemia cells" Blood 86(11):4228-4233 (1995).
Watson A. J. et al. "Lessons from genetically engineered animal models. VII. Apoptosis in intestinal epithelium: lessons from transgenic and knockout mice" Am. J. Physiol. Gastrointest. Liver Physiol. 278(1):G1-G5 (2000).
Wheeler C. M. "Preventative vaccines for cervial cancer" Salud Publica de Mexico 39(4) (1997) 9 pages.
Whitnall M. H. et al. "In vivo radioprotection by 5-androstenediol: stimulation of the innate immune system " Radiation Research 156(3):283-293 (2001).
Wolska et al. "Toll-like receptors and their role in carcinogensis and anti-tumor treatment" Cell Mol Biol Letters 14:248-272 2009.
Wong G. H. W. "Protective roles of cytokines against radiation: induction of mitochondrial MnSOD" Biochimica et Biophysica Acta 1271:205-209 (1995).
Yang et al. "Antigen replacement of domains D2 and D3 in flagellin promotes mucosal IgA production and attenuates flagellin-induced inflammatory response after intranasal immunization" Human Vaccines and Immunotherap 9:5 1084-1092 2013.
Leigh et al., "A Flagellin-Derived Toll-Like Receptor 5 Agonist Stimulates Cytotoxic Lymphocyte-Mediated Tumor Immunity," PLOS One, 2014, vol. 9, No. 1, pp. 1-10.
International Search Report and Written Opinion, Application No. PCT/US2015/042684, dated Nov. 19, 2015, 12 pages.
Alavanja M. CR. "Biologic damage resulting from exposure to tobacco smoke from radon: implication for preventive interventions" Oncogene 21:7365-7375 (2002).
Andreassen C. N. et al. "Chemical radioprotection: a critical review of amifostine as a cytoprotector in radiotherapy" Seminars in Radiation Oncology 13(1):62-72 (2003).
Androstenediol and Androstenedione Wikipedia (online). URL: < http://en. wikipedia.org/wiki/Androstenediol> [Retrieved from the Internet: Dec. 5, 2006] 4 pages.
Bachmann M. F. et al. "Recall proliferation potential of memory CD8+ T cells and antiviral protection" The Journal of Immunology 175:4677-4685 (2005).
Ben-Yedidia T. et al. "Intranasal administration of peptide vaccine protects human/mouse radiation chimera from influenza infection" International Immunology 11(7):1043-1051 (1998).
Booth D. et. al. "Transforming growth factor-B3 protects murine small intestinal crypt stem cells and animal survival after irradiation possibly by reducing stem-cell cycling" Int. J. Cancer 86(1):53-59 (2000).
Borges H. L. et al. "DNA damage-induced cell death: lessons from the central nervous system" Cell Research 18:17-26 (2008).
Bulinski J. C. et al. "Overexpression of MAP4 inhibits organelle motility and trafficking in vivo" Journal of Cell Sciences 110:3055-3064 (1997).
Burdelya L. G. et al. "An agonist of toll-like receptor 5 has radioprotective activity in mouse and primate models" Science 320:226-230 (2008).
Cai et al. "Activation of toll-like receptor 5 on breast cancer cells by flagellin suppresses cell proliferation and tumor growth" Cancer Res 71 (7): 2466-2475 2011.

(56) References Cited

OTHER PUBLICATIONS

Cai et al. "Activation of toll-like receptor 5 on breast cancer cells by flagellin suppresses tumor development and growth" Cancer Res 70: #3819 Apr. 2010.
Carnes B. A. et al. "Mortality of atomic bomb survivors predicted from laboratory animals" Radiation Research 160 (2):159-167 (2003) Abstract.
Caron G. et. al. "Direct stimulation of human T cells via TLR5 and TLR7/8: Flagellin and R-848 up-regulate proliferation and IFN-y production by memory CD4+ T cells" The Journal of Immunology 175(3):1551-1557 (2005).
Coffman et al. Vaccine Adjuvants: Pulling Innate Immunity to Work Immunity vol. 33 Oct. 29, 2010 pp. 492-503.
Dummer et al. "An exploratory study of systemic administration of the toll-like receptor-7 agonist 852A in patients with refractory metastic melanoma" Clin Cancer Res 14(3): 856-864 2008.
Eaves-Pyles T. D. et al. "*Salmonella* flagellin-dependent proinflammatory responses are localized to the conserved amino and carboxyl regions of the protein" The Journal of Immunology 167(12):7009-7016 (2001).
Eaves-Pyles T. et al. "Flagellin a novel mediator of *Salmonella*-induced epithelial activation and systemic inflammation: IKBa degradation induction of nitric oxide synthase induction of proinflammatory mediators and cardiovascular dysfunction" The Journal of Immunology 166(2):1248-1260 (2001).
Efferson C. L. et al. "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15" Anticancer Research 25:715-724 (2005).
Egan L. J. et al. "IkB-kinase13-dependent NF-k13 activation provides radioprotection to the intestinal epithelium" PNAS 101(8):2452-2457 (2004).
Elewaut D. et al. "NF-KB is a central regulator of the intestinal epithelial cell innate immune response induced by infection with enteroinvasive bacteria" The Journal of Immunology 163:1457-1466 (1999).
Etter et al. "The combination of chemotherapy and intraperitoneal MegaFas ligand improves treatment of ovarian carcinoma" Gynecologic Oncol 107: 14-21 2007.
Foldes G. et al. "Toll-like receptor modulation in cardiovascular disease: a target for intervention?" Expert Opinion on Investigational Drugs 15(8):857-871 (2006).
Fukuzawa N. et al. "A TLR5 agonist inhibits acute renal ischemic failure" The Journal of Immunology 187:3831-3839 (2011).
GenBank databases NCBI Accession No. M84972 Apr. 26, 1993 [online] [retrieved on Sep. 29, 2011] Retrieved from the Internet: <URL: http://www.ncbi.nlm.nih.gov/nuccore/M84972>.
Gewirtz A.T. et. al. "Cutting edge: Bacterial flagellin activates basolaterally expressed TLR5 to induce epithelial proinflammatory gene expression" The Journal of Immunology 167(4):1882-1885 (2001).
Grdina D. J. et al. "Relationships between cytoprotection and mutation prevention by WR-1065" Military Medicine 167(2):51-53 (2002).
Guan K. L. et al. "Eukaryotic proteins expressed in *Escherichia coli*: an improved thrombin cleavage and purification procedure of fusion proteins with glutathione S-transferase" Analytical Biochemistry 192:262-267 (1991).
Gudkov A. V. et al. "The role of p53 in determining sensitivity to radiotherapy" Nat. Rev. Cancer 3:117-129 (2003).
Guicciardi et al., Life and Death by Death Receptors, FASEB J, 2009, vol. 23, No. 6, pp. 1625-1637.
Haimovitz-Friedman A. et al. "Ionizing radiation acts on cellular membranes to generate ceramide and apoptosis" J. Exp. Med. 180:525-535 (1994).
Hall "Physics and Chemisty of Radiation Absorption" Radiobiology for the Radiobiologist pp. 5-15 5th ed. Lippincott Williams and Wilkins Philadelphia PA (2000).
Herbert J. M. et al. "Involvement of u-PA in the anti-apoptotic activity of TGF-beta for vascular smooth muscle cells" FEBS Letters 413(3):401-404 (1997).
Honko A. N. et al. "Effects of flagellin on innate and adaptive immunity" Immunologic Research 33(1):83-101 (2005).
Jung C. W. et al. "Antiproliferative effect of a vitamin D3 analog EB1089 on HL-60 cells by the induction of TGF-beta receptor" Leukemia Research 23(12):1105-1112 (1999).
Kemp G. et al. "Amifostine pretreatment for protection against cyclophosphamide-induced and cisplatininduced toxicities: results of a randomized control in patients with advanced ovarian cancer" Journal of Clinical Oncolouv 14 (7):2101-2112 (1996).
Krieg A.M. "Development of TLR9 agonists for cancer therapy" J Clinical Invest 117(5): 1184-1194 2007.
Kyte J. et al. "A simple method for displaying the hydropathic character of a protein" J. Mol. Biol. 157:105-132 (1982).
Lehnert B. E. et al. "A new mechanism for DNA alterations induced by alpha particles such as those emitted by radon and radon progeny" Environmental Health Perspectives 105(5):1095-1101 (1997).
Li G. et al. "A special issue on DNA damage responses and genome maintenance" Cell Research 18(1):1-2 (2008).
Li J. et al. "Evolutionary origin and radiation of the avian-adapted non-motile *Salmonellae*" Journal of Medical Microbiology 38(2):129-139 (1993).
McQuiston J. R. et al. "Sequencing and comparative analysis of flagellin genes fliC fljB and flpA from *Salmonella*" Journal of Clinical Microbiology 42(5):1923-1932 (2004).
Melby T. E. et al. "The symmetrical structure of structural maintenance of chromosomes (SMC) and MukB proteins: Long antiparallel coiled coils folded at a flexible hinge" The Journal of Cell Biology 142(6):1595-1604 (1998).
Mercurio F. et al. "NF-kB as a primary regulator of the stress response" Oncogene 18:6163-6171 (1999).
Murley J. S. et al. "Delayed cytoprotection after enhancement of Sod2 (MnSOD) gene expression in SA-NH mouse sarcoma cells exposed to WR-1065 the active metabolite of amifostine" Radiation Research 158(1):101-109 (2002).
Murley J. S. et al. "Delayed radioprotection by NFKB-mediated induction of Sod2 (MnSOD) in SA-NH tumor cells after exposure to clinically used thiol-containing drugs" Radiation Research 162(5):536-546 (2004).
Mutlu-Turkoglu U. et al. "The effect of selenium and/or vitamin E treatments on radiation-induced intestinal injury in rats" Life Sciences 66(20):1905-1913 (2000).
Neish A. S. "TLRS in the Gut. II. Flagellin-induced inflammation and antiapoptosis" American Journal of Physiology: Gastrointestinal and Liver Physiology 292(2):G462-G466 (2006).
Newton S. M. C. et al. "Immune response to cholera toxin epitope inserted in *Salmonella* flagellin" Science 244:70-72 (1989).
Offringa "Tumour immunology—Exploitation of the weapon of immune destruction for cancer therapy: taking aim before firing" Current Opinion in Immunology 2005 17:159-162.
Panda D. et al. "Stabilization of microtubule dynamics by estramustine by binding to a novel site in tubulin: A possible mechanistic basis for its antitumor action" Proc. Natl. Acad. Sci. USA 94(20):10560-10564 (1997).
U.S. Appl. No. 13/979,104, U.S. Pat. No. 9,376,473, filed Feb. 3, 2014.
U.S. Appl. No. 15/631,427, filed Jun. 23, 2017.
U.S. Appl. No. 15/500,133, filed Jan. 30, 2017.
U.S. Appl. No. 13/110,704, U.S. Pat. No. 8,932,609, filed May 18, 2011.
U.S. Appl. No. 14/284,354, U.S. Pat. No. 8,871,215, filed May 21, 2014.
U.S. Appl. No. 14/559,669, U.S. Pat. No. 9,139,623, filed Dec. 3, 2014.
U.S. Appl. No. 14/828,111, U.S. Pat. No. 9,228,000, filed Aug. 17, 2015.
U.S. Appl. No. 14/949,492, U.S. Pat. No. 9,457,061, filed Nov. 23, 2015.
U.S. Appl. No. 15/254,695, filed Sep. 1, 2016.
U.S. Appl. No. 13/530,580, U.S. Pat. No. 8,618,059, filed Jun. 22, 2012.

(56) References Cited

OTHER PUBLICATIONS

U.S. Appl. No. 14/088,097, U.S. Pat. No. 9,006,180, filed Nov. 22, 2013.
U.S. Appl. No. 15/519,462, filed Apr. 14, 2017.
U.S. Appl. No. 13/056,973, U.S. Pat. No. 8,324,163, filed Jan. 31, 2011.

FIG. 1A

```
Q53970  1 MAQVINTNSLLLTQNNLNKSQSSLSSAIERLSSGLRINSAKDDAAGQAIANRFTSNIKGLTQASRNAND
P72151  1 MALTVNTNIASLNTQRNLNASSNDLNTSLQRLTTGYRINSAKDDAAGLQISNRLSNQISGLNVATRNAND
Q5X5M6  1 MAQVINTNVASLTAQRNLGVSGNMMQTSIQRLSSGLRINSAKDDAAGLAISQRMTAQIRGMNQAVRNAND
Q6VMV6  1 MAQVINTNSLLLTQNNLNKSQSSLSSAIERLSSGLRINSAKDDAAGQAIANRFTANIKGLTQASRNAND
P13713  1 MAQVINTNSLSLMAQNNLNKSQSSLGTAIERLSSGLRINSAKDDAAGQAIANRFTANIKGLTQASRNAND
Q93RK8  1 --MRINHNIAALNTSRQLNAGSNSAAKNMEKLSSGLRINRAGDDAAGLAISEKMRSQIRGLDMASKNAQD
Q02551  1 --MKVNTNIISLKTQEYLRKNNEGMTQAQRRLASGKRINSSLDDAAGLAVVTRMNVKSTGLDAASKNSSM
Q09012  1 MAQVINTNSLSLLTQNNLNKSQSSLSSAIERLSSGLRINSAKDDAAGQAIANRFTANIKGLTQASRNAND
Q8GNT8  1 MAQVINTNSLSLMAQNNLNKSQSALGTAIERLSSGLRINSAKDDAAGQAISNRFTANINGLTQASRNAND
Q9FAE7  1 MASTINTNVSSLTAQRNLSLSQSSLINTSIQRLSSGLRINSAKDDAAGLAISERFTSQIRGLNQAVRNAND
Q8ZF76  1 MA-VINTNSLLLTQNNLNKSQSSLGTAIERLSSGLRINSAKDDAAGQAIANRFTSNIKGLTQAARNAND
Q7N5J4  1 MAQVINTNSLSLLTQNNLNRSQGTLGSAIERLSSGLRINSAKDDAAGQAIANRFTANVRGLTQAARNAND
O33578  1 -MTTINTNIGAIAAQANMTKVNDQFNTAMTRLSTGLRINAAKDDAAGMAIGEKMTAQVMGLNQAIRNAQD
Q56826  1 MASVINTNDSALLAQNNLTKSKGILGSAIERLSSGLRINSAKDDAAGQAIANRFTANVKGLTQAARNAND
P42273  1 MAQVINTNYLSIVTQNNLNRSQSALGNAIERLSSGMRINSAKDDAAGQAIANRFTSNINGLTQASRNAND
O31059  1 --MVVQHNMQAANASRMLGITTGDQSKSTEKLSSGFKINRAADDAAGLSISEKMRKQIRGLDQASTNASD
Q7VZC2  1 MAAVINTNYLSIVAQNNLNKSQSALGSAIERLSSGLRINSAKDDAAGQAIANRFTANVKGLTQAARNAND
Q9F4A4  1 --MIINHNMNALNAHRNMMGNIATAGKSMEKLSSGLRINRAGDDAAGLAISEKMRGQIRGLDQASRNAQD
Q8P9C4  1 MAQVINTNVMSLNAQRNLNTNSSSMALSIQQLSSGKRITSASVDAAGLAISERFTTQIRGLDVASRNAND
Q82UA3  1 MPQVINTNIASLNAQRNLNVSQNSLSTALQRLSSGLRINSAADDAAGLAISERMTSQIRGMNQAARNAND
Q84IC5  1 -GFRINTNGASLNAQVNAGLNSRNLDSSLARLSSGLRINSAADDASGLAIADSLKTQANSLGAINNAND
             :.  ::            :          *:::*.:.:**.: :*:::.* .:.   *   *  *:..
```

C=indicates a conserved amino acid important for TLR5 activity

FIG. 1A (continued)

```
Q53970  71  GISIAQTTEGALNEINNNLQRVRELSVQATNGTNSDSDLKSIQDEIQQRLEEIDRVSNQTQFNGVKVLSQ
P72151  71  GISLAQTAEGALQQSTNILQRIRDLALQSANGSNSDADRAALQKEVAAQQAELTRISDTTTFGGRKLLDG
Q5X5M6  71  GISLAQVAEGAMQETTNILQRMRELSVQAANSTNNSSDRASIQSEISQLKSELERIAQNTEFNGQRILDG
Q6VMV6  71  GISVAQTTEGALNEINNNLQRVRELTVQATNGTNSDSDLSSIQAEITQRLEEIDRVSEQTQFNGVKVLAE
P13713  71  GISLAQTTEGALNEINEVNDNLQNIRRLTVQAQNGSNSTSDLKSIQDEITQRLSEINRISEQTDFNGVKVLSS
Q93RK8  69  GISLIQTSEGALNETHSILQRMSELATQAANDTNTDSDRSELQKEMDQLASEVTRISTDTEFNTKKLLDG
Q02551  71  GIDLLQTADSALSSMSSILQRMRQLAVQSSNGSFSDEDRKQYTAEFGSLIKELDHVADTTNYNNIKLLDQ
Q09012  69  GISVAQTTEGALSEINNNLQRIRELSVQATNGTNSDSDLNSIQDEITQRLSEIDRVSNQTQFNGVKVLAS
Q8GNT8  71  GISVAQTTEGALNEVNDNLQNIRRLTVQAQNGSNSSSDLQSIQDEITQRLSEIDRISQQTDFNGVKVLSK
Q9FAE7  71  GISLAQTAEGALKSTGDILQRVRELAVQSANATNSSGDRKAIQAEVGQLLSEMDRIAGNTEFNGQKLLDG
Q8ZF76  70  GISIAQTTEGSLNEINNNLQRVRELTVQAQNGSNSSDLDSIQDEISLRLAEIDRVSDQTQFNGKKVLAE
Q7N5J4  71  GISIAQTTEGALNEINTNLQRIRELTVQSONGSNSESDIKSIQEEVTQRLKEIDRISEQTQFNGVRVLRE
O33578  70  GKNLVDTTEGAHVEVSSMLQRLRELAVQSSNDTNTAADRGSLAAEGKQLIAEINRVAESTTFNGMKVLDG
Q56826  71  GISIAQTTEGALNEINNNLQRIRELTVQSENGSNSKSDLDSIQKEVTQRLEEIDRISTQTQFNGVKVLSG
P42273  71  GISVSQTTEGALNEINNNLQRIRELTVQAKNGTNSNSDINSIQNEVNQRLDEINRVSEQTQFNGVKVLSG
O31059  69  GISAVQTAEGALTEVHSMLQRMNELAVQAANGTNSESDRSSIQDEINQLTTEIDRVAETTKFNETYLLKG
Q7VZC2  71  GISLIQTAEGALNEINNNLQRIRELTVQASNGTNSASDIDSIQQEVNQRLEEINRIAEQTDFNGIKVLKS
Q9F4A4  69  GISLIQTAETHSILQRMRELSVQAANDTNVAVDRTAIQDEINSLTEEINRISGDTEFNTQKLLDG
Q8P9C4  71  GISLAQTAEGAMVEIGNNLQRIRELSVQSANATNSATDREALNSEVKQLTSEIDRVANQTSFNGTKLLNG
Q82UA3  71  GISLAQTAEGALVEIGNNLQRIRELAVQSANATNSEDDREALQKEVTQLIDEIQRVGEQTSFNGTKLLDG
Q84IC5  70  ANSMLQIADKAMDEQLKLILDTIKVKATQAAQDGQTAKTRAMIQGEINKLMEELDNIANTTTYNGKQLLSG
                *                                   *.   . *.  *   * .    .   .*
                                                       CCC  C  C                            C
```

C=indicates a conserved amino acid important for TLR5 activity

FIG. 1A (continued)

```
Q53970  141  DNQ-MK---IQVGANDG-------------ETITIDLQ----------KID-VKSLG-----LDGFN
P72151  141  SFGTTS--FQVGSNAY--------------ETIDISLQNASASAIGSYQVG-SNGAGTVASVAGTA
Q5X5M6  141  SFSGAS--FQVGANSN--------------QTINFSIG----------SIK-ASSIGGIATATGTE
Q6VMV6  141  NNE-MK---IQVGANDG-------------ETITINLA----------KID-AKTLG-----LDGFN
P13713  141  DQK-LT---IQVGANDG-------------ETTDIDLK----------KID-AKQLG-----MDTF-
Q93RK8  139  TAQNLT--FQIGANEG--------------QTMSLSIN----------KMD-SE---------SLK
Q02551  139  TATGAATQVSIQASDKAN------------DLINIDLFNAKGLSAGTITLGSGSTVAGYSALSVAD
Q09012  141  DQT-MK---IQVGANDG-------------ETIEIALD----------KID-AKTLG-----LDNFS
Q8GNT8  141  DQK-LT---IQVGANDG-------------ETIDIDLK----------NIN-AQSLG-----LDKFN
Q9FAE7  141  SFGSAT--FQVGANAN--------------QTITATTGNFRTNNY-GAQLT-ASASG--AATSGAS
Q8ZF76  140  NTT-MS---IQVGANDG-------------ETIDINLQ----------KID-SKSLG-----LGSYS
Q7N5J4  141  DSK-MT---IQVGANDN-------------EVIDIDLK----------KID-KEALN-----LGKFT
O33578  140  SFTGKQ--LQIGADSG--------------QTMAINVDSAAATDIGAHKISSASTVVADAALTDTT
Q56826  141  DVTEMK--IQVGANDN--------------ETIGIKLG----------KIN-SEKLN-----LKEFS
P42273  141  EKSKMT--IQVGTNDN--------------EVIEFNLD----------KID-NDTLG-----VASDK
O31059  139  GNGDRT--VRVYAHDAGLVGSLSQNTTKATFQMRKLEIGDSYTIGGTTYKIG-AETVK--EAMTALK
Q7VZC2  141  NATDMTLSIQVGAKDN--------------ETIDIKID----------RNS-NWNLY----DAVGT
Q9F4A4  139  GFKG-E--FQIGANSN--------------QTVKLDIG----------NMS-AA-------SLG
Q8P9C4  139  DFSGAL--FQVGADAG--------------QTIGINS----------IVDAN-VDSLG--KANFAAS
Q82UA3  141  SFASQI--FQVGANEG--------------ETIDFTD----------STN-SAKVGQTRFETGAV
Q84IC5  140  SFSNAQ--FQIGDKAN--------------QTVNATIG---------STN-SAKVGQTRFETGAV
```

C=indicates a conserved amino acid important for TLR5 activity

FIG. 1B

```
Q53970  410  PLASIDSALSKVDAVRSSLGAIQNRFDSAITNLGNTVTNLNSARSRIEDADYATEVSNMSKAQILQQAGTSVLAQANQVPQNVLSLLR--
P72151  401  AIAVVDNALAAIDAQRADLGAVQNRFKNTIDNLTNISENATNARSRIKDTDFAAETAALSKNQVLQQAGTAILAQANQLPQAVLSLLR--
Q5X5M6  387  AIKRIDAAALNSVNSNRANMGALQNRFESTIANLQNVSDNLSAARSRIQDADYAAEMASLTKNQILQQAGTAMLAQANSLPQSVLSLLGR-
Q6VMV6  400  PLETIDKRALAKVDNLRSDLGAVQNRFDSAITNLGNTVNNLSSARSRIRDADYATEVSNMSRAQILQQAGTSVLAQANQTTQNVLSLLQG-
P13713  264  PLATLDKALAQVDGLRSSLGAVQNRFDSVINNLNSTVNNLSASQSRIQDADYATEVSNMSRANILQQAGTSVLAQANQSTQNVLSLLR--
Q93RK8  245  ALTTIXTALDTVSSERAKLGAVQNRLEHTINNLGTSSENLTSABSRIRDVDMASEMMEYTKNNILTQASQAMLAQANQQPQQVLQLLKG-
Q02551  481  VIGLADAALTKIMKQRADMGAYYNRLEYTAKGLMGAYENMQASESRIRDADMAEEVVSLITTKQILVQSGTAMLAQANMKPNSVLKLLQQI
Q09012  437  PLSKLDEALAKVDKLRSSLGLGAVQNRFDSAITNLGNTVNDLSSARSRIQDADYATEVSNMSRAQILQQAGTSVLAQANQTTQNVLSLLR--
Q8GNT8  329  PLATLDKALSQVDILRSGLGAVQNRFDSVINNLNSTVNNLSASRSRIQDADYATEVSNMSRAQILQQAGTSVLAQANQSTQNVLSLLR--
Q9FAE7  405  AIKIIDAAALSAVNQQRASFGALQSRFETTVNNLQSTSENMSASRSRIQDADFAAETANLSRSQILQQAGTAMVAQANQLPQGVLSLLK--
Q8ZF76  282  PLETLDDAIKQVDGLRSSLGAVQNRFESASAVTNLNNTVTNLTSARSRIEDADYATEVSNMSRAQILQQAGTSVLSQANQVPQTVLSLLN--
Q7N5J4  268  PLETLDSALAQVDSLRSSLGAIQNRLESTVNNLNNTVNNLSAARSRIEDADYATEVSNMSRGQILQQAGTAVLAQAMQVPQNVMSLLR--
O33578  405  AIGVIDVALSKISQSRSELGAVSNRLDSTISNLTNISTSVQAAKSQVMDADFAAESTNLARSQILSQASTAMLAQANSSKQNVLSLLRG-
Q56826  226  PLDTLDKALAQVDDNRSSLGAVQNRLESTVNNLNNTVNNLNNTVNNLSAARSRIEDADYAVEVSNMSRGQILQQAGTSVLAQANQVPQTVLSLLR--
P42273  280  ALATLDNAISKVDESRSKLGAIQNRFQSTINNLNNTVNNLSASRSRILDADYATEVSNMSKNQILQQAGTAVLAQANQVPQTVLSLLR--
O31059  385  AIDAISDALAKVSAQRSALGSIQNRLEHSIANLDNVVENTNAAESRIRDTDMADEMVTYSKNNILMQAGQSMLAQANQATQGVLSILQ-
Q7V2C2  304  ALSKLDDAMKAVDEQRSSLGAIQNRFESTVANLNNTITNLSAARSRIEDSDYATEVSNMTKNQILQQAGTSVLAQANQVPQNVSLLR--
Q9F4A4  326  SIKTINSAIEQVSTQRSKLGAVQNRLEHTINNLNTSSENLTAAESRVRDVDMAKEMMAFSKNNILSQAAQAMLGQANQPQGVLQLLR--
Q8P9C4  312  ALEIVDKALTSVNSSRADMGAVQNRFTSTLANLAATSENLTASRSRIADTDYAKTTAELTRTQILQQAGTAMLAQAKSVFQNVLSLLQ-
Q82UA3  192  ----IDDALKIVNSTRADLGAIQNRFSSAIANLQTSAENLSASRSRIQDADFAAETAALTRAQILQQAGVAMLSQANALPNNVLSLLR--
Q84IC5  403  VMDIADTAIANLDTIRANIGATQNQITSTINNISVTQVNVKAAESQIRDVDFASEKSANYSKANILAQSGSYAMAQANAASQNVLRLLQ--
                 *    *.    *:   * :.  *   ..     ::   ..   **::  * * *     .:..***  *.:  :.::*
              CC     C          C                                  C
```

C=indicates a conserved amino acid important for TLR5 activity

FIG. 6
A
502 0.1 µg
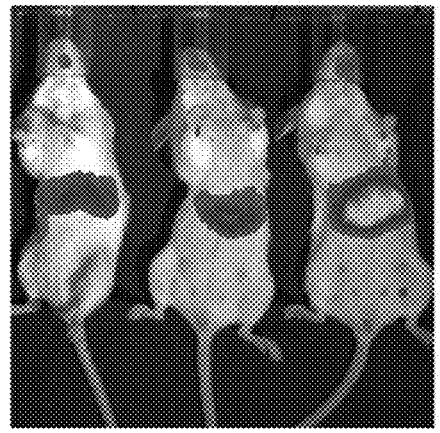
B
S33 0.1 µg
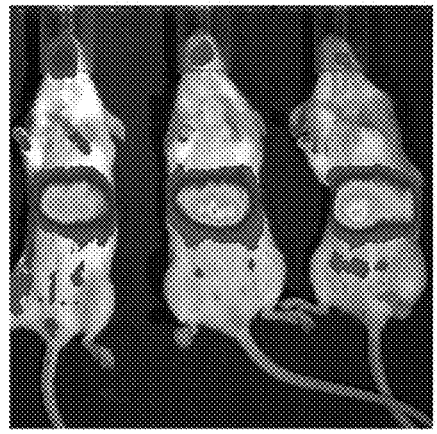

FIG. 7 (cont.)
E
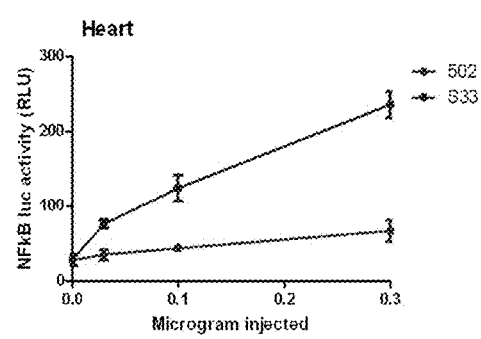
F
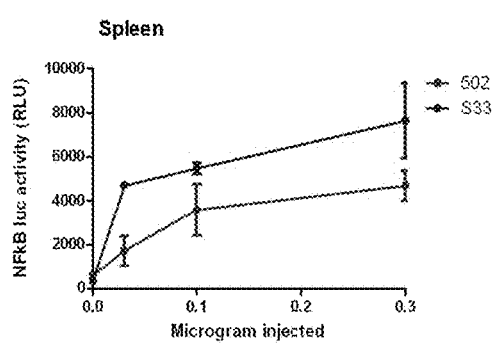
G
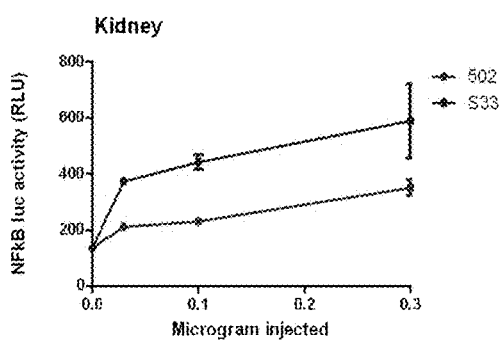
H
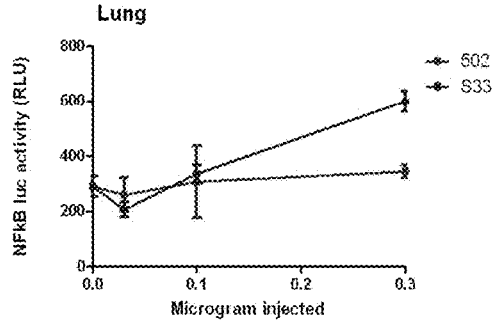

A

| Time hr | Average CBLB502, ng/ml | |
|---|---|---|
| | 1 µg/kg | 2 µg/kg |
| 0.08 | 1.030 | 2.453 |
| 0.25 | 0.069 | 0.178 |
| 0.5 | 0.015 | 0.021 |
| 1 | BLQ | 0.005 |
| 2 | BLQ | BLQ |
| 4 | BLQ | BLQ |
| 8 | BLQ | BLQ |
| 24 | BLQ | BLQ |

| Time hr | Average 33MX, ng/ml | |
|---|---|---|
| | 1 µg/kg | 2 µg/kg |
| 0.08 | 1.218 | 3.029 |
| 0.25 | 0.139 | 0.343 |
| 0.5 | 0.034 | 0.064 |
| 1 | 0.020 | 0.036 |
| 2 | 0.008 | 0.015 |
| 4 | BLQ | BLQ |
| 8 | BLQ | BLQ |
| 24 | BLQ | BLQ |

| Time hr | STDEV CBLB502, ng/ml | |
|---|---|---|
| | 1 µg/kg | 2 µg/kg |
| 0.08 | 0.823 | 1.051 |
| 0.25 | 0.025 | 0.037 |
| 0.5 | 0.010 | 0.004 |
| 1 | ND | 0.011 |
| 2 | ND | ND |
| 4 | ND | ND |
| 8 | ND | ND |
| 24 | ND | ND |

| Time hr | STDEV 33MX, ng/ml | |
|---|---|---|
| | 1 µg/kg | 2 µg/kg |
| 0.08 | 0.224 | 0.789 |
| 0.25 | 0.029 | 0.153 |
| 0.5 | 0.006 | 0.011 |
| 1 | 0.010 | 0.008 |
| 2 | 0.001 | 0.010 |
| 4 | ND | ND |
| 8 | ND | ND |
| 24 | ND | ND |

B

SEQUENCE LISTING

<160> NUMBER OF SEQ ID NOS: 294

<210> SEQ ID NO 1
<211> LENGTH: 505
<212> TYPE: PRT
<213> ORGANISM: Salmonella dublin

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
        195                 200                 205

Asp Ile Asn Ser Gly Ala Val Val Thr Asp Ala Ala Pro Asp Lys
    210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
        275                 280                 285

Thr Gly Asp Asp Gly Asn Gly Lys Val Ser Thr Thr Ile Asn Gly Glu
    290                 295                 300

```
Lys Val Thr Leu Thr Val Ala Asp Ile Ala Thr Gly Ala Ala Asp Val
305                 310                 315                 320

Asn Ala Ala Thr Leu Gln Ser Ser Lys Asn Val Tyr Thr Ser Val Val
            325                 330                 335

Asn Gly Gln Phe Thr Phe Asp Asp Lys Thr Lys Asn Glu Ser Ala Lys
        340                 345                 350

Leu Ser Asp Leu Glu Ala Asn Asn Ala Val Lys Gly Glu Ser Lys Ile
    355                 360                 365

Thr Val Asn Gly Ala Glu Tyr Thr Ala Asn Ala Thr Gly Asp Lys Ile
370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
            405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
    435                 440                 445

Asn Leu Gly Asn Thr Val Thr Asn Leu Asn Ser Ala Arg Ser Arg Ile
    450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 2
<211> LENGTH: 329
<212> TYPE: PRT
<213> ORGANISM: Artificial Sequence
<220> FEATURE:
<223> OTHER INFORMATION: Synthetic sequence

<400> SEQUENCE: 2

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160
```

Asn Gln Thr Gln Phe Asn Gly Val Lys Val Leu Ser Gln Asp Asn Gln
            165                 170                 175

Met Lys Ile Gln Val Gly Ala Asn Asp Gly Glu Thr Ile Thr Ile Asp
        180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu Gly Asn Thr Val Thr Asn Leu Asn Ser Ala Arg Ser Arg Ile
        275                 280                 285

Glu Asp Ala Asp Tyr Ala Thr Glu Val Ser Asn Met Ser Lys Ala Gln
    290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
            325

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence

<400> SEQUENCE: 3
taatacgact cactataggg g                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
attgcgcaga ccactgaagg                                                20

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Leu Val Pro Arg Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

```
<400> SEQUENCE: 6

Asp Asp Asp Asp Lys
1               5

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence

<400> SEQUENCE: 7

Ser Ser Gly Leu Arg Ile Asn Ser Ala Lys Asp Asp Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic sequence

<400> SEQUENCE: 8

Glu Asp Ala Asp Tyr Ala
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic sequence

<400> SEQUENCE: 9

Ala Ala Ser Ala Gly Ala Gly Gln Gly Gly Gly Gly Ser Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic sequence

<400> SEQUENCE: 10

Glu Gly Lys Ser Ser Gly Ser Gly Ser Glu Ser Lys Ser Thr
1               5                   10

<210> SEQ ID NO 11
<211> LENGTH: 22
<212> TYPE: PRT
<213> ORGANISM: Artificial Sequence
<220> FEATURE:
<223> OTHER INFORMATION: Synthetic sequence

<400> SEQUENCE: 11

Gly Gly Gly Arg Thr Ser Ser Ala Ala Ser Ala Gly Ala Gly Gln
1               5                   10                  15

Gly Gly Gly Gly Ser Gly
            20

<210> SEQ ID NO 12
<211> LENGTH: 4
<212> TYPE: PRT
<213> ORGANISM: Artificial Sequence
<220> FEATURE:
```

<223> OTHER INFORMATION: Synthetic sequence

<400> SEQUENCE: 12

Gly Pro Ser Gly
1

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence

<400> SEQUENCE: 13

Gly Ser Ala Gly Ser Ala Ala Gly Ser Gly Glu Phe
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic sequence

<400> SEQUENCE: 14

Gly Ser Pro Gly
1

<210> SEQ ID NO 15
<211> LENGTH: 18
<212> TYPE: PRT
<213> ORGANISM: Artificial Sequence
<220> FEATURE:
<223> OTHER INFORMATION: Synthetic sequence

<400> SEQUENCE: 15

Lys Glu Ser Gly Ser Val Ser Ser Glu Gln Leu Ala Gln Phe Arg Ser
1               5                   10                  15

Leu Asp

<210> SEQ ID NO 16
<211> LENGTH: 16
<212> TYPE: PRT
<213> ORGANISM: Artificial Sequence
<220> FEATURE:
<223> OTHER INFORMATION: Synthetic sequence

<400> SEQUENCE: 16

Ser Pro Gly Ile Ser Gly Gly Gly Gly Ile Leu Asp Ser Met Gly
1               5                   10                  15

<210> SEQ ID NO 17
<211> LENGTH: 300
<212> TYPE: PRT
<213> ORGANISM: Artificial Sequence
<220> FEATURE:
<223> OTHER INFORMATION: Synthetic sequence

<400> SEQUENCE: 17

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
            50                  55                  60

Leu Thr Gln Ala Ser Arg Asn Ala Asn Asp Gly Ile Ser Ile Ala Gln
 65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
                100                 105                 110

Leu Lys Ser Ile Gln Asp Glu Ile Gln Gln Arg Leu Glu Glu Ile Asp
            115                 120                 125

Arg Val Ser Asn Gln Thr Gln Phe Asn Gly Val Lys Val Leu Ser Gln
            130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
                180                 185                 190

Asp Ser Met Gly Thr Leu Ile Asn Glu Asp Ala Ala Ala Lys Lys
            195                 200                 205

Ser Thr Ala Asn Pro Leu Ala Ser Ile Asp Ser Ala Leu Ser Lys Val
210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
                260                 265                 270

Lys Ala Gln Ile Leu Gln Gln Ala Gly Thr Ser Val Leu Ala Gln Ala
            275                 280                 285

Asn Gln Val Pro Gln Asn Val Leu Ser Leu Leu Arg
            290                 295                 300

<210> SEQ ID NO 18
<211> LENGTH: 48
<212> TYPE: DNA
<213> ORGANISM: Artificial Sequence
<220> FEATURE:
<223> OTHER INFORMATION: Synthetic sequence

<400> SEQUENCE: 18
gcagattctg cagcaggctg gttgataatc tggcgcaggc taaccagg         48

<210> SEQ ID NO 19
<211> LENGTH: 60
<212> TYPE: DNA
<213> ORGANISM: Artificial Sequence
<220> FEATURE:
<223> OTHER INFORMATION: Synthetic sequence

<400> SEQUENCE: 19
tctaaagcgc agattctgca gcaggctggt acttccgttc tggcgcaggc taaccaggtt    60

<210> SEQ ID NO 20
<211> LENGTH: 48
<212> TYPE: DNA
<213> ORGANISM: Artificial Sequence
<220> FEATURE:

<223> OTHER INFORMATION: Synthetic sequence

<400> SEQUENCE: 20
cctggttagc ctgcgccaga ttatcaacca gcctgctgca gaatctgc    48

<210> SEQ ID NO 21
<211> LENGTH: 936
<212> TYPE: DNA
<213> ORGANISM: Artificial Sequence
<220> FEATURE:
<223> OTHER INFORMATION: Synthetic sequence

<400> SEQUENCE: 21

```
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcgggatc tgtacgacct ggttccgcgc   180
ggtagcgcga aggatccgtc tggtctgcgt atcaacagcg cgaaagacga tgcggcaggc   240
caggcgattg ctaaccgctt cacttctaat atcaaaggtc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta cgggactaa ctctgattcc   420
gatctgaaat ctatccagga tgaaattcag caacgtctgg aagaaatcga tcgcgtttct   480
aatcagactc aatttaacgg tgttaaagtc ctgtctcagg acaaccagat gaaaatccag   540
gttggtgcta acgatggtga accattacc atcgatctgc aaaaaattga tgtgaaaagc   600
cttggccttg atgggttcaa tgttaattcc ccgggaattt ccggtggtgg tggtggaatt   660
ctagactcca tgggtacatt aatcaatgaa gacgctgccg cagccaagaa aagtaccgct   720
aacccactgg cttcaattga ttctgcattg tcaaaagtgg acgcagttcg ttcttctctg   780
ggggcaattc aaaaccgttt tgattcagcc attaccaacc ttggcaatac ggtaaccaat   840
ctgaactccg cgcgtagccg tatcgaagat gctgactatg caacggaagt ttctaatatg   900
tctaaagcgc agattctgca gcaggctggt tgataa                              936
```

<210> SEQ ID NO 22
<211> LENGTH: 281
<212> TYPE: PRT
<213> ORGANISM: Artificial Sequence
<220> FEATURE:
<223> OTHER INFORMATION: Synthetic sequence

<400> SEQUENCE: 22

```
Met Arg Gly Ser His His His His His His Gly Met Ala Ser Met Thr
1               5                   10                  15
Gly Gly Gln Gln Met Gly Arg Asp Leu Tyr Asp Leu Val Pro Arg Gly
            20                  25                  30
Ser Ala Lys Asp Pro Ser Gly Leu Arg Ile Asn Ser Ala Lys Asp Asp
        35                  40                  45
Ala Ala Gly Gln Ala Ile Ala Asn Arg Phe Thr Ser Asn Ile Lys Gly
    50                  55                  60
Leu Thr Gln Ala Ser Arg Asn Ala Asn Asp Gly Ile Ser Ile Ala Gln
65                  70                  75                  80
Thr Thr Glu Gly Ala Leu Asn Glu Ile Asn Asn Leu Gln Arg Val
                85                  90                  95
Arg Glu Leu Ser Val Gln Ala Thr Asn Gly Thr Asn Ser Asp Ser Asp
            100                 105                 110
```

```
Leu Lys Ser Ile Gln Asp Glu Ile Gln Gln Arg Leu Glu Glu Ile Asp
            115                 120                 125
Arg Val Ser Asn Gln Thr Gln Phe Asn Gly Val Lys Val Leu Ser Gln
130                 135                 140
Asp Asn Gln Met Lys Ile Gln Val Gly Ala Asn Asp Gly Glu Thr Ile
145                 150                 155                 160
Thr Ile Asp Leu Gln Lys Ile Asp Val Lys Ser Leu Gly Leu Asp Gly
                165                 170                 175
Phe Asn Val Asn Ser Pro Gly Ile Ser Gly Gly Gly Gly Ile Leu
            180                 185                 190
Asp Ser Met Gly Thr Leu Ile Asn Glu Asp Ala Ala Ala Lys Lys
            195                 200                 205
Ser Thr Ala Asn Pro Leu Ala Ser Ile Asp Ser Ala Leu Ser Lys Val
            210                 215                 220
Asp Ala Val Arg Ser Ser Leu Gly Ala Ile Gln Asn Arg Phe Asp Ser
225                 230                 235                 240
Ala Ile Thr Asn Leu Gly Asn Thr Val Thr Asn Leu Asn Ser Ala Arg
                245                 250                 255
Ser Arg Ile Glu Asp Ala Asp Tyr Ala Thr Glu Val Ser Asn Met Ser
            260                 265                 270
Lys Ala Gln Ile Leu Gln Gln Ala Gly
            275                 280

<210> SEQ ID NO 23
<211> LENGTH: 329
<212> TYPE: PRT
<213> ORGANISM: Artificial Sequence
<220> FEATURE:
<223> OTHER INFORMATION: Synthetic sequence

<400> SEQUENCE: 23

Met Ala Gln Val Ile Asn Thr Asn Ser Leu Ser Leu Thr Gln Asn
1               5                   10                  15
Asn Leu Asn Lys Ser Gln Ser Ser Leu Ser Ser Ala Ile Glu Arg Leu
            20                  25                  30
Ser Ser Gly Leu Arg Ile Asn Ser Ala Lys Asp Asp Ala Ala Gly Gln
        35                  40                  45
Ala Ile Ala Asn Arg Phe Thr Ser Asn Ile Lys Gly Leu Thr Gln Ala
50                  55                  60
Ser Arg Asn Ala Asn Asp Gly Ile Ser Ile Ala Gln Thr Thr Glu Gly
65                  70                  75                  80
Ala Leu Asn Glu Ile Asn Asn Asn Leu Gln Arg Val Arg Glu Leu Ser
                85                  90                  95
Val Gln Ala Thr Asn Gly Thr Asn Ser Asp Ser Asp Leu Lys Ser Ile
            100                 105                 110
Gln Asp Glu Ile Gln Gln Arg Leu Glu Glu Ile Asp Arg Val Ser Asn
        115                 120                 125
Gln Thr Gln Phe Asn Gly Val Lys Val Leu Ser Gln Asp Asn Gln Met
130                 135                 140
Lys Ile Gln Val Gly Ala Asn Asp Gly Glu Thr Ile Thr Ile Asp Leu
145                 150                 155                 160
Gln Lys Ile Asp Val Lys Ser Leu Gly Leu Asp Gly Phe Asn Val Asn
                165                 170                 175
Ser Pro Gly Ile Ser Gly Gly Gly Gly Ile Leu Asp Ser Met Gly
            180                 185                 190
```

```
Thr Leu Ile Asn Glu Asp Ala Ala Ala Ala Lys Lys Ser Thr Ala Asn
            195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
            245                 250                 255

Asp Ala Asp Tyr Ala Thr Glu Val Ser Asn Met Ser Lys Ala Gln Ile
            260                 265                 270

Leu Gln Gln Ala Gly Thr Ser Val Leu Ala Gln Ala Asn Gln Val Pro
    275                 280                 285

Gln Asn Val Leu Ser Leu Leu Val Pro Arg Gly Ser His His His
    290                 295                 300

His His Gly Met Ala Ser Met Thr Gly Gly Gln Gln Met Gly Arg Asp
305                 310                 315                 320

Leu Tyr Asp Asp Asp Lys Asp Pro
            325

<210> SEQ ID NO 24
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 24
atggcacaag tcattaatac aaacagcctg tcgctgttga cccagaataa cctgaacaaa      60
tctcagtcct cactgagttc cgctattgag cgtctgtcct ctggtctgcg tatcaacagc     120
gcgaaagacg atgcggcagg ccaggcgatt gctaaccgct tcacttctaa tatcaaaggt     180
ctgactcagg cttcccgtaa cgctaacgac ggcatttcta ttgcgcagac cactgaaggt     240
gcgctgaatg aaatcaacaa caacctgcag cgtgtgcgtg agttgtctgt tcaggccact     300
aacgggacta actctgattc cgatctgaaa tctatccagg atgaaattca gcaacgtctg     360
gaagaaatcg atcgcgtttc taatcagact caatttaacg gtgttaaagt cctgtctcag     420
gacaaccaga tgaaaatcca ggttggtgct aacgatggtg aaaccattac catcgatctg     480
caaaaaattg atgtgaaaag ccttggcctt gatgggttca atgttaattc cccgggaatt     540
tccggtggtg gtggtggaat tctagactcc atgggtacat taatcaatga agacgctgcc     600
gcagccaaga aaagtaccgc taacccactg gcttcaattg attctgcatt gtcaaaagtg     660
gacgcagttc gttcttctct gggggcaatt caaaaccgtt ttgattcagc cattaccaac     720
cttggcaata cggtaaccaa tctgaactcc gcgcgtagcc gtatcgaaga tgctgactat     780
gcaacggaag tttctaatat gtctaaagcg cagattctgc agcaggctgg tacttccgtt     840
ctggcgcagg ctaaccaggt tccgcaaaac gtcctctctt tactggttcc gcggggttct     900
catcatcatc atcatcatgg tatggctagc atgactggtg gacagcaaat gggtcgggat     960
ctgtacgacg atgacgataa ggatccgtaa gtcgacaagc ttgcg              1005

<210> SEQ ID NO 25
<211> LENGTH: 31
<212> TYPE: DNA
<213> ORGANISM: Artificial Sequence
<220> FEATURE:
<223> OTHER INFORMATION: Synthetic sequence
```

<400> SEQUENCE: 25
cgaaagacca tatggcaggc caggcgattg c                                    31

<210> SEQ ID NO 26
<211> LENGTH: 33
<212> TYPE: DNA
<213> ORGANISM: Artificial Sequence
<220> FEATURE:
<223> OTHER INFORMATION: Synthetic sequence

<400> SEQUENCE: 26
cgcaagcttg tcgacttacg gatccttatc gtc                                  33

<210> SEQ ID NO 27
<211> LENGTH: 952
<212> TYPE: DNA
<213> ORGANISM: Artificial Sequence
<220> FEATURE:
<223> OTHER INFORMATION: Synthetic sequence

<400> SEQUENCE: 27

```
taatacgact cactataggg gaattgtgag cggataacaa ttcccctcta gaaataattt      60
tgtttaactt taagaaggag atatacatat ggcaggccag gcgattgcta accgcttcac     120
ttctaatatc aaaggtctga ctcaggcttc ccgtaacgct aacgacggca tttctattgc     180
gcagaccact gaaggtgcgc tgaatgaaat caacaacaac ctgcagcgtg tgcgtgagtt     240
gtctgttcag gccactaacg ggactaactc tgattccgat ctgaaatcta tccaggatga     300
aattcagcaa cgtctggaag aaatcgatcg cgtttctaat cagactcaat ttaacggtgt     360
taaagtcctg tctcaggaca accagatgaa atccaggtt ggtgctaacg atggtgaaac     420
cattaccatc gatctgcaaa aaattgatgt gaaaagcctt ggccttgatg ggttcaatgt     480
taattccccg ggaatttccg gtggtggtgg tggaattcta gactccatgg gtacattaat     540
caatgaagac gctgccgcag ccaagaaaag taccgctaac ccactggctt caattgattc     600
tgcattgtca aaagtggacg cagttcgttc ttctctgggg gcaattcaaa accgctttga     660
ttcagccatt accaaccttg gcaatacggt aaccaatctg aactccgcgc gtagccgtat     720
cgaagatgct gactatgcaa cggaagtttc taatatgtct aaagcgcaga ttctgcagca     780
ggctggtact tccgttctgg cgcaggctaa ccaggttccg caaaacgtcc tctctttact     840
ggttccgcgg ggttctcatc atcatcatca tcatggtatg gctagcatga ctggtggaca     900
gcaaatgggt cgggatctgt acgacgatga cgataaggat ccgtaagtcg ac             952
```

<210> SEQ ID NO 28
<211> LENGTH: 285
<212> TYPE: PRT
<213> ORGANISM: Artificial Sequence
<220> FEATURE:
<223> OTHER INFORMATION: Synthetic sequence

<400> SEQUENCE: 28

```
Met Ala Gly Gln Ala Ile Ala Asn Arg Phe Thr Ser Asn Ile Lys Gly
1               5                   10                  15

Leu Thr Gln Ala Ser Arg Asn Ala Asn Asp Gly Ile Ser Ile Ala Gln
            20                  25                  30

Thr Thr Glu Gly Ala Leu Asn Glu Ile Asn Asn Asn Leu Gln Arg Val
        35                  40                  45

Arg Glu Leu Ser Val Gln Ala Thr Asn Gly Thr Asn Ser Asp Ser Asp
    50                  55                  60
```

Leu Lys Ser Ile Gln Asp Glu Ile Gln Arg Leu Glu Glu Ile Asp
65                  70                  75                  80

Arg Val Ser Asn Gln Thr Gln Phe Asn Gly Val Lys Val Leu Ser Gln
                85                  90                  95

Asp Asn Gln Met Lys Ile Gln Val Gly Ala Asn Asp Gly Glu Thr Ile
            100                 105                 110

Thr Ile Asp Leu Gln Lys Ile Asp Val Lys Ser Leu Gly Leu Asp Gly
        115                 120                 125

Phe Asn Val Asn Ser Pro Gly Ile Ser Gly Gly Gly Gly Ile Leu
130                 135                 140

Asp Ser Met Gly Thr Leu Ile Asn Glu Asp Ala Ala Ala Lys Lys
145                 150                 155                 160

Ser Thr Ala Asn Pro Leu Ala Ser Ile Asp Ser Ala Leu Ser Lys Val
                165                 170                 175

Asp Ala Val Arg Ser Ser Leu Gly Ala Ile Gln Asn Arg Phe Asp Ser
            180                 185                 190

Ala Ile Thr Asn Leu Gly Asn Thr Val Thr Asn Leu Asn Ser Ala Arg
        195                 200                 205

Ser Arg Ile Glu Asp Ala Asp Tyr Ala Thr Glu Val Ser Asn Met Ser
210                 215                 220

Lys Ala Gln Ile Leu Gln Gln Ala Gly Thr Ser Val Leu Ala Gln Ala
225                 230                 235                 240

Asn Gln Val Pro Gln Asn Val Leu Ser Leu Leu Val Pro Arg Gly Ser
                245                 250                 255

His His His His His His Gly Met Ala Ser Met Thr Gly Gly Gln Gln
            260                 265                 270

Met Gly Arg Asp Leu Tyr Asp Asp Asp Lys Asp Pro
        275                 280                 285

<210> SEQ ID NO 29
<211> LENGTH: 765
<212> TYPE: DNA
<213> ORGANISM: Artificial Sequence
<220> FEATURE:
<223> OTHER INFORMATION: Synthetic sequence

<400> SEQUENCE: 29
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca caacaacct gcagcgtgtg      180 cgtgagttgt ctgttcaggc cactaacggg actaactctg attccgatct gaaatctatc     240
ggaccatcag gtcaggatga aattcagcaa cgtctggaag aaatcgatcg cgtttctaat     300
cagactcaat taacggtgt taaagtcctg tctcaggaca accagatgaa atccaggtt      360 ggtgctaacg atggtgaaac cattaccatc gatctgcaaa aaattgatgt gaaaagcctt     420
ggccttgatg ggttcaatgt taattccccg ggaagtaccg ctaacccact ggcttcaatt     480
gattctgcat tgtcaaaagt ggacgcagtt cgttcttctc tgggggcaat tcaaaaccgc     540
tttgattcag ccattaccaa ccttggcaat acggtaacca atctgaactc cgcgcgtagc     600
cgtatcgaag atgctgacta tgcaacggaa gtttctaata tgtctaaagc gcagattctg     660
cagcaggctg gtacttccgt tctggcgcag gctaaccagg ttccgcaaaa cgtcctctct     720
ttactggttc cgcggggttc tcatcatcat catcatcatg gttaa                    765

```
<210> SEQ ID NO 30
<211> LENGTH: 254
<212> TYPE: PRT
<213> ORGANISM: Artificial Sequence
<220> FEATURE:
<223> OTHER INFORMATION: Synthetic sequence

<400> SEQUENCE: 30

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gly Pro Ser Gly Gln Asp Glu Ile Gln Gln Arg Leu Glu Glu Ile Asp
                85                  90                  95

Arg Val Ser Asn Gln Thr Gln Phe Asn Gly Val Lys Val Leu Ser Gln
            100                 105                 110

Asp Asn Gln Met Lys Ile Gln Val Gly Ala Asn Asp Gly Glu Thr Ile
        115                 120                 125

Thr Ile Asp Leu Gln Lys Ile Asp Val Lys Ser Leu Gly Leu Asp Gly
    130                 135                 140

Phe Asn Val Asn Ser Pro Gly Ser Thr Ala Asn Pro Leu Ala Ser Ile
145                 150                 155                 160

Asp Ser Ala Leu Ser Lys Val Asp Ala Val Arg Ser Ser Leu Gly Ala
                165                 170                 175

Ile Gln Asn Arg Phe Asp Ser Ala Ile Thr Asn Leu Gly Asn Thr Val
            180                 185                 190

Thr Asn Leu Asn Ser Ala Arg Ser Arg Ile Glu Asp Ala Asp Tyr Ala
        195                 200                 205

Thr Glu Val Ser Asn Met Ser Lys Ala Gln Ile Leu Gln Gln Ala Gly
    210                 215                 220

Thr Ser Val Leu Ala Gln Ala Asn Gln Val Pro Gln Asn Val Leu Ser
225                 230                 235                 240

Leu Leu Val Pro Arg Gly Ser His His His His His Gly
                245                 250

<210> SEQ ID NO 31
<211> LENGTH: 32
<212> TYPE: DNA
<213> ORGANISM: Artificial Sequence
<220> FEATURE:
<223> OTHER INFORMATION: Synthetic sequence

<400> SEQUENCE: 31
gatatacata tgagcgggtt acggatcaac ag                                    32

<210> SEQ ID NO 32
<211> LENGTH: 29
<212> TYPE: DNA
<213> ORGANISM: Artificial Sequence
<220> FEATURE:
<223> OTHER INFORMATION: Synthetic sequence

<400> SEQUENCE: 32
```

```
agatctcccg gggaattaac attgaaccc                                    29
```

<210> SEQ ID NO 33
<211> LENGTH: 816
<212> TYPE: DNA
<213> ORGANISM: Artificial Sequence
<220> FEATURE:
<223> OTHER INFORMATION: Synthetic sequence

<400> SEQUENCE: 33

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac tggaccatca   300
ggtgaaattc agcaacgtct ggaagaaatc gatcgcgttt ctaatcagac tcaatttaac   360
ggtgttaaag tcctgtctca ggacaaccag atgaaaatcc aggttggtgc taacgatggt   420
gaaaccatta ccatcgatct gcaaaaaatt gatgtgaaaa gccttggcct tgatgggttc   480
aatgttaatt ccccgggaag taccgctaac ccactggctt caattgattc tgcattgtca   540
aaagtggacg cagttcgttc ttctctgggg gcaattcaaa accgctttga ttcagccatt   600
accaaccttg gcaatacggt aaccaatctg aactccgcgc gtagccgtat cgaagatgct   660
gactatgcaa cggaagtttc taatatgtct aaagcgcaga ttctgcagca ggctggtact   720
tccgttctgg cgcaggctaa ccaggttccg caaaacgtcc tctctttact ggttccgcgg   780
ggttctcatc atcatcatca tcatggttaa gtcgac                             816
```

<210> SEQ ID NO 34
<211> LENGTH: 240
<212> TYPE: PRT
<213> ORGANISM: Artificial Sequence
<220> FEATURE:
<223> OTHER INFORMATION: Synthetic sequence

<400> SEQUENCE: 34

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Gly Pro Ser Gly Glu Ile Gln Gln Arg Leu Glu Glu
65                  70                  75                  80

Ile Asp Arg Val Ser Asn Gln Thr Gln Phe Asn Gly Val Lys Val Leu
                85                  90                  95

Ser Gln Asp Asn Gln Met Lys Ile Gln Val Gly Ala Asn Asp Gly Glu
            100                 105                 110

Thr Ile Thr Ile Asp Leu Gln Lys Ile Asp Val Lys Ser Leu Gly Leu
        115                 120                 125

Asp Gly Phe Asn Val Asn Ser Pro Gly Ser Thr Ala Asn Pro Leu Ala
    130                 135                 140

Ser Ile Asp Ser Ala Leu Ser Lys Val Asp Ala Val Arg Ser Ser Leu
```

```
             145                 150                 155                 160
         Gly Ala Ile Gln Asn Arg Phe Asp Ser Ala Ile Thr Asn Leu Gly Asn
                         165                 170                 175

Thr Val Thr Asn Leu Asn Ser Ala Arg Ser Arg Ile Glu Asp Ala Asp
                         180                 185                 190

Tyr Ala Thr Glu Val Ser Asn Met Ser Lys Ala Gln Ile Leu Gln Gln
                         195                 200                 205

Ala Gly Thr Ser Val Leu Ala Gln Ala Asn Gln Val Pro Gln Asn Val
                         210                 215                 220

Leu Ser Leu Leu Val Pro Arg Gly Ser His His His His His His Gly
         225                 230                 235                 240

<210> SEQ ID NO 35
<211> LENGTH: 275
<212> TYPE: PRT
<213> ORGANISM: Artificial Sequence
<220> FEATURE:
<223> OTHER INFORMATION: Synthetic sequence

<400> SEQUENCE: 35

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
                20                  25                  30

Ser Arg Asn Ala Asn Asp Gly Ile Ser Ile Ala Gln Thr Thr Glu Gly
            35                  40                  45

Ala Leu Asn Glu Ile Asn Asn Asn Leu Gln Arg Val Arg Glu Leu Ser
        50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
                100                 105                 110

Lys Ile Gln Val Gly Ala Asn Asp Gly Glu Thr Ile Thr Ile Asp Leu
            115                 120                 125

Gln Lys Ile Asp Val Lys Ser Leu Gly Leu Asp Gly Phe Asn Val Asn
        130                 135                 140

Ser Pro Gly Ile Ser Gly Gly Gly Gly Ile Leu Asp Ser Met Gly
145                 150                 155                 160

Thr Leu Ile Asn Glu Asp Ala Ala Ala Lys Lys Ser Thr Ala Asn
                165                 170                 175

Pro Leu Ala Ser Ile Asp Ser Ala Leu Ser Lys Val Asp Ala Val Arg
                180                 185                 190

Ser Ser Leu Gly Ala Ile Gln Asn Arg Phe Asp Ser Ala Ile Thr Asn
            195                 200                 205

Leu Gly Asn Thr Val Thr Asn Leu Asn Ser Ala Arg Ser Arg Ile Glu
        210                 215                 220

Asp Ala Asp Tyr Ala Thr Glu Val Ser Asn Met Ser Lys Ala Gln Ile
225                 230                 235                 240

Leu Gln Gln Ala Gly Thr Ser Val Leu Ala Gln Ala Asn Gln Val Pro
                245                 250                 255

Gln Asn Val Leu Ser Leu Leu Val Pro Arg Gly Ser His His His His
                260                 265                 270

His His Gly
```

<210> SEQ ID NO 36
<211> LENGTH: 828
<212> TYPE: DNA
<213> ORGANISM: Artificial Sequence
<220> FEATURE:
<223> OTHER INFORMATION: Synthetic sequence

<400> SEQUENCE: 36

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca caacaaccct gcagcgtgtg     180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aatttccggt ggtggtggtg gaattctaga ctccatgggt     480
acattaatca atgaagacgc tgccgcagcc aagaaaagta ccgctaaccc actggcttca     540
attgattctg cattgtcaaa agtggacgca gttcgttctt ctctggggc  aattcaaaac     600
cgctttgatt cagccattac caaccttggc aatacggtaa ccaatctgaa ctccgcgcgt     660
agccgtatcg aagatgctga ctatgcaacg gaagtttcta atatgtctaa agcgcagatt     720
ctgcagcagg ctggtacttc cgttctggcg caggctaacc aggttccgca aaacgtcctc     780
tctttactgg ttccgcgggg ttctcatcat catcatcatc atggttaa                  828
```

<210> SEQ ID NO 37
<211> LENGTH: 41
<212> TYPE: DNA
<213> ORGANISM: Artificial Sequence
<220> FEATURE:
<223> OTHER INFORMATION: Synthetic sequence

<400> SEQUENCE: 37

```
tctagacccg ggaagtaccg ctaacccact ggcttcaatt g              41
```

<210> SEQ ID NO 38
<211> LENGTH: 40
<212> TYPE: DNA
<213> ORGANISM: Artificial Sequence
<220> FEATURE:
<223> OTHER INFORMATION: Synthetic sequence

<400> SEQUENCE: 38

```
ccagtcatgt cgacttaacc atgatgatga tgatgatgag              40
```

<210> SEQ ID NO 39
<211> LENGTH: 55
<212> TYPE: DNA
<213> ORGANISM: Artificial Sequence
<220> FEATURE:
<223> OTHER INFORMATION: Synthetic sequence

<400> SEQUENCE: 39

```
ctcatcatca tcatcatcat ggttaagtcg acaagcttgc ggccgcagag ctcgc              55
```

<210> SEQ ID NO 40
<211> LENGTH: 846

```
<212> TYPE: DNA
<213> ORGANISM: Artificial Sequence
<220> FEATURE:
<223> OTHER INFORMATION: Synthetic sequence

<400> SEQUENCE: 40
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caaccctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg     660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846

<210> SEQ ID NO 41
<211> LENGTH: 753
<212> TYPE: DNA
<213> ORGANISM: Artificial Sequence
<220> FEATURE:
<223> OTHER INFORMATION: Synthetic sequence

<400> SEQUENCE: 41
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg ttttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aaccccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggaagt ttctaatatg tctaaagcgc agattctgca gcaggctggt    660
acttccgttc tggcgcaggc taaccaggtt ccgcaaaacg tcctctcttt actggttccg    720
cggggttctc atcatcatca tcatcatggt taa                                 753

<210> SEQ ID NO 42
<211> LENGTH: 250
<212> TYPE: PRT
<213> ORGANISM: Artificial Sequence
<220> FEATURE:
```

<223> OTHER INFORMATION: Synthetic sequence

<400> SEQUENCE: 42

| | | | | | | | | | | | | | |
|---|---|---|---|---|---|---|---|---|---|---|---|---|---|
| Met | Ser | Gly | Leu | Arg | Ile | Asn | Ser | Ala | Lys | Asp | Asp | Ala | Ala | Gly | Gln |
| 1 | | | | 5 | | | | | 10 | | | | | 15 |

Met Ser Gly Leu Arg Ile Asn Ser Ala Lys Asp Asp Ala Ala Gly Gln
 1               5                   10                  15

Ala Ile Ala Asn Arg Phe Thr Ser Asn Ile Lys Gly Leu Thr Gln Ala
             20                  25                  30

Ser Arg Asn Ala Asn Asp Gly Ile Ser Ile Ala Gln Thr Thr Glu Gly
         35                  40                  45

Ala Leu Asn Glu Ile Asn Asn Asn Leu Gln Arg Val Arg Glu Leu Ser
     50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                 85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 43
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 43
atggcacaag tcattaatac aaacagcctg tcgctgttga cccagaataa cctgaacaaa    60
tctcagtcct cactgagttc cgctattgag cgtctgtcct ctggtctgcg tatcaacggc   120
gcgaaagacg atgcggcagg ccaggcgatt gctaaccgct tcacttctaa tatcaaaggt   180
ctgactcagg cttcccgtaa cgctaacgac ggcattttcta ttgcgcagac cactgaaggt   240
gcgctgaatg aaatcaacaa caacctgcag cgtgtgcgtg agttgtctgt tcaggccact   300
aacgggacta actctgattc cgatctgaaa tctatccagg atgaaattca gcaacgtctg   360
gaagaaatcg atcgcgtttc taatcagact caatttaacg gtgttaaagt cctgtctcag   420
gacaaccaga tgaaaatcca ggttggtgct aacgatggtg aaaccattac catcgatctg   480
caaaaaattg atgtgaaaag ccttggcctt gatgggttca tgttaattc cccgggaatt   540

```
tccggtggtg gtggtggaat tctagactcc atgggtacat taatcaatga agacgctgcc    600
gcagccaaga aaagtaccgc taacccactg gcttcaattg attctgcatt gtcaaaagtg    660
gacgcagttc gttcttctct gggggcaatt caaaaccgct ttgattcagc cattaccaac    720 cttgcaata cggtaaccaa tctgaactcc gcgcgtagcc gtatcgaaga tgctgactat    780
gcaacggaag tttctaatat gtctaaagcg cagattctgc agcaggctgg tacttccgtt    840
ctggcgcagg ctaaccaggt tccgcaaaac gtcctctctt tactggttcc gcggggttct    900
catcatcatc atcatcatgg tatggctagc atgactggtg gacagcaaat gggtcgggat    960
ctgtacgacg atgacgataa ggatccgtaa gtcgacaagc ttgcg                   1005
```

<210> SEQ ID NO 44
<211> LENGTH: 329
<212> TYPE: PRT
<213> ORGANISM: Artificial Sequence
<220> FEATURE:
<223> OTHER INFORMATION: Synthetic sequence

<400> SEQUENCE: 44

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Gly Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Ile Leu Asp Ser Met Gly
            180                 185                 190

Thr Leu Ile Asn Glu Asp Ala Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Thr Glu Val Ser Asn Met Ser Lys Ala Gln Ile
            260                 265                 270

Leu Gln Gln Ala Gly Thr Ser Val Leu Ala Gln Ala Asn Gln Val Pro
```

275                 280                 285
Gln Asn Val Leu Ser Leu Leu Val Pro Arg Gly Ser His His His
            290                 295                 300

His His Gly Met Ala Ser Met Thr Gly Gly Gln Gln Met Gly Arg Asp
305                 310                 315                 320

Leu Tyr Asp Asp Asp Asp Lys Asp Pro
            325

<210> SEQ ID NO 45
<211> LENGTH: 36
<212> TYPE: DNA
<213> ORGANISM: Artificial Sequence
<220> FEATURE:
<223> OTHER INFORMATION: Synthetic sequence

<400> SEQUENCE: 45
ctctggtcat atgatcaaca gcgcgaaaga cgatgc                       36

<210> SEQ ID NO 46
<211> LENGTH: 46
<212> TYPE: DNA
<213> ORGANISM: Artificial Sequence
<220> FEATURE:
<223> OTHER INFORMATION: Synthetic sequence

<400> SEQUENCE: 46
tctagagtcg actattaagc cataccatga tgatgatgat gatgag             46

<210> SEQ ID NO 47
<211> LENGTH: 918
<212> TYPE: DNA
<213> ORGANISM: Artificial Sequence
<220> FEATURE:
<223> OTHER INFORMATION: Synthetic sequence

<400> SEQUENCE: 47
taatacgact cactataggg gaattgtgag cggataacaa ttcccctcta gaaataattt    60
tgtttaactt taagaaggag atatacatat gatcaacagc gcgaaagacg atgcggcagg   120
ccaggcgatt gctaaccgct tcacttctaa tatcaaaggt ctgactcagg cttcccgtaa   180
cgctaacgac ggcatttcta ttgcgcagac cactgaaggt gcgctgaatg aaatcaacaa   240
caacctgcag cgtgtgcgtg agttgtctgt tcaggccact aacgggacta actctgattc   300
cgatctgaaa tctatccagg atgaaattca gcaacgtctg aagaaatcg atcgcgtttc    360 taatcagact caatttaacg gtgttaaagt cctgtctcag gacaaccaga tgaaaatcca   420
ggttggtgct aacgatggtg aaaccattac catcgatctg caaaaaattg atgtgaaaag   480
ccttggcctt gatgggttca atgttaattc cccgggaatt tccggtggtg gtggtggaat   540
tctagactcc atgggtacat aatcaatga agacgctgcc gcagccaaga aaagtaccgc    600
taacccactg gcttcaattg attctgcatt gtcaaaagtg gacgcagttc gttcttctct   660 ggggggcaatt caaaaccgct tgattcagc cattaccaac cttggcaata cggtaaccaa   720
tctgaactcc gcgcgtagcc gtatcgaaga tgctgactat gcaacggaag tttctaatat   780
gtctaaagcg cagattctgc agcaggctgg tacttccgtt ctggcgcagg ctaaccaggt   840
tccgcaaaac gtcctctctt tactggttcc gcggggttct catcatcatc atcatcatgg   900
tatggcttaa tagtcgac                                                918

<210> SEQ ID NO 48

<211> LENGTH: 273
<212> TYPE: PRT
<213> ORGANISM: Artificial Sequence
<220> FEATURE:
<223> OTHER INFORMATION: Synthetic sequence

<400> SEQUENCE: 48

Met Ile Asn Ser Ala Lys Asp Asp Ala Ala Gly Gln Ala Ile Ala Asn
1               5                   10                  15

Arg Phe Thr Ser Asn Ile Lys Gly Leu Thr Gln Ala Ser Arg Asn Ala
            20                  25                  30

Asn Asp Gly Ile Ser Ile Ala Gln Thr Thr Glu Gly Ala Leu Asn Glu
        35                  40                  45

Ile Asn Asn Asn Leu Gln Arg Val Arg Glu Leu Ser Val Gln Ala Thr
50                  55                  60

Asn Gly Thr Asn Ser Asp Ser Asp Leu Lys Ser Ile Gln Asp Glu Ile
65                  70                  75                  80

Gln Gln Arg Leu Glu Glu Ile Asp Arg Val Ser Asn Gln Thr Gln Phe
                85                  90                  95

Asn Gly Val Lys Val Leu Ser Gln Asp Asn Gln Met Lys Ile Gln Val
            100                 105                 110

Gly Ala Asn Asp Gly Glu Thr Ile Thr Ile Asp Leu Gln Lys Ile Asp
        115                 120                 125

Val Lys Ser Leu Gly Leu Asp Gly Phe Asn Val Asn Ser Pro Gly Ile
130                 135                 140

Ser Gly Gly Gly Gly Ile Leu Asp Ser Met Gly Thr Leu Ile Asn
145                 150                 155                 160

Glu Asp Ala Ala Ala Ala Lys Lys Ser Thr Ala Asn Pro Leu Ala Ser
                165                 170                 175

Ile Asp Ser Ala Leu Ser Lys Val Asp Ala Val Arg Ser Ser Leu Gly
            180                 185                 190

Ala Ile Gln Asn Arg Phe Asp Ser Ala Ile Thr Asn Leu Gly Asn Thr
        195                 200                 205

Val Thr Asn Leu Asn Ser Ala Arg Ser Arg Ile Glu Asp Ala Asp Tyr
210                 215                 220

Ala Thr Glu Val Ser Asn Met Ser Lys Ala Gln Ile Leu Gln Gln Ala
225                 230                 235                 240

Gly Thr Ser Val Leu Ala Gln Ala Asn Gln Val Pro Gln Asn Val Leu
                245                 250                 255

Ser Leu Leu Val Pro Arg Gly Ser His His His His His Gly Met
            260                 265                 270

Ala

<210> SEQ ID NO 49
<211> LENGTH: 333
<212> TYPE: PRT
<213> ORGANISM: Artificial Sequence
<220> FEATURE:
<223> OTHER INFORMATION: Synthetic sequence

<400> SEQUENCE: 49

Met Arg Gly Ser His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

```
Leu Leu Thr Gln Asn Asn Leu Asn Lys Ser Gln Ser Ser Leu Ser Ser
         50                  55                  60
Ala Ile Glu Arg Leu Ser Ser Gly Leu Arg Ile Asn Ser Ala Lys Asp
 65                  70                  75                  80
Asp Ala Ala Gly Gln Ala Ile Ala Asn Arg Phe Thr Ser Asn Ile Lys
                 85                  90                  95
Gly Leu Thr Gln Ala Ser Arg Asn Ala Asn Asp Gly Ile Ser Ile Ala
            100                 105                 110
Gln Thr Thr Glu Gly Ala Leu Asn Glu Ile Asn Asn Leu Gln Arg
            115                 120                 125
Val Arg Glu Leu Ser Val Gln Ala Thr Asn Gly Thr Asn Ser Asp Ser
        130                 135                 140
Asp Leu Lys Ser Ile Gln Asp Glu Ile Gln Gln Arg Leu Glu Glu Ile
145                 150                 155                 160
Asp Arg Val Ser Asn Gln Thr Gln Phe Asn Gly Val Lys Val Leu Ser
                165                 170                 175
Gln Asp Asn Gln Met Lys Ile Gln Val Gly Ala Asn Asp Gly Glu Thr
            180                 185                 190
Ile Thr Ile Asp Leu Gln Lys Ile Asp Val Lys Ser Leu Gly Leu Asp
        195                 200                 205
Gly Phe Asn Val Asn Ser Pro Gly Ile Ser Gly Gly Gly Gly Ile
    210                 215                 220
Leu Asp Ser Met Gly Thr Leu Ile Asn Glu Asp Ala Ala Ala Ala Lys
225                 230                 235                 240
Lys Ser Thr Ala Asn Pro Leu Ala Ser Ile Asp Ser Ala Leu Ser Lys
                245                 250                 255
Val Asp Ala Val Arg Ser Ser Leu Gly Ala Ile Gln Asn Arg Phe Asp
            260                 265                 270
Ser Ala Ile Thr Asn Leu Gly Asn Thr Val Thr Asn Leu Asn Ser Ala
        275                 280                 285
Arg Ser Arg Ile Glu Asp Ala Asp Tyr Ala Thr Glu Val Ser Asn Met
    290                 295                 300
Ser Lys Ala Gln Ile Leu Gln Gln Ala Gly Thr Ser Val Leu Ala Gln
305                 310                 315                 320
Ala Asn Gln Val Pro Gln Asn Val Leu Ser Leu Leu Arg
                325                 330

<210> SEQ ID NO 50
<211> LENGTH: 1002
<212> TYPE: DNA
<213> ORGANISM: Artificial Sequence
<220> FEATURE:
<223> OTHER INFORMATION: Synthetic sequence

<400> SEQUENCE: 50
atgcggggtt ctcatcatca tcatcatcat ggtatggcta gcatgactgg tggacagcaa    60
atgggtcggg atctgtacga cctggttccg cgcggtagcg cgaaggatcc gatggcacaa   120
gtcattaata caaacagcct gtcgctgttg acccagaata acctgaacaa atctcagtcc   180
tcactgagtt ccgctattga gcgtctgtcc tctggtctgc gtatcaacag cgcgaaagac   240
gatgcggcag gccaggcgat tgctaaccgc ttcacttcta atatcaaagg tctgactcag   300
gcttcccgta acgctaacga cggcatttct attgcgcaga ccactgaagg tgcgctgaat   360
gaaatcaaca caacctgca gcgtgtgcgt gagttgtctg ttcaggccac taacgggact   420
```

```
aactctgatt ccgatctgaa atctatccag gatgaaattc agcaacgtct ggaagaaatc      480
gatcgcgttt ctaatcagac tcaatttaac ggtgttaaag tcctgtctca ggacaaccag      540
atgaaaatcc aggttggtgc taacgatggt gaaaccatta ccatcgatct gcaaaaaatt      600
gatgtgaaaa gccttggcct tgatgggttc aatgttaatt ccccgggaat ttccggtggt      660
ggtggtggaa ttctagactc catgggtaca ttaatcaatg aagacgctgc cgcagccaag      720
aaaagtaccg ctaacccact ggcttcaatt gattctgcat tgtcaaaagt ggacgcagtt      780
cgttcttctc tgggggcaat tcaaaaccgt tttgattcag ccattaccaa ccttggcaat      840
acggtaacca atctgaactc cgcgcgtagc cgtatcgaag atgctgacta tgcaacggaa      900
gtttctaata tgtctaaagc gcagattctg cagcaggctg gtacttccgt tctggcgcag      960
gctaaccagg ttccgcaaaa cgtcctctct ttactgcgtt aa                        1002
```

<210> SEQ ID NO 51
<211> LENGTH: 42
<212> TYPE: DNA
<213> ORGANISM: Artificial Sequence
<220> FEATURE:
<223> OTHER INFORMATION: Synthetic sequence

<400> SEQUENCE: 51

```
ggcaattcaa aaccgttttg attaagccat taccaacctt gg                         42
```

<210> SEQ ID NO 52
<211> LENGTH: 42
<212> TYPE: DNA
<213> ORGANISM: Artificial Sequence
<220> FEATURE:
<223> OTHER INFORMATION: Synthetic sequence

<400> SEQUENCE: 52

```
ccaaggttgg taatggctta atcaaaacgg ttttgaattg cc                         42
```

<210> SEQ ID NO 53
<211> LENGTH: 906
<212> TYPE: DNA
<213> ORGANISM: Artificial Sequence
<220> FEATURE:
<223> OTHER INFORMATION: Synthetic sequence

<400> SEQUENCE: 53

```
taatacgact cactataggg gaattgtgag cggataacaa ttcccctcta gaataatttt      60
gtttaacttt aagaaggaga tatacatatg cggggttctc atcatcatca tcatcatggt     120
atggctagca tgactggtgg acagcaaatg ggtcgggatc tgtacgacct ggttccgcgc     180
ggtagcgcga aggatccgat ggcacaagtc attaatacaa acagcctgtc gctgttgacc     240
cagaataacc tgaacaaatc tcagtcctca ctgagttccg ctattgagcg tctgtcctct     300
ggtctgcgta tcaacagcgc gaaagacgat gcggcaggcc aggcgattgc taaccgcttc     360
acttctaata tcaaaggtct gactcaggct tcccgtaacg ctaacgacgg catttctatt     420
gcgcagacca ctgaaggtgc gctgaatgaa atcaacaaca acctgcagcg tgtgcgtgag     480
ttgtctgttc aggccactaa cggactaac tctgattccg atctgaaatc tatccaggat     540
gaaattcagc aacgtctgga agaaatcgat cgcgtttcta atcagactca atttaacggt     600
gttaaagtcc tgtctcagga caaccagatg aaaatccagg ttggtgctaa cgatggtgaa     660
accattacca tcgatctgca aaaaattgat gtgaaaagcc ttggccttga tgggttcaat     720
gttaattccc cgggaatttc cggtggtggt ggtggaattc tagactccat gggtacatta     780
```

```
atcaatgaag acgctgccgc agccaagaaa agtaccgcta acccactggc ttcaattgat    840
tctgcattgt caaaagtgga cgcagttcgt tcttctctgg gggcaattca aaaccgtttt    900
gattaa                                                                906
```

<210> SEQ ID NO 54
<211> LENGTH: 272
<212> TYPE: PRT
<213> ORGANISM: Artificial Sequence
<220> FEATURE:
<223> OTHER INFORMATION: Synthetic sequence

<400> SEQUENCE: 54

```
Met Arg Gly Ser His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Ile
    210                 215                 220

Leu Asp Ser Met Gly Thr Leu Ile Asn Glu Asp Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270
```

<210> SEQ ID NO 55
<211> LENGTH: 45
<212> TYPE: DNA
<213> ORGANISM: Artificial Sequence
<220> FEATURE:
<223> OTHER INFORMATION: Synthetic sequence

<400> SEQUENCE: 55

```
caatctgaac tccgcgcgtt gacgtatcta agatgctgac tatgc              45
```

<210> SEQ ID NO 56
<211> LENGTH: 45
<212> TYPE: DNA
<213> ORGANISM: Artificial Sequence
<220> FEATURE:
<223> OTHER INFORMATION: Synthetic sequence

<400> SEQUENCE: 56
gcatagtcag catcttagat acgtcaacgc gcggagttca gattg            45

<210> SEQ ID NO 57
<211> LENGTH: 966
<212> TYPE: DNA
<213> ORGANISM: Artificial Sequence
<220> FEATURE:
<223> OTHER INFORMATION: Synthetic sequence

<400> SEQUENCE: 57
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcggatcc tgtacgacct ggttccgcgc   180
ggtagcgcga aggatccgat ggcacaagtc attaatacaa acagcctgtc gctgttgacc   240
cagaataacc tgaacaaatc tcagtcctca ctgagttccg ctattgagcg tctgtcctct   300
ggtctgcgta tcaacagcgc gaaagacgat gcggcaggcc aggcgattgc taaccgcttc   360
acttctaata tcaaaggtct gactcaggct tcccgtaacg ctaacgacgg catttctatt   420
gcgcagacca ctgaaggtgc gctgaatgaa atcaacaaca cctgcagcg tgtgcgtgag   480 ttgtctgttc aggccactaa cgggactaac tctgattccg atctgaaatc tatccaggat   540
gaaattcagc aacgtctgga agaaatcgat cgcgtttcta atcagactca atttaacggt   600
gttaaagtcc tgtctcagga caaccagatg aaaatccagg ttggtgctaa cgatggtgaa   660
accattacca tcgatctgca aaaaattgat gtgaaaagcc ttggccttga tgggttcaat   720
gttaattccc cgggaatttc cggtggtggt ggtggaattc tagactccat gggtacatta   780
atcaatgaag acgctgccgc agccaagaaa agtaccgcta ccccactggc ttcaattgat   840
tctgcattgt caaaagtgga cgcagttcgt tcttctctgg gggcaattca aaaccgtttt   900
gattcagcca ttaccaacct tggcaatacg gtaaccaatc tgaactccgc gcgttgacgt   960
atctaa                                                              966

<210> SEQ ID NO 58
<211> LENGTH: 289
<212> TYPE: PRT
<213> ORGANISM: Artificial Sequence
<220> FEATURE:
<223> OTHER INFORMATION: Synthetic sequence

<400> SEQUENCE: 58

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

```
Ala Ile Glu Arg Leu Ser Ser Gly Leu Arg Ile Asn Ser Ala Lys Asp
 65                  70                  75                  80

Asp Ala Ala Gly Gln Ala Ile Ala Asn Arg Phe Thr Ser Asn Ile Lys
                 85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg

<210> SEQ ID NO 59
<211> LENGTH: 48
<212> TYPE: DNA
<213> ORGANISM: Artificial Sequence
<220> FEATURE:
<223> OTHER INFORMATION: Synthetic sequence

<400> SEQUENCE: 59
cgtagccgta tcgaagatgc ttaataggca acggaagttt ctaatatg                48

<210> SEQ ID NO 60
<211> LENGTH: 48
<212> TYPE: DNA
<213> ORGANISM: Artificial Sequence
<220> FEATURE:
<223> OTHER INFORMATION: Synthetic sequence

<400> SEQUENCE: 60
catattagaa acttccgttg cctattaagc atcttcgata cggctacg                48

<210> SEQ ID NO 61
<211> LENGTH: 978
<212> TYPE: DNA
<213> ORGANISM: Artificial Sequence
<220> FEATURE:
<223> OTHER INFORMATION: Synthetic sequence

<400> SEQUENCE: 61
taatacgact cactataggg gaattgtgag cggataacaa ttcccctcta gaataatttt    60
```

```
gtttaacttt aagaaggaga tatacatatg cggggttctc atcatcatca tcatcatggt    120
atggctagca tgactggtgg acagcaaatg gtcgggatc tgtacgacct ggttccgcgc    180
ggtagcgcga aggatccgat ggcacaagtc attaatacaa acagcctgtc gctgttgacc    240
cagaataacc tgaacaaatc tcagtcctca ctgagttccg ctattgagcg tctgtcctct    300
ggtctgcgta tcaacagcgc gaaagacgat gcggcaggcc aggcgattgc taaccgcttc    360
acttctaata tcaaaggtct gactcaggct tcccgtaacg ctaacgacgg catttctatt    420
gcgcagacca ctgaaggtgc gctgaatgaa atcaacaaca acctgcagcg tgtgcgtgag    480
ttgtctgttc aggccactaa cgggactaac tctgattccg atctgaaatc tatccaggat    540
gaaattcagc aacgtctgga agaaatcgat cgcgtttcta atcagactca atttaacggt    600
gttaaagtcc tgtctcagga caaccagatg aaaatccagg ttggtgctaa cgatggtgaa    660
accattacca tcgatctgca aaaaattgat gtgaaaagcc ttggccttga tgggttcaat    720
gttaattccc cgggaatttc cggtggtggt ggtggaattc tagactccat gggtacatta    780
atcaatgaag acgctgccgc agccaagaaa agtaccgcta acccactggc ttcaattgat    840
tctgcattgt caaaagtgga cgcagttcgt tcttctctgg gggcaattca aaaccgtttt    900
gattcagcca ttaccaacct tggcaatacg gtaaccaatc tgaactccgc gcgtagccgt    960
atcgaagatg cttaatag                                                  978
```

<210> SEQ ID NO 62  
<211> LENGTH: 295  
<212> TYPE: PRT  
<213> ORGANISM: Artificial Sequence  
<220> FEATURE:  
<223> OTHER INFORMATION: Synthetic sequence

<400> SEQUENCE: 62

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190
```

```
Ile Thr Ile Asp Leu Gln Lys Ile Asp Val Lys Ser Leu Gly Leu Asp
            195                 200                 205

Gly Phe Asn Val Asn Ser Pro Gly Ile Ser Gly Gly Gly Gly Ile
210                 215                 220

Leu Asp Ser Met Gly Thr Leu Ile Asn Glu Asp Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
            275                 280                 285

Arg Ser Arg Ile Glu Asp Ala
    290                 295
```

<210> SEQ ID NO 63
<211> LENGTH: 990
<212> TYPE: DNA
<213> ORGANISM: Artificial Sequence
<220> FEATURE:
<223> OTHER INFORMATION: Synthetic sequence

<400> SEQUENCE: 63

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggtc tgactcaggc ttcccgtaac     300
gctaacgacg gcatttctat tgcgcagacc actgaaggtg cgctgaatga atcaacaac      360
aacctgcagc gtgtgcgtga gttgtctgtt caggccacta cgggactaa ctctgattcc     420
gatctgaaat ctatccagga tgaaattcag caacgtctgg aagaaatcga tcgcgtttct     480
aatcagactc aatttaacgg tgttaaagtc ctgtctcagg acaaccagat gaaaatccag     540
gttggtgcta cgatggtga aaccattacc atcgatctgc aaaaaattga tgtgaaaagc     600
cttggccttg atgggttcaa tgttaattcc ccgggaattt ccggtggtgg tggtggaatt     660
ctagactcca tgggtacatt aatcaatgaa gacgctgccg cagccaagaa aagtaccgct     720
aacccactgg cttcaattga ttctgcattg tcaaaagtgg acgcagttcg ttcttctctg     780
ggggcaattc aaaaccgttt tgattcagcc attaccaacc ttggcaatac ggtaaccaat     840
ctgaactccg cgcgtagccg tatcgaagat gctgactatg caacggaagt ttctaatatg     900
tctaaagcgc agattctgca gcaggctggt acttccgttc tggcgcaggc taaccaggtt     960
ccgcaaaacg tcctctcttt actgcgttaa                                     990
```

<210> SEQ ID NO 64
<211> LENGTH: 33
<212> TYPE: DNA
<213> ORGANISM: Artificial Sequence
<220> FEATURE:
<223> OTHER INFORMATION: Synthetic sequence

<400> SEQUENCE: 64

```
cgataaggat catatggcac aagtcattaa tac                                   33
```

<210> SEQ ID NO 65

<211> LENGTH: 78
<212> TYPE: DNA
<213> ORGANISM: Artificial Sequence
<220> FEATURE:
<223> OTHER INFORMATION: Synthetic sequence

<400> SEQUENCE: 65

```
agatctgtcg acttaaccat gatgatgatg atgatgagaa ccccgcggaa ccagtgcata      60
gtcagcatct tcgatacg                                                   78
```

<210> SEQ ID NO 66
<211> LENGTH: 918
<212> TYPE: DNA
<213> ORGANISM: Artificial Sequence
<220> FEATURE:
<223> OTHER INFORMATION: Synthetic sequence

<400> SEQUENCE: 66

```
taatacgact cactataggg gaattgtgag cggataacaa ttcccctcta gaataatttt      60
gtttaacttt aagaaggaga tatacatatg gcacaagtca ttaatacaaa cagcctgtcg     120
ctgttgaccc agaataacct gaacaaatct cagtcctcac tgagttccgc tattgagcgt     180
ctgtcctctg gtctgcgtat caacagcgcg aaagacgatg cggcaggcca ggcgattgct     240
aaccgcttca cttctaatat caaaggtctg actcaggctt cccgtaacgc taacgacggc     300
atttctattg cgcagaccac tgaaggtgcg ctgaatgaaa tcaacaacaa cctgcagcgt     360
gtgcgtgagt tgtctgttca ggccactaac gggactaact ctgattccga tctgaaatct     420
atccaggatg aaattcagca acgtctggaa gaaatcgatc gcgtttctaa tcagactcaa     480
tttaacggtg ttaaagtcct gtctcaggac aaccagatga aaatccaggt tggtgctaac     540
gatggtgaaa ccattaccat cgatctgcaa aaaattgatg tgaaaagcct tggccttgat     600
gggttcaatg ttaattcccc gggaatttcc ggtggtggtg gtggaattct agactccatg     660
ggtacattaa tcaatgaaga cgctgccgca gccaagaaaa gtaccgctaa cccactggct     720
tcaattgatt ctgcattgtc aaaagtggac gcagttcgtt cttctctggg ggcaattcaa     780
aaccgttttg attcagccat taccaacctt ggcaatacgg taaccaatct gaactccgcg     840
cgtagccgta tcgaagatgc tgactatgca ctggttccgc ggggttctca tcatcatcat     900
catcatggtt aagtcgac                                                  918
```

<210> SEQ ID NO 67
<211> LENGTH: 274
<212> TYPE: PRT
<213> ORGANISM: Artificial Sequence
<220> FEATURE:
<223> OTHER INFORMATION: Synthetic sequence

<400> SEQUENCE: 67

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80
```

Ala Leu Asn Glu Ile Asn Asn Asn Leu Gln Arg Val Arg Glu Leu Ser
             85                  90                  95

Val Gln Ala Thr Asn Gly Thr Asn Ser Asp Ser Asp Leu Lys Ser Ile
        100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Ile Leu Asp Ser Met Gly
                180                 185                 190

Thr Leu Ile Asn Glu Asp Ala Ala Ala Lys Lys Ser Thr Ala Asn
            195                 200                 205

Pro Leu Ala Ser Ile Asp Ser Ala Leu Ser Lys Val Asp Ala Val Arg
        210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Leu Val Pro Arg Gly Ser His His His His His
                260                 265                 270

His Gly

<210> SEQ ID NO 68
<211> LENGTH: 40
<212> TYPE: DNA
<213> ORGANISM: Artificial Sequence
<220> FEATURE:
<223> OTHER INFORMATION: Synthetic sequence

<400> SEQUENCE: 68
agatctccgc ggaaccagac cagcctgctg cagaatctgc                            40

<210> SEQ ID NO 69
<211> LENGTH: 795
<212> TYPE: DNA
<213> ORGANISM: Artificial Sequence
<220> FEATURE:
<223> OTHER INFORMATION: Synthetic sequence

<400> SEQUENCE: 69
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcattcct attgcgcaga ccactgaagg tgcgctgaat     240
gaaatcaaca caaacctgca gcgtgtgcgt gagttgtctg ttcaggccac taacgggact     300
aactctgatt ccgatctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600

```
gcaattcaaa accgctttga ttcagccatt accaaccttg gcaatacggt aaccaatctg      660
aactccgcgc gtagccgtat cgaagatgct gactatgcaa cggaagtttc taatatgtct      720
aaagcgcaga ttctgcagca ggctggtctg gttccgcggg ttctcatca tcatcatcat      780 catggttaag tcgac                                                       795
```

<210> SEQ ID NO 70
<211> LENGTH: 702
<212> TYPE: DNA
<213> ORGANISM: Artificial Sequence
<220> FEATURE:
<223> OTHER INFORMATION: Synthetic sequence

<400> SEQUENCE: 70

```
atgagcgggt tacggatcaa cagcgcgaaa gacgatgcgg caggccaggc gattgctaac       60
cgcttcactt ctaatatcaa aggtctgact caggcttccc gtaacgctaa cgacggcatt      120
tctattgcgc agaccactga aggtgcgctg aatgaaatca caacaaccct gcagcgtgtg      180
cgtgagttgt ctgttcaggc cactaacggg actaactctg attccgatct gaaatctatc      240
caggatgaaa ttcagcaacg tctggaagaa atcgatcgcg tttctaatca gactcaattt      300
aacggtgtta aagtcctgtc tcaggacaac cagatgaaaa tccaggttgg tgctaacgat      360
ggtgaaacca ttaccatcga tctgcaaaaa attgatgtga aaagccttgg ccttgatggg      420
ttcaatgtta attccccggg aagtaccgct aacccactgg cttcaattga ttctgcattg      480
tcaaaagtgg acgcagttcg ttcttctctg ggggcaattc aaaaccgctt tgattcagcc      540
attaccaacc ttggcaatac ggtaaccaat ctgaactccg cgcgtagccg tatcgaagat      600
gctgactatg caacggaagt ttctaatatg tctaaagcgc agattctgca gcaggctggt      660
ctggttccgc ggggttctca tcatcatcat catcatggtt aa                         702
```

<210> SEQ ID NO 71
<211> LENGTH: 233
<212> TYPE: PRT
<213> ORGANISM: Artificial Sequence
<220> FEATURE:
<223> OTHER INFORMATION: Synthetic sequence

<400> SEQUENCE: 71

Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

```
Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Leu Val Pro Arg
    210                 215                 220

Gly Ser His His His His His His Gly
225                 230

<210> SEQ ID NO 72
<211> LENGTH: 120
<212> TYPE: DNA
<213> ORGANISM: Artificial Sequence
<220> FEATURE:
<223> OTHER INFORMATION: Synthetic sequence

<400> SEQUENCE: 72
aacccactgg cttcaattga ttctgcattg tcaaaagtgg acgcagttcg ttcttctctg      60
ggggcaattc aaaaccgttt tgattcagcc attaccgccc ttggcaatac ggtaaccaat     120

<210> SEQ ID NO 73
<211> LENGTH: 40
<212> TYPE: PRT
<213> ORGANISM: Artificial Sequence
<220> FEATURE:
<223> OTHER INFORMATION: Synthetic sequence

<400> SEQUENCE: 73

Asn Pro Leu Ala Ser Ile Asp Ser Ala Leu Ser Lys Val Asp Ala Val
1               5                   10                  15

Arg Ser Ser Leu Gly Ala Ile Gln Asn Arg Phe Asp Ser Ala Ile Thr
            20                  25                  30

Ala Leu Gly Asn Thr Val Thr Asn
        35                  40

<210> SEQ ID NO 74
<211> LENGTH: 46
<212> TYPE: DNA
<213> ORGANISM: Artificial Sequence
<220> FEATURE:
<223> OTHER INFORMATION: Synthetic sequence

<400> SEQUENCE: 74
gttcgttctt ctctgggggc aattgattca gccattaccg cccttg                    46

<210> SEQ ID NO 75
<211> LENGTH: 46
<212> TYPE: DNA
<213> ORGANISM: Artificial Sequence
<220> FEATURE:
<223> OTHER INFORMATION: Synthetic sequence

<400> SEQUENCE: 75
caagggcggt aatggctgaa tcaattgccc ccagagaaga acgaac                    46

<210> SEQ ID NO 76
<211> LENGTH: 783
```

```
<212> TYPE: DNA
<213> ORGANISM: Artificial Sequence
<220> FEATURE:
<223> OTHER INFORMATION: Synthetic sequence

<400> SEQUENCE: 76
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca acaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattgatt cagccattac cgcccttggc aatacggtaa ccaatctgaa ctccgcgcgt   660
agccgtatcg aagatgctga ctatgcaacg gaagtttcta atatgtctaa agcgcagatt   720
ctgcagcagg ctggtctggt tccgcggggt tctcatcatc atcatcatca tggttaagtc   780
gac                                                                783

<210> SEQ ID NO 77
<211> LENGTH: 229
<212> TYPE: PRT
<213> ORGANISM: Artificial Sequence
<220> FEATURE:
<223> OTHER INFORMATION: Synthetic sequence

<400> SEQUENCE: 77

Met Ser Gly Leu Arg Ile Asn Ser Ala Lys Asp Asp Ala Ala Gly Gln
  1               5                  10                  15
Ala Ile Ala Asn Arg Phe Thr Ser Asn Ile Lys Gly Leu Thr Gln Ala
                 20                  25                  30
Ser Arg Asn Ala Asn Asp Gly Ile Ser Ile Ala Gln Thr Thr Glu Gly
             35                  40                  45
Ala Leu Asn Glu Ile Asn Asn Asn Leu Gln Arg Val Arg Glu Leu Ser
         50                  55                  60
Val Gln Ala Thr Asn Gly Thr Asn Ser Asp Ser Asp Leu Lys Ser Ile
 65                  70                  75                  80
Gln Asp Glu Ile Gln Gln Arg Leu Glu Glu Ile Asp Arg Val Ser Asn
                 85                  90                  95
Gln Thr Gln Phe Asn Gly Val Lys Val Leu Ser Gln Asp Asn Gln Met
            100                 105                 110
Lys Ile Gln Val Gly Ala Asn Asp Gly Glu Thr Ile Thr Ile Asp Leu
        115                 120                 125
Gln Lys Ile Asp Val Lys Ser Leu Gly Leu Asp Gly Phe Asn Val Asn
    130                 135                 140
Ser Pro Gly Ser Thr Ala Asn Pro Leu Ala Ile Asp Ser Ala Leu
145                 150                 155                 160
Ser Lys Val Asp Ala Val Arg Ser Ser Leu Gly Ala Ile Asp Ser Ala
                165                 170                 175
Ile Thr Ala Leu Gly Asn Thr Val Thr Asn Leu Asn Ser Ala Arg Ser
```

```
            180                 185                 190
Arg Ile Glu Asp Ala Asp Tyr Ala Thr Glu Val Ser Asn Met Ser Lys
            195                 200                 205

Ala Gln Ile Leu Gln Gln Ala Gly Leu Val Pro Arg Gly Ser His His
            210                 215                 220

His His His His Gly
225

<210> SEQ ID NO 78
<211> LENGTH: 654
<212> TYPE: DNA
<213> ORGANISM: Artificial Sequence
<220> FEATURE:
<223> OTHER INFORMATION: Synthetic sequence

<400> SEQUENCE: 78
atgagcgggt tacggatcaa cagcgcgaaa gacgatgcgg caggccaggc gattgctaac        60
cgcttcactt ctaatatcaa aggtctgact caggcttccc gtaacgctaa cgacggcatt      120
tctattgcgc agaccactga aggtgcgctg aatgaaatca caacaaccct gcagcgtgtg      180
cgtgagttgt ctgttcaggc cactaacggg actaactctg attccgatct gaaatctatc      240
caggatgaaa ttcagcaacg tctggaagaa atcgatcgcg tttctaatca gactcaattt      300
aacggtgtta aagtcctgtc tcaggacaac cagatgaaaa tccaggttgg tgctaacgat      360
ggtgaaacca ttaccatcga tctgcaaaaa attgatgtga aaagccttgg ccttgatggg      420
ttcaatgtta attccccggg aagtaccgct aacccactgg cttcaattga ttctgcattg      480
tcaaaagtgg acgcagttcg ttcttctctg ggggcaattc aaaaccgctt tgattcagcc      540
attaccaacc ttggcaatac ggtaaccaat ctgaactccg cgcgtagccg tatcgaagat      600
gctgactatg cactggttcc gcggggttct catcatcatc atcatcatgg ttaa            654

<210> SEQ ID NO 79
<211> LENGTH: 217
<212> TYPE: PRT
<213> ORGANISM: Artificial Sequence
<220> FEATURE:
<223> OTHER INFORMATION: Synthetic sequence

<400> SEQUENCE: 79

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140
```

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
            165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
            195                 200                 205

Gly Ser His His His His His Gly
    210                 215

<210> SEQ ID NO 80
<211> LENGTH: 714
<212> TYPE: DNA
<213> ORGANISM: Artificial Sequence
<220> FEATURE:
<223> OTHER INFORMATION: Synthetic sequence

<400> SEQUENCE: 80
atgagtaaag gagaagaact tttcactgga gttgtcccaa ttcttgttga attagatggt      60
gatgttaatg ggcacaaatt ttctgtcagt ggagagggtg aaggtgatgc aacatacgga    120
aaacttaccc ttaaatttat ttgcactact ggaaaactac ctgttccatg ccaacactt    180
gtcactactc tgacgtatgg tgttcaatgc ttttcccgtt atccggatca tatgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga tacccttgtt    360
aatcgtatcg agttaaaagg tattgatttt aaagaagatg aaacattctc ggacacaaa    420
ctcgagtaca actataactc acacaatgta tacatcacgg cagacaaaca aaagaatgga    480
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct tttgaaagat cccaacgaaa agcgtgacca catggtcctt    660
cttgagtttg taactgctgc tgggattaca catggcatgg atgaactata caaa          714

<210> SEQ ID NO 81
<211> LENGTH: 238
<212> TYPE: PRT
<213> ORGANISM: Artificial Sequence
<220> FEATURE:
<223> OTHER INFORMATION: Synthetic sequence

<400> SEQUENCE: 81

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val

```
              100                 105                 110
Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Leu
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235
```

<210> SEQ ID NO 82
<211> LENGTH: 717
<212> TYPE: DNA
<213> ORGANISM: Artificial Sequence
<220> FEATURE:
<223> OTHER INFORMATION: Synthetic sequence

<400> SEQUENCE: 82

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactc tgacgtatgg tgttcaatgc ttttcccgtt atccggatca catgaaacgg   240
catgactttt tcaagagtgc catgcccgaa ggttatgtac aggaacgcac tatatctttc   300
aaagatgacg ggaactacaa gacgcgtgct gaagtcaagt ttgaaggtga tacccttgtt   360
aatcgtatcg agttaaaagg tattgatttt aaagaagatg gaaacattct cggacacaaa   420
ctcgagtaca ctataactca cacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct tttgaaagat cccaacgaaa agcgtgacca catggtcctt   660
cttgagtttg taactgctgc tgggattaca catggcatgg atgaactata caaataa     717
```

<210> SEQ ID NO 83
<211> LENGTH: 54
<212> TYPE: DNA
<213> ORGANISM: Artificial Sequence
<220> FEATURE:
<223> OTHER INFORMATION: Synthetic sequence

<400> SEQUENCE: 83

```
tctagacggc cgatctcagg taagaatgga atcaaagcta acttcaaaat tcgc           54
```

<210> SEQ ID NO 84
<211> LENGTH: 20
<212> TYPE: PRT
<213> ORGANISM: Artificial Sequence
<220> FEATURE:
<223> OTHER INFORMATION: Synthetic sequence

<400> SEQUENCE: 84

Asn Val Tyr Ile Pro Ile Ser Gly Lys Asn Gly Ile Lys Ala Asn Phe
1               5                   10                  15

Lys Ile Arg His
            20

<210> SEQ ID NO 85
<211> LENGTH: 45
<212> TYPE: DNA
<213> ORGANISM: Artificial Sequence
<220> FEATURE:
<223> OTHER INFORMATION: Synthetic sequence

<400> SEQUENCE: 85
agatctccgc ggtttgtata gttcatccat gccatgtgta atccc                45

<210> SEQ ID NO 86
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 86
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg    660 aactccgcgc gtagccgtat cgaagatgct gactatgcac tggttccgcc gatctcaggt   720
aagaatggaa tcaaagctaa cttcaaaatt cgccacaaca ttgaagatgg atccgttcaa   780
ctagcagacc attatcaaca aaatactcca attggcgatg gccctgtcct tttaccagac   840
aaccattacc tgtcgacaca atctgcccct ttgaaagatc caacgaaaaa gcgtgaccac   900
atggtccttc ttgagtttgt aactgctgct gggattacac atggcatgga tgaactatac   960
aaaccgcggg gttctcatca tcatcatcat catggttaag tcgac               1005

<210> SEQ ID NO 87
<211> LENGTH: 912
<212> TYPE: DNA
<213> ORGANISM: Artificial Sequence
<220> FEATURE:
<223> OTHER INFORMATION: Synthetic sequence

<400> SEQUENCE: 87
atgagcgggt tacgatcaa cagcgcgaaa gacgatgcgg caggccaggc gattgctaac     60
cgcttcactt ctaatatcaa aggtctgact caggcttccc gtaacgctaa cgacggcatt   120

```
tctattgcgc agaccactga aggtgcgctg aatgaaatca acaacaacct gcagcgtgtg      180
cgtgagttgt ctgttcaggc cactaacggg actaactctg attccgatct gaaatctatc      240
caggatgaaa ttcagcaacg tctggaagaa atcgatcgcg tttctaatca gactcaattt      300
aacggtgtta aagtcctgtc tcaggacaac cagatgaaaa tccaggttgg tgctaacgat      360
ggtgaaacca ttaccatcga tctgcaaaaa attgatgtga aaagccttgg ccttgatggg      420
ttcaatgtta attccccggg aagtaccgct aacccactgg cttcaattga ttctgcattg      480
tcaaaagtgg acgcagttcg ttcttctctg ggggcaattc aaaaccgctt tgattcagcc      540
attaccaacc ttggcaatac ggtaaccaat ctgaactccg cgcgtagccg tatcgaagat      600
gctgactatg cactggttcc gccgatctca ggtaagaatg gaatcaaagc taacttcaaa      660
attcgccaca acattgaaga tggatccgtt caactagcag accattatca acaaaatact      720
ccaattggcg atggccctgt ccttttacca gacaaccatt acctgtcgac acaatctgcc      780
cttttgaaag atcccaacga aaagcgtgac cacatggtcc ttcttgagtt tgtaactgct      840
gctgggatta cacatggcat ggatgaacta tacaaaccgc ggggttctca tcatcatcat      900
catcatggtt aa                                                         912
```

<210> SEQ ID NO 88
<211> LENGTH: 303
<212> TYPE: PRT
<213> ORGANISM: Artificial Sequence
<220> FEATURE:
<223> OTHER INFORMATION: Synthetic sequence

<400> SEQUENCE: 88

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Pro
        195                 200                 205

Ile Ser Gly Lys Asn Gly Ile Lys Ala Asn Phe Lys Ile Arg His Asn
    210                 215                 220
```

```
Ile Glu Asp Gly Ser Val Gln Leu Ala Asp His Tyr Gln Gln Asn Thr
225                 230                 235                 240

Pro Ile Gly Asp Gly Pro Val Leu Leu Pro Asp Asn His Tyr Leu Ser
                245                 250                 255

Thr Gln Ser Ala Leu Leu Lys Asp Pro Asn Glu Lys Arg Asp His Met
            260                 265                 270

Val Leu Leu Glu Phe Val Thr Ala Ala Gly Ile Thr His Gly Met Asp
        275                 280                 285

Glu Leu Tyr Lys Pro Arg Gly Ser His His His His His His Gly
    290                 295                 300
```

<210> SEQ ID NO 89
<211> LENGTH: 585
<212> TYPE: DNA
<213> ORGANISM: Artificial Sequence
<220> FEATURE:
<223> OTHER INFORMATION: Synthetic sequence

<400> SEQUENCE: 89

```
atgagtaccg ctaacccact ggcttcaatt gattctgcat tgtcaaaagt ggacgcagtt    60
cgttcttctc tgggggcaat tcaaaaccgc tttgattcag ccattaccaa ccttggcaat   120
acggtaacca atctgaactc cgcgcgtagc cgtatcgaag atgctgacta tgcatccccg   180
ggaagcgggt tacggatcaa cagcgcgaaa gacgatgcgg caggccaggc gattgctaac   240
cgcttcactt ctaatatcaa aggtctgact caggcttccc gtaacgctaa cgacggcatt   300
tctattgcgc agaccactga aggtgcgctg aatgaaatca acaacaacct gcagcgtgtg   360
cgtgagttgt ctgttcaggc cactaacggg actaactctg attccgatct gaatctatc   420
caggatgaaa ttcagcaacg tctggaagaa atcgatcgcg tttctaatca gactcaattt   480
aacggtgtta aagtcctgtc tcaggacaac cagatgaaaa tccaggttgg tgctaacgat   540
ggtctggttc cgcggggttc tcatcatcat catcatcatg gttaa               585
```

<210> SEQ ID NO 90
<211> LENGTH: 194
<212> TYPE: PRT
<213> ORGANISM: Artificial Sequence
<220> FEATURE:
<223> OTHER INFORMATION: Synthetic sequence

<400> SEQUENCE: 90

```
Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu
            100                 105                 110

Ile Asn Asn Asn Leu Gln Arg Val Arg Glu Leu Ser Val Gln Ala Thr
        115                 120                 125
```

```
Asn Gly Thr Asn Ser Asp Ser Asp Leu Lys Ser Ile Gln Asp Glu Ile
            130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Leu Val Pro Arg Gly Ser His His His His
            180                 185                 190

His Gly

<210> SEQ ID NO 91
<211> LENGTH: 678
<212> TYPE: DNA
<213> ORGANISM: Artificial Sequence
<220> FEATURE:
<223> OTHER INFORMATION: Synthetic sequence

<400> SEQUENCE: 91
taatacgact cactataggg gaattgtgag cggataacaa ttcccctcta gaataatttt      60
gtttaacttt aagaaggaga tatacatatg agtaccgcta acccactggc ttcaattgat    120
tctgcattgt caaaagtgga cgcagttcgt tcttctctgg gggcaattca aaaccgcttt    180
gattcagcca ttaccaacct tggcaatacg gtaaccaatc tgaactccgc gcgtagccgt    240
atcgaagatg ctgactatgc atccccggga agcgggttac ggatcaacag cgcgaaagac    300
gatgcggcag gccaggcgat tgctaaccgc ttcacttcta atatcaaagg tctgactcag    360
gcttcccgta acgctaacga cggcatttct attgcgcaga ccactgaagg tgcgctgaat    420
gaaatcaaca caaacctgca gcgtgtgcgt gagttgtctg ttcaggccac taacgggact    480
aactctgatt ccgatctgaa atctatccag gatgaaattc agcaacgtct ggaagaaatc    540
gatcgcgttt ctaatcagac tcaatttaac ggtgttaaag tcctgtctca ggacaaccag    600
atgaaaatcc aggttggtgc taacgatggt ctggttccgc ggggttctca tcatcatcat    660
catcatggtt aagtcgac                                                  678

<210> SEQ ID NO 92
<211> LENGTH: 40
<212> TYPE: DNA
<213> ORGANISM: Artificial Sequence
<220> FEATURE:
<223> OTHER INFORMATION: Synthetic sequence

<400> SEQUENCE: 92
tctagacata tgagtaccgc taacccactg gcttcaattg                           40

<210> SEQ ID NO 93
<211> LENGTH: 38
<212> TYPE: DNA
<213> ORGANISM: Artificial Sequence
<220> FEATURE:
<223> OTHER INFORMATION: Synthetic sequence

<400> SEQUENCE: 93
gcttcccggg gatgcatagt cagcatcttc gatacggc                             38

<210> SEQ ID NO 94
<211> LENGTH: 34
<212> TYPE: DNA
<213> ORGANISM: Artificial Sequence
<220> FEATURE:
```

<223> OTHER INFORMATION: Synthetic sequence

<400> SEQUENCE: 94
gcatccccgg gaagcgggtt acggatcaac agcg                                    34

<210> SEQ ID NO 95
<211> LENGTH: 50
<212> TYPE: DNA
<213> ORGANISM: Artificial Sequence
<220> FEATURE:
<223> OTHER INFORMATION: Synthetic sequence

<400> SEQUENCE: 95
agatctccgc ggaaccagac catcgttagc accaacctgg attttcatct                   50

<210> SEQ ID NO 96
<211> LENGTH: 654
<212> TYPE: DNA
<213> ORGANISM: Artificial Sequence
<220> FEATURE:
<223> OTHER INFORMATION: Synthetic sequence

<400> SEQUENCE: 96
atgagtaccg ctaacccact ggcttcaatt gattctgcat tgtcaaaagt ggacgcagtt        60
cgttcttctc tgggggcaat tcaaaaccgc tttgattcag ccattaccaa ccttggcaat       120
acggtaacca atctgaactc cgcgcgtagc cgtatcgaag atgctgacta tgcatccccg       180
ggaagcgggt tacggatcaa cagcgcgaaa gacgatgcgg caggccaggc gattgctaac       240
cgcttcactt ctaatatcaa aggtctgact caggcttccc gtaacgctaa cgacggcatt       300
tctattgcgc agaccactga aggtgcgctg aatgaaatca acaacaacct gcagcgtgtg       360
cgtgagttgt ctgttcaggc cactaacggg actaactctg attccgatct gaaatctatc       420
caggatgaaa ttcagcaacg tctggaagaa atcgatcgcg tttctaatca gactcaattt       480
aacggtgtta agtcctgtc tcaggacaac cagatgaaaa tccaggttgg tgctaacgat       540
ggtgaaacca ttaccatcga tctgcaaaaa attgatgtga aaagccttgg ccttgatggg       600
ttcaatgtta atctggttcc gcggggttct catcatcatc atcatcatgg ttaa            654

<210> SEQ ID NO 97
<211> LENGTH: 217
<212> TYPE: PRT
<213> ORGANISM: Artificial Sequence
<220> FEATURE:
<223> OTHER INFORMATION: Synthetic sequence

<400> SEQUENCE: 97

Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu

```
            100                 105                 110
Ile Asn Asn Asn Leu Gln Arg Val Arg Glu Leu Ser Val Gln Ala Thr
            115                 120                 125

Asn Gly Thr Asn Ser Asp Ser Asp Leu Lys Ser Ile Gln Asp Glu Ile
        130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Glu Thr Ile Thr Ile Asp Leu Gln Lys Ile Asp
            180                 185                 190

Val Lys Ser Leu Gly Leu Asp Gly Phe Asn Val Asn Leu Val Pro Arg
        195                 200                 205

Gly Ser His His His His His His Gly
        210                 215
```

<210> SEQ ID NO 98
<211> LENGTH: 747
<212> TYPE: DNA
<213> ORGANISM: Artificial Sequence
<220> FEATURE:
<223> OTHER INFORMATION: Synthetic sequence

<400> SEQUENCE: 98

```
taatacgact cactataggg gaattgtgag cggataacaa ttcccctcta gaataatttt     60
gtttaacttt aagaaggaga tatacatatg agtaccgcta acccactggc ttcaattgat    120
tctgcattgt caaaagtgga cgcagttcgt tcttctctgg gggcaattca aaaccgcttt    180
gattcagcca ttaccaacct tggcaatacg gtaaccaatc tgaactccgc gcgtagccgt    240
atcgaagatg ctgactatgc atccccggga agcgggttac ggatcaacag cgcgaaagac    300
gatgcggcag ccaggcgat tgctaaccgc ttcacttcta atatcaaagg tctgactcag    360
gcttcccgta acgctaacga cggcatttct attgcgcaga ccactgaagg tgcgctgaat    420
gaaatcaaca caaccctgca gcgtgtgcgt gagttgtctg ttcaggccac taacgggact    480
aactctgatt ccgatctgaa atctatccag gatgaaattc agcaacgtct ggaagaaatc    540
gatcgcgttt ctaatcagac tcaatttaac ggtgttaaag tcctgtctca ggacaaccag    600
atgaaaatcc aggttggtgc taacgatggt gaaaccatta ccatcgatct gcaaaaaatt    660
gatgtgaaaa gccttggcct tgatgggttc aatgttaatc tggttccgcg gggttctcat    720
catcatcatc atcatggtta agtcgac                                        747
```

<210> SEQ ID NO 99
<211> LENGTH: 45
<212> TYPE: DNA
<213> ORGANISM: Artificial Sequence
<220> FEATURE:
<223> OTHER INFORMATION: Synthetic sequence

<400> SEQUENCE: 99

```
agatctccgc ggaaccagat taacattgaa cccatcaagg ccaag                     45
```

<210> SEQ ID NO 100
<211> LENGTH: 38
<212> TYPE: DNA
<213> ORGANISM: Artificial Sequence
<220> FEATURE:
<223> OTHER INFORMATION: Synthetic sequence

<400> SEQUENCE: 100
cccgttatcc ggatcacatg aaacggcatg acttttttc                                38

<210> SEQ ID NO 101
<211> LENGTH: 38
<212> TYPE: DNA
<213> ORGANISM: Artificial Sequence
<220> FEATURE:
<223> OTHER INFORMATION: Synthetic sequence

<400> SEQUENCE: 101
gaaaaagtca tgccgtttca tgtgatccgg ataacggg                                 38

<210> SEQ ID NO 102
<211> LENGTH: 21
<212> TYPE: DNA
<213> ORGANISM: Artificial Sequence
<220> FEATURE:
<223> OTHER INFORMATION: Synthetic sequence

<400> SEQUENCE: 102
ctgttccatg gccaacactt g                                                   21

<210> SEQ ID NO 103
<211> LENGTH: 46
<212> TYPE: DNA
<213> ORGANISM: Artificial Sequence
<220> FEATURE:
<223> OTHER INFORMATION: Synthetic sequence

<400> SEQUENCE: 103
tctagacata tgagtaaagg agaagaactt ttcactggag ttgtcc                        46

<210> SEQ ID NO 104
<211> LENGTH: 63
<212> TYPE: DNA
<213> ORGANISM: Artificial Sequence
<220> FEATURE:
<223> OTHER INFORMATION: Synthetic sequence

<400> SEQUENCE: 104
ggcctatgcg gccgcagtaa aggagaagaa cttttcactg gagttgtccc aattcttgtt         60
gaa                                                                      63

<210> SEQ ID NO 105
<211> LENGTH: 57
<212> TYPE: DNA
<213> ORGANISM: Artificial Sequence
<220> FEATURE:
<223> OTHER INFORMATION: Synthetic sequence

<400> SEQUENCE: 105
agatctatta tgcggcctg ataggccttg tttgtctgcc gtgatgtata cattgtg             57

<210> SEQ ID NO 106
<211> LENGTH: 18
<212> TYPE: PRT
<213> ORGANISM: Artificial Sequence
<220> FEATURE:
<223> OTHER INFORMATION: Synthetic sequence

<400> SEQUENCE: 106

Ser His Asn Val Tyr Ile Thr Ala Asp Lys Gln Gly Leu Ser Gly Arg
1               5                   10                  15

Asn Met

<210> SEQ ID NO 107
<211> LENGTH: 1494
<212> TYPE: DNA
<213> ORGANISM: Artificial Sequence
<220> FEATURE:
<223> OTHER INFORMATION: Synthetic sequence

<400> SEQUENCE: 107

```
taatacgact cactataggg gaattgtgag cggataacaa ttcccctcta gaataatttt      60
gtttaacttt aagaaggaga tatacatatg agtaaaggag aagaactttt cactggagtt     120
gtcccaattc ttgttgaatt agatggtgat gttaatgggc acaaattttc tgtcagtgga     180
gagggtgaag gtgatgcaac atacggaaaa cttaccctta aatttatttg cactactgga     240
aaactacctg ttccatggcc aacacttgtc actactctga cgtatggtgt tcaatgcttt     300
tcccgttatc cggatcacat gaaacggcat gactttttca agagtgccat gcccgaaggt     360
tatgtacagg aacgcactat atctttcaaa gatgacggga actacaagac gcgtgctgaa     420
gtcaagtttg aaggtgatac ccttgttaat cgtatcgagt taaaaggtat tgattttaaa     480
gaagatggaa acattctcgg acacaaactc gagtacaact ataactcaca caatgtatac     540
atcacggcag acaaacaagg cctatcaggc gcattatga gcgggttacg atcaacagc      600
gcgaaagaca tgcggcagg ccaggcgatt gctaaccgct tcacttctaa tatcaaaggt     660
ctgactcagg cttcccgtaa cgctaacgac ggcatttcta ttgcgcagac cactgaaggt     720
gcgctgaatg aaatcaacaa caacctgcag cgtgtgcgtg agttgtctgt tcaggccact     780
aacgggacta actctgattc cgatctgaaa tctatccagg atgaaattca gcaacgtctg     840
gaagaaatcg atcgcgtttc taatcagact caatttaacg gtgttaaagt cctgtctcag     900
gacaaccaga tgaaaatcca ggttggtgct aacgatggtg aaaccattac catcgatctg     960
caaaaaattg atgtgaaaag ccttggcctt gatgggttca atgttaattc cccgggaagt    1020
accgctaacc cactggcttc aattgattct gcattgtcaa aagtggacgc agttcgttct    1080
tctctggggg caattcaaaa ccgctttgat tcagccatta ccaaccttgg caatacggta    1140
accaatctga actccgcgcg tagccgtatc gaagatgctg actatgcact ggttccgccg    1200
atctcaggta agaatggaat caaagctaac ttcaaaattc gccacaacat gaagatgga    1260
tccgttcaac tagcagacca ttatcaacaa atactccaa ttggcgatgg ccctgtcctt    1320
ttaccagaca accattacct gtcgacacaa tctgcccttt tgaaagatcc caacgaaaag    1380
cgtgaccaca tggtccttct tgagtttgta actgctgctg ggattacaca tggcatggat    1440
gaactataca aaccgcgggg ttctcatcat catcatcatc atggttaagt cgac           1494
```

<210> SEQ ID NO 108
<211> LENGTH: 1401
<212> TYPE: DNA
<213> ORGANISM: Artificial Sequence
<220> FEATURE:
<223> OTHER INFORMATION: Synthetic sequence

<400> SEQUENCE: 108

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactc tgacgtatgg tgttcaatgc ttttcccgtt atccggatca catgaaacgg     240
```

-continued

```
catgactttt tcaagagtgc catgcccgaa ggttatgtac aggaacgcac tatatctttc    300
aaagatgacg ggaactacaa gacgcgtgct gaagtcaagt ttgaaggtga tacccttgtt    360
aatcgtatcg agttaaaagg tattgatttt aaagaagatg gaaacattct cggacacaaa    420
ctcgagtaca actataactc acacaatgta tacatcacgg cagacaaaca aggcctatca    480
ggccgcatta tgagcgggtt acggatcaac agcgcgaaag acgatgcggc aggccaggcg    540
attgctaacc gcttcacttc taatatcaaa ggtctgactc aggcttcccg taacgctaac    600
gacggcattt ctattgcgca gaccactgaa ggtgcgctga atgaaatcaa caacaacctg    660
cagcgtgtgc gtgagttgtc tgttcaggcc actaacggga ctaactctga ttccgatctg    720
aaatctatcc aggatgaaat tcagcaacgt ctggaagaaa tcgatcgcgt ttctaatcag    780
actcaattta acggtgttaa agtcctgtct caggacaacc agatgaaaat ccaggttggt    840
gctaacgatg gtgaaaccat taccatcgat ctgcaaaaaa ttgatgtgaa aagccttggc    900
cttgatgggt tcaatgttaa ttccccggga agtaccgcta acccactggc ttcaattgat    960
tctgcattgt caaaagtgga cgcagttcgt tcttctctgg gggcaattca aaaccgcttt   1020
gattcagcca ttaccaacct tggcaatacg gtaaccaatc tgaactccgc gcgtagccgt   1080
atcgaagatg ctgactatgc actggttccg ccgatctcag gtaagaatgg aatcaaagct   1140
aacttcaaaa ttcgccacaa cattgaagat ggatccgttc aactagcaga ccattatcaa   1200
caaaatactc caattggcga tggccctgtc cttttaccag acaaccatta cctgtcgaca   1260
caatctgccc ttttgaaaga tcccaacgaa aagcgtgacc acatggtcct tcttgagttt   1320
gtaactgctg ctgggattac acatggcatg gatgaactat acaaaccgcg gggttctcat   1380
catcatcatc atcatggtta a                                             1401
```

<210> SEQ ID NO 109
<211> LENGTH: 466
<212> TYPE: PRT
<213> ORGANISM: Artificial Sequence
<220> FEATURE:
<223> OTHER INFORMATION: Synthetic sequence

<400> SEQUENCE: 109

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Gly Leu Ser
```

```
            145                 150                 155                 160
        Gly Arg Ile Met Ser Gly Leu Arg Ile Asn Ser Ala Lys Asp Asp Ala
                            165                 170                 175

Ala Gly Gln Ala Ile Ala Asn Arg Phe Thr Ser Asn Ile Lys Gly Leu
                            180                 185                 190

Thr Gln Ala Ser Arg Asn Ala Asn Asp Gly Ile Ser Ile Ala Gln Thr
                            195                 200                 205

Thr Glu Gly Ala Leu Asn Glu Ile Asn Asn Leu Gln Arg Val Arg
                            210                 215                 220

Glu Leu Ser Val Gln Ala Thr Asn Gly Thr Asn Ser Asp Ser Asp Leu
        225                 230                 235                 240

Lys Ser Ile Gln Asp Glu Ile Gln Gln Arg Leu Glu Glu Ile Asp Arg
                            245                 250                 255

Val Ser Asn Gln Thr Gln Phe Asn Gly Val Lys Val Leu Ser Gln Asp
                            260                 265                 270

Asn Gln Met Lys Ile Gln Val Gly Ala Asn Asp Gly Glu Thr Ile Thr
                            275                 280                 285

Ile Asp Leu Gln Lys Ile Asp Val Lys Ser Leu Gly Leu Asp Gly Phe
                            290                 295                 300

Asn Val Asn Ser Pro Gly Ser Thr Ala Asn Pro Leu Ala Ser Ile Asp
        305                 310                 315                 320

Ser Ala Leu Ser Lys Val Asp Ala Val Arg Ser Ser Leu Gly Ala Ile
                            325                 330                 335

Gln Asn Arg Phe Asp Ser Ala Ile Thr Asn Leu Gly Asn Thr Val Thr
                            340                 345                 350

Asn Leu Asn Ser Ala Arg Ser Arg Ile Glu Asp Ala Asp Tyr Ala Leu
                            355                 360                 365

Val Pro Pro Ile Ser Gly Lys Asn Gly Ile Lys Ala Asn Phe Lys Ile
                            370                 375                 380

Arg His Asn Ile Glu Asp Gly Ser Val Gln Leu Ala Asp His Tyr Gln
        385                 390                 395                 400

Gln Asn Thr Pro Ile Gly Asp Gly Pro Val Leu Leu Pro Asp Asn His
                            405                 410                 415

Tyr Leu Ser Thr Gln Ser Ala Leu Leu Lys Asp Pro Asn Glu Lys Arg
                            420                 425                 430

Asp His Met Val Leu Leu Glu Phe Val Thr Ala Ala Gly Ile Thr His
                            435                 440                 445

Gly Met Asp Glu Leu Tyr Lys Pro Arg Gly Ser His His His His
                            450                 455                 460

His Gly
        465

<210> SEQ ID NO 110
<211> LENGTH: 124
<212> TYPE: DNA
<213> ORGANISM: Artificial Sequence
<220> FEATURE:
<223> OTHER INFORMATION: Synthetic sequence

<400> SEQUENCE: 110
cttggccttg atgggttcaa tgttaattcc ccgggaattt ccggtggtgg tggtggaatt      60
acattaatca atgaagacgc tgccgcagcc aagaaaagta ccgctaaccc actggcttca     120
attg                                                                  124
```

<210> SEQ ID NO 111
<211> LENGTH: 41
<212> TYPE: PRT
<213> ORGANISM: Artificial Sequence
<220> FEATURE:
<223> OTHER INFORMATION: Synthetic sequence

<400> SEQUENCE: 111

Leu Gly Leu Asp Gly Phe Asn Val Asn Ser Pro Gly Ile Ser Gly Gly
1               5                   10                  15

Gly Gly Gly Ile Thr Leu Ile Asn Glu Asp Ala Ala Ala Lys Lys
            20                  25                  30

Ser Thr Ala Asn Pro Leu Ala Ser Ile
        35                  40

<210> SEQ ID NO 112
<211> LENGTH: 72
<212> TYPE: DNA
<213> ORGANISM: Artificial Sequence
<220> FEATURE:
<223> OTHER INFORMATION: Synthetic sequence

<400> SEQUENCE: 112
agatctccgc ggaaccagta aagagaggac gttttgcgga acctggtttg catagtcagc     60
atcttcgata cg                                                        72

<210> SEQ ID NO 113
<211> LENGTH: 777
<212> TYPE: DNA
<213> ORGANISM: Artificial Sequence
<220> FEATURE:
<223> OTHER INFORMATION: Synthetic sequence

<400> SEQUENCE: 113
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgttttga ttcagccatt accaaccttg caatacggt aaccaatctg    660 aactccgcgc gtagccgtat cgaagatgct gactatgcaa accaggttcc gcaaaacgtc    720
ctctctttac tggttccgcg gggttctcat catcatcatc atcatggtta agtcgac      777

<210> SEQ ID NO 114
<211> LENGTH: 684
<212> TYPE: DNA
<213> ORGANISM: Artificial Sequence
<220> FEATURE:
<223> OTHER INFORMATION: Synthetic sequence

<400> SEQUENCE: 114
atgagcgggt tacggatcaa cagcgcgaaa gacgatgcgg caggccaggc gattgctaac     60

```
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgttt tgattcagcc    540
attaccaacc ttggcaatac ggtaaccaat ctgaactccg cgcgtagccg tatcgaagat    600
gctgactatg caaaccaggt tccgcaaaac gtcctctctt tactggttcc gcggggttct    660
catcatcatc atcatcatgg ttaa                                           684
```

<210> SEQ ID NO 115
<211> LENGTH: 227
<212> TYPE: PRT
<213> ORGANISM: Artificial Sequence
<220> FEATURE:
<223> OTHER INFORMATION: Synthetic sequence

<400> SEQUENCE: 115

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Asn Gln Val Pro
        195                 200                 205

Gln Asn Val Leu Ser Leu Leu Val Pro Arg Gly Ser His His His His
    210                 215                 220

His His Gly
225
```

<210> SEQ ID NO 116
<211> LENGTH: 42
<212> TYPE: DNA
<213> ORGANISM: Artificial Sequence
<220> FEATURE:
<223> OTHER INFORMATION: Synthetic sequence

<400> SEQUENCE: 116

```
agatctcccg gggaaccatc gttagcacca acctggattt tc                            42
```

<210> SEQ ID NO 117
<211> LENGTH: 777
<212> TYPE: DNA
<213> ORGANISM: Artificial Sequence
<220> FEATURE:
<223> OTHER INFORMATION: Synthetic sequence

<400> SEQUENCE: 117

```
taatacgact cactataggg gaattgtgag cggataacaa ttcccctcta gaataatttt         60
gtttaacttt aagaaggaga tatacatatg agcgggttac ggatcaacag cgcgaaagac        120
gatgcggcag gccaggcgat tgctaaccgc ttcacttcta atatcaaagg tctgactcag        180
gcttcccgta acgctaacga cggcatttct attgcgcaga ccactgaagg tgcgctgaat        240
gaaatcaaca acaacctgca gcgtgtgcgt gagttgtctg ttcaggccac taacgggact        300
aactctgatt ccgatctgaa atctatccag gatgaaattc agcaacgtct ggaagaaatc        360
gatcgcgttt ctaatcagac tcaatttaac ggtgttaaag tcctgtctca ggacaaccag        420
atgaaaatcc aggttggtgc taacgatggt tccccgggaa gtaccgctaa cccactggct        480
tcaattgatt ctgcattgtc aaaagtggac gcagttcgtt cttctctggg ggcaattcaa        540
aaccgctttg attcagccat taccaacctt ggcaatacgg taaccaatct gaactccgcg        600
cgtagccgta tcgaagatgc tgactatgca acggaagttt ctaatatgtc taaagcgcag        660
attctgcagc aggctggtac ttccgttctg cgcgcaggcta accaggttcc gcaaaacgtc        720
ctctctttac tggttccgcg gggttctcat catcatcatc atcatggtta agtcgac           777
```

<210> SEQ ID NO 118
<211> LENGTH: 684
<212> TYPE: DNA
<213> ORGANISM: Artificial Sequence
<220> FEATURE:
<223> OTHER INFORMATION: Synthetic sequence

<400> SEQUENCE: 118

```
atgagcgggt tacggatcaa cagcgcgaaa gacgatgcgg caggccaggc gattgctaac         60
cgcttcactt ctaatatcaa aggtctgact caggcttccc gtaacgctaa cgacggcatt        120
tctattgcgc agaccactga aggtgcgctg aatgaaatca acaacaacct gcagcgtgtg        180
cgtgagttgt ctgttcaggc cactaacggg actaactctg attccgatct gaaatctatc        240
caggatgaaa ttcagcaacg tctggaagaa atcgatcgcg tttctaatca gactcaattt        300
aacggtgtta aagtcctgtc tcaggacaac cagatgaaaa tccaggttgg tgctaacgat        360
ggttccccgg gaagtaccgc taacccactg gcttcaattg attctgcatt gtcaaaagtg        420
gacgcagttc gttcttctct gggggcaatt caaaaccgct ttgattcagc cattaccaac        480
cttggcaata cggtaaccaa tctgaactcc gcgcgtagcc gtatcgaaga tgctgactat        540
gcaacggaag tttctaatat gtctaaagcg cagattctgc agcaggctgg tacttccgtt        600
ctggcgcagg ctaaccaggt tccgcaaaac gtcctctctt tactggttcc gcggggttct        660
```

```
catcatcatc atcatcatgg ttaa                                            684
```

```
<210> SEQ ID NO 119
<211> LENGTH: 227
<212> TYPE: PRT
<213> ORGANISM: Artificial Sequence
<220> FEATURE:
<223> OTHER INFORMATION: Synthetic sequence

<400> SEQUENCE: 119
```

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Ser Pro Gly Ser Thr Ala Asn
        115                 120                 125

Pro Leu Ala Ser Ile Asp Ser Ala Leu Ser Lys Val Asp Ala Val Arg
    130                 135                 140

Ser Ser Leu Gly Ala Ile Gln Asn Arg Phe Asp Ser Ala Ile Thr Asn
145                 150                 155                 160

Leu Gly Asn Thr Val Thr Asn Leu Asn Ser Ala Arg Ser Arg Ile Glu
                165                 170                 175

Asp Ala Asp Tyr Ala Thr Glu Val Ser Asn Met Ser Lys Ala Gln Ile
            180                 185                 190

Leu Gln Gln Ala Gly Thr Ser Val Leu Ala Gln Ala Asn Gln Val Pro
        195                 200                 205

Gln Asn Val Leu Ser Leu Leu Val Pro Arg Gly Ser His His His His
    210                 215                 220

His His Gly
225

```
<210> SEQ ID NO 120
<211> LENGTH: 90
<212> TYPE: DNA
<213> ORGANISM: Artificial Sequence
<220> FEATURE:
<223> OTHER INFORMATION: Synthetic sequence

<400> SEQUENCE: 120
```

```
agatctccgc ggaaccagca ggttattctg ggtcaacagc gacaggctgt tgtattaat    60 gacttgtgca tagtcagcat cttcgatacg                                    90
```

```
<210> SEQ ID NO 121
<211> LENGTH: 795
<212> TYPE: DNA
<213> ORGANISM: Artificial Sequence
<220> FEATURE:
<223> OTHER INFORMATION: Synthetic sequence
```

<400> SEQUENCE: 121

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac taacgggact     300
aactctgatt ccgatctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaacctg gcaatacggt aaccaatctg      660
aactccgcgc gtagccgtat cgaagatgct gactatgcac aagtcattaa tacaaacagc     720
ctgtcgctgt tgacccagaa taacctgctg gttccgcggg gttctcatca tcatcatcat     780
catggttaag tcgac                                                       795
```

<210> SEQ ID NO 122
<211> LENGTH: 702
<212> TYPE: DNA
<213> ORGANISM: Artificial Sequence
<220> FEATURE:
<223> OTHER INFORMATION: Synthetic sequence

<400> SEQUENCE: 122

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg ggggcaattc aaaaccgctt tgattcagcc     540
attaccaacc ttgcaatac ggtaaccaat ctgaactccg cgcgtagccg tatcgaagat      600
gctgactatg cacaagtcat taatacaaac agcctgtcgc tgttgaccca gaataacctg     660
ctggttccgc ggggttctca tcatcatcat catcatggtt aa                         702
```

<210> SEQ ID NO 123
<211> LENGTH: 233
<212> TYPE: PRT
<213> ORGANISM: Artificial Sequence
<220> FEATURE:
<223> OTHER INFORMATION: Synthetic sequence

<400> SEQUENCE: 123

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30
```

```
Ser Arg Asn Ala Asn Asp Gly Ile Ser Ile Ala Gln Thr Thr Glu Gly
         35                  40                  45

Ala Leu Asn Glu Ile Asn Asn Asn Leu Gln Arg Val Arg Glu Leu Ser
 50                  55                  60

Val Gln Ala Thr Asn Gly Thr Asn Ser Asp Ser Asp Leu Lys Ser Ile
 65                  70                  75                  80

Gln Asp Glu Ile Gln Gln Arg Leu Glu Glu Ile Asp Arg Val Ser Asn
             85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Gln Val Ile Asn
        195                 200                 205

Thr Asn Ser Leu Ser Leu Leu Thr Gln Asn Asn Leu Leu Val Pro Arg
    210                 215                 220

Gly Ser His His His His His Gly
225                 230

<210> SEQ ID NO 124
<211> LENGTH: 49
<212> TYPE: DNA
<213> ORGANISM: Artificial Sequence
<220> FEATURE:
<223> OTHER INFORMATION: Synthetic sequence

<400> SEQUENCE: 124
gctgactatg caacggcagt ttctgctatg tctgcagcgc agattctgc          49

<210> SEQ ID NO 125
<211> LENGTH: 49
<212> TYPE: DNA
<213> ORGANISM: Artificial Sequence
<220> FEATURE:
<223> OTHER INFORMATION: Synthetic sequence

<400> SEQUENCE: 125
gcagaatctg cgctgcagac atagcagaaa ctgccgttgc atagtcagc          49

<210> SEQ ID NO 126
<211> LENGTH: 795
<212> TYPE: DNA
<213> ORGANISM: Artificial Sequence
<220> FEATURE:
<223> OTHER INFORMATION: Synthetic sequence

<400> SEQUENCE: 126
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag ccaggcgat tgctaaccgc ttcacttcta atatcaaagg tctgactcag   180
```

```
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggcagtttc tgctatgtct    720
gcagcgcaga ttctgcagca ggctggtctg gttccgcggg gttctcatca tcatcatcat    780
catggttaag tcgac                                                    795

<210> SEQ ID NO 127
<211> LENGTH: 702
<212> TYPE: DNA
<213> ORGANISM: Artificial Sequence
<220> FEATURE:
<223> OTHER INFORMATION: Synthetic sequence

<400> SEQUENCE: 127
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca caacaacct gcagcgtgtg    180 cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggcagt ttctgctatg tctgcagcgc agattctgca gcaggctggt    660
ctggttccgc ggggttctca tcatcatcat catcatggtt aa                       702

<210> SEQ ID NO 128
<211> LENGTH: 233
<212> TYPE: PRT
<213> ORGANISM: Artificial Sequence
<220> FEATURE:
<223> OTHER INFORMATION: Synthetic sequence

<400> SEQUENCE: 128

Met Ser Gly Leu Arg Ile Asn Ser Ala Lys Asp Asp Ala Ala Gly Gln
  1               5                  10                  15

Ala Ile Ala Asn Arg Phe Thr Ser Asn Ile Lys Gly Leu Thr Gln Ala
                 20                  25                  30

Ser Arg Asn Ala Asn Asp Gly Ile Ser Ile Ala Gln Thr Thr Glu Gly
             35                  40                  45

Ala Leu Asn Glu Ile Asn Asn Asn Leu Gln Arg Val Arg Glu Leu Ser
         50                  55                  60
```

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Ala Val Ser
        195                 200                 205

Ala Met Ser Ala Ala Gln Ile Leu Gln Gln Ala Gly Leu Val Pro Arg
    210                 215                 220

Gly Ser His His His His His His Gly
225                 230

<210> SEQ ID NO 129
<211> LENGTH: 54
<212> TYPE: DNA
<213> ORGANISM: Artificial Sequence
<220> FEATURE:
<223> OTHER INFORMATION: Synthetic sequence

<400> SEQUENCE: 129
gtttctaata tgtctaaagc ggcgattctg ggagcggctg gtctggttcc gcgg        54

<210> SEQ ID NO 130
<211> LENGTH: 54
<212> TYPE: DNA
<213> ORGANISM: Artificial Sequence
<220> FEATURE:
<223> OTHER INFORMATION: Synthetic sequence

<400> SEQUENCE: 130
ccgcggaacc agaccagccg ctcccagaat cgccgcttta gacatattag aaac        54

<210> SEQ ID NO 131
<211> LENGTH: 795
<212> TYPE: DNA
<213> ORGANISM: Artificial Sequence
<220> FEATURE:
<223> OTHER INFORMATION: Synthetic sequence

<400> SEQUENCE: 131
taatacgact cactataggg gaattgtgag cggataacaa ttcccctcta gaataatttt        60
gtttaacttt aagaaggaga tatacatatg agcgggttac ggatcaacag cgcgaaagac       120
gatgcggcag gccaggcgat tgctaaccgc ttcacttcta atatcaaagg tctgactcag       180
gcttcccgta acgctaacga cggcattttt attgcgcaga ccactgaagg tgcgctgaat       240
gaaatcaaca caacctgca gcgtgtgcgt gagttgtctg ttcaggccac taacgggact       300
aactctgatt ccgatctgaa atctatccag gatgaaattc agcaacgtct ggaagaaatc       360

```
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg caatacggt aaccaatctg     660 aactccgcgc gtagccgtat cgaagatgct gactatgcaa cggaagtttc taatatgtct    720
aaagcggcga ttctgggagc ggctggtctg gttccgcggg gttctcatca tcatcatcat    780
catggttaag tcgac                                                    795
```

```
<210> SEQ ID NO 132
<211> LENGTH: 702
<212> TYPE: DNA
<213> ORGANISM: Artificial Sequence
<220> FEATURE:
<223> OTHER INFORMATION: Synthetic sequence

<400> SEQUENCE: 132
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca caacaacct gcagcgtgtg     180 cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aaccccactgg cttcaattga ttctgcattg    480
tcaaaagtgg acgcagttcg ttcttctctg ggggcaattc aaaaccgctt tgattcagcc    540
attaccaacc ttgcaatac ggtaaccaat ctgaactccg cgcgtagccg tatcgaagat     600
gctgactatg caacggaagt ttctaatatg tctaaagcgg cgattctggg agcggctggt    660
ctggttccgc ggggttctca tcatcatcat catcatggtt aa                       702
```

```
<210> SEQ ID NO 133
<211> LENGTH: 233
<212> TYPE: PRT
<213> ORGANISM: Artificial Sequence
<220> FEATURE:
<223> OTHER INFORMATION: Synthetic sequence

<400> SEQUENCE: 133

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
```

```
              100                 105                 110
Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Ala Ile Leu Gly Ala Ala Gly Leu Val Pro Arg
    210                 215                 220

Gly Ser His His His His His His Gly
225                 230
```

<210> SEQ ID NO 134
<211> LENGTH: 25
<212> TYPE: DNA
<213> ORGANISM: Artificial Sequence
<220> FEATURE:
<223> OTHER INFORMATION: Synthetic sequence

<400> SEQUENCE: 134
tctagaggat ccggcaggcc aggcg                                 25

<210> SEQ ID NO 135
<211> LENGTH: 22
<212> TYPE: DNA
<213> ORGANISM: Artificial Sequence
<220> FEATURE:
<223> OTHER INFORMATION: Synthetic sequence

<400> SEQUENCE: 135
cgcaagcttg tcgacttaac gc                                    22

<210> SEQ ID NO 136
<211> LENGTH: 970
<212> TYPE: DNA
<213> ORGANISM: Artificial Sequence
<220> FEATURE:
<223> OTHER INFORMATION: Synthetic sequence

<400> SEQUENCE: 136
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcgggatc tgtacgacct ggttccgcgc   180
ggtagcgcga aggatccggc aggccaggcg attgctaacc gcttcacttc taatatcaaa   240
ggtctgactc aggcttcccg taacgctaac gacggcattt ctattgcgca gaccactgaa   300
ggtgcgctga tgaaatcaa caacaacctg cagcgtgtgc gtgagttgtc tgttcaggcc   360
actaacggga ctaactctga ttccgatctg aaatctatcc aggatgaaat tcagcaacgt   420
ctggaagaaa tcgatcgcgt ttctaatcag actcaattta acggtgttaa agtcctgtct   480
caggacaacc agatgaaaat ccaggttggt gctaacgatg gtgaaccat accatcgat   540 ctgcaaaaaa ttgatgtgaa aagccttggc cttgatgggt tcaatgttaa ttccccggga   600

```
atttccggtg gtggtggtgg aattctagac tccatgggta cattaatcaa tgaagacgct    660
gccgcagcca agaaaagtac cgctaaccca ctggcttcaa ttgattctgc attgtcaaaa    720
gtggacgcag ttcgttcttc tctgggggca attcaaaacc gttttgattc agccattacc    780
aaccttggca atacggtaac caatctgaac tccgcgcgta ccgtatcga agatgctgac     840 tatgcaacgg aagtttctaa tatgtctaaa gcgcagattc tgcagcaggc tggtacttcc    900
gttctggcgc aggctaacca ggttccgcaa aacgtcctct ctttactgcg ttaagtcgac    960
aagcttgcgg                                                           970
```

<210> SEQ ID NO 137
<211> LENGTH: 288
<212> TYPE: PRT
<213> ORGANISM: Artificial Sequence
<220> FEATURE:
<223> OTHER INFORMATION: Synthetic sequence

<400> SEQUENCE: 137

```
Met Arg Gly Ser His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ala Gly Gln Ala Ile Ala Asn Arg Phe Thr Ser
        35                  40                  45

Asn Ile Lys Gly Leu Thr Gln Ala Ser Arg Asn Ala Asn Asp Gly Ile
    50                  55                  60

Ser Ile Ala Gln Thr Thr Glu Gly Ala Leu Asn Glu Ile Asn Asn Asn
65                  70                  75                  80

Leu Gln Arg Val Arg Glu Leu Ser Val Gln Ala Thr Asn Gly Thr Asn
                85                  90                  95

Ser Asp Ser Asp Leu Lys Ser Ile Gln Asp Glu Ile Gln Gln Arg Leu
            100                 105                 110

Glu Glu Ile Asp Arg Val Ser Asn Gln Thr Gln Phe Asn Gly Val Lys
        115                 120                 125

Val Leu Ser Gln Asp Asn Gln Met Lys Ile Gln Val Gly Ala Asn Asp
    130                 135                 140

Gly Glu Thr Ile Thr Ile Asp Leu Gln Lys Ile Asp Val Lys Ser Leu
145                 150                 155                 160

Gly Leu Asp Gly Phe Asn Val Asn Ser Pro Gly Ile Ser Gly Gly Gly
                165                 170                 175

Gly Gly Ile Leu Asp Ser Met Gly Thr Leu Ile Asn Glu Asp Ala Ala
            180                 185                 190

Ala Ala Lys Lys Ser Thr Ala Asn Pro Leu Ala Ser Ile Asp Ser Ala
        195                 200                 205

Leu Ser Lys Val Asp Ala Val Arg Ser Ser Leu Gly Ala Ile Gln Asn
    210                 215                 220

Arg Phe Asp Ser Ala Ile Thr Asn Leu Gly Asn Thr Val Thr Asn Leu
225                 230                 235                 240

Asn Ser Ala Arg Ser Arg Ile Glu Asp Ala Asp Tyr Ala Thr Glu Val
                245                 250                 255

Ser Asn Met Ser Lys Ala Gln Ile Leu Gln Gln Ala Gly Thr Ser Val
            260                 265                 270

Leu Ala Gln Ala Asn Gln Val Pro Gln Asn Val Leu Ser Leu Leu Arg
        275                 280                 285
```

<210> SEQ ID NO 138
<211> LENGTH: 1236
<212> TYPE: DNA
<213> ORGANISM: Artificial Sequence
<220> FEATURE:
<223> OTHER INFORMATION: Synthetic sequence

<400> SEQUENCE: 138

| | | | | | |
|---|---|---|---|---|---|
| taatacgact | cactataggg | gaattgtgag | cggataacaa | ttcccctcta | gaataatttt | 60 |
| gtttaacttt | aagaaggaga | tatacatatg | agtaaaggag | aagaactttt | cactggagtt | 120 |
| gtcccaattc | ttgttgaatt | agatggtgat | gttaatgggc | acaaattttc | tgtcagtgga | 180 |
| gagggtgaag | gtgatgcaac | atacggaaaa | cttaccctta | aatttatttg | cactactgga | 240 |
| aaactacctg | ttccatggcc | aacacttgtc | actactctga | cgtatggtgt | tcaatgcttt | 300 |
| tcccgttatc | cggatcacat | gaaacggcat | gactttttca | agagtgccat | gcccgaaggt | 360 |
| tatgtacagg | aacgcactat | atctttcaaa | gatgacggga | actacaagac | gcgtgctgaa | 420 |
| gtcaagtttg | aaggtgatac | ccttgttaat | cgtatcgagt | taaaaggtat | tgattttaaa | 480 |
| gaagatggaa | acattctcgg | acacaaactc | gagtacaact | ataactcaca | caatgtatac | 540 |
| atcacggcag | acaaacaagg | cctatcaggc | cgcattatga | gcgggttacg | gatcaacagc | 600 |
| gcgaaagacg | atgcggcagg | ccaggcgatt | gctaaccgct | tcacttctaa | tatcaaaggt | 660 |
| ctgactcagg | cttcccgtaa | cgctaacgac | ggcatttcta | ttgcgcagac | cactgaaggt | 720 |
| gcgctgaatg | aaatcaacaa | caacctgcag | cgtgtgcgtg | agttgtctgt | tcaggccact | 780 |
| aacgggacta | actctgattc | cgatctgaaa | tctatccagg | atgaaattca | gcaacgtctg | 840 |
| gaagaaatcg | atcgcgtttc | taatcagact | caatttaacg | gtgttaaagt | cctgtctcag | 900 |
| gacaaccaga | tgaaaatcca | ggttggtgct | aacgatggtg | aaaccattac | catcgatctg | 960 |
| caaaaaattg | atgtgaaaag | ccttggcctt | gatgggttca | atgttaattc | cccgggaagt | 1020 |
| accgctaacc | cactggcttc | aattgattct | gcattgtcaa | agtggacgc | agttcgttct | 1080 |
| tctctggggg | caattcaaaa | ccgctttgat | tcagccatta | ccaaccttgg | caatacggta | 1140 |
| accaatctga | actccgcgcg | tagccgtatc | gaagatgctg | actatgcact | ggttccgcgg | 1200 |
| ggttctcatc | atcatcatca | tcatggttaa | gtcgac | | | 1236 |

<210> SEQ ID NO 139
<211> LENGTH: 1143
<212> TYPE: DNA
<213> ORGANISM: Artificial Sequence
<220> FEATURE:
<223> OTHER INFORMATION: Synthetic sequence

<400> SEQUENCE: 139

| | | | | | |
|---|---|---|---|---|---|
| atgagtaaag | gagaagaact | tttcactgga | gttgtcccaa | ttcttgttga | attagatggt | 60 |
| gatgttaatg | ggcacaaatt | ttctgtcagt | ggagagggtg | aaggtgatgc | aacatacgga | 120 |
| aaacttaccc | ttaaatttat | ttgcactact | ggaaaactac | ctgttccatg | gccaacactt | 180 |
| gtcactactc | tgacgtatgg | tgttcaatgc | ttttcccgtt | atccggatca | catgaaacgg | 240 |
| catgactttt | tcaagagtgc | catgcccgaa | ggttatgtac | aggaacgcac | tatatctttc | 300 |
| aaagatgacg | ggaactacaa | gacgcgtgct | gaagtcaagt | ttgaaggtga | tacccttgtt | 360 |
| aatcgtatcg | agttaaaagg | tattgatttt | aaagaagatg | gaaacattct | cggacacaaa | 420 |
| ctcgagtaca | actataactc | acacaatgta | tacatcacgg | cagacaaaca | aggcctatca | 480 |
| ggccgcatta | tgagcgggtt | acggatcaac | agcgcgaaag | acgatgcggc | aggccaggcg | 540 |

```
attgctaacc gcttcacttc taatatcaaa ggtctgactc aggcttcccg taacgctaac     600
gacggcattt ctattgcgca gaccactgaa ggtgcgctga atgaaatcaa caacaacctg     660
cagcgtgtgc gtgagttgtc tgttcaggcc actaacggga ctaactctga ttccgatctg     720
aaatctatcc aggatgaaat tcagcaacgt ctggaagaaa tcgatcgcgt ttctaatcag     780
actcaattta acgtgttaa agtcctgtct caggacaacc agatgaaaat ccaggttggt      840
gctaacgatg tgaaaccat taccatcgat ctgcaaaaaa ttgatgtgaa aagccttggc      900
cttgatgggt tcaatgttaa ttccccggga agtaccgcta acccactggc ttcaattgat     960
tctgcattgt caaaagtgga cgcagttcgt tcttctctgg gggcaattca aaaccgcttt    1020
gattcagcca ttaccaacct tggcaatacg gtaaccaatc tgaactccgc gcgtagccgt    1080
atcgaagatg ctgactatgc actggttccg cggggttctc atcatcatca tcatcatggt    1140
taa                                                                   1143
```

<210> SEQ ID NO 140
<211> LENGTH: 380
<212> TYPE: PRT
<213> ORGANISM: Artificial Sequence
<220> FEATURE:
<223> OTHER INFORMATION: Synthetic sequence

<400> SEQUENCE: 140

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Gly Leu Ser
145                 150                 155                 160

Gly Arg Ile Met Ser Gly Leu Arg Ile Asn Ser Ala Lys Asp Asp Ala
                165                 170                 175

Ala Gly Gln Ala Ile Ala Asn Arg Phe Thr Ser Asn Ile Lys Gly Leu
            180                 185                 190

Thr Gln Ala Ser Arg Asn Ala Asn Asp Gly Ile Ser Ile Ala Gln Thr
        195                 200                 205

Thr Glu Gly Ala Leu Asn Glu Ile Asn Asn Asn Leu Gln Arg Val Arg
    210                 215                 220

Glu Leu Ser Val Gln Ala Thr Asn Gly Thr Asn Ser Asp Ser Asp Leu
225                 230                 235                 240

Lys Ser Ile Gln Asp Glu Ile Gln Gln Arg Leu Glu Glu Ile Asp Arg
```

```
            245                 250                 255
Val Ser Asn Gln Thr Gln Phe Asn Gly Val Lys Val Leu Ser Gln Asp
        260                 265                 270

Asn Gln Met Lys Ile Gln Val Gly Ala Asn Asp Gly Glu Thr Ile Thr
    275                 280                 285

Ile Asp Leu Gln Lys Ile Asp Val Lys Ser Leu Gly Leu Asp Gly Phe
290                 295                 300

Asn Val Asn Ser Pro Gly Ser Thr Ala Asn Pro Leu Ala Ser Ile Asp
305                 310                 315                 320

Ser Ala Leu Ser Lys Val Asp Ala Val Arg Ser Leu Gly Ala Ile
            325                 330                 335

Gln Asn Arg Phe Asp Ser Ala Ile Thr Asn Leu Gly Asn Thr Val Thr
                340                 345                 350

Asn Leu Asn Ser Ala Arg Ser Arg Ile Glu Asp Ala Asp Tyr Ala Leu
            355                 360                 365

Val Pro Arg Gly Ser His His His His His His Gly
        370                 375                 380

<210> SEQ ID NO 141
<211> LENGTH: 36
<212> TYPE: DNA
<213> ORGANISM: Artificial Sequence
<220> FEATURE:
<223> OTHER INFORMATION: Synthetic sequence

<400> SEQUENCE: 141
tctagaggat ccgtctggtc tgcgtatcaa cagcgc                              36

<210> SEQ ID NO 142
<211> LENGTH: 996
<212> TYPE: DNA
<213> ORGANISM: Artificial Sequence
<220> FEATURE:
<223> OTHER INFORMATION: Synthetic sequence

<400> SEQUENCE: 142
taatacgact cactataggg gaattgtgag cggataacaa ttcccctcta gaataatttt     60
gtttaacttt aagaaggaga tatacatatg cggggttctc atcatcatca tcatcatggt    120
atggctagca tgactggtgg acagcaaatg ggtcgggatc tgtacgacct ggttccgcgc    180
ggtagcgcga aggatccgtc tggtctgcgt atcaacagcg cgaaagacga tgcggcaggc    240
caggcgattg ctaaccgctt cacttctaat atcaaaggtc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta cgggactaa ctctgattcc    420 gatctgaaat ctatccagga tgaaattcag caacgtctgg aagaaatcga tcgcgtttct    480
aatcagactc aatttaacgg tgttaaagtc ctgtctcagg acaaccagat gaaaatccag    540
gttggtgcta acgatggtga accattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa aagtaccgct    720
aacccactgg cttcaattga ttctgcattg tcaaagtgg acgcagttcg ttcttctctg    780
ggggcaattc aaaaccgttt tgattcagcc attaccaacc ttggcaatac ggtaaccaat    840
ctgaactccg cgcgtagccg tatcgaagat gctgactatg caacggaagt ttctaatatg    900
tctaaagcgc agattctgca gcaggctggt acttccgttc tggcgcaggc taaccaggtt    960
```

```
ccgcaaaacg tcctctcttt actgcgttaa gtcgac                              996
```

<210> SEQ ID NO 143
<211> LENGTH: 903
<212> TYPE: DNA
<213> ORGANISM: Artificial Sequence
<220> FEATURE:
<223> OTHER INFORMATION: Synthetic sequence

<400> SEQUENCE: 143

```
atgcggggtt ctcatcatca tcatcatcat ggtatggcta gcatgactgg tggacagcaa    60
atgggtcggg atctgtacga cctggttccg cgcggtagcg cgaaggatcc gtctggtctg   120
cgtatcaaca gcgcgaaaga cgatgcggca ggccaggcga ttgctaaccg cttcacttct   180
aatatcaaag gtctgactca ggcttcccgt aacgctaacg acggcatttc tattgcgcag   240
accactgaag gtgcgctgaa tgaaatcaac aacaacctgc agcgtgtgcg tgagttgtct   300
gttcaggcca ctaacgggac taactctgat tccgatctga atctatcca ggatgaaatt   360
cagcaacgtc tggaagaaat cgatcgcgtt tctaatcaga ctcaatttaa cggtgttaaa   420
gtcctgtctc aggacaacca gatgaaaatc caggttggtg ctaacgatgg tgaaaccatt   480
accatcgatc tgcaaaaaat tgatgtgaaa agccttggcc ttgatgggtt caatgttaat   540
tccccgggaa tttccggtgg tggtggtgga attctagact ccatgggtac attaatcaat   600
gaagacgctg ccgcagccaa gaaaagtacc gctaacccac tggcttcaat tgattctgca   660
ttgtcaaaag tggacgcagt tcgttcttct ctgggggcaa ttcaaaaccg ttttgattca   720
gccattacca accttggcaa tacggtaacc aatctgaact ccgcgcgtag ccgtatcgaa   780
gatgctgact atgcaacgga agtttctaat atgtctaaag cgcagattct gcagcaggct   840
ggtacttccg ttctggcgca ggctaaccag gttccgcaaa acgtcctctc tttactgcgt   900
taa                                                                 903
```

<210> SEQ ID NO 144
<211> LENGTH: 300
<212> TYPE: PRT
<213> ORGANISM: Artificial Sequence
<220> FEATURE:
<223> OTHER INFORMATION: Synthetic sequence

<400> SEQUENCE: 144

```
Met Arg Gly Ser His His His His His His Gly Met Ala Ser Met Thr
1               5                   10                  15
Gly Gly Gln Gln Met Gly Arg Asp Leu Tyr Asp Leu Val Pro Arg Gly
            20                  25                  30
Ser Ala Lys Asp Pro Ser Gly Leu Arg Ile Asn Ser Ala Lys Asp Asp
        35                  40                  45
Ala Ala Gly Gln Ala Ile Ala Asn Arg Phe Thr Ser Asn Ile Lys Gly
    50                  55                  60
Leu Thr Gln Ala Ser Arg Asn Ala Asn Asp Gly Ile Ser Ile Ala Gln
65                  70                  75                  80
Thr Thr Glu Gly Ala Leu Asn Glu Ile Asn Asn Asn Leu Gln Arg Val
                85                  90                  95
Arg Glu Leu Ser Val Gln Ala Thr Asn Gly Thr Asn Ser Asp Ser Asp
            100                 105                 110
Leu Lys Ser Ile Gln Asp Glu Ile Gln Gln Arg Leu Glu Glu Ile Asp
        115                 120                 125
```

```
Arg Val Ser Asn Gln Thr Gln Phe Asn Gly Val Lys Val Leu Ser Gln
        130                 135                 140
Asp Asn Gln Met Lys Ile Gln Val Gly Ala Asn Asp Gly Glu Thr Ile
145                 150                 155                 160
Thr Ile Asp Leu Gln Lys Ile Asp Val Lys Ser Leu Gly Leu Asp Gly
                165                 170                 175
Phe Asn Val Asn Ser Pro Gly Ile Ser Gly Gly Gly Ile Leu
            180                 185                 190
Asp Ser Met Gly Thr Leu Ile Asn Glu Asp Ala Ala Ala Lys Lys
        195                 200                 205
Ser Thr Ala Asn Pro Leu Ala Ser Ile Asp Ser Ala Leu Ser Lys Val
210                 215                 220
Asp Ala Val Arg Ser Ser Leu Gly Ala Ile Gln Asn Arg Phe Asp Ser
225                 230                 235                 240
Ala Ile Thr Asn Leu Gly Asn Thr Val Thr Asn Leu Asn Ser Ala Arg
                245                 250                 255
Ser Arg Ile Glu Asp Ala Asp Tyr Ala Thr Glu Val Ser Asn Met Ser
            260                 265                 270
Lys Ala Gln Ile Leu Gln Gln Ala Gly Thr Ser Val Leu Ala Gln Ala
        275                 280                 285
Asn Gln Val Pro Gln Asn Val Leu Ser Leu Leu Arg
        290                 295                 300

<210> SEQ ID NO 145
<211> LENGTH: 44
<212> TYPE: DNA
<213> ORGANISM: Artificial Sequence
<220> FEATURE:
<223> OTHER INFORMATION: Synthetic sequence

<400> SEQUENCE: 145
agatctccgc ggaaccagtg catagtcagc atcttcgata cggc          44

<210> SEQ ID NO 146
<211> LENGTH: 747
<212> TYPE: DNA
<213> ORGANISM: Artificial Sequence
<220> FEATURE:
<223> OTHER INFORMATION: Synthetic sequence

<400> SEQUENCE: 146
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttg gcaatacggt aaccaatctg   660
aactccgcgc gtagccgtat cgaagatgct gactatgcac tggttccgcg gggttctcat   720
```
catcatcatc atcatggtta agtcgac 747

<210> SEQ ID NO 147
<211> LENGTH: 654
<212> TYPE: DNA
<213> ORGANISM: Artificial Sequence
<220> FEATURE:
<223> OTHER INFORMATION: Synthetic sequence

<400> SEQUENCE: 147
atgagcgggt tacggatcaa cagcgcgaaa gacgatgcgg caggccaggc gattgctaac    60
cgcttcactt ctaatatcaa aggtctgact caggcttccc gtaacgctaa cgacggcatt   120
tctattgcgc agaccactga aggtgcgctg aatgaaatca caacaacct gcagcgtgtg    180
cgtgagttgt ctgttcaggc cactaacggg actaactctg attccgatct gaaatctatc   240
caggatgaaa ttcagcaacg tctggaagaa atcgatcgcg tttctaatca gactcaattt   300
aacggtgtta aagtcctgtc tcaggacaac cagatgaaaa tccaggttgg tgctaacgat   360
ggtgaaacca ttaccatcga tctgcaaaaa attgatgtga aaagccttgg ccttgatggg   420
ttcaatgtta attccccggg aagtaccgct aacccactgg cttcaattga ttctgcattg   480
tcaaaagtgg acgcagttcg ttcttctctg ggggcaattc aaaaccgctt tgattcagcc   540
attaccaacc ttggcaatac ggtaaccaat ctgaactccg cgcgtagccg tatcgaagat   600
gctgactatg cactggttcc gcggggttct catcatcatc atcatcatgg ttaa           654

<210> SEQ ID NO 148
<211> LENGTH: 217
<212> TYPE: PRT
<213> ORGANISM: Artificial Sequence
<220> FEATURE:
<223> OTHER INFORMATION: Synthetic sequence

<400> SEQUENCE: 148

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
        195                 200                 205

Gly Ser His His His His His His Gly
    210                 215

<210> SEQ ID NO 149
<211> LENGTH: 753
<212> TYPE: DNA
<213> ORGANISM: Artificial Sequence
<220> FEATURE:
<223> OTHER INFORMATION: Synthetic sequence

<400> SEQUENCE: 149

```
atgagcgggt tacggatcaa cagcgcgaaa gacgatgcgg caggccaggc gattgctaac      60
cgcttcactt ctaatatcaa aggtctgact caggcttccc gtaacgctgc agacggcatt     120
tctattgcgc agaccactga aggtgcgctg aatgaaatca caacaacct gcagcgtgtg     180
cgtgagttgt ctgttcaggc cactgccggg gctaacgctg atgccgctct gaaagctatc     240
caggctgaaa ttcagcaacg tctggaagaa atcgatcgcg tttctcagca gactcaagct     300
gccgctgtta aagtcctgtc tcaggacaac gcaatggcaa tccaggttgg tgctaacgat     360
ggtgccgcta ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg ggggcaattc aaaaccgctt tgattcagcc     540
attaccaacc ttggcaatac ggtaaccaat ctgaactccg cgcgtagccg tatcgaagat     600
gctgactatg caacggaagt ttctcaaatg tctaaagcgc agattctgca gcaggctggt     660
acttccgttc tggcgcaggc taaccaggtt ccgcaaaacg tcctctcttt actggttccg     720
cggggttctc atcatcatca tcatcatggt taa                                  753
```

<210> SEQ ID NO 150
<211> LENGTH: 250
<212> TYPE: PRT
<213> ORGANISM: Artificial Sequence
<220> FEATURE:
<223> OTHER INFORMATION: Synthetic sequence

<400> SEQUENCE: 150

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80

Gln Ala Glu Ile Gln Gln Arg Leu Glu Glu Ile Asp Arg Val Ser Gln
                85                  90                  95

Gln Thr Gln Ala Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

```
Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
            165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
            195                 200                 205

Gln Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 151
<211> LENGTH: 846
<212> TYPE: DNA
<213> ORGANISM: Artificial Sequence
<220> FEATURE:
<223> OTHER INFORMATION: Synthetic sequence

<400> SEQUENCE: 151
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctgcaga cggcatttct attgcgcaga ccactgaagg tgcgctgaat    240
gaaatcaaca caaacctgca gcgtgtgcgt gagttgtctg ttcaggccac tgccggggct    300
aacgctgatg ccgctctgaa agctatccag gctgaaattc agcaacgtct ggaagaaatc    360
gatcgcgttt ctcagcagac tcaagctgcc gctgttaaag tcctgtctca ggacaacgca    420
atggcaatcc aggttggtgc taacgatggt gccgctatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggaagtttc tcaaatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846

<210> SEQ ID NO 152
<211> LENGTH: 795
<212> TYPE: DNA
<213> ORGANISM: Artificial Sequence
<220> FEATURE:
<223> OTHER INFORMATION: Synthetic sequence

<400> SEQUENCE: 152
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctgcaga cggcatttct attgcgcaga ccactgaagg tgcgctgaat    240
```

```
gaaatcaaca acaacctgca gcgtgtgcgt gagttgtctg ttcaggccac tgccggggct    300
aacgctgatg ccgctctgaa agctatccag gctgaaattc agcaacgtct ggaagaaatc    360
gatcgcgttt ctcagcagac tcaagctgcc gctgttaaag tcctgtctca ggacaacgca    420
atggcaatcc aggttggtgc taacgatggt gccgctatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg caatacggt aaccaatctg     660 aactccgcgc gtagccgtat cgaagatgct gactatgcaa cggaagtttc tcaaatgtct    720
aaagcgcaga ttctgcagca ggctggtctg gttccgcggg gttctcatca tcatcatcat    780
catggttaag tcgac                                                     795

<210> SEQ ID NO 153
<211> LENGTH: 702
<212> TYPE: DNA
<213> ORGANISM: Artificial Sequence
<220> FEATURE:
<223> OTHER INFORMATION: Synthetic sequence

<400> SEQUENCE: 153
atgagcgggt tacggatcaa cagcgcgaaa gacgatgcgg caggccaggc gattgctaac     60
cgcttcactt ctaatatcaa aggtctgact caggcttccc gtaacgctgc agacggcatt    120
tctattgcgc agaccactga aggtgcgctg aatgaaatca caacaacct gcagcgtgtg     180 cgtgagttgt ctgttcaggc cactgccggg gctaacgctg atgccgctct gaaagctatc    240
caggctgaaa ttcagcaacg tctggaagaa atcgatcgcg tttctcagca gactcaagct    300
gccgctgtta aagtcctgtc tcaggacaac gcaatggcaa tccaggttgg tgctaacgat    360
ggtgccgcta ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttgcaatac ggtaaccaat ctgaactccg cgcgtagccg tatcgaagat     600
gctgactatg caacggaagt ttctcaaatg tctaaagcgc agattctgca gcaggctggt    660
ctggttccgc ggggttctca tcatcatcat catcatggtt aa                       702

<210> SEQ ID NO 154
<211> LENGTH: 233
<212> TYPE: PRT
<213> ORGANISM: Artificial Sequence
<220> FEATURE:
<223> OTHER INFORMATION: Synthetic sequence

<400> SEQUENCE: 154

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80
```

Gln Ala Glu Ile Gln Gln Arg Leu Glu Glu Ile Asp Arg Val Ser Gln
                85                  90                  95

Gln Thr Gln Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
            115                 120                 125

Gln Lys Ile Asp Val Lys Ser Leu Gly Leu Asp Gly Phe Asn Val Asn
130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
            195                 200                 205

Gln Met Ser Lys Ala Gln Ile Leu Gln Gln Ala Gly Leu Val Pro Arg
        210                 215                 220

Gly Ser His His His His His His Gly
225                 230

<210> SEQ ID NO 155
<211> LENGTH: 990
<212> TYPE: DNA
<213> ORGANISM: Artificial Sequence
<220> FEATURE:
<223> OTHER INFORMATION: Synthetic sequence

<400> SEQUENCE: 155
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgcagaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggtc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccactc aagggactaa ctctgattcc     420
gatctgaaat ctatccagga tgaaattcag caacgtctgg aagaaatcga tcgcgtttct     480
cagcagactc aatttaacgg tgttaaagtc ctgtctcagg acaaccagat gaaaatccag     540
gttggtgcta acgatggtga accattacc atcgatctgc aaaaaattga tgtgaaaagc     600
cttggccttg atgggttcaa tgttaattcc ccgggaattt ccgtggtgg tggtggaatt     660 ctagactcca tgggtacatt aatcaatgaa gacgctgccg cagccaagaa agtaccgct     720 aacccactgg cttcaattga ttctgcattg tcaaaagtgg acgcagttcg ttcttctctg     780
ggggcaattc aaaaccgttt tgattcagcc attaccaacc ttggcaatac ggtaaccaat     840
ctgaactccg cgcgtagccg tatcgaagat gctgactatg caacggaagt ttctcaaatg     900
tctaaagcgc agattctgca gcaggctggt acttccgttc tggcgcaggc taaccaggtt     960
ccgcaaaacg tcctctcttt actgcgttaa                                      990

<210> SEQ ID NO 156
<211> LENGTH: 180
<212> TYPE: DNA

<213> ORGANISM: Artificial Sequence
<220> FEATURE:
<223> OTHER INFORMATION: Synthetic sequence

<400> SEQUENCE: 156

```
aacccactgg cttcaattga ttctgcattg tcaaaagtgg acgcagttcg ttcttctctg      60
ggggcaattc aaaaccgttt tgattcagcc attaccgccc ttggcgctac ggtaaccgct     120
ctggcctccg cgcgtagcgc tatcgaagat gctgactatg caacggaagt ttctcaaatg     180
```

<210> SEQ ID NO 157
<211> LENGTH: 60
<212> TYPE: PRT
<213> ORGANISM: Artificial Sequence
<220> FEATURE:
<223> OTHER INFORMATION: Synthetic sequence

<400> SEQUENCE: 157

```
Asn Pro Leu Ala Ser Ile Asp Ser Ala Leu Ser Lys Val Asp Ala Val
1               5                   10                  15
Arg Ser Ser Leu Gly Ala Ile Gln Asn Arg Phe Asp Ser Ala Ile Thr
            20                  25                  30
Ala Leu Gly Ala Thr Val Thr Ala Leu Ala Ser Ala Arg Ser Ala Ile
        35                  40                  45
Glu Asp Ala Asp Tyr Ala Thr Glu Val Ser Asn Met
    50                  55                  60
```

<210> SEQ ID NO 158
<211> LENGTH: 50
<212> TYPE: DNA
<213> ORGANISM: Artificial Sequence
<220> FEATURE:
<223> OTHER INFORMATION: Synthetic sequence

<400> SEQUENCE: 158

```
gcagttcgtt cttctctggg ggcaattgat tcagccatta ccgcccttgg                50
```

<210> SEQ ID NO 159
<211> LENGTH: 50
<212> TYPE: DNA
<213> ORGANISM: Artificial Sequence
<220> FEATURE:
<223> OTHER INFORMATION: Synthetic sequence

<400> SEQUENCE: 159

```
ccaagggcgg taatggctga atcaattgcc cccagagaag aacgaactgc                50
```

<210> SEQ ID NO 160
<211> LENGTH: 1066
<212> TYPE: DNA
<213> ORGANISM: Artificial Sequence
<220> FEATURE:
<223> OTHER INFORMATION: Synthetic sequence

<400> SEQUENCE: 160

```
taatacgact cactataggg gaattgtgag cggataacaa ttcccctcta gaaataattt      60
tgtttaactt taagaaggag atatacatat gcggggttct catcatcatc atcatcatgg    120
tatggctagc atgactggtg gacagcaaat gggtcgggat ctgtacgacg atgacgataa    180
ggatccgatg gcacaagtca ttaatacaaa cagcctgtcg ctgttgaccc agaataacct    240
gaacaaatct cagtcctcac tgagttccgc tattgagcgt ctgtcctctg gtctgcgtat    300
caacagcgcg aaagacgatg cggcaggcca ggcgattgct aaccgcttca cttctaatat    360
```

```
caaaggtctg actcaggctt cccgtaacgc taacgacggc atttctattg cgcagaccac    420
tgaaggtgcg ctgaatgaaa tcaacaacaa cctgcagcgt gtgcgtgagt tgtctgttca    480
ggccactaac gggactaact ctgattccga tctgaaatct atccaggatg aaattcagca    540
acgtctggaa gaaatcgatc gcgttttctaa tcagactcaa tttaacggtg ttaaagtcct    600
gtctcaggac aaccagatga aaatccaggt tggtgctaac gatggtgaaa ccattaccat    660
cgatctgcaa aaaattgatg tgaaaagcct tggccttgat gggttcaatg ttaattcccc    720
gggaatttcc ggtggtggtg gtggaattct agactccatg ggtacattaa tcaatgaaga    780
cgctgccgca gccaagaaaa gtaccgctaa cccactggct tcaattgatt ctgcattgtc    840
aaaagtggac gcagttcgtt cttctctggg ggcaattgat tcagccatta ccgcccttgg    900
cgctacggta accgctctgg cctccgcggc tagccgtatc gaagatgctg actatgcaac    960
ggaagtttct aatatgtcta agcgcagat tctgcagcag gctggtactt ccgttctggc    1020
gcaggctaac caggttccgc aaaacgtcct ctctttactg cgttaa                  1066
```

<210> SEQ ID NO 161
<211> LENGTH: 325
<212> TYPE: PRT
<213> ORGANISM: Artificial Sequence
<220> FEATURE:
<223> OTHER INFORMATION: Synthetic sequence

<400> SEQUENCE: 161

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
130                 135                 140

Ile Gln Asp Glu Ile Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240
```

```
Asn Pro Leu Ala Ser Ile Asp Ser Ala Leu Ser Lys Val Asp Ala Val
                245                 250                 255

Arg Ser Ser Leu Gly Ala Ile Asp Ser Ala Ile Thr Ala Leu Gly Ala
            260                 265                 270

Thr Val Thr Ala Leu Ala Ser Ala Ala Ser Arg Ile Glu Asp Ala Asp
        275                 280                 285

Tyr Ala Thr Glu Val Ser Asn Met Ser Lys Ala Gln Ile Leu Gln Gln
    290                 295                 300

Ala Gly Thr Ser Val Leu Ala Gln Ala Asn Gln Val Pro Gln Asn Val
305                 310                 315                 320

Leu Ser Leu Leu Arg
                325

<210> SEQ ID NO 162
<211> LENGTH: 180
<212> TYPE: DNA
<213> ORGANISM: Artificial Sequence
<220> FEATURE:
<223> OTHER INFORMATION: Synthetic sequence

<400> SEQUENCE: 162
aacccactgg cttcaattga ttctgcattg tcaaaagtgg acgcagttcg ttcttctctg    60
ggggcaattg caaaggcttt tgattcagcc attaccgccc ttggcgctac ggtaaccgct   120
ctggcctccg cgcgtagcgc tatcgaagat gctgactatg caacggaagt ttctcaaatg   180

<210> SEQ ID NO 163
<211> LENGTH: 60
<212> TYPE: PRT
<213> ORGANISM: Artificial Sequence
<220> FEATURE:
<223> OTHER INFORMATION: Synthetic sequence

<400> SEQUENCE: 163

Asn Pro Leu Ala Ser Ile Asp Ser Ala Leu Ser Lys Val Asp Ala Val
1               5                   10                  15

Arg Ser Ser Leu Gly Ala Ile Ala Lys Ala Phe Asp Ser Ala Ile Thr
            20                  25                  30

Ala Leu Gly Ala Thr Val Thr Ala Leu Ala Ser Ala Arg Ser Ala Ile
        35                  40                  45

Glu Asp Ala Asp Tyr Ala Thr Glu Val Ser Asn Met
    50                  55                  60

<210> SEQ ID NO 164
<211> LENGTH: 50
<212> TYPE: DNA
<213> ORGANISM: Artificial Sequence
<220> FEATURE:
<223> OTHER INFORMATION: Synthetic sequence

<400> SEQUENCE: 164
cgttcttctc tggggggcaat tgcaaaggct tttgattcag ccattaccgc              50

<210> SEQ ID NO 165
<211> LENGTH: 50
<212> TYPE: DNA
<213> ORGANISM: Artificial Sequence
<220> FEATURE:
<223> OTHER INFORMATION: Synthetic sequence

<400> SEQUENCE: 165
```

```
gcggtaatgg ctgaatcaaa agcctttgca attgccccca gagaagaacg        50
```

<210> SEQ ID NO 166
<211> LENGTH: 1078
<212> TYPE: DNA
<213> ORGANISM: Artificial Sequence
<220> FEATURE:
<223> OTHER INFORMATION: Synthetic sequence

<400> SEQUENCE: 166

```
taatacgact cactataggg gaattgtgag cggataacaa ttcccctcta gaaataattt    60
tgtttaactt taagaaggag atatacatat gcggggttct catcatcatc atcatcatgg   120
tatggctagc atgactggtg gacagcaaat gggtcgggat ctgtacgacg atgacgataa   180
ggatccgatg gcacaagtca ttaatacaaa cagcctgtcg ctgttgaccc agaataacct   240
gaacaaatct cagtcctcac tgagttccgc tattgagcgt ctgtcctctg gtctgcgtat   300
caacagcgcg aaagacgatg cggcaggcca ggcgattgct aaccgcttca cttctaatat   360
caaaggtctg actcaggctt cccgtaacgc taacgacggc atttctattg cgcagaccac   420
tgaaggtgcg ctgaatgaaa tcaacaacaa cctgcagcgt gtgcgtgagt tgtctgttca   480
ggccactaac gggactaact ctgattccga tctgaaatct atccaggatg aaattcagca   540
acgtctggaa gaaatcgatc gcgtttctaa tcagactcaa tttaacggtg ttaaagtcct   600
gtctcaggac aaccagatga aaatccaggt tggtgctaac gatggtgaaa ccattaccat   660
cgatctgcaa aaaattgatg tgaaaagcct tggccttgat gggttcaatg ttaattcccc   720
gggaatttcc ggtggtggtg gtggaattct agactccatg ggtacattaa tcaatgaaga   780
cgctgccgca gccaagaaaa gtaccgctaa cccactggct tcaattgatt ctgcattgtc   840
aaaagtggac gcagttcgtt cttctctggg ggcaattgca aaggcttttg attcagccat   900
taccgccctt ggcgctacgg taaccgctct ggcctccgcg gctagccgta tcgaagatgc   960
tgactatgca acggaagttt ctaatatgtc taaagcgcag attctgcagc aggctggtac  1020
ttccgttctg gcgcaggcta accaggttcc gcaaaacgtc ctctctttac tgcgttaa    1078
```

<210> SEQ ID NO 167
<211> LENGTH: 329
<212> TYPE: PRT
<213> ORGANISM: Artificial Sequence
<220> FEATURE:
<223> OTHER INFORMATION: Synthetic sequence

<400> SEQUENCE: 167

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110
```

```
Gly Ala Leu Asn Glu Ile Asn Asn Asn Leu Gln Arg Val Arg Glu Leu
            115                 120                 125

Ser Val Gln Ala Thr Asn Gly Thr Asn Ser Asp Ser Asp Leu Lys Ser
        130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Ala Lys Ala Phe Asp Ser Ala Ile Thr
            260                 265                 270

Ala Leu Gly Ala Thr Val Thr Ala Leu Ala Ser Ala Ala Ser Arg Ile
        275                 280                 285

Glu Asp Ala Asp Tyr Ala Thr Glu Val Ser Asn Met Ser Lys Ala Gln
290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325
```

<210> SEQ ID NO 168
<211> LENGTH: 903
<212> TYPE: DNA
<213> ORGANISM: Artificial Sequence
<220> FEATURE:
<223> OTHER INFORMATION: Synthetic sequence

<400> SEQUENCE: 168

```
atgcggggtt ctcatcatca tcatcatcat ggtatggcta gcatgactgg tggacagcaa    60
atgggtcggg atctgtacga cctggttccg cgcggtagcg cgaaggatcc gtctggtctg   120
cgtatcaaca gcgcgaaaga cgatgcggca ggccaggcga ttgctaaccg cttcacttct   180
aatatcaaag gtctgactca ggcttcccgt aacgctgcag acggcatttc tattgcgcag   240
accactgaag gtgcgctgaa tgaaatcaac aacaacctgc agcgtgtgcg tgagttgtct   300
gttcaggcca ctaacgggac taactctgat tccgatctga atctatccag gatgaaatt   360
cagcaacgtc tggaagaaat cgatcgcgtt tctaatcaga ctcaagctaa cggtgttaaa   420
gtcctgtctc aggacaacgc aatgaaaatc caggttggtg ctaacgatgg tgccgctatt   480
accatcgatc tgcaaaaaat tgatgtgaaa agccttggcc ttgatgggtt caatgttaat   540
tccccgggaa tttccggtgg tggtggtgga attctagact ccatgggtac attaatcaat   600
gaagacgctg ccgcagccaa gaaaagtacc gctaacccac tggcttcaat tgattctgca   660
ttgtcaaaag tggacgcagt tcgttcttct ctggggggcaa ttcaagctcg ttttgccgcg   720
gccattgcta accttggcaa tacggtaacc aatctgaact ccgcgcgtag ccgtatcgaa   780
gatgctgact atgcaacgga agtttctaat atgtctaaag cgcagattct gcagcaggct   840
```

```
          ggtacttccg ttctggcgca ggctaaccag gttccgcaaa acgtcctctc tttactgcgt    900
taa                                                                 903
```

<210> SEQ ID NO 169
<211> LENGTH: 300
<212> TYPE: PRT
<213> ORGANISM: Artificial Sequence
<220> FEATURE:
<223> OTHER INFORMATION: Synthetic sequence

<400> SEQUENCE: 169

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Ala Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Ala Asn Gly Val Lys Val Leu Ser Gln
    130                 135                 140

Asp Asn Ala Met Lys Ile Gln Val Gly Ala Asn Asp Gly Ala Ala Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
            180                 185                 190

Asp Ser Met Gly Thr Leu Ile Asn Glu Asp Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Ala Arg Phe Ala Ala
225                 230                 235                 240

Ala Ile Ala Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
    290                 295                 300
```

<210> SEQ ID NO 170
<211> LENGTH: 996
<212> TYPE: DNA
<213> ORGANISM: Artificial Sequence
<220> FEATURE:
<223> OTHER INFORMATION: Synthetic sequence

```
<400> SEQUENCE: 170
taatacgact cactataggg gaattgtgag cggataacaa ttcccctcta gaataatttt      60
gtttaacttt aagaaggaga tatacatatg cggggttctc atcatcatca tcatcatggt    120
atggctagca tgactggtgg acagcaaatg ggtcggatc tgtacgacct ggttccgcgc     180
ggtagcgcga aggatccgtc tggtctgcgt atcaacagcg cgaaagacga tgcggcaggc    240
caggcgattg ctaaccgctt cacttctaat atcaaaggtc tgactcaggc ttcccgtaac    300
gctgcagacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aagctaacgg tgttaaagtc ctgtctcagg acaacgcaat gaaaatccag    540
gttggtgcta acgatggtgc cgctattacc atcgatctgc aaaaaattga tgtgaaaagc    600
cttggccttg atgggttcaa tgttaattcc ccgggaattt ccgtggtgg tggtggaatt    660 ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aagctcgttt tgccgcggcc attgctaacc ttggcaatac ggtaaccaat    840
ctgaactccg cgcgtagccg tatcgaagat gctgactatg caacgaagt ttctaatatg     900 tctaaagcgc agattctgca gcaggctggt acttccgttc tggcgcaggc taaccaggtt    960
ccgcaaaacg tcctctcttt actgcgttaa gtcgac                               996

<210> SEQ ID NO 171
<211> LENGTH: 79
<212> TYPE: DNA
<213> ORGANISM: Artificial Sequence
<220> FEATURE:
<223> OTHER INFORMATION: Synthetic sequence

<400> SEQUENCE: 171
agatctgtcg acttaaccat gatgatgatg atgatgagaa ccccgcggaa ccagtaaaga     60
gaggacgttt tgcggaacc                                                  79

<210> SEQ ID NO 172
<211> LENGTH: 846
<212> TYPE: DNA
<213> ORGANISM: Artificial Sequence
<220> FEATURE:
<223> OTHER INFORMATION: Synthetic sequence

<400> SEQUENCE: 172
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaatta gcaacgtct ggaagaaatc     360 gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
```

```
ccactggctt caattgattc tgcattgtca aaagtggacg cagttcgttc ttctctgggg    600
gcaattcaag ctcgttttgc cgcggccatt gctaaccttg caatacggt aaccaatctg    660 aactccgcgc gtagccgtat cgaagatgct gactatgcaa cggaagtttc taatatgtct   720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846
```

<210> SEQ ID NO 173
<211> LENGTH: 250
<212> TYPE: PRT
<213> ORGANISM: Artificial Sequence
<220> FEATURE:
<223> OTHER INFORMATION: Synthetic sequence

<400> SEQUENCE: 173

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Ala Arg
                165                 170                 175

Phe Ala Ala Ala Ile Ala Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250
```

<210> SEQ ID NO 174
<211> LENGTH: 47
<212> TYPE: DNA
<213> ORGANISM: Artificial Sequence
<220> FEATURE:
<223> OTHER INFORMATION: Synthetic sequence

<400> SEQUENCE: 174
agatctcata tgagcgggtt acggatcaac agcgcgaaag acgatgc    47

<210> SEQ ID NO 175
<211> LENGTH: 846
<212> TYPE: DNA
<213> ORGANISM: Artificial Sequence
<220> FEATURE:
<223> OTHER INFORMATION: Synthetic sequence

<400> SEQUENCE: 175

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctgcaga cggcatttct attgcgcaga ccactgaagg tgcgctgaat   240
gaaatcaaca acaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaagctaac ggtgttaaag tcctgtctca ggacaacgca   420
atgaaaatcc aggttggtgc taacgatggt gccgctatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                             846
```

<210> SEQ ID NO 176
<211> LENGTH: 250
<212> TYPE: PRT
<213> ORGANISM: Artificial Sequence
<220> FEATURE:
<223> OTHER INFORMATION: Synthetic sequence

<400> SEQUENCE: 176

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Ala Asn Gly Val Lys Val Leu Ser Gln Asp Asn Ala Met
            100                 105                 110

Lys Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

```
Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
            165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
            195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250
```

<210> SEQ ID NO 177
<211> LENGTH: 270
<212> TYPE: DNA
<213> ORGANISM: Artificial Sequence
<220> FEATURE:
<223> OTHER INFORMATION: Synthetic sequence

<400> SEQUENCE: 177

```
aacccactgg cttcaattga ttctgcattg tcaaaagtgg acgcagttcg ttcttctctg    60
ggggcaattc aaaaccgttt tgattcagcc attaccaacc ttggcaatac ggtaaccaat   120
ctgaactccg cgcgtagccg tatcgaagat gctgactatg caacggaagt ttctcaaatg   180
tctaaagcgc agattctgca gcaggctggt acttccgttc tggcgcaggc taaccaggtt   240
ccgcaaaacg tcctctcttt actgcgttaa                                    270
```

<210> SEQ ID NO 178
<211> LENGTH: 60
<212> TYPE: DNA
<213> ORGANISM: Artificial Sequence
<220> FEATURE:
<223> OTHER INFORMATION: Synthetic sequence

<400> SEQUENCE: 178

```
attaccaacc ttggcaatac ggtaaccaat ctgaactccg cgcgtagccg tatcgaagat    60
```

<210> SEQ ID NO 179
<211> LENGTH: 20
<212> TYPE: PRT
<213> ORGANISM: Artificial Sequence
<220> FEATURE:
<223> OTHER INFORMATION: Synthetic sequence

<400> SEQUENCE: 179

```
Ile Thr Asn Leu Gly Asn Thr Val Thr Asn Leu Asn Ser Ala Arg Ser
1               5                   10                  15

Arg Ile Glu Asp
            20
```

<210> SEQ ID NO 180
<211> LENGTH: 46
<212> TYPE: DNA
<213> ORGANISM: Artificial Sequence
<220> FEATURE:
<223> OTHER INFORMATION: Synthetic sequence

<400> SEQUENCE: 180

|  |  |
|---|---|
| ccttggcaat acggtaaccg ctctggcctc cgcgcgtagc cgtatc | 46 |

<210> SEQ ID NO 181
<211> LENGTH: 46
<212> TYPE: DNA
<213> ORGANISM: Artificial Sequence
<220> FEATURE:
<223> OTHER INFORMATION: Synthetic sequence

<400> SEQUENCE: 181

|  |  |
|---|---|
| gatacggcta cgcgcggagg ccagagcggt taccgtattg ccaagg | 46 |

<210> SEQ ID NO 182
<211> LENGTH: 60
<212> TYPE: DNA
<213> ORGANISM: Artificial Sequence
<220> FEATURE:
<223> OTHER INFORMATION: Synthetic sequence

<400> SEQUENCE: 182

|  |  |
|---|---|
| acggtaaccg ctctggcctc cgcgcgtagc cgtatcgaag atgctgacta tgcaacggaa | 60 |

<210> SEQ ID NO 183
<211> LENGTH: 20
<212> TYPE: PRT
<213> ORGANISM: Artificial Sequence
<220> FEATURE:
<223> OTHER INFORMATION: Synthetic sequence

<400> SEQUENCE: 183

Thr Val Thr Ala Leu Ala Ser Ala Arg Ser Arg Ile Glu Asp Ala Asp
1               5                   10                  15

Tyr Ala Thr Glu
            20

<210> SEQ ID NO 184
<211> LENGTH: 34
<212> TYPE: DNA
<213> ORGANISM: Artificial Sequence
<220> FEATURE:
<223> OTHER INFORMATION: Synthetic sequence

<400> SEQUENCE: 184

|  |  |
|---|---|
| gctctggcct ccgcggctag ccgtatcgaa gatg | 34 |

<210> SEQ ID NO 185
<211> LENGTH: 34
<212> TYPE: DNA
<213> ORGANISM: Artificial Sequence
<220> FEATURE:
<223> OTHER INFORMATION: Synthetic sequence

<400> SEQUENCE: 185

|  |  |
|---|---|
| catcttcgat acggctagcc gcggaggcca gagc | 34 |

<210> SEQ ID NO 186
<211> LENGTH: 60
<212> TYPE: DNA
<213> ORGANISM: Artificial Sequence
<220> FEATURE:
<223> OTHER INFORMATION: Synthetic sequence

<400> SEQUENCE: 186

|  |  |
|---|---|
| caaaaccgtt ttgattcagc cattaccaac cttggcaata cggtaaccgc tctggcctcc | 60 |

<210> SEQ ID NO 187
<211> LENGTH: 20
<212> TYPE: PRT
<213> ORGANISM: Artificial Sequence
<220> FEATURE:
<223> OTHER INFORMATION: Synthetic sequence

<400> SEQUENCE: 187

Gln Asn Arg Phe Asp Ser Ala Ile Thr Asn Leu Gly Asn Thr Val Thr
1               5                   10                  15

Ala Leu Ala Ser
            20

<210> SEQ ID NO 188
<211> LENGTH: 48
<212> TYPE: DNA
<213> ORGANISM: Artificial Sequence
<220> FEATURE:
<223> OTHER INFORMATION: Synthetic sequence

<400> SEQUENCE: 188
gttttgattc agccattacc gcccttggcg ctacggtaac cgctctgg            48

<210> SEQ ID NO 189
<211> LENGTH: 48
<212> TYPE: DNA
<213> ORGANISM: Artificial Sequence
<220> FEATURE:
<223> OTHER INFORMATION: Synthetic sequence

<400> SEQUENCE: 189
ccagagcggt taccgtagcg ccaagggcgg taatggctga atcaaaac            48

<210> SEQ ID NO 190
<211> LENGTH: 39
<212> TYPE: DNA
<213> ORGANISM: Artificial Sequence
<220> FEATURE:
<223> OTHER INFORMATION: Synthetic sequence

<400> SEQUENCE: 190
caacagcgcg aaagccgatg cgggaggcca ggcgattgc                      39

<210> SEQ ID NO 191
<211> LENGTH: 39
<212> TYPE: DNA
<213> ORGANISM: Artificial Sequence
<220> FEATURE:
<223> OTHER INFORMATION: Synthetic sequence

<400> SEQUENCE: 191
gcaatcgcct ggcctcccgc atcggctttc gcgctgttg                      39

<210> SEQ ID NO 192
<211> LENGTH: 846
<212> TYPE: DNA
<213> ORGANISM: Artificial Sequence
<220> FEATURE:
<223> OTHER INFORMATION: Synthetic sequence

<400> SEQUENCE: 192
taatacgact cactataggg gaattgtgag cggataacaa ttcccctcta gaataatttt    60
gtttaacttt aagaaggaga tatacatatg agcgggttac ggatcaacag cgcgaaagcc   120
gatgcgggag gccaggcgat tgctaaccgc ttcacttcta atatcaaagg tctgactcag   180

```
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846
```

<210> SEQ ID NO 193
<211> LENGTH: 250
<212> TYPE: PRT
<213> ORGANISM: Artificial Sequence
<220> FEATURE:
<223> OTHER INFORMATION: Synthetic sequence

<400> SEQUENCE: 193

```
Met Ser Gly Leu Arg Ile Asn Ser Ala Lys Ala Asp Ala Gly Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240
```

Arg Gly Ser His His His His His His Gly
            245                 250

<210> SEQ ID NO 194
<211> LENGTH: 43
<212> TYPE: DNA
<213> ORGANISM: Artificial Sequence
<220> FEATURE:
<223> OTHER INFORMATION: Synthetic sequence

<400> SEQUENCE: 194
gtctgttcag gccactgccg gggctaactc tgattccgat ctg         43

<210> SEQ ID NO 195
<211> LENGTH: 43
<212> TYPE: DNA
<213> ORGANISM: Artificial Sequence
<220> FEATURE:
<223> OTHER INFORMATION: Synthetic sequence

<400> SEQUENCE: 195
cagatcggaa tcagagttag ccccggcagt ggcctgaaca gac         43

<210> SEQ ID NO 196
<211> LENGTH: 846
<212> TYPE: DNA
<213> ORGANISM: Artificial Sequence
<220> FEATURE:
<223> OTHER INFORMATION: Synthetic sequence

<400> SEQUENCE: 196
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac tgccggggct     300
aactctgatt ccgatctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaaccttg gcaatacggt aaccaatctg     660
aactccgcgc gtagccgtat cgaagatgct gactatgcaa cggaagtttc taatatgtct     720
aaagcgcaga ttctgcagca ggctggtact tccgttctgg cgcaggctaa ccaggttccg     780
caaaacgtcc tctctttact ggttccgcgg ggttctcatc atcatcatca tcatggttaa     840
gtcgac                                                                846

<210> SEQ ID NO 197
<211> LENGTH: 250
<212> TYPE: PRT
<213> ORGANISM: Artificial Sequence
<220> FEATURE:
<223> OTHER INFORMATION: Synthetic sequence

<400> SEQUENCE: 197

Met Ser Gly Leu Arg Ile Asn Ser Ala Lys Asp Asp Ala Ala Gly Gln

```
            1               5                  10                 15
Ala Ile Ala Asn Arg Phe Thr Ser Asn Ile Lys Gly Leu Thr Gln Ala
                20                  25                 30
Ser Arg Asn Ala Asn Asp Gly Ile Ser Ile Ala Gln Thr Thr Glu Gly
            35                  40                 45
Ala Leu Asn Glu Ile Asn Asn Leu Gln Arg Val Arg Glu Leu Ser
50                  55                  60
Val Gln Ala Thr Ala Gly Ala Asn Ser Asp Ser Asp Leu Lys Ser Ile
65                  70                  75                 80
Gln Asp Glu Ile Gln Gln Arg Leu Glu Glu Ile Asp Arg Val Ser Asn
                85                  90                 95
Gln Thr Gln Phe Asn Gly Val Lys Val Leu Ser Gln Asp Asn Gln Met
                100                 105                110
Lys Ile Gln Val Gly Ala Asn Asp Gly Glu Thr Ile Thr Ile Asp Leu
                115                 120                125
Gln Lys Ile Asp Val Lys Ser Leu Gly Leu Asp Gly Phe Asn Val Asn
                130                 135                140
Ser Pro Gly Ser Thr Ala Asn Pro Leu Ala Ser Ile Asp Ser Ala Leu
145                 150                 155                160
Ser Lys Val Asp Ala Val Arg Ser Ser Leu Gly Ala Ile Gln Asn Arg
                165                 170                175
Phe Asp Ser Ala Ile Thr Asn Leu Gly Asn Thr Val Thr Asn Leu Asn
                180                 185                190
Ser Ala Arg Ser Arg Ile Glu Asp Ala Asp Tyr Ala Thr Glu Val Ser
                195                 200                205
Asn Met Ser Lys Ala Gln Ile Leu Gln Gln Ala Gly Thr Ser Val Leu
            210                 215                220
Ala Gln Ala Asn Gln Val Pro Gln Asn Val Leu Ser Leu Leu Val Pro
225                 230                 235                240
Arg Gly Ser His His His His His His Gly
                245                 250

<210> SEQ ID NO 198
<211> LENGTH: 45
<212> TYPE: DNA
<213> ORGANISM: Artificial Sequence
<220> FEATURE:
<223> OTHER INFORMATION: Synthetic sequence

<400> SEQUENCE: 198
ctgattccga tctgaaagct atccaggctg aaattcagca acgtc           45

<210> SEQ ID NO 199
<211> LENGTH: 45
<212> TYPE: DNA
<213> ORGANISM: Artificial Sequence
<220> FEATURE:
<223> OTHER INFORMATION: Synthetic sequence

<400> SEQUENCE: 199
gacgttgctg aatttcagcc tggatagctt tcagatcgga atcag           45

<210> SEQ ID NO 200
<211> LENGTH: 846
<212> TYPE: DNA
<213> ORGANISM: Artificial Sequence
<220> FEATURE:
<223> OTHER INFORMATION: Synthetic sequence
```

<400> SEQUENCE: 200

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac tgccggggct     300
aactctgatt ccgatctgaa agctatccag gctgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaacctg gcaatacggt aaccaatctg      660
aactccgcgc gtagccgtat cgaagatgct gactatgcaa cggaagtttc taatatgtct     720
aaagcgcaga ttctgcagca ggctggtact tccgttctgg cgcaggctaa ccaggttccg     780
caaaacgtcc tctctttact ggttccgcgg ggttctcatc atcatcatca tcatggttaa     840
gtcgac                                                                846
```

<210> SEQ ID NO 201
<211> LENGTH: 753
<212> TYPE: DNA
<213> ORGANISM: Artificial Sequence
<220> FEATURE:
<223> OTHER INFORMATION: Synthetic sequence

<400> SEQUENCE: 201

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactgccggg gctaactctg attccgatct gaaagctatc     240
caggctgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg ggggcaattc aaaaccgctt tgattcagcc     540
attaccaacc ttggcaatac ggtaaccaat ctgaactccg cgcgtagccg tatcgaagat     600
gctgactatg caacggaagt ttctaatatg tctaaagcgc agattctgca gcaggctggt     660
acttccgttc tggcgcaggc taaccaggtt ccgcaaaacg tcctctcttt actggttccg     720
cggggttctc atcatcatca tcatcatggt taa                                  753
```

<210> SEQ ID NO 202
<211> LENGTH: 250
<212> TYPE: PRT
<213> ORGANISM: Artificial Sequence
<220> FEATURE:
<223> OTHER INFORMATION: Synthetic sequence

<400> SEQUENCE: 202

Met Ser Gly Leu Arg Ile Asn Ser Ala Lys Asp Asp Ala Ala Gly Gln

```
            1               5               10              15
          Ala Ile Ala Asn Arg Phe Thr Ser Asn Ile Lys Gly Leu Thr Gln Ala
                          20              25              30
          Ser Arg Asn Ala Asn Asp Gly Ile Ser Ile Ala Gln Thr Thr Glu Gly
                      35              40              45
          Ala Leu Asn Glu Ile Asn Asn Leu Gln Arg Val Arg Glu Leu Ser
           50              55              60
          Val Gln Ala Thr Ala Gly Ala Asn Ser Asp Ser Asp Leu Lys Ala Ile
           65              70              75              80
          Gln Ala Glu Ile Gln Gln Arg Leu Glu Glu Ile Asp Arg Val Ser Asn
                          85              90              95
          Gln Thr Gln Phe Asn Gly Val Lys Val Leu Ser Gln Asp Asn Gln Met
                          100             105             110
          Lys Ile Gln Val Gly Ala Asn Asp Gly Glu Thr Ile Thr Ile Asp Leu
                          115             120             125
          Gln Lys Ile Asp Val Lys Ser Leu Gly Leu Asp Gly Phe Asn Val Asn
                          130             135             140
          Ser Pro Gly Ser Thr Ala Asn Pro Leu Ala Ser Ile Asp Ser Ala Leu
           145             150             155             160
          Ser Lys Val Asp Ala Val Arg Ser Ser Leu Gly Ala Ile Gln Asn Arg
                          165             170             175
          Phe Asp Ser Ala Ile Thr Asn Leu Gly Asn Thr Val Thr Asn Leu Asn
                          180             185             190
          Ser Ala Arg Ser Arg Ile Glu Asp Ala Asp Tyr Ala Thr Glu Val Ser
                          195             200             205
          Asn Met Ser Lys Ala Gln Ile Leu Gln Gln Ala Gly Thr Ser Val Leu
                          210             215             220
          Ala Gln Ala Asn Gln Val Pro Gln Asn Val Leu Ser Leu Leu Val Pro
           225             230             235             240
          Arg Gly Ser His His His His His His Gly
                          245             250

<210> SEQ ID NO 203
<211> LENGTH: 45
<212> TYPE: DNA
<213> ORGANISM: Artificial Sequence
<220> FEATURE:
<223> OTHER INFORMATION: Synthetic sequence

<400> SEQUENCE: 203
gccactaacg ggactaacgc tgatgccgct ctgaaatcta tccag              45

<210> SEQ ID NO 204
<211> LENGTH: 45
<212> TYPE: DNA
<213> ORGANISM: Artificial Sequence
<220> FEATURE:
<223> OTHER INFORMATION: Synthetic sequence

<400> SEQUENCE: 204
ctggatagat ttcagagcgg catcagcgtt agtcccgtta gtggc              45

<210> SEQ ID NO 205
<211> LENGTH: 846
<212> TYPE: DNA
<213> ORGANISM: Artificial Sequence
<220> FEATURE:
<223> OTHER INFORMATION: Synthetic sequence
```

<400> SEQUENCE: 205

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac taacgggact     300
aacgctgatg ccgctctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaacctg gcaatacggt aaccaatctg      660
aactccgcgc gtagccgtat cgaagatgct gactatgcaa cggaagtttc taatatgtct     720
aaagcgcaga ttctgcagca ggctggtact tccgttctgg cgcaggctaa ccaggttccg     780
caaaacgtcc tctctttact ggttccgcgg ggttctcatc atcatcatca tcatggttaa     840
gtcgac                                                                846
```

<210> SEQ ID NO 206
<211> LENGTH: 250
<212> TYPE: PRT
<213> ORGANISM: Artificial Sequence
<220> FEATURE:
<223> OTHER INFORMATION: Synthetic sequence

<400> SEQUENCE: 206

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ala Asp Ala Ala Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
```

```
                195                 200                 205
Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 207
<211> LENGTH: 45
<212> TYPE: DNA
<213> ORGANISM: Artificial Sequence
<220> FEATURE:
<223> OTHER INFORMATION: Synthetic sequence

<400> SEQUENCE: 207

```
gccactgccg gggctaacgc tgatgccgct ctgaaagcta tccag            45
```

<210> SEQ ID NO 208
<211> LENGTH: 45
<212> TYPE: DNA
<213> ORGANISM: Artificial Sequence
<220> FEATURE:
<223> OTHER INFORMATION: Synthetic sequence

<400> SEQUENCE: 208

```
ctggatagct ttcagagcgg catcagcgtt agccccggca gtggc            45
```

<210> SEQ ID NO 209
<211> LENGTH: 846
<212> TYPE: DNA
<213> ORGANISM: Artificial Sequence
<220> FEATURE:
<223> OTHER INFORMATION: Synthetic sequence

<400> SEQUENCE: 209

```
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag ccaggcgat tgctaaccgc ttcacttcta atatcaaagg tctgactcag     180
gcttcccgta acgctaacga cggcatttct attgcgcaga ccactgaagg tgcgctgaat    240
gaaatcaaca caacctgca gcgtgtgcgt gagttgtctg ttcaggccac tgccggggct    300
aacgctgatg ccgctctgaa agctatccag gctgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 210
<211> LENGTH: 250
<212> TYPE: PRT

<213> ORGANISM: Artificial Sequence
<220> FEATURE:
<223> OTHER INFORMATION: Synthetic sequence

<400> SEQUENCE: 210

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Ala Gly Ala Asn Ala Asp Ala Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 211
<211> LENGTH: 846
<212> TYPE: DNA
<213> ORGANISM: Artificial Sequence
<220> FEATURE:
<223> OTHER INFORMATION: Synthetic sequence

<400> SEQUENCE: 211

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac taacgggact     300
aactctgatt ccgatctgaa agctatccag gctgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
```

-continued

```
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 212
<211> LENGTH: 250
<212> TYPE: PRT
<213> ORGANISM: Artificial Sequence
<220> FEATURE:
<223> OTHER INFORMATION: Synthetic sequence

<400> SEQUENCE: 212

```
Met Ser Gly Leu Arg Ile Asn Ser Ala Lys Asp Asp Ala Ala Gly Gln
 1               5                  10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250
```

<210> SEQ ID NO 213
<211> LENGTH: 45
<212> TYPE: DNA
<213> ORGANISM: Artificial Sequence
<220> FEATURE:

<223> OTHER INFORMATION: Synthetic sequence

<400> SEQUENCE: 213
ctatccagga tgaaattcag gcacgtctgg cagaaatcga tcgcg        45

<210> SEQ ID NO 214
<211> LENGTH: 45
<212> TYPE: DNA
<213> ORGANISM: Artificial Sequence
<220> FEATURE:
<223> OTHER INFORMATION: Synthetic sequence

<400> SEQUENCE: 214
cgcgatcgat ttctgccaga cgtgcctgaa tttcatcctg gatag        45

<210> SEQ ID NO 215
<211> LENGTH: 846
<212> TYPE: DNA
<213> ORGANISM: Artificial Sequence
<220> FEATURE:
<223> OTHER INFORMATION: Synthetic sequence

<400> SEQUENCE: 215

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca caaacctgca gcgtgtgcgt gagttgtctg ttcaggccac taacgggact     300
aactctgatt ccgatctgaa atctatccag gatgaaattc aggcacgtct ggcagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaaccttg caatacggt aaccaatctg     660
aactccgcgc gtagccgtat cgaagatgct gactatgcaa cggaagtttc taatatgtct     720
aaagcgcaga ttctgcagca ggctggtact tccgttctgg cgcaggctaa ccaggttccg     780
caaaacgtcc tctctttact ggttccgcgg ggttctcatc atcatcatca tcatggttaa     840
gtcgac                                                                846
```

<210> SEQ ID NO 216
<211> LENGTH: 250
<212> TYPE: PRT
<213> ORGANISM: Artificial Sequence
<220> FEATURE:
<223> OTHER INFORMATION: Synthetic sequence

<400> SEQUENCE: 216

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

```
Val Gln Ala Thr Asn Gly Thr Asn Ser Asp Ser Asp Leu Lys Ser Ile
 65                  70                  75                  80

Gln Asp Glu Ile Gln Ala Arg Leu Ala Glu Ile Asp Arg Val Ser Asn
             85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 217
<211> LENGTH: 59
<212> TYPE: DNA
<213> ORGANISM: Artificial Sequence
<220> FEATURE:
<223> OTHER INFORMATION: Synthetic sequence

<400> SEQUENCE: 217
ggaagaaatc gatgccgttt ctgctgcgac tcaatttaac ggtgttaaag tcctgtctc      59

<210> SEQ ID NO 218
<211> LENGTH: 59
<212> TYPE: DNA
<213> ORGANISM: Artificial Sequence
<220> FEATURE:
<223> OTHER INFORMATION: Synthetic sequence

<400> SEQUENCE: 218
gagacaggac tttaacaccg ttaaattgag tcgcagcaga aacggcatcg atttcttcc      59

<210> SEQ ID NO 219
<211> LENGTH: 846
<212> TYPE: DNA
<213> ORGANISM: Artificial Sequence
<220> FEATURE:
<223> OTHER INFORMATION: Synthetic sequence

<400> SEQUENCE: 219
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
```

```
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatgccgttt ctgctgcgac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 220
<211> LENGTH: 250
<212> TYPE: PRT
<213> ORGANISM: Artificial Sequence
<220> FEATURE:
<223> OTHER INFORMATION: Synthetic sequence

<400> SEQUENCE: 220

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Ala Val Ser Ala
                85                  90                  95

Ala Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 221
<211> LENGTH: 53
<212> TYPE: DNA
<213> ORGANISM: Artificial Sequence
<220> FEATURE:
<223> OTHER INFORMATION: Synthetic sequence

<400> SEQUENCE: 221
cagcaacgtc tggaagaaat cgatgccgtt tctaatcaga ctcaatttaa cgg      53

<210> SEQ ID NO 222
<211> LENGTH: 53
<212> TYPE: DNA
<213> ORGANISM: Artificial Sequence
<220> FEATURE:
<223> OTHER INFORMATION: Synthetic sequence

<400> SEQUENCE: 222
ccgttaaatt gagtctgatt agaaacggca tcgatttctt ccagacgttg ctg      53

<210> SEQ ID NO 223
<211> LENGTH: 753
<212> TYPE: DNA
<213> ORGANISM: Artificial Sequence
<220> FEATURE:
<223> OTHER INFORMATION: Synthetic sequence

<400> SEQUENCE: 223
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca caacaacct gcagcgtgtg      180 cgtgagttgt ctgttcaggc cactaacggg actaactctg attccgatct gaaatctatc     240
caggatgaaa ttcagcaacg tctggaagaa atcgatgccg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg gggcaattc aaaaccgctt tgattcagcc      540
attaccaacc ttggcaatac ggtaaccaat ctgaactccg cgcgtagccg tatcgaagat     600
gctgactatg caacggaagt ttctaatatg tctaaagcgc agattctgca gcaggctggt     660
acttccgttc tggcgcaggc taaccaggtt ccgcaaaacg tcctctcttt actggttccg     720
cggggttctc atcatcatca tcatcatggt taa                                  753

<210> SEQ ID NO 224
<211> LENGTH: 846
<212> TYPE: DNA
<213> ORGANISM: Artificial Sequence
<220> FEATURE:
<223> OTHER INFORMATION: Synthetic sequence

<400> SEQUENCE: 224
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240

```
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatgccgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                                846
```

<210> SEQ ID NO 225
<211> LENGTH: 250
<212> TYPE: PRT
<213> ORGANISM: Artificial Sequence
<220> FEATURE:
<223> OTHER INFORMATION: Synthetic sequence

<400> SEQUENCE: 225

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Ala Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 226
<211> LENGTH: 53
<212> TYPE: DNA
<213> ORGANISM: Artificial Sequence
<220> FEATURE:
<223> OTHER INFORMATION: Synthetic sequence

<400> SEQUENCE: 226

```
cgtttctaat cagactcaat ttgccgctgt taaagtcctg tctcaggaca acc        53
```

<210> SEQ ID NO 227
<211> LENGTH: 53
<212> TYPE: DNA
<213> ORGANISM: Artificial Sequence
<220> FEATURE:
<223> OTHER INFORMATION: Synthetic sequence

<400> SEQUENCE: 227

```
ggttgtcctg agacaggact ttaacagcgg caaattgagt ctgattagaa acg        53
```

<210> SEQ ID NO 228
<211> LENGTH: 846
<212> TYPE: DNA
<213> ORGANISM: Artificial Sequence
<220> FEATURE:
<223> OTHER INFORMATION: Synthetic sequence

<400> SEQUENCE: 228

```
taatacgact cactataggg gaattgtgag cggataacaa ttcccctcta gaataatttt     60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttgcc gctgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aagtggacg cagttcgttc ttctctgggg   600
gcaattcaaa accgctttga ttcagccatt accaaccttg gcaatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                               846
```

<210> SEQ ID NO 229
<211> LENGTH: 250
<212> TYPE: PRT
<213> ORGANISM: Artificial Sequence
<220> FEATURE:
<223> OTHER INFORMATION: Synthetic sequence

<400> SEQUENCE: 229

```
Met Ser Gly Leu Arg Ile Asn Ser Ala Lys Asp Asp Ala Ala Gly Gln
 1               5                  10                  15

Ala Ile Ala Asn Arg Phe Thr Ser Asn Ile Lys Gly Leu Thr Gln Ala
```

```
            20                  25                  30
Ser Arg Asn Ala Asn Asp Gly Ile Ser Ile Ala Gln Thr Thr Glu Gly
            35                  40                  45

Ala Leu Asn Glu Ile Asn Asn Asn Leu Gln Arg Val Arg Glu Leu Ser
        50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Ala Ala Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 230
<211> LENGTH: 52
<212> TYPE: DNA
<213> ORGANISM: Artificial Sequence
<220> FEATURE:
<223> OTHER INFORMATION: Synthetic sequence

<400> SEQUENCE: 230
gttaaagtcc tgtctcagga caacgcgatg gcaatccagg ttggtgctaa cg          52

<210> SEQ ID NO 231
<211> LENGTH: 52
<212> TYPE: DNA
<213> ORGANISM: Artificial Sequence
<220> FEATURE:
<223> OTHER INFORMATION: Synthetic sequence

<400> SEQUENCE: 231
cgttagcacc aacctggatt gccatcgcgt tgtcctgaga caggacttta ac          52

<210> SEQ ID NO 232
<211> LENGTH: 846
<212> TYPE: DNA
<213> ORGANISM: Artificial Sequence
<220> FEATURE:
<223> OTHER INFORMATION: Synthetic sequence

<400> SEQUENCE: 232
taatacgact cactataggg gaattgtgag cggataacaa ttcccctcta gaataatttt    60
```

```
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaacgcg    420
atggcaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg caatacggt aaccaatctg    660 aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                                846
```

<210> SEQ ID NO 233
<211> LENGTH: 250
<212> TYPE: PRT
<213> ORGANISM: Artificial Sequence
<220> FEATURE:
<223> OTHER INFORMATION: Synthetic sequence

<400> SEQUENCE: 233

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Ala Met
            100                 105                 110

Ala Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
```

```
                210               215                220
Ala Gln Ala Asn Gln Val Pro Gln Asn Val Leu Ser Leu Leu Val Pro
225                 230                 235                 240

Arg Gly Ser His His His His His Gly
                245                 250

<210> SEQ ID NO 234
<211> LENGTH: 53
<212> TYPE: DNA
<213> ORGANISM: Artificial Sequence
<220> FEATURE:
<223> OTHER INFORMATION: Synthetic sequence

<400> SEQUENCE: 234
gatgaaaatc caggttggtg ctagcgctgc tgaaaccatt accatcgatc tgc          53

<210> SEQ ID NO 235
<211> LENGTH: 53
<212> TYPE: DNA
<213> ORGANISM: Artificial Sequence
<220> FEATURE:
<223> OTHER INFORMATION: Synthetic sequence

<400> SEQUENCE: 235
gcagatcgat ggtaatggtt tcagcagcgc tagcaccaac ctggattttc atc          53

<210> SEQ ID NO 236
<211> LENGTH: 846
<212> TYPE: DNA
<213> ORGANISM: Artificial Sequence
<220> FEATURE:
<223> OTHER INFORMATION: Synthetic sequence

<400> SEQUENCE: 236
taatacgact cactataggg gaattgtgag cggataacaa ttcccctcta gaataatttt     60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc tagcgctgct gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                             846

<210> SEQ ID NO 237
<211> LENGTH: 250
<212> TYPE: PRT
<213> ORGANISM: Artificial Sequence
<220> FEATURE:
<223> OTHER INFORMATION: Synthetic sequence
```

<400> SEQUENCE: 237

| | | | | | | | | | | | | | | |
|---|---|---|---|---|---|---|---|---|---|---|---|---|---|---|
|Met|Ser|Gly|Leu|Arg|Ile|Asn|Ser|Ala|Lys|Asp|Asp|Ala|Ala|Gly|Gln|
|1| | | |5| | | | |10| | | | |15|
|Ala|Ile|Ala|Asn|Arg|Phe|Thr|Ser|Asn|Ile|Lys|Gly|Leu|Thr|Gln|Ala|
| | | | |20| | | | |25| | | | |30| |
|Ser|Arg|Asn|Ala|Asn|Asp|Gly|Ile|Ser|Ile|Ala|Gln|Thr|Thr|Glu|Gly|
| | |35| | | | | |40| | | | | |45| |
|Ala|Leu|Asn|Glu|Ile|Asn|Asn|Asn|Leu|Gln|Arg|Val|Arg|Glu|Leu|Ser|
| |50| | | | | |55| | | | | |60| | |
|Val|Gln|Ala|Thr|Asn|Gly|Thr|Asn|Ser|Asp|Ser|Asp|Leu|Lys|Ser|Ile|
|65| | | | |70| | | | |75| | | | |80|
|Gln|Asp|Glu|Ile|Gln|Gln|Arg|Leu|Glu|Glu|Ile|Asp|Arg|Val|Ser|Asn|
| | | | |85| | | | |90| | | | |95| |
|Gln|Thr|Gln|Phe|Asn|Gly|Val|Lys|Val|Leu|Ser|Gln|Asp|Asn|Gln|Met|
| | | |100| | | | |105| | | | |110| | |
|Lys|Ile|Gln|Val|Gly|Ala|Ser|Ala|Ala|Glu|Thr|Ile|Thr|Ile|Asp|Leu|
| | |115| | | | |120| | | | |125| | | |
|Gln|Lys|Ile|Asp|Val|Lys|Ser|Leu|Gly|Leu|Asp|Gly|Phe|Asn|Val|Asn|
| |130| | | | |135| | | | |140| | | | |
|Ser|Pro|Gly|Ser|Thr|Ala|Asn|Pro|Leu|Ala|Ser|Ile|Asp|Ser|Ala|Leu|
|145| | | | |150| | | | |155| | | | |160|
|Ser|Lys|Val|Asp|Ala|Val|Arg|Ser|Ser|Leu|Gly|Ala|Ile|Gln|Asn|Arg|
| | | | |165| | | | |170| | | | |175| |
|Phe|Asp|Ser|Ala|Ile|Thr|Asn|Leu|Gly|Asn|Thr|Val|Thr|Asn|Leu|Asn|
| | | |180| | | | |185| | | | |190| | |
|Ser|Ala|Arg|Ser|Arg|Ile|Glu|Asp|Ala|Asp|Tyr|Ala|Thr|Glu|Val|Ser|
| | |195| | | | |200| | | | |205| | | |
|Asn|Met|Ser|Lys|Ala|Gln|Ile|Leu|Gln|Gln|Ala|Gly|Thr|Ser|Val|Leu|
| |210| | | | |215| | | | |220| | | | |
|Ala|Gln|Ala|Asn|Gln|Val|Pro|Gln|Asn|Val|Leu|Ser|Leu|Leu|Val|Pro|
|225| | | | |230| | | | |235| | | | |240|
|Arg|Gly|Ser|His|His|His|His|His|His|Gly| | | | | | |
| | | |245| | | | | |250| | | | | | |

<210> SEQ ID NO 238
<211> LENGTH: 56
<212> TYPE: DNA
<213> ORGANISM: Artificial Sequence
<220> FEATURE:
<223> OTHER INFORMATION: Synthetic sequence

<400> SEQUENCE: 238
gccgtatcga agatgctgac gctggagcgg aagttgctaa tatgtctaaa gcgcag    56

<210> SEQ ID NO 239
<211> LENGTH: 56
<212> TYPE: DNA
<213> ORGANISM: Artificial Sequence
<220> FEATURE:
<223> OTHER INFORMATION: Synthetic sequence

<400> SEQUENCE: 239
ctgcgcttta gacatattag caacttccgc tccagcgtca gcatcttcga tacggc    56

<210> SEQ ID NO 240
<211> LENGTH: 846
<212> TYPE: DNA

<213> ORGANISM: Artificial Sequence
<220> FEATURE:
<223> OTHER INFORMATION: Synthetic sequence

<400> SEQUENCE: 240

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca acaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttgg caatacggta accaatctg    660
aactccgcgc gtagccgtat cgaagatgct gacgctggag cggaagttgc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                              846
```

<210> SEQ ID NO 241
<211> LENGTH: 250
<212> TYPE: PRT
<213> ORGANISM: Artificial Sequence
<220> FEATURE:
<223> OTHER INFORMATION: Synthetic sequence

<400> SEQUENCE: 241

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175
```

```
Phe Asp Ser Ala Ile Thr Asn Leu Gly Asn Thr Val Thr Asn Leu Asn
                180                 185                 190

Ser Ala Arg Ser Arg Ile Glu Asp Ala Asp Ala Gly Ala Glu Val Ala
            195                 200                 205

Asn Met Ser Lys Ala Gln Ile Leu Gln Gln Ala Gly Thr Ser Val Leu
        210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 242
<211> LENGTH: 3
<212> TYPE: PRT
<213> ORGANISM: Artificial Sequence
<220> FEATURE:
<223> OTHER INFORMATION: Synthetic sequence

<400> SEQUENCE: 242

Ser Pro Gly
1

<210> SEQ ID NO 243
<211> LENGTH: 293
<212> TYPE: PRT
<213> ORGANISM: Artificial Sequence
<220> FEATURE:
<223> OTHER INFORMATION: Synthetic sequence

<400> SEQUENCE: 243

Met Gly His His His His His His Ser Gly Met Glu Phe Asn Met
1               5                   10                  15

Arg Ile Asn Thr Asn Val Ala Ala Met Asn Thr Tyr Ser Arg Leu Thr
            20                  25                  30

Ala Ala Asn Thr Ala Lys Ser Asn Ser Leu Ala Lys Leu Ser Ser Gly
        35                  40                  45

Leu Arg Ile Asn Lys Ala Gly Asp Asp Ala Ala Gly Leu Ala Ile Ser
    50                  55                  60

Glu Lys Met Lys Ser Gln Ile Gly Gly Leu Thr Gln Ala Lys Arg Asn
65                  70                  75                  80

Ala Gln Asp Gly Ile Ser Leu Val Gln Thr Ala Glu Gly Ala Leu Asn
                85                  90                  95

Glu Thr His Ser Ile Leu Glu Arg Met Arg Asp Leu Ala Val Gln Gly
            100                 105                 110

Ser Asn Gly Thr Leu Thr Ser Ser Asp Arg Gly Ser Ile Asn Lys Glu
        115                 120                 125

Leu Lys Ala Leu His Gln Glu Leu Thr Arg Ile Ser Asn Thr Thr Glu
    130                 135                 140

Phe Asn Thr Gln Lys Leu Phe Ser Gln Thr Lys Gln Lys Ser Val Thr
145                 150                 155                 160

Phe Thr Phe Gln Ile Gly Ala Asn Ala Gly Gln Thr Leu Ser Val Ala
                165                 170                 175

Ile Thr Ala Met Ser Gly Glu Ala Leu Leu Val Ser Thr Asp Ala Lys
            180                 185                 190

Phe Ser Leu Asn Ala Ala Gly Thr Asn Ala Gly Ala Met Ile Lys Ser
        195                 200                 205

Ile Asp Ala Ala Ile Ala Lys Val Ser Asp Gln Arg Ala Asp Leu Gly
    210                 215                 220
```

```
Ala Val Gln Asn Arg Leu Glu His Thr Ile Asn Asn Leu Thr Ala Thr
225                 230                 235                 240

Asn Glu Asn Leu Ser Asp Ala Asn Ser Arg Ile Arg Asp Val Asp Met
            245                 250                 255

Ala Glu Glu Met Met Thr Phe Thr Lys Ser Asn Ile Leu Ser Gln Ala
        260                 265                 270

Ala Thr Ser Met Leu Ala Gln Ala Asn Ala Met Pro Asn Ser Val Leu
    275                 280                 285

Asn Leu Leu Gln Gly
    290

<210> SEQ ID NO 244
<211> LENGTH: 280
<212> TYPE: PRT
<213> ORGANISM: Artificial Sequence
<220> FEATURE:
<223> OTHER INFORMATION: Synthetic sequence

<400> SEQUENCE: 244

Met Gly His His His His His Ser Gly Met Arg Ile Asn His Asn
1               5                   10                  15

Ile Ser Ala Leu Asn Ala Trp Arg Asn Ile Asp Gln Thr Gln Tyr Ser
            20                  25                  30

Met Ser Lys Thr Leu Glu Arg Leu Ser Ser Gly Leu Arg Ile Asn Arg
        35                  40                  45

Ala Gly Asp Asp Ala Ala Gly Leu Ala Ile Ser Glu Lys Met Arg Gly
    50                  55                  60

Gln Ile Lys Gly Leu Asn Met Ala Ile Lys Asn Ala Gln Asp Ala Ile
65                  70                  75                  80

Ser Leu Ile Gln Thr Ala Glu Gly Ala Leu Thr Glu Val His Ser Ile
                85                  90                  95

Leu Gln Arg Met Arg Glu Leu Ala Val Gln Ala Ala Ser Asp Thr Asn
            100                 105                 110

Thr Asn Val Asp Arg Glu Gln Ile Gln Lys Glu Ile Asp Gln Leu Arg
        115                 120                 125

Glu Glu Ile Asp Arg Ile Ala Arg Thr Thr Glu Phe Asn Thr Lys Lys
    130                 135                 140

Leu Leu Asp Gly Lys Leu Glu Gly Phe Arg Ser Gln Val Asp Ala Lys
145                 150                 155                 160

Val Val Thr Gly Gly Asn Ile Asn Val Gln Leu Gly Thr Val Ser Ser
                165                 170                 175

Lys Ala Val Glu Gly Thr Tyr Val Ile Glu Val Gly Ala Ala Glu Arg
            180                 185                 190

Ala Ile Met Val Val Asp Ala Ala Ile His Arg Val Ser Thr Ala Arg
        195                 200                 205

Ala Ala Leu Gly Ala Ile Gln Asn Arg Leu Glu His Thr Ile Ser Asn
    210                 215                 220

Leu Gly Val Ala Ala Glu Asn Leu Thr Ala Ala Glu Ser Arg Ile Arg
225                 230                 235                 240

Asp Ala Asp Met Ala Lys Glu Met Met Glu Phe Thr Lys Gln Gln Ile
                245                 250                 255

Leu Leu Gln Ser Ser Met Ala Met Leu Ala Gln Ser Asn Thr Leu Pro
            260                 265                 270

Gln Asn Val Leu Gln Leu Met Arg
        275                 280
```

```
<210> SEQ ID NO 245
<211> LENGTH: 168
<212> TYPE: PRT
<213> ORGANISM: Artificial Sequence
<220> FEATURE:
<223> OTHER INFORMATION: Synthetic sequence

<400> SEQUENCE: 245
```

Met Gly His His His His His His Ser Gly Leu Asn Met Ala Ile Lys
1               5                   10                  15

Asn Ala Gln Asp Ala Ile Ser Leu Ile Gln Thr Ala Glu Gly Ala Leu
            20                  25                  30

Thr Glu Val His Ser Ile Leu Gln Arg Met Arg Glu Leu Ala Val Gln
        35                  40                  45

Ala Ala Ser Asp Thr Asn Thr Asn Val Asp Arg Glu Gln Ile Gln Lys
    50                  55                  60

Glu Ile Asp Gln Leu Arg Glu Glu Ile Asp Arg Ile Ala Arg Thr Thr
65                  70                  75                  80

Glu Phe Asn Thr Lys Lys Leu Leu Asp Gly Lys Leu Glu Gly Phe Arg
                85                  90                  95

Ser Gln Val Asp Ala Lys Val Val Thr Gly Gly Asn Ile Asn Val Gln
            100                 105                 110

Leu Gly Thr Val Ser Ser Lys Ala Val Glu Gly Thr Tyr Val Ile Glu
        115                 120                 125

Val Gly Ala Ala Glu Arg Ala Ile Met Val Val Asp Ala Ala Ile His
    130                 135                 140

Arg Val Ser Thr Ala Arg Ala Ala Leu Gly Ala Ile Gln Asn Arg Leu
145                 150                 155                 160

Glu His Thr Ile Ser Asn Leu Gly
                165

```
<210> SEQ ID NO 246
<211> LENGTH: 285
<212> TYPE: PRT
<213> ORGANISM: Artificial Sequence
<220> FEATURE:
<223> OTHER INFORMATION: Synthetic sequence

<400> SEQUENCE: 246
```

Met Gly His His His His His His Ser Gly Met Ser Leu Arg Ile Asn
1               5                   10                  15

Asn Asn Ile Glu Ala Leu Asn Ala Trp Arg Ala Leu Asn Ser Thr Ser
            20                  25                  30

Asn Ala Leu Gln Lys Ser Met Glu Lys Leu Ser Ser Gly Leu Arg Ile
        35                  40                  45

Asn Arg Ala Gly Asp Asp Ala Ala Gly Leu Ala Ile Ser Glu Lys Leu
    50                  55                  60

Arg Ala Gln Ile Arg Gly Leu Asn Gln Ala Ile Arg Asn Ala Gln Asp
65                  70                  75                  80

Gly Ile Ser Leu Ile Gln Thr Ala Glu Gly Gly Leu Ser Glu Ile Gln
                85                  90                  95

Asn Ile Leu Gln Arg Met Arg Glu Leu Gly Val Gln Ala Ala Asn Gly
            100                 105                 110

Thr Leu Asn Asn Gln Asp Ile Ser Ala Ile Thr Thr Glu Leu Asn Gln
        115                 120                 125

Leu Phe Asn Glu Ile Asp Arg Ile Ala Gly Ala Thr Glu Phe Asn Thr

```
                130             135             140
Lys Asn Leu Leu Ala Val Ser Thr Gly Leu Val Val Thr Leu Gln Val
145                 150                 155                 160

Gly Ala Asn Ala Gly Gln Val Ile Ala Phe Thr Ile Asp Asn Ala Gly
                165                 170                 175

Thr Ala Ser Leu Gly Leu Ser Ser Ala Asp Leu Ala Ile Asn Asp Asn
            180                 185                 190

Ala Ser Ala Ser Ala Phe Ile Ser Lys Val Asp Ser Ala Leu Gln Lys
            195                 200                 205

Val Ser Thr Tyr Arg Ala Asn Leu Gly Ser Ile Gln Asn Arg Leu Glu
        210                 215                 220

His Thr Ile Ala Asn Leu Gly Ile Ala Ser Glu Asn Leu Ser Ala Ser
225                 230                 235                 240

Glu Ser Arg Ile Arg Asp Val Asp Met Ala Ala Glu Met Met Asn Phe
                245                 250                 255

Thr Lys Asn Gln Ile Leu Gln Gln Ala Gly Val Ala Ile Leu Ala Gln
                260                 265                 270

Ala Asn Gln Ala Pro Gln Ala Val Leu Gln Leu Leu Arg
            275                 280                 285

<210> SEQ ID NO 247
<211> LENGTH: 171
<212> TYPE: PRT
<213> ORGANISM: Artificial Sequence
<220> FEATURE:
<223> OTHER INFORMATION: Synthetic sequence

<400> SEQUENCE: 247

Met Gly His His His His His His Ser Gly Leu Asn Gln Ala Ile Arg
1               5                   10                  15

Asn Ala Gln Asp Gly Ile Ser Leu Ile Gln Thr Ala Glu Gly Gly Leu
                20                  25                  30

Ser Glu Ile Gln Asn Ile Leu Gln Arg Met Arg Glu Leu Gly Val Gln
            35                  40                  45

Ala Ala Asn Gly Thr Leu Asn Asn Gln Asp Ile Ser Ala Ile Thr Thr
50              55                  60

Glu Leu Asn Gln Leu Phe Asn Glu Ile Asp Arg Ile Ala Gly Ala Thr
65              70                  75                  80

Glu Phe Asn Thr Lys Asn Leu Leu Ala Val Ser Thr Gly Leu Val Val
                85                  90                  95

Thr Leu Gln Val Gly Ala Asn Ala Gly Gln Val Ile Ala Phe Thr Ile
            100                 105                 110

Asp Asn Ala Gly Thr Ala Ser Leu Gly Leu Ser Ser Ala Asp Leu Ala
        115                 120                 125

Ile Asn Asp Asn Ala Ser Ala Ser Ala Phe Ile Ser Lys Val Asp Ser
    130                 135                 140

Ala Leu Gln Lys Val Ser Thr Tyr Arg Ala Asn Leu Gly Ser Ile Gln
145                 150                 155                 160

Asn Arg Leu Glu His Thr Ile Ala Asn Leu Gly
                165                 170

<210> SEQ ID NO 248
<211> LENGTH: 146
<212> TYPE: PRT
<213> ORGANISM: Artificial Sequence
<220> FEATURE:
<223> OTHER INFORMATION: Synthetic sequence
```

<400> SEQUENCE: 248

Met Gly His His His His His Ser Gly Leu Asn Gln Ala Ile Arg
1               5                   10                  15

Asn Ala Gln Asp Gly Ile Ser Leu Ile Gln Thr Ala Glu Gly Leu
            20                  25                  30

Ser Glu Ile Gln Asn Ile Leu Gln Arg Met Arg Glu Leu Gly Val Gln
        35                  40                  45

Ala Ala Asn Gly Thr Leu Asn Gln Asp Ile Ala Ile Thr Thr
50                  55                  60

Glu Leu Asn Gln Leu Phe Asn Glu Ile Asp Arg Ile Ala Gly Ala Thr
65                  70                  75                  80

Glu Phe Asn Thr Lys Asn Leu Leu Ala Ala Gly Thr Ala Ser Leu Gly
                85                  90                  95

Leu Ser Ser Ala Asp Leu Ala Ile Asn Asp Asn Ala Ser Ala Ser Ala
            100                 105                 110

Phe Ile Ser Lys Val Asp Ser Ala Leu Gln Lys Val Ser Thr Tyr Arg
            115                 120                 125

Ala Asn Leu Gly Ser Ile Gln Asn Arg Leu Glu His Thr Ile Ala Asn
130                 135                 140

Leu Gly
145

<210> SEQ ID NO 249
<211> LENGTH: 116
<212> TYPE: PRT
<213> ORGANISM: Artificial Sequence
<220> FEATURE:
<223> OTHER INFORMATION: Synthetic sequence

<400> SEQUENCE: 249

Met Gly His His His His His Ser Ala Ser Ala Phe Ile Ser Lys
1               5                   10                  15

Val Asp Ser Ala Leu Gln Lys Val Ser Thr Tyr Arg Ala Asn Leu Gly
            20                  25                  30

Ser Ile Gln Asn Arg Leu Glu His Thr Ile Ala Asn Leu Gly Pro Asp
        35                  40                  45

Gly Leu Asn Gln Ala Ile Arg Asn Ala Gln Asp Gly Ile Ser Leu Ile
50                  55                  60

Gln Thr Ala Glu Gly Gly Leu Ser Glu Ile Gln Asn Ile Leu Gln Arg
65                  70                  75                  80

Met Arg Glu Leu Gly Val Gln Ala Ala Asn Gly Thr Leu Asn Asn Gln
                85                  90                  95

Asp Ile Ser Ala Ile Thr Thr Glu Leu Asn Gln Leu Phe Asn Glu Ile
            100                 105                 110

Asp Arg Ile Ala
            115

<210> SEQ ID NO 250
<211> LENGTH: 103
<212> TYPE: PRT
<213> ORGANISM: Artificial Sequence
<220> FEATURE:
<223> OTHER INFORMATION: Synthetic sequence

<400> SEQUENCE: 250

Met Gly His His His His His Ser Asn Asn Gln Asp Ile Ser Ala
1               5                   10                  15

```
Ile Thr Thr Glu Leu Asn Gln Leu Phe Asn Glu Ile Asp Arg Ile Ala
         20                  25                  30

Gly Ala Thr Gly Ser Gly Leu Ser Glu Ile Gln Asn Ile Leu Gln
         35                  40                  45

Arg Met Arg Glu Leu Gly Val Gln Ala Ala Asn Gly Thr Leu Asn Gly
 50                  55                  60

Gly Ser Ala Ser Ala Phe Ile Ser Lys Val Asp Ser Ala Leu Gln Lys
 65                  70                  75                  80

Val Ser Thr Tyr Arg Ala Asn Leu Gly Ser Ile Gln Asn Arg Leu Glu
             85                  90                  95

His Thr Ile Ala Asn Leu Gly
            100
```

<210> SEQ ID NO 251
<211> LENGTH: 170
<212> TYPE: PRT
<213> ORGANISM: Artificial Sequence
<220> FEATURE:
<223> OTHER INFORMATION: Synthetic sequence

<400> SEQUENCE: 251

```
Met Gly His His His His His His Ser Gly Leu Ala Gln Ala Ser Arg
 1               5                  10                  15

Asn Ala Gln Asp Ala Ile Ser Ile Ala Gln Thr Ala Glu Gly Ala Leu
             20                  25                  30

Asp Glu Thr Gln Ser Ile Leu Gln Arg Val Arg Glu Leu Gly Val Gln
         35                  40                  45

Gly Ala Asn Gly Thr Leu Thr Ala Asp Asp Ile Asn Ala Leu Gln Ala
 50                  55                  60

Glu Val Asp Gln Leu Ile Ala Glu Ile Asp Arg Ile Ala Gly Ala Thr
 65                  70                  75                  80

Glu Phe Asn Thr Gln Asn Leu Leu Asp Gly Ser Phe Thr Thr Lys Ala
             85                  90                  95

Phe Gln Val Gly Ala Asn Ser Gly Gln Asn Met Thr Leu Thr Ile Gly
            100                 105                 110

Lys Met Asp Thr Thr Leu Gly Leu Ser Ser Ala Asp Leu Ala Ile
            115                 120                 125

Asn Asp Asn Ala Phe Ala Asn Gly Ala Ile Ser Thr Val Asp Ser Ala
        130                 135                 140

Leu Gln Lys Val Ser Ala Glu Arg Ala Lys Leu Gly Ala Ile Gln Asn
145                 150                 155                 160

Arg Leu Glu His Thr Ile Ala Asn Leu Gly
            165                 170
```

<210> SEQ ID NO 252
<211> LENGTH: 170
<212> TYPE: PRT
<213> ORGANISM: Artificial Sequence
<220> FEATURE:
<223> OTHER INFORMATION: Synthetic sequence

<400> SEQUENCE: 252

```
Met Gly His His His His His His Ser Gly Leu Ala Gln Ala Ser Arg
 1               5                  10                  15

Gln Ala Gln Asp Ala Ile Ser Ile Ala Gln Thr Ala Glu Gly Ala Leu
             20                  25                  30

Asp Glu Thr Gln Ser Ile Leu Gln Arg Val Arg Glu Leu Gly Val Gln
```

```
Gly Ala Asp Gly Thr Leu Thr Ala Asp Asp Ile Asp Ala Leu Gln Ala
         35                  40                  45
    50                  55                  60

Glu Val Asp Gln Leu Ile Ala Glu Ile Asp Arg Ile Ala Gly Ala Thr
 65                  70                  75                  80

Glu Phe Ala Thr Gln Lys Leu Leu Asp Gly Ser Phe Thr Thr Lys Ala
                 85                  90                  95

Phe Gln Val Gly Ala Ala Ser Gly Gln Asp Val Thr Leu Thr Ile Gly
                100                 105                 110

Lys Val Asp Thr Thr Thr Leu Gly Leu Ser Ser Ala Asp Leu Ala Ile
                115                 120                 125

Asp Ser Ala Ala Phe Ala Asp Gly Ala Ile Ser Thr Val Asp Ser Ala
            130                 135                 140

Leu Gln Lys Val Ser Ala Glu Arg Ala Lys Leu Gly Ala Ile Gln Asn
145                 150                 155                 160

Arg Leu Glu His Thr Ile Ala Gln Leu Gly
                165                 170

<210> SEQ ID NO 253
<211> LENGTH: 174
<212> TYPE: PRT
<213> ORGANISM: Artificial Sequence
<220> FEATURE:
<223> OTHER INFORMATION: Synthetic peptide accession number Q53970

<400> SEQUENCE: 253

Met Ala Gln Val Ile Asn Thr Asn Ser Leu Ser Leu Leu Thr Gln Asn
  1               5                  10                  15

Asn Leu Asn Lys Ser Gln Ser Ser Leu Ser Ser Ala Ile Glu Arg Leu
                 20                  25                  30

Ser Ser Gly Leu Arg Ile Asn Ser Ala Lys Asp Asp Ala Ala Gly Gln
             35                  40                  45

Ala Ile Ala Asn Arg Phe Thr Ser Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ser
                 85                  90                  95

Val Gln Ala Thr Asn Gly Thr Asn Ser Asp Ser Asp Leu Lys Ser Ile
                100                 105                 110

Gln Asp Glu Ile Gln Gln Arg Leu Glu Glu Ile Asp Arg Val Ser Asn
            115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170

<210> SEQ ID NO 254
<211> LENGTH: 189
<212> TYPE: PRT
<213> ORGANISM: Artificial Sequence
<220> FEATURE:
<223> OTHER INFORMATION: Synthetic peptide accession number P72151

<400> SEQUENCE: 254
```

```
Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
            20                  25                  30

Thr Thr Gly Tyr Arg Ile Asn Ser Ala Lys Asp Asp Ala Ala Gly Leu
            35                  40                  45

Gln Ile Ser Asn Arg Leu Ser Asn Gln Ile Ser Gly Leu Asn Val Ala
        50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Gln Ala Glu Leu Thr Arg Ile Ser Asp
        115                 120                 125

Thr Thr Thr Phe Gly Gly Arg Lys Leu Leu Asp Gly Ser Phe Gly Thr
    130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala
            180                 185

<210> SEQ ID NO 255
<211> LENGTH: 179
<212> TYPE: PRT
<213> ORGANISM: Artificial Sequence
<220> FEATURE:
<223> OTHER INFORMATION: Synthetic peptide accession number Q5X5M6

<400> SEQUENCE: 255

Met Ala Gln Val Ile Asn Thr Asn Val Ala Ser Leu Thr Ala Gln Arg
1               5                   10                  15

Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
            35                  40                  45

Ala Ile Ser Gln Arg Met Thr Ala Gln Ile Arg Gly Met Asn Gln Ala
        50                  55                  60

Val Arg Asn Ala Asn Asp Gly Ile Ser Leu Ala Gln Val Ala Glu Gly
65                  70                  75                  80

Ala Met Gln Glu Thr Thr Asn Ile Leu Gln Arg Met Arg Glu Leu Ser
                85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Gly Ile Ala Thr Ala Thr
                165                 170                 175
```

Gly Thr Glu

<210> SEQ ID NO 256
<211> LENGTH: 174
<212> TYPE: PRT
<213> ORGANISM: Artificial Sequence
<220> FEATURE:
<223> OTHER INFORMATION: Synthetic peptide accession number Q6VMV6

<400> SEQUENCE: 256

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Asn Glu Ile Asn Asn Asn Leu Gln Arg Val Arg Glu Leu Thr
                85                  90                  95

Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170
```

<210> SEQ ID NO 257
<211> LENGTH: 173
<212> TYPE: PRT
<213> ORGANISM: Artificial Sequence
<220> FEATURE:
<223> OTHER INFORMATION: Synthetic peptide accession number P13713

<400> SEQUENCE: 257

```
Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Lys Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125
```

Gln Thr Asp Phe Asn Gly Val Lys Val Leu Ser Ser Asp Gln Lys Leu
            130                 135                 140

Thr Ile Gln Val Gly Ala Asn Asp Gly Glu Thr Thr Asp Ile Asp Leu
145                 150                 155                 160

Lys Lys Ile Asp Ala Lys Gln Leu Gly Met Asp Thr Phe
                165                 170

<210> SEQ ID NO 258
<211> LENGTH: 168
<212> TYPE: PRT
<213> ORGANISM: Artificial Sequence
<220> FEATURE:
<223> OTHER INFORMATION: Synthetic peptide accession number Q93RK8

<400> SEQUENCE: 258

Met Arg Ile Asn His Asn Ile Ala Ala Leu Asn Thr Ser Arg Gln Leu
1               5                   10                  15

Asn Ala Gly Ser Asn Ser Ala Ala Lys Asn Met Glu Lys Leu Ser Ser
                20                  25                  30

Gly Leu Arg Ile Asn Arg Ala Gly Asp Asp Ala Ala Gly Leu Ala Ile
            35                  40                  45

Ser Glu Lys Met Arg Ser Gln Ile Arg Gly Leu Asp Met Ala Ser Lys
        50                  55                  60

Asn Ala Gln Asp Gly Ile Ser Leu Ile Gln Thr Ser Glu Gly Ala Leu
65                  70                  75                  80

Asn Glu Thr His Ser Ile Leu Gln Arg Met Ser Glu Leu Ala Thr Gln
                85                  90                  95

Ala Ala Asn Asp Thr Asn Thr Asp Ser Asp Arg Ser Glu Leu Gln Lys
                100                 105                 110

Glu Met Asp Gln Leu Ala Ser Glu Val Thr Arg Ile Ser Thr Asp Thr
            115                 120                 125

Glu Phe Asn Thr Lys Lys Leu Leu Asp Gly Thr Ala Gln Asn Leu Thr
        130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165

<210> SEQ ID NO 259
<211> LENGTH: 192
<212> TYPE: PRT
<213> ORGANISM: Artificial Sequence
<220> FEATURE:
<223> OTHER INFORMATION: Synthetic peptide accession number Q02551

<400> SEQUENCE: 259

Met Lys Val Asn Thr Asn Ile Ile Ser Leu Lys Thr Gln Glu Tyr Leu
1               5                   10                  15

Arg Lys Asn Asn Glu Gly Met Thr Gln Ala Gln Arg Leu Ala Ser
                20                  25                  30

Gly Lys Arg Ile Asn Ser Ser Leu Asp Asp Ala Ala Gly Leu Ala Val
            35                  40                  45

Val Thr Arg Met Asn Val Lys Ser Thr Gly Leu Asp Ala Ala Ser Lys
        50                  55                  60

Asn Ser Ser Met Gly Ile Asp Leu Leu Gln Thr Ala Asp Ser Ala Leu
65                  70                  75                  80

Ser Ser Met Ser Ser Ile Leu Gln Arg Met Arg Gln Leu Ala Val Gln
                85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
        115                 120                 125

Asn Tyr Asn Asn Ile Lys Leu Leu Asp Gln Thr Ala Thr Gly Ala Ala
130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190

<210> SEQ ID NO 260
<211> LENGTH: 174
<212> TYPE: PRT
<213> ORGANISM: Artificial Sequence
<220> FEATURE:
<223> OTHER INFORMATION: Synthetic peptide accession number Q09012

<400> SEQUENCE: 260

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Ser
                85                  90                  95

Val Gln Ala Thr Asn Gly Thr Asn Ser Asp Ser Asp Leu Asn Ser Ile
            100                 105                 110

Gln Asp Glu Ile Thr Gln Arg Leu Ser Glu Ile Asp Arg Val Ser Asn
        115                 120                 125

Gln Thr Gln Phe Asn Gly Val Lys Val Leu Ala Ser Asp Gln Thr Met
    130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 261
<211> LENGTH: 174
<212> TYPE: PRT
<213> ORGANISM: Artificial Sequence
<220> FEATURE:
<223> OTHER INFORMATION: Synthetic peptide accession number Q8GNT8

<400> SEQUENCE: 261

Met Ala Gln Val Ile Asn Thr Asn Ser Leu Ser Leu Met Ala Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln

```
            35                  40                  45
Ala Ile Ser Asn Arg Phe Thr Ala Asn Ile Asn Gly Leu Thr Gln Ala
 50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Ser Asp Leu Gln Ser Ile
            100                 105                 110

Gln Asp Glu Ile Thr Gln Arg Leu Ser Glu Ile Asp Arg Ile Ser Gln
            115                 120                 125

Gln Thr Asp Phe Asn Gly Val Lys Val Leu Ser Lys Asp Gln Lys Leu
        130                 135                 140

Thr Ile Gln Val Gly Ala Asn Asp Gly Glu Thr Ile Thr Ile Asp Leu
145                 150                 155                 160

Lys Asn Ile Asn Ala Gln Ser Leu Gly Leu Asp Lys Phe Asn
                165                 170
```

<210> SEQ ID NO 262
<211> LENGTH: 186
<212> TYPE: PRT
<213> ORGANISM: Artificial Sequence
<220> FEATURE:
<223> OTHER INFORMATION: Synthetic peptide accession number Q9FAE7

<400> SEQUENCE: 262

```
Met Ala Ser Thr Ile Asn Thr Asn Val Ser Ser Leu Thr Ala Gln Arg
 1               5                  10                  15

Asn Leu Ser Leu Ser Gln Ser Ser Leu Asn Thr Ser Ile Gln Arg Leu
                20                  25                  30

Ser Ser Gly Leu Arg Ile Asn Ser Ala Lys Asp Asp Ala Ala Gly Leu
            35                  40                  45

Ala Ile Ser Glu Arg Phe Thr Ser Gln Ile Arg Gly Leu Asn Gln Ala
 50                  55                  60

Val Arg Asn Ala Asn Asp Gly Ile Ser Leu Ala Gln Thr Ala Glu Gly
 65                  70                  75                  80

Ala Leu Lys Ser Thr Gly Asp Ile Leu Gln Arg Val Arg Glu Leu Ala
                 85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
            115                 120                 125

Asn Thr Glu Phe Asn Gly Gln Lys Leu Leu Asp Gly Ser Phe Gly Ser
        130                 135                 140

Ala Thr Phe Gln Val Gly Ala Asn Ala Asn Gln Thr Ile Thr Ala Thr
145                 150                 155                 160

Thr Gly Asn Phe Arg Thr Asn Tyr Gly Ala Gln Leu Thr Ala Ser
                165                 170                 175

Ala Ser Gly Ala Ala Thr Ser Gly Ala Ser
                180                 185
```

<210> SEQ ID NO 263
<211> LENGTH: 173
<212> TYPE: PRT
<213> ORGANISM: Artificial Sequence
<220> FEATURE:
<223> OTHER INFORMATION: Synthetic peptide accession number Q8ZF76

<400> SEQUENCE: 263

Met Ala Val Ile Asn Thr Asn Ser Leu Ser Leu Leu Thr Gln Asn Asn
1               5                   10                  15

Leu Asn Lys Ser Gln Ser Ser Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ala
    50                  55                  60

Arg Asn Ala Asn Asp Gly Ile Ser Ile Ala Gln Thr Thr Glu Gly Ser
65                  70                  75                  80

Leu Asn Glu Ile Asn Asn Asn Leu Gln Arg Val Arg Glu Leu Thr Val
                85                  90                  95

Gln Ala Gln Asn Gly Ser Asn Ser Ser Ser Asp Leu Asp Ser Ile Gln
            100                 105                 110

Asp Glu Ile Ser Leu Arg Leu Ala Glu Ile Asp Arg Val Ser Asp Gln
        115                 120                 125

Thr Gln Phe Asn Gly Lys Lys Val Leu Ala Glu Asn Thr Thr Met Ser
130                 135                 140

Ile Gln Val Gly Ala Asn Asp Gly Glu Thr Ile Asp Ile Asn Leu Gln
145                 150                 155                 160

Lys Ile Asp Ser Lys Ser Leu Gly Leu Gly Ser Tyr Ser
                165                 170

<210> SEQ ID NO 264
<211> LENGTH: 174
<212> TYPE: PRT
<213> ORGANISM: Artificial Sequence
<220> FEATURE:
<223> OTHER INFORMATION: Synthetic peptide accession number Q7N5J4

<400> SEQUENCE: 264

Met Ala Gln Val Ile Asn Thr Asn Ser Leu Ser Leu Leu Thr Gln Asn
1               5                   10                  15

Asn Leu Asn Arg Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Arg Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Thr Asn Leu Gln Arg Ile Arg Glu Leu Thr
                85                  90                  95

Val Gln Ser Gln Asn Gly Ser Asn Ser Glu Ser Asp Ile Lys Ser Ile
            100                 105                 110

Gln Glu Glu Val Thr Gln Arg Leu Lys Glu Ile Asp Arg Ile Ser Glu
        115                 120                 125

Gln Thr Gln Phe Asn Gly Val Arg Val Leu Arg Glu Asp Ser Lys Met
130                 135                 140

Thr Ile Gln Val Gly Ala Asn Asp Asn Glu Val Ile Asp Ile Asp Leu
145                 150                 155                 160

Lys Lys Ile Asp Lys Glu Ala Leu Asn Leu Gly Lys Phe Thr
                165                 170

<210> SEQ ID NO 265
<211> LENGTH: 189
<212> TYPE: PRT
<213> ORGANISM: Artificial Sequence
<220> FEATURE:
<223> OTHER INFORMATION: Synthetic peptide accession number O33578

<400> SEQUENCE: 265

```
Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
                20                  25                  30

Thr Gly Leu Arg Ile Asn Ala Ala Lys Asp Asp Ala Ala Gly Met Ala
            35                  40                  45

Ile Gly Glu Lys Met Thr Ala Gln Val Met Gly Leu Asn Gln Ala Ile
50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185
```

<210> SEQ ID NO 266
<211> LENGTH: 175
<212> TYPE: PRT
<213> ORGANISM: Artificial Sequence
<220> FEATURE:
<223> OTHER INFORMATION: Synthetic peptide accession number Q56826

<400> SEQUENCE: 266

```
Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Val Lys Gly Leu Thr Gln Ala
50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125
```

```
Gln Thr Gln Phe Asn Gly Ile Lys Val Leu Asn Gly Asp Val Thr Glu
            130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 267
<211> LENGTH: 175
<212> TYPE: PRT
<213> ORGANISM: Artificial Sequence
<220> FEATURE:
<223> OTHER INFORMATION: Synthetic peptide accession number P42273

<400> SEQUENCE: 267

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175

<210> SEQ ID NO 268
<211> LENGTH: 200
<212> TYPE: PRT
<213> ORGANISM: Artificial Sequence
<220> FEATURE:
<223> OTHER INFORMATION: Synthetic peptide accession number O31059

<400> SEQUENCE: 268

Met Val Val Gln His Asn Met Gln Ala Ala Asn Ala Ser Arg Met Leu
1               5                   10                  15

Gly Ile Thr Thr Gly Asp Gln Ser Lys Ser Thr Glu Lys Leu Ser Ser
            20                  25                  30

Gly Phe Lys Ile Asn Arg Ala Ala Asp Asp Ala Ala Gly Leu Ser Ile
        35                  40                  45

Ser Glu Lys Met Arg Lys Gln Ile Arg Gly Leu Asp Gln Ala Ser Thr
    50                  55                  60

Asn Ala Ser Asp Gly Ile Ser Ala Val Gln Thr Ala Glu Gly Ala Leu
65                  70                  75                  80

Thr Glu Val His Ser Met Leu Gln Arg Met Asn Glu Leu Ala Val Gln
```

```
            85                  90                  95
Ala Ala Asn Gly Thr Asn Ser Glu Ser Asp Arg Ser Ser Ile Gln Asp
            100                 105                 110

Glu Ile Asn Gln Leu Thr Thr Glu Ile Asp Arg Val Ala Glu Thr Thr
            115                 120                 125

Lys Phe Asn Glu Thr Tyr Leu Leu Lys Gly Gly Asn Gly Asp Arg Thr
            130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Tyr Lys Ile Gly Ala Glu Thr Val
                180                 185                 190

Lys Glu Ala Met Thr Ala Leu Lys
            195                 200
```

<210> SEQ ID NO 269
<211> LENGTH: 177
<212> TYPE: PRT
<213> ORGANISM: Artificial Sequence
<220> FEATURE:
<223> OTHER INFORMATION: Synthetic peptide accession number Q7VZC2

<400> SEQUENCE: 269

```
Met Ala Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Ser Asn Gly Thr Asn Ser Ala Ser Asp Ile Asp Ser Ile
            100                 105                 110

Gln Gln Glu Val Asn Gln Arg Leu Glu Glu Ile Asn Arg Ile Ala Glu
        115                 120                 125

Gln Thr Asp Phe Asn Gly Ile Lys Val Leu Lys Ser Asn Ala Thr Asp
    130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr
```

<210> SEQ ID NO 270
<211> LENGTH: 167
<212> TYPE: PRT
<213> ORGANISM: Artificial Sequence
<220> FEATURE:
<223> OTHER INFORMATION: Synthetic peptide accession number Q9F4A4

<400> SEQUENCE: 270

Met Ile Ile Asn His Asn Met Asn Ala Leu Asn Ala His Arg Asn Met

-continued

```
                1               5                  10                 15
Met Gly Asn Ile Ala Thr Ala Gly Lys Ser Met Glu Lys Leu Ser Ser
                20                 25                 30

Gly Leu Arg Ile Asn Arg Ala Gly Asp Asp Ala Ala Gly Leu Ala Ile
                35                 40                 45

Ser Glu Lys Met Arg Gly Gln Ile Arg Gly Leu Asp Gln Ala Ser Arg
                50                 55                 60

Asn Ala Gln Asp Gly Ile Ser Leu Ile Gln Thr Ala Glu Gly Ala Leu
65                 70                 75                 80

Ala Glu Thr His Ser Ile Leu Gln Arg Met Arg Glu Leu Ser Val Gln
                85                 90                 95

Ser Ala Asn Asp Thr Asn Val Ala Val Asp Arg Thr Ala Ile Gln Asp
                100                105                110

Glu Ile Asn Ser Leu Thr Glu Glu Ile Asn Arg Ile Ser Gly Asp Thr
                115                120                125

Glu Phe Asn Thr Gln Lys Leu Leu Asp Gly Gly Phe Lys Gly Glu Phe
                130                135                140

Gln Ile Gly Ala Asn Ser Asn Gln Thr Val Lys Leu Asp Ile Gly Asn
145                150                155                160

Met Ser Ala Ala Ser Leu Gly
                165
```

<210> SEQ ID NO 271
<211> LENGTH: 178
<212> TYPE: PRT
<213> ORGANISM: Artificial Sequence
<220> FEATURE:
<223> OTHER INFORMATION: Synthetic peptide accession number Q8P9C4

<400> SEQUENCE: 271

```
Met Ala Gln Val Ile Asn Thr Asn Val Met Ser Leu Asn Ala Gln Arg
1               5                  10                 15

Asn Leu Asn Thr Asn Ser Ser Met Ala Leu Ser Ile Gln Gln Leu
                20                 25                 30

Ser Ser Gly Lys Arg Ile Thr Ser Ala Ser Val Asp Ala Ala Gly Leu
                35                 40                 45

Ala Ile Ser Glu Arg Phe Thr Thr Gln Ile Arg Gly Leu Asp Val Ala
                50                 55                 60

Ser Arg Asn Ala Asn Asp Gly Ile Ser Leu Ala Gln Thr Ala Glu Gly
65                 70                 75                 80

Ala Met Val Glu Ile Gly Asn Asn Leu Gln Arg Ile Arg Glu Leu Ser
                85                 90                 95

Val Gln Ser Ala Asn Ala Thr Asn Ser Ala Thr Asp Arg Glu Ala Leu
                100                105                110

Asn Ser Glu Val Lys Gln Leu Thr Ser Glu Ile Asp Arg Val Ala Asn
                115                120                125

Gln Thr Ser Phe Asn Gly Thr Lys Leu Leu Asn Gly Asp Phe Ser Gly
                130                135                140

Ala Leu Phe Gln Val Gly Ala Asp Ala Gly Gln Thr Ile Gly Ile Asn
145                150                155                160

Ser Ile Val Asp Ala Asn Val Asp Ser Leu Gly Lys Ala Asn Phe Ala
                165                170                175

Ala Ser
```

<210> SEQ ID NO 272

<211> LENGTH: 161
<212> TYPE: PRT
<213> ORGANISM: Artificial Sequence
<220> FEATURE:
<223> OTHER INFORMATION: Synthetic peptide accession number Q82UA3

<400> SEQUENCE: 272

```
Met Pro Gln Val Ile Asn Thr Asn Ile Ala Ser Leu Asn Ala Gln Arg
1               5                   10                  15

Asn Leu Asn Val Ser Gln Asn Ser Leu Ser Thr Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Met Thr Ser Gln Ile Arg Gly Met Asn Gln Ala
    50                  55                  60

Ala Arg Asn Ala Asn Asp Gly Ile Ser Leu Ala Gln Thr Ala Glu Gly
65                  70                  75                  80

Ala Leu Val Glu Ile Gly Asn Asn Leu Gln Arg Ile Arg Glu Leu Ala
                85                  90                  95

Val Gln Ser Ala Asn Ala Thr Asn Ser Glu Asp Asp Arg Glu Ala Leu
            100                 105                 110

Gln Lys Glu Val Thr Gln Leu Ile Asp Glu Ile Gln Arg Val Gly Glu
        115                 120                 125

Gln Thr Ser Phe Asn Gly Thr Lys Leu Leu Asp Gly Ser Phe Ala Ser
    130                 135                 140

Gln Ile Phe Gln Val Gly Ala Asn Glu Gly Glu Thr Ile Asp Phe Thr
145                 150                 155                 160

Asp
```

<210> SEQ ID NO 273
<211> LENGTH: 178
<212> TYPE: PRT
<213> ORGANISM: Artificial Sequence
<220> FEATURE:
<223> OTHER INFORMATION: Synthetic peptide accession number Q84IC5

<400> SEQUENCE: 273

```
Gly Phe Arg Ile Asn Thr Asn Gly Ala Ser Leu Asn Ala Gln Val Asn
1               5                   10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Asp Ala Ser Gly Leu Ala
        35                  40                  45

Ile Ala Asp Ser Leu Lys Thr Gln Ala Asn Ser Leu Gly Gln Ala Ile
    50                  55                  60

Asn Asn Ala Asn Asp Ala Asn Ser Met Leu Gln Ile Ala Asp Lys Ala
65                  70                  75                  80

Met Asp Glu Gln Leu Lys Ile Leu Asp Thr Ile Lys Val Lys Ala Thr
                85                  90                  95

Gln Ala Ala Gln Asp Gly Gln Thr Ala Lys Thr Arg Ala Met Ile Gln
            100                 105                 110

Gly Glu Ile Asn Lys Leu Met Glu Glu Leu Asp Asn Ile Ala Asn Thr
        115                 120                 125

Thr Thr Tyr Asn Gly Lys Gln Leu Leu Ser Gly Ser Phe Ser Asn Ala
    130                 135                 140

Gln Phe Gln Ile Gly Asp Lys Ala Asn Gln Thr Val Asn Ala Thr Ile
145                 150                 155                 160
```

```
Gly Ser Thr Asn Ser Ala Lys Val Gly Gln Thr Arg Phe Glu Thr Gly
                165                 170                 175

Ala Val

<210> SEQ ID NO 274
<211> LENGTH: 88
<212> TYPE: PRT
<213> ORGANISM: Artificial Sequence
<220> FEATURE:
<223> OTHER INFORMATION: Synthetic polypeptide accession number Q53970

<400> SEQUENCE: 274

Pro Leu Ala Ser Ile Asp Ser Ala Leu Ser Lys Val Asp Ala Val Arg
1               5                   10                  15

Ser Ser Leu Gly Ala Ile Gln Asn Arg Phe Asp Ser Ala Ile Thr Asn
                20                  25                  30

Leu Gly Asn Thr Val Thr Asn Leu Asn Ser Ala Arg Ser Arg Ile Glu
            35                  40                  45

Asp Ala Asp Tyr Ala Thr Glu Val Ser Asn Met Ser Lys Ala Gln Ile
        50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85

<210> SEQ ID NO 275
<211> LENGTH: 88
<212> TYPE: PRT
<213> ORGANISM: Artificial Sequence
<220> FEATURE:
<223> OTHER INFORMATION: Synthetic peptide accession number P72151

<400> SEQUENCE: 275

Ala Ile Ala Val Val Asp Asn Ala Leu Ala Ala Ile Asp Ala Gln Arg
1               5                   10                  15

Ala Asp Leu Gly Ala Val Gln Asn Arg Phe Lys Asn Thr Ile Asp Asn
                20                  25                  30

Leu Thr Asn Ile Ser Glu Asn Ala Thr Asn Ala Arg Ser Arg Ile Lys
            35                  40                  45

Asp Thr Asp Phe Ala Ala Glu Thr Ala Ala Leu Ser Lys Asn Gln Val
        50                  55                  60

Leu Gln Gln Ala Gly Thr Ala Ile Leu Ala Gln Ala Asn Gln Leu Pro
65                  70                  75                  80

Gln Ala Val Leu Ser Leu Leu Arg
                85

<210> SEQ ID NO 276
<211> LENGTH: 89
<212> TYPE: PRT
<213> ORGANISM: Artificial Sequence
<220> FEATURE:
<223> OTHER INFORMATION: Synthetic peptide accession number Q5X5M6

<400> SEQUENCE: 276

Ala Ile Lys Arg Ile Asp Ala Ala Leu Asn Ser Val Asn Ser Asn Arg
1               5                   10                  15

Ala Asn Met Gly Ala Leu Gln Asn Arg Phe Glu Ser Thr Ile Ala Asn
                20                  25                  30

Leu Gln Asn Val Ser Asp Asn Leu Ser Ala Ala Arg Ser Arg Ile Gln
```

```
                35                  40                  45

Asp Ala Asp Tyr Ala Ala Glu Met Ala Ser Leu Thr Lys Asn Gln Ile
 50                  55                  60

Leu Gln Gln Ala Gly Thr Ala Met Leu Ala Gln Ala Asn Ser Leu Pro
 65                  70                  75                  80

Gln Ser Val Leu Ser Leu Leu Gly Arg
                85

<210> SEQ ID NO 277
<211> LENGTH: 89
<212> TYPE: PRT
<213> ORGANISM: Artificial Sequence
<220> FEATURE:
<223> OTHER INFORMATION: Synthetic peptide accession number Q6VMV6

<400> SEQUENCE: 277

Pro Leu Glu Thr Ile Asp Lys Ala Leu Ala Lys Val Asp Asn Leu Arg
 1               5                  10                  15

Ser Asp Leu Gly Ala Val Gln Asn Arg Phe Asp Ser Ala Ile Thr Asn
                20                  25                  30

Leu Gly Asn Thr Val Asn Asn Leu Ser Ser Ala Arg Ser Arg Ile Arg
            35                  40                  45

Asp Ala Asp Tyr Ala Thr Glu Val Ser Asn Met Ser Arg Ala Gln Ile
 50                  55                  60

Leu Gln Gln Ala Gly Thr Ser Val Leu Ala Gln Ala Asn Gln Thr Thr
 65                  70                  75                  80

Gln Asn Val Leu Ser Leu Leu Gln Gly
                85

<210> SEQ ID NO 278
<211> LENGTH: 88
<212> TYPE: PRT
<213> ORGANISM: Artificial Sequence
<220> FEATURE:
<223> OTHER INFORMATION: Synthetic peptide accession number P13713

<400> SEQUENCE: 278

Pro Leu Ala Thr Leu Asp Lys Ala Leu Ala Gln Val Asp Gly Leu Arg
 1               5                  10                  15

Ser Ser Leu Gly Ala Val Gln Asn Arg Phe Asp Ser Val Ile Asn Asn
                20                  25                  30

Leu Asn Ser Thr Val Asn Asn Leu Ser Ala Ser Gln Ser Arg Ile Gln
            35                  40                  45

Asp Ala Asp Tyr Ala Thr Glu Val Ser Asn Met Ser Arg Ala Asn Ile
 50                  55                  60

Leu Gln Gln Ala Gly Thr Ser Val Leu Ala Gln Ala Asn Gln Ser Thr
 65                  70                  75                  80

Gln Asn Val Leu Ser Leu Leu Arg
                85

<210> SEQ ID NO 279
<211> LENGTH: 89
<212> TYPE: PRT
<213> ORGANISM: Artificial Sequence
<220> FEATURE:
<223> OTHER INFORMATION: Synthetic peptide accession number Q93RK8
<220> FEATURE:
<221> NAME/KEY: misc_feature
<222> LOCATION: (6)..(6)
<223> OTHER INFORMATION: Xaa can be any naturally occurring amino acid
```

<400> SEQUENCE: 279

Ala Leu Thr Thr Ile Xaa Thr Ala Ile Asp Thr Val Ser Ser Glu Arg
1               5                   10                  15

Ala Lys Leu Gly Ala Val Gln Asn Arg Leu Glu His Thr Ile Asn Asn
            20                  25                  30

Leu Gly Thr Ser Ser Glu Asn Leu Thr Ser Ala Asx Ser Arg Ile Arg
        35                  40                  45

Asp Val Asp Met Ala Ser Glu Met Met Glu Tyr Thr Lys Asn Asn Ile
    50                  55                  60

Leu Thr Gln Ala Ser Gln Ala Met Leu Ala Gln Ala Asn Gln Gln Pro
65                  70                  75                  80

Gln Gln Val Leu Gln Leu Leu Lys Gly
                85

<210> SEQ ID NO 280
<211> LENGTH: 90
<212> TYPE: PRT
<213> ORGANISM: Artificial Sequence
<220> FEATURE:
<223> OTHER INFORMATION: Synthetic peptide accession number Q02551

<400> SEQUENCE: 280

Val Ile Gly Leu Ala Asp Ala Ala Leu Thr Lys Ile Met Lys Gln Arg
1               5                   10                  15

Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
        35                  40                  45

Asp Ala Asp Met Ala Glu Glu Val Val Ser Leu Thr Thr Lys Gln Ile
    50                  55                  60

Leu Val Gln Ser Gly Thr Ala Met Leu Ala Gln Ala Asn Met Lys Pro
65                  70                  75                  80

Asn Ser Val Leu Lys Leu Leu Gln Gln Ile
                85                  90

<210> SEQ ID NO 281
<211> LENGTH: 88
<212> TYPE: PRT
<213> ORGANISM: Artificial Sequence
<220> FEATURE:
<223> OTHER INFORMATION: Synthetic peptide accession number Q09012

<400> SEQUENCE: 281

Pro Leu Ser Lys Leu Asp Glu Ala Leu Ala Lys Val Asp Lys Leu Arg
1               5                   10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Arg
                85

<210> SEQ ID NO 282
<211> LENGTH: 88

```
<212> TYPE: PRT
<213> ORGANISM: Artificial Sequence
<220> FEATURE:
<223> OTHER INFORMATION: Synthetic peptide accession number Q8GNT8

<400> SEQUENCE: 282

Pro Leu Ala Thr Leu Asp Lys Ala Leu Ser Gln Val Asp Ile Leu Arg
1               5                   10                  15

Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85

<210> SEQ ID NO 283
<211> LENGTH: 88
<212> TYPE: PRT
<213> ORGANISM: Artificial Sequence
<220> FEATURE:
<223> OTHER INFORMATION: Synthetic peptide accession number Q9FAE7

<400> SEQUENCE: 283

Ala Leu Lys Ile Ile Asp Ala Ala Leu Ser Ala Val Asn Gln Gln Arg
1               5                   10                  15

Ala Ser Phe Gly Ala Leu Gln Ser Arg Phe Glu Thr Thr Val Asn Asn
            20                  25                  30

Leu Gln Ser Thr Ser Glu Asn Met Ser Ala Ser Arg Ser Arg Ile Gln
        35                  40                  45

Asp Ala Asp Phe Ala Ala Glu Thr Ala Asn Leu Ser Arg Ser Gln Ile
    50                  55                  60

Leu Gln Gln Ala Gly Thr Ala Met Val Ala Gly Ala Asn Gln Leu Pro
65                  70                  75                  80

Gln Gly Val Leu Ser Leu Leu Lys
                85

<210> SEQ ID NO 284
<211> LENGTH: 88
<212> TYPE: PRT
<213> ORGANISM: Artificial Sequence
<220> FEATURE:
<223> OTHER INFORMATION: Synthetic peptide accession number Q8ZF76

<400> SEQUENCE: 284

Pro Leu Glu Thr Leu Asp Asp Ala Ile Lys Gln Val Asp Gly Leu Arg
1               5                   10                  15

Ser Ser Leu Gly Ala Val Gln Asn Arg Phe Glu Ser Ala Val Thr Asn
            20                  25                  30

Leu Asn Asn Thr Val Thr Asn Leu Thr Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ser Gln Ala Asn Gln Val Pro
65                  70                  75                  80

Gln Thr Val Leu Ser Leu Leu Asn
```

<210> SEQ ID NO 285
<211> LENGTH: 88
<212> TYPE: PRT
<213> ORGANISM: Artificial Sequence
<220> FEATURE:
<223> OTHER INFORMATION: Synthetic peptide accession number Q7N5J4

<400> SEQUENCE: 285

Pro Leu Glu Thr Leu Asp Ser Ala Leu Ala Gln Val Asp Ser Leu Arg
1               5                   10                  15

Ser Ser Leu Gly Ala Ile Gln Asn Arg Leu Glu Ser Thr Val Asn Asn
                20                  25                  30

Leu Asn Asn Thr Val Asn Asn Leu Ser Ala Ala Arg Ser Arg Ile Glu
            35                  40                  45

Asp Ala Asp Tyr Ala Thr Glu Val Ser Asn Met Ser Arg Gly Gln Ile
        50                  55                  60

Leu Gln Gln Ala Gly Thr Ala Val Leu Ala Gln Ala Met Gln Val Pro
65                  70                  75                  80

Gln Asn Val Met Ser Leu Leu Arg
                85

<210> SEQ ID NO 286
<211> LENGTH: 89
<212> TYPE: PRT
<213> ORGANISM: Artificial Sequence
<220> FEATURE:
<223> OTHER INFORMATION: Synthetic peptide accession number O33578

<400> SEQUENCE: 286

Ala Ile Gly Val Ile Asp Val Ala Leu Ser Lys Ile Ser Gln Ser Arg
1               5                   10                  15

Ser Glu Leu Gly Ala Val Ser Asn Arg Leu Asp Ser Thr Ile Ser Asn
                20                  25                  30

Leu Thr Asn Ile Ser Thr Ser Val Gln Ala Ala Lys Ser Gln Val Met
            35                  40                  45

Asp Ala Asp Phe Ala Ala Glu Ser Thr Asn Leu Ala Arg Ser Gln Ile
        50                  55                  60

Leu Ser Gln Ala Ser Thr Ala Met Leu Ala Gln Ala Asn Ser Ser Lys
65                  70                  75                  80

Gln Asn Val Leu Ser Leu Leu Arg Gly
                85

<210> SEQ ID NO 287
<211> LENGTH: 88
<212> TYPE: PRT
<213> ORGANISM: Artificial Sequence
<220> FEATURE:
<223> OTHER INFORMATION: Synthetic peptide accession number Q56826

<400> SEQUENCE: 287

Pro Leu Asp Thr Leu Asp Lys Ala Leu Ala Gln Val Asp Asp Asn Arg
1               5                   10                  15

Ser Ser Leu Gly Ala Val Gln Asn Arg Leu Glu Ser Thr Val Asn Asn
                20                  25                  30

Leu Asn Asn Thr Val Asn Asn Leu Ser Ala Ala Arg Ser Arg Ile Glu
            35                  40                  45

Asp Ala Asp Tyr Ala Val Glu Val Ser Asn Met Ser Arg Gly Gln Ile
        50                  55                  60

```
Leu Gln Gln Ala Gly Thr Ser Val Leu Ala Gln Ala Asn Gln Val Pro
 65                  70                  75                  80

Gln Thr Val Leu Ser Leu Leu Arg
                85

<210> SEQ ID NO 288
<211> LENGTH: 88
<212> TYPE: PRT
<213> ORGANISM: Artificial Sequence
<220> FEATURE:
<223> OTHER INFORMATION: Synthetic peptide accession number P42273

<400> SEQUENCE: 288

Ala Leu Ala Thr Leu Asp Asn Ala Ile Ser Lys Val Asp Glu Ser Arg
  1               5                  10                  15

Ser Lys Leu Gly Ala Ile Gln Asn Arg Phe Gln Ser Thr Ile Asn Asn
                20                  25                  30

Leu Asn Asn Thr Val Asn Asn Leu Ser Ala Ser Arg Ser Arg Ile Leu
            35                  40                  45

Asp Ala Asp Tyr Ala Thr Glu Val Ser Asn Met Ser Lys Asn Gln Ile
     50                  55                  60

Leu Gln Gln Ala Gly Thr Ala Val Leu Ala Gln Ala Asn Gln Val Pro
 65                  70                  75                  80

Gln Thr Val Leu Ser Leu Leu Arg
                85

<210> SEQ ID NO 289
<211> LENGTH: 88
<212> TYPE: PRT
<213> ORGANISM: Artificial Sequence
<220> FEATURE:
<223> OTHER INFORMATION: Synthetic peptide accession number O31059

<400> SEQUENCE: 289

Ala Ile Asp Ala Ile Ser Asp Ala Leu Ala Lys Val Ser Ala Gln Arg
  1               5                  10                  15

Ser Ala Leu Gly Ser Ile Gln Asn Arg Leu Glu His Ser Ile Ala Asn
                20                  25                  30

Leu Asp Asn Val Val Glu Asn Thr Asn Ala Ala Glu Ser Arg Ile Arg
            35                  40                  45

Asp Thr Asp Met Ala Asp Glu Met Val Thr Tyr Ser Lys Asn Asn Ile
     50                  55                  60

Leu Met Gln Ala Gly Gln Ser Met Leu Ala Gln Ala Asn Gln Ala Thr
 65                  70                  75                  80

Gln Gly Val Leu Ser Ile Leu Gln
                85

<210> SEQ ID NO 290
<211> LENGTH: 88
<212> TYPE: PRT
<213> ORGANISM: Artificial Sequence
<220> FEATURE:
<223> OTHER INFORMATION: Synthetic peptide accession number Q7VZC2

<400> SEQUENCE: 290

Ala Leu Ser Lys Leu Asp Asp Ala Met Lys Ala Val Asp Glu Gln Arg
  1               5                  10                  15

Ser Ser Leu Gly Ala Ile Gln Asn Arg Phe Glu Ser Thr Val Ala Asn
                20                  25                  30
```

```
Leu Asn Asn Thr Ile Thr Asn Leu Ser Ala Ala Arg Ser Arg Ile Glu
            35                  40                  45

Asp Ser Asp Tyr Ala Thr Glu Val Ser Asn Met Thr Lys Asn Gln Ile
 50                  55                  60

Leu Gln Gln Ala Gly Thr Ser Val Leu Ala Gln Ala Asn Gln Val Pro
 65                  70                  75                  80

Gln Asn Val Leu Ser Leu Leu Arg
                85
```

<210> SEQ ID NO 291
<211> LENGTH: 88
<212> TYPE: PRT
<213> ORGANISM: Artificial Sequence
<220> FEATURE:
<223> OTHER INFORMATION: Synthetic peptide accession number Q9F4A4

<400> SEQUENCE: 291

```
Ser Ile Lys Thr Ile Asn Ser Ala Ile Glu Gln Val Ser Thr Gln Arg
 1               5                  10                  15

Ser Lys Leu Gly Ala Val Gln Asn Arg Leu Glu His Thr Ile Asn Asn
            20                  25                  30

Leu Asn Thr Ser Ser Glu Asn Leu Thr Ala Ala Glu Ser Arg Val Arg
            35                  40                  45

Asp Val Asp Met Ala Lys Glu Met Met Ala Phe Ser Lys Asn Asn Ile
 50                  55                  60

Leu Ser Gln Ala Ala Gln Ala Met Leu Gly Gln Ala Asn Gln Gln Pro
 65                  70                  75                  80

Gln Gly Val Leu Gln Leu Leu Arg
                85
```

<210> SEQ ID NO 292
<211> LENGTH: 88
<212> TYPE: PRT
<213> ORGANISM: Artificial Sequence
<220> FEATURE:
<223> OTHER INFORMATION: Synthetic peptide accession number Q8P9C4

<400> SEQUENCE: 292

```
Ala Leu Glu Ile Val Asp Lys Ala Leu Thr Ser Val Asn Ser Ser Arg
 1               5                  10                  15

Ala Asp Met Gly Ala Val Gln Asn Arg Phe Thr Ser Thr Leu Ala Asn
            20                  25                  30

Leu Ala Ala Thr Ser Glu Asn Leu Thr Ala Ser Arg Ser Arg Ile Ala
            35                  40                  45

Asp Thr Asp Tyr Ala Lys Thr Thr Ala Glu Leu Thr Arg Thr Gln Ile
 50                  55                  60

Leu Gln Gln Ala Gly Thr Ala Met Leu Ala Gln Ala Lys Ser Val Pro
 65                  70                  75                  80

Gln Asn Val Leu Ser Leu Leu Gln
                85
```

<210> SEQ ID NO 293
<211> LENGTH: 84
<212> TYPE: PRT
<213> ORGANISM: Artificial Sequence
<220> FEATURE:
<223> OTHER INFORMATION: Synthetic peptide accession number Q82UA3

<400> SEQUENCE: 293

```
Ile Asp Asp Ala Leu Lys Ile Val Asn Ser Thr Arg Ala Asp Leu Gly
```

```
1               5                   10                  15
Ala Ile Gln Asn Arg Phe Ser Ser Ala Ile Ala Asn Leu Gln Thr Ser
                20                  25                  30
Ala Glu Asn Leu Ser Ala Ser Arg Ser Arg Ile Gln Asp Ala Asp Phe
                35                  40                  45
Ala Ala Glu Thr Ala Ala Leu Thr Arg Ala Gln Ile Leu Gln Gln Ala
        50                  55                  60
Gly Val Ala Met Leu Ser Gln Ala Asn Ala Leu Pro Asn Asn Val Leu
65                  70                  75                  80

Ser Leu Leu Arg

<210> SEQ ID NO 294
<211> LENGTH: 89
<212> TYPE: PRT
<213> ORGANISM: Artificial Sequence
<220> FEATURE:
<223> OTHER INFORMATION: Synthetic peptide accession number Q84IC5

<400> SEQUENCE: 294

Val Met Asp Ile Ala Asp Thr Ala Ile Ala Asn Leu Asp Thr Ile Arg
1               5                   10                  15
Ala Asn Ile Gly Ala Thr Gln Asn Gln Ile Thr Ser Thr Ile Asn Asn
                20                  25                  30
Ile Ser Val Thr Gln Val Asn Val Lys Ala Ala Glu Ser Gln Ile Arg
        35                  40                  45
Asp Val Asp Phe Ala Ser Glu Lys Ser Ala Asn Tyr Ser Lys Ala Asn
        50                  55                  60
Ile Leu Ala Gln Ser Gly Ser Tyr Ala Met Ala Gln Ala Asn Ala Ala
65                  70                  75                  80
Ser Gln Asn Val Leu Arg Leu Leu Gln
                85
```

FLAGELLIN COMPOSITIONS AND USES

CROSS-REFERENCE TO RELATED APPLICATIONS

This application is the 371 National Stage entry of International Patent Application No. PCT/US2015/042684, filed Jul. 29, 2015, which claims the benefit of U.S. Provisional Patent Application Nos. 62/031,116, filed Jul. 30, 2014; 62/110,744, filed Feb. 2, 2015; and 62/117,366, filed Feb. 17, 2015, the entire contents of which are herein incorporated by reference.

FIELD OF THE INVENTION

This invention relates to methods and compositions that are useful for the treatment, prevention, and/or diagnosis, of various diseases, including cancer and radiation-related ailments.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CLE-016PC-SequenceListing.txt; date recorded: Jul. 28, 2015; file size: 245 KB).

BACKGROUND

Toll-like receptors (TLRs) are type I membrane glycoproteins that are key receptors in innate immunity. The 10 TLRs known in humans recognize different microbial antigens, and when activated by ligand binding, mediate rapid production of cytokines and chemokines. In addition to their role in host defense, TLRs play a role in cancer progression and development and cell protection.

TLR5 binds flagellin, a globular protein that arranges itself in a hollow cylinder to form the filament in bacterial flagella. Binding of flagellin to TLR5 initiates a cascade of pro-inflammatory molecules, notably NF-κB and its targets. TLR5 agonists derived from flagellin have been developed as therapies various diseases. However, these molecules may suffer from specific limitations, including for example, unsatisfactory binding and signaling. Additionally, many possible hosts already produce anti-flagellin antibodies that also target the TLR5 agonist derivatives, thereby clearing the therapeutics from the body and limiting their efficacy. Moreover, as intrinsically immunogenic bacterial proteins flagellin derivatives may possess disadvantageous antigenicity and immunogenicity, and therefore warrant improvement.

SUMMARY OF THE INVENTION

Accordingly, the present invention provides flagellin-related compositions and methods that overcome limitations observed among this group of biologics.

The present invention is based, in part, of the discovery that minimized constructs of flagellin-related compositions can exhibit reduced immunogenicity and improve pharmacokinetics while still retaining the ability to active TLR5 signaling.

In one aspect, the invention provides a flagellin-related composition that retains the ability to activate TLR5 signaling. In a further embodiment, the flagellin-related composition comprises mutations that decrease the antigenicity and immunogenicity of the construct. In a further embodiment, the flagellin-related composition is not recognized by flagellin (FliC) neutralizing antibodies. In yet a further embodiment, the flagellin-related composition activates TLR5 signaling at a level the same as or similar to that of a full-length flagellin-related composition. In a further embodiment, the flagellin-related composition demonstrates improved pharmacokinetics compared with a full length flagellin-related composition. In yet a further embodiment, the flagellin-related composition demonstrates increased retention in the host.

In some embodiments, the flagellin-related composition is derived from CBLB502 (SEQ ID NO: 2). In a further embodiment, the flagellin-related composition comprises a truncation in one or more domains. In a further embodiment, the flagellin-related composition comprises a deletion in a N-terminal domain. In yet a further embodiment, the flagellin-related composition comprises a deletion in the ND0 domain. In yet a further embodiment, the flagellin-related composition comprises a deletion of the entire ND0 domain. In a further embodiment, the flagellin-related composition comprises a deletion in a C-terminal domain. In yet another embodiment, the flagellin-related composition comprises a deletion in the CD0 domain. In yet another embodiment, the flagellin-related composition retains amino acids 470-485 of the CD0 domain. In yet a further embodiment, the flagellin-related composition is CBLB502-S33 (SEQ ID NO: 17).

In some embodiments, the flagellin-related composition comprises mutations in epitopes recognized by neutralizing anti-CBLB502 antibodies. In some embodiments, the flagellin-related composition comprises one or more mutations in the epitopes recognized by neutralizing anti-CBLB502 antibodies which inhibit the ability of the antibodies to neutralize the composition. In yet a further embodiment, the flagellin-related composition comprises a truncation and mutations in one or more epitopes recognized by anti-CBLB502 neutralizing antibodies. In a further embodiment, the mutations comprise replacement of the epitope residues with alanine. In a further embodiment, the mutations are selected from one or more of D42A, A45G, N68A, N100A, T102A, S104A, S106A, D107A, S110A, D113A, Q117A, E120A, R124A, N127A, Q128A, F131A, N132A, G133A, Q142A, K144A, D151A, G152A, E153A, T154A, Q439A, N440A, R441A, D443A, S444A, T447A, N448A, N451A, N455A, N457A, R460A, Y468A; A469G; T470A; S473A, and N474Q. In a further embodiment, the mutated epitopes comprise one or more of the following residues: E153, S444, T154, N440, Q142, F131, D443, N68, T447, S110, Q117, R124, D113, E120, N127, and Q128. In a further embodiment, the flagellin-related composition is CBLB502-S33MX/"CBLB543" (SEQ ID NO: 150). In yet a further embodiment, the flagellin-related composition is CBLB502-485CT/"BCLB533" (SEQ ID NO: 71).

In some embodiments, the flagellin-related composition comprises a tag. In yet a further embodiment, the tag is attached to the N-terminus of the flagellin-related composition. In yet another embodiment, the tag is attached to the C-terminus of the flagellin-related composition.

In some embodiments, the flagellin-related composition comprises a flexible linker. In a further embodiment, the flexible linker comprises SEQ ID NO: 16. In yet a further embodiment, the flexible linker comprises SEQ ID NO: 242.

In some embodiments, the flagellin-related composition is encoded by any one of the nucleotide sequences listed in Table 1. In a further embodiment, the flagellin-related composition comprises any one of the polypeptides listed in Table 1.

In some embodiments, the flagellin-related composition activates TLR5 signaling. In a further embodiment, the flagellin-related composition induces expression of NF-κB. In yet a further embodiment, the minimized flagellin-related composition induces expression of one or more of cytokines. In yet a further embodiment, the cytokines are selected from IL-6, IL-12, keratinocyte chemoattractant (KC), IL-10, G-CSF, MCP-1, TNF-α, MIG, and MIP-2.

In one aspect, the invention provides a pharmaceutical composition comprising the flagellin-related composition of the invention with a pharmaceutically accepted carrier.

In one aspect, the invention provides a method of stimulating TLR5 signaling comprising administering a flagellin-related composition of the invention to a subject in need thereof. In some embodiments, the subject has cancer. In a further embodiment, the tumor expresses TLR5. In a further embodiment, the tumor does not express TLR5. In yet a further embodiment, the cancer is selected from breast cancer, lung cancer, colon cancer, kidney cancer, liver cancer, ovarian cancer, prostate cancer, testicular cancer, genitourinary tract cancer, lymphatic system cancer, rectal cancer, pancreatic cancer, esophageal cancer, stomach cancer, cervical cancer, thyroid cancer, skin cancer, leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma, acute and chronic myelogenous leukemias, myelodysplastic syndrome, myeloid leukemia, promyelocytic leukemia, astrocytoma, neuroblastoma, glioma, schwannomas, fibrosarcoma, rhabdomyoscarcoma, osteosarcoma, xenoderma pigmentosum, keratoactanthoma, seminoma, thyroid follicular cancer, teratocarcinoma, and cancers of the gastrointestinal tract or the abdominopelvic cavity.

In some embodiments, the subject suffers from radiation-induced damage. In a further embodiment, the subject has been subjected to a lethal dose of radiation. In yet a further embodiment, the subject is undergoing radiation treatment. In another embodiment, the flagellin-related composition is administered prior to exposure to radiation. In yet another embodiment, the flagellin-related composition is administered during exposure to radiation. In yet another embodiment, the flagellin-related composition is administered after exposure to radiation.

In some embodiments, the subject suffers from reperfusion injury. In a further embodiment the reperfusion is caused by an injury. In a further embodiment, the injury is ischemia or hypoxia. In a further embodiment, the flagellin-related composition is administered prior to the influx of oxygen. In a further embodiment, the flagellin-related composition is administered during the influx of oxygen. In a further embodiment, the flagellin-related composition is administered after the influx of oxygen.

In various embodiments, the flagellin-related composition is administered in conjunction with other therapeutics and/or treatments. In a further embodiment, the flagellin-related composition is administered in conjunction with chemotherapy. In a further embodiment, the flagellin-related composition is administered with radiation treatment. In a further embodiment, the flagellin-related composition is administered in conjunction with an antioxidant. In a further embodiment, the flagellin-related composition is administered in conjunction with amifostine and/or vitamin E. In some embodiments, the flagellin-related composition is administered prior to administration of other therapeutics and/or treatments. In further embodiments, the flagellin-related composition is administered at the same time as other therapeutics and/or treatments. In yet further embodiments, the flagellin-related composition is administered after administration of other therapeutics and/or treatments.

In one aspect, the invention provides a method of treating cancer comprising administering a flagellin-related composition of the invention to a subject in need thereof.

In one aspect, the invention provides a method of treating radiation-induced damage comprising administering a flagellin-related composition of the invention to a subject in need thereof.

In one aspect, the invention provides a method of treating reperfusion injury comprising administering a flagellin-related composition of the invention to a subject in need thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIGS. 1A and 1B show the 13 conserved amino acids of flagellin that may be important for TLR5 activity. FIGS. 1A and 1B show a comparison of amino acid sequences of the conserved amino (FIG. 1A) and carboxy (FIG. 1B) terminus from 21 species of bacteria. The 13 conserved amino acids important for TLR5 activity are shown with indicated by the letter "C" at the bottom of each column. The amino acid sequences are identified by their accession numbers from TrEMBL (first letter=Q) or Swiss-Prot (first letter=P). With respect to FIG. 1A, SEQ ID Nos: 253-273 correspond to the sequences listed on the figure from top to bottom, respectively. With respect to FIG. 1B, SEQ ID Nos: 274-294 correspond to the sequences listed on the figure from top to bottom, respectively.

DIM2, (C) DIM 1, (D) PIM, and (E) SY3 constructs. The activity was measured in the mouse liver, spleen, large intestine, and bladder.

Figure 5:
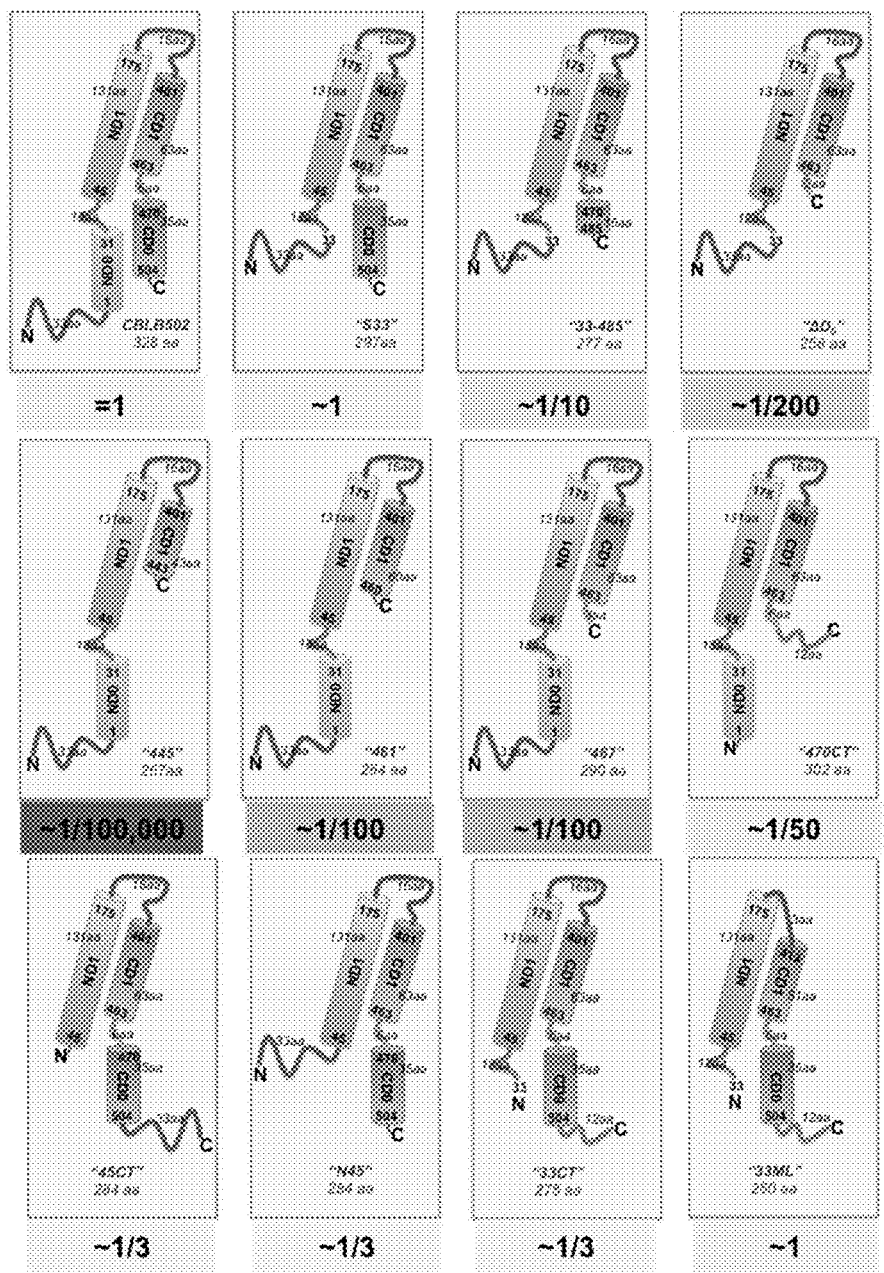

FIG. 5 shows the iterative minimization of the flagellin-related composition, CBLB502. The constructs S33 and 33ML retain nearly full signaling activity in vitro. The schematic shows domain organization including spacer and tag.

Figure 4:
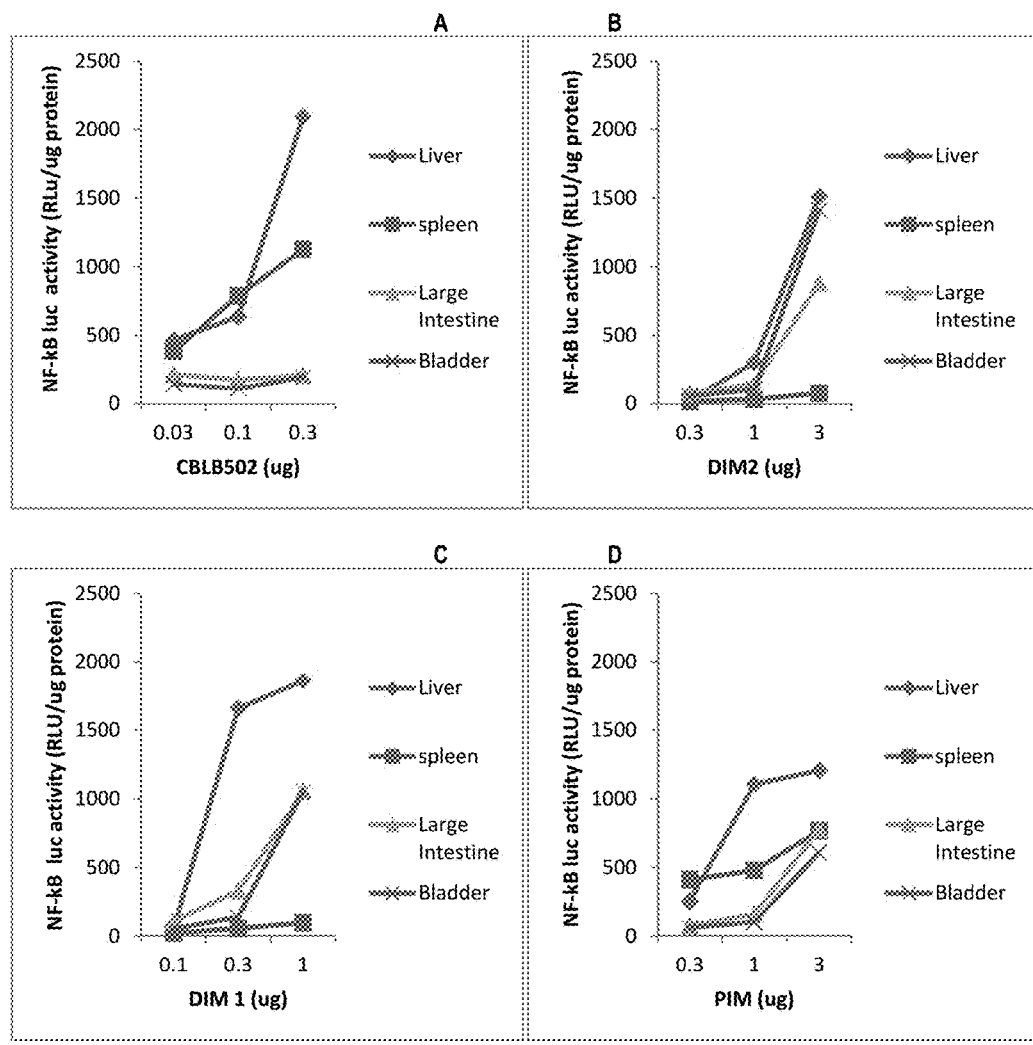
FIG. 4, panels A-E show the signaling efficiency of CBLB502 mutants in NF-κB luciferase reporter mice. The graphs show the NF-κB luciferase activity in reporter mice after subcutaneous administration of the (A) CBLB502, (B)
Figure 4:
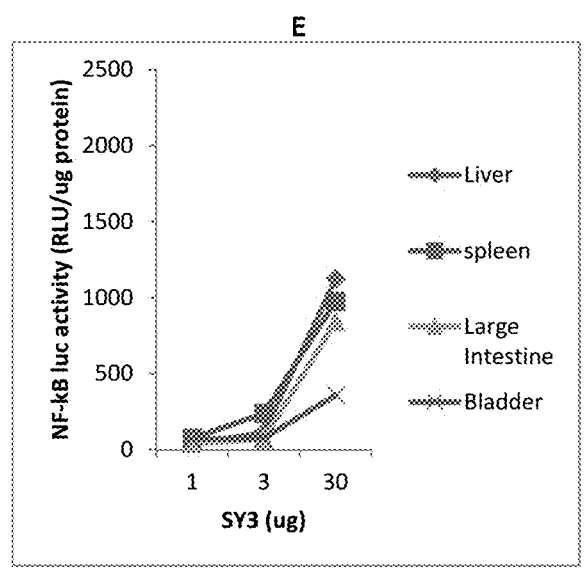

FIG. 6 panels A and B show that a minimized variant CBLB502-S33 shows substantially higher signaling activity in vivo compared to CBLB502. NF-kB-luciferase reporter mice were injected (s.c) with 0.1 μg of CBLB502 (A) or S33 (B) and imaged 3 hours later. The measurements in individual organs are illustrated in FIG. 4.

Figure 7:
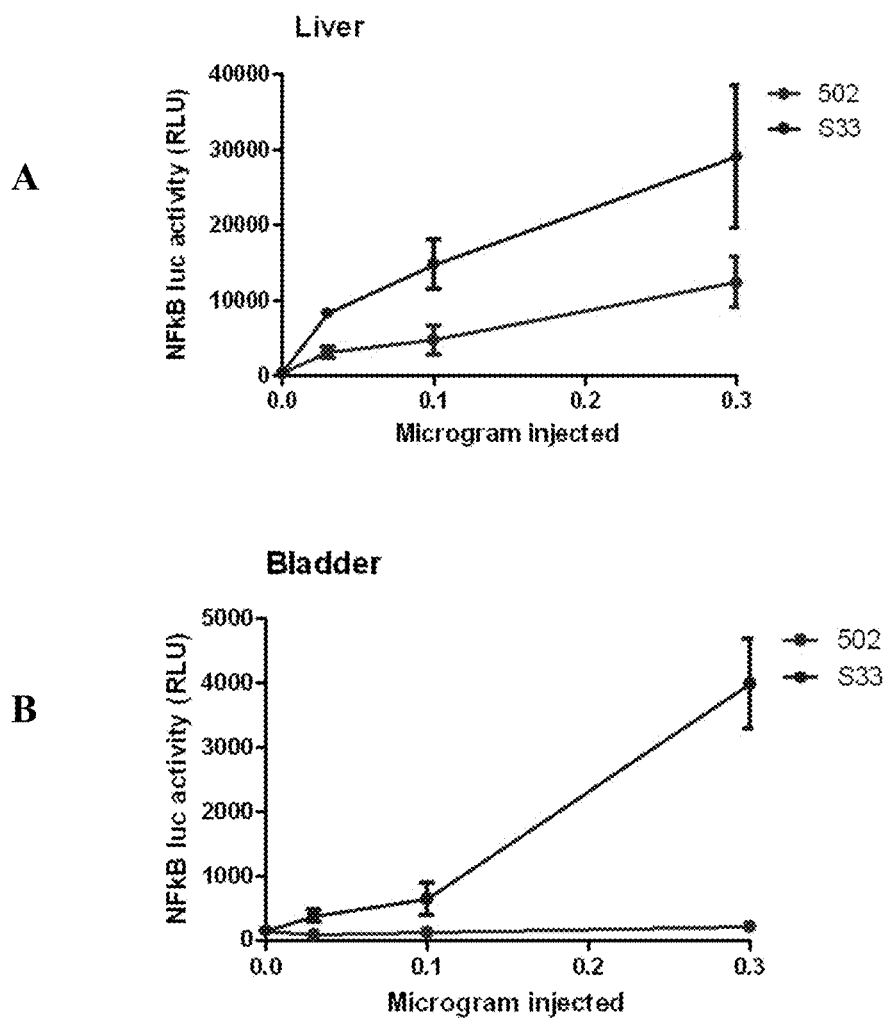
Figure 7:
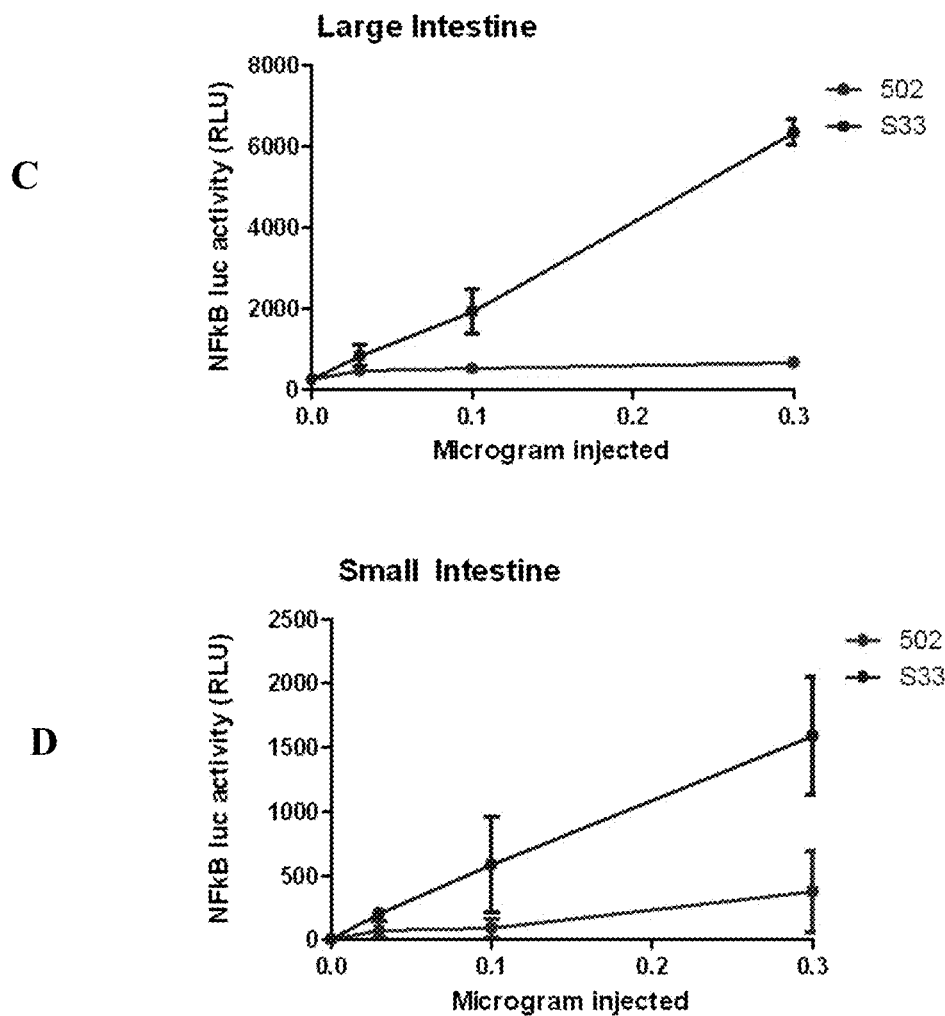

FIG. 7 panels A-H show that a minimized variant CBLB502-S33 shows substantially higher signaling activity in vivo compared to CBLB502, and the effect was particularly strong in bladder and large intestine. Signaling efficiency of the CBLB502 and CBLB502-S33 in NF-kB luciferase reporter mice (s.c. injection at indicated doses and collection of organs 3 hours later) was established by the analysis of luciferase activity in collected organs.

Figure 8:
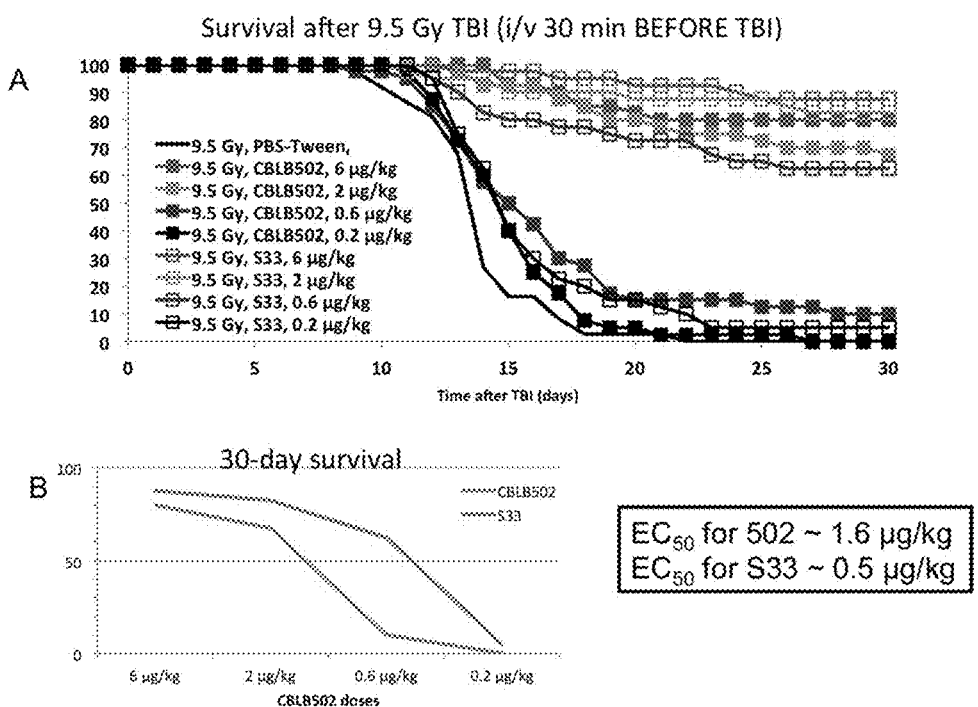

FIG. 8 panels A and B show that a minimized variant CBLB502-S33 shows higher potency in protection against lethal irradiation in mice, as compared to CBLB502. Panel A. Kaplan-Meyer plot showing survival dynamics in C57/BL6 mice injected with CBLB502 or CBLB502-S33, 30 min prior to total body irradiation at 9.5 Gy (compared with vehicle control. Panel B. Dose dependence for the 30-day % survival.

Figure 9:
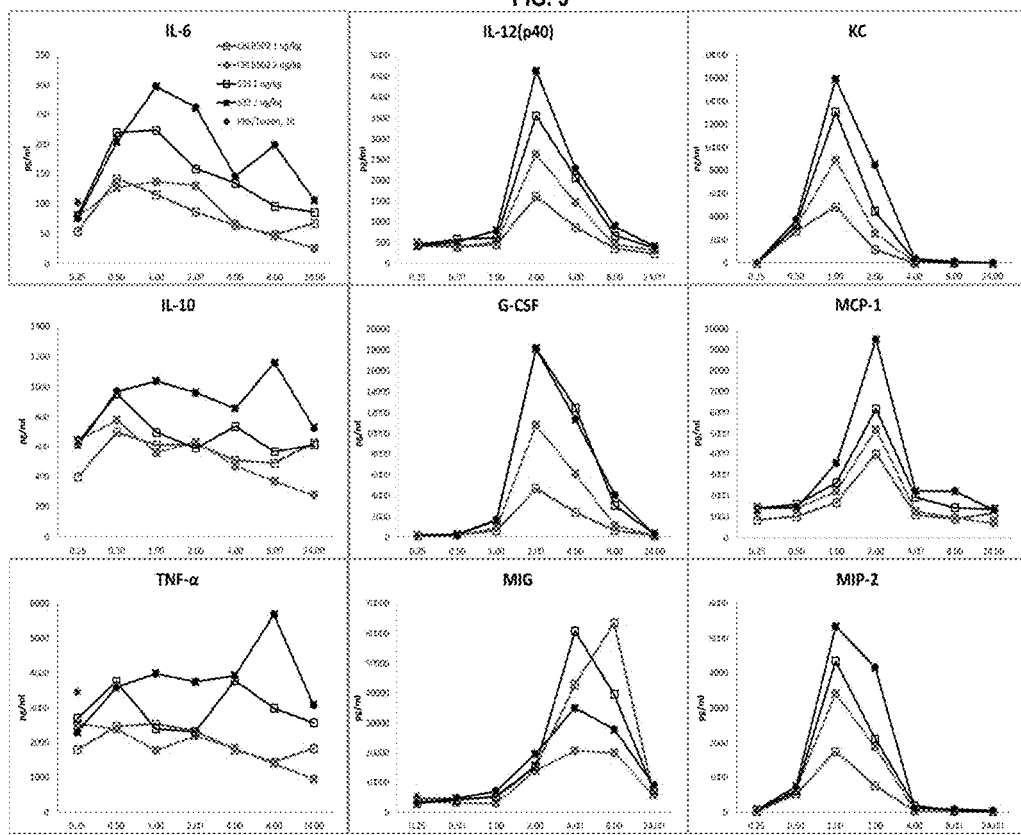

FIG. 9 shows the higher signaling and radioprotective activity of CBLB502-S33 correlates with higher cytokine production (PD analysis) in mice compared to CBLB502, including mechanistically essential biomarkers G-CSF and IL-6. Mice were injected with either 1 μg/kg or 2 μg/kg of CBLB502 or S33.

Figure 10:
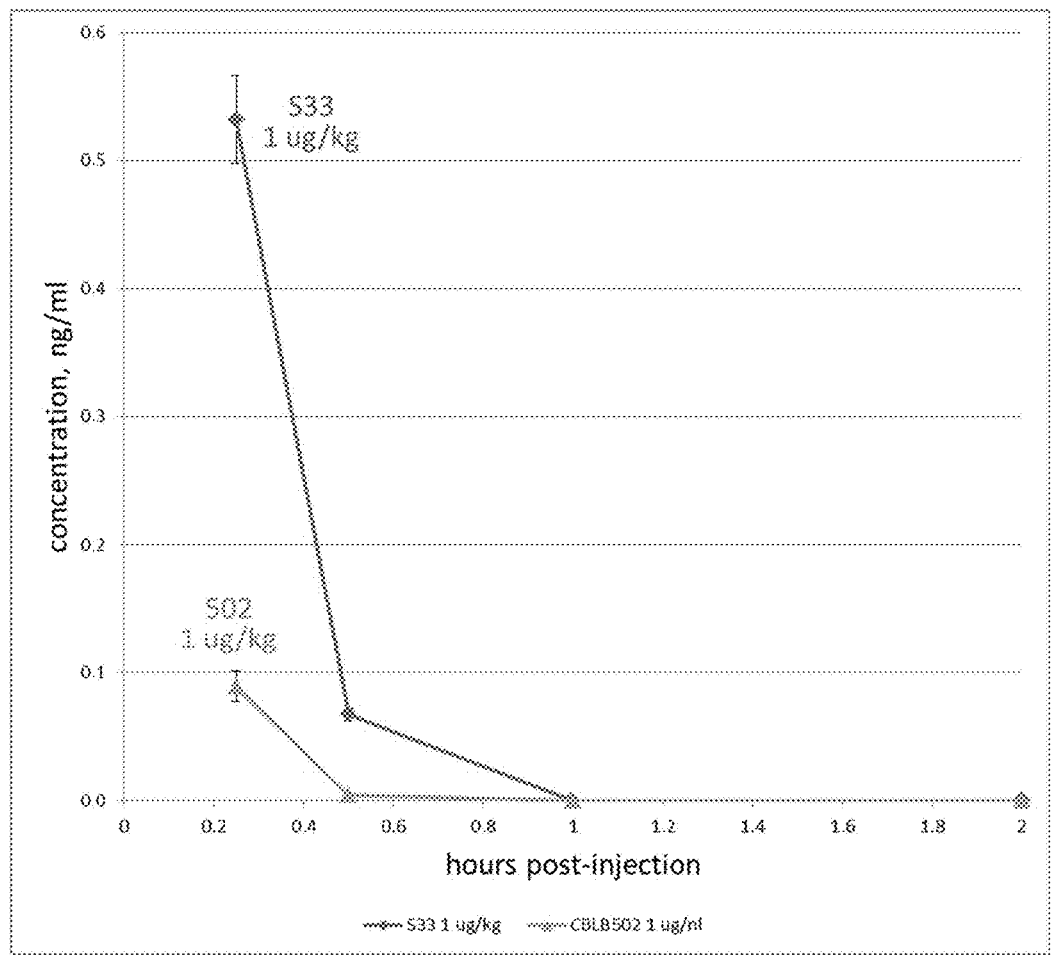

FIG. 10 shows that the minimized variant CBLB502-S33 displays better PK (higher levels in plasma) in mice compared to CBLB502.

Figure 11:
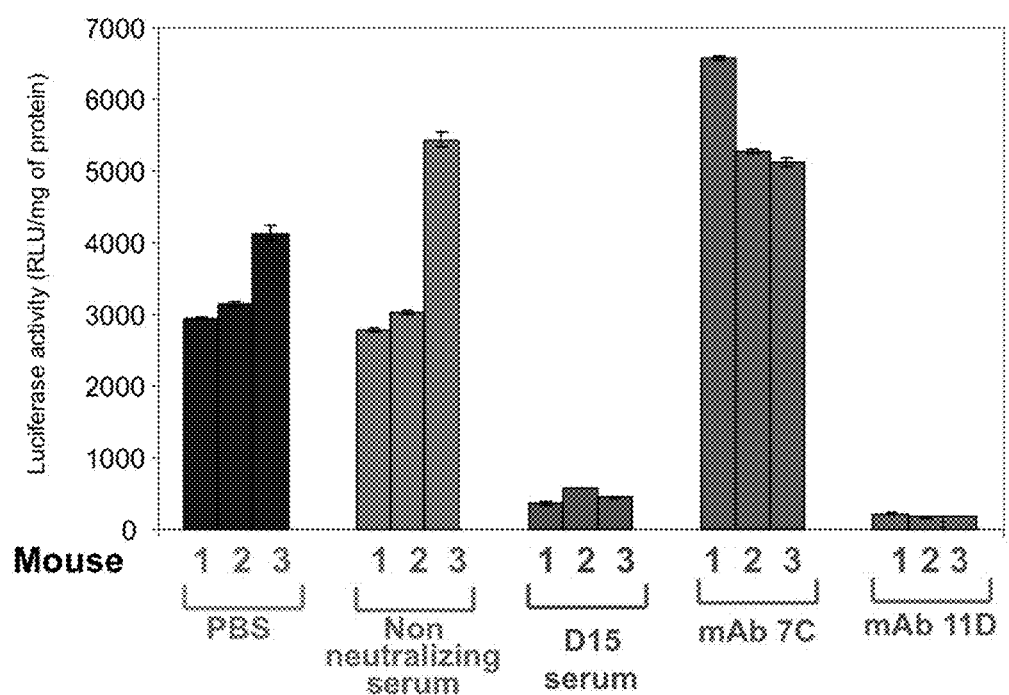

FIG. 11 shows the suppression of luciferase activity in murine liver lysates as a measurement of the in vivo neutralization of CBLB502 by injection of antisera and antibodies (neutralizing and not neutralizing) in reporter mice (3 mice/group). PBS, non-neutralizing human serum, neutralizing serum (D15), the non-neutralizing monoclonal antibody 7C, or the neutralizing monoclonal antibody 11D were administered to the mice intravenously. An hour after, the CBLB502 construct was administered subcutaneously. The amount of luciferase activity was measured three hours after administration of CBLB502. Murine serum samples were collected before administration of CBLB502. Human sera were diluted 10-fold with PBS for injections. Both monoclonal antibodies, 7C and 11D were injected at a concentration of 2 mg/ml in PBS.

Figure 12:
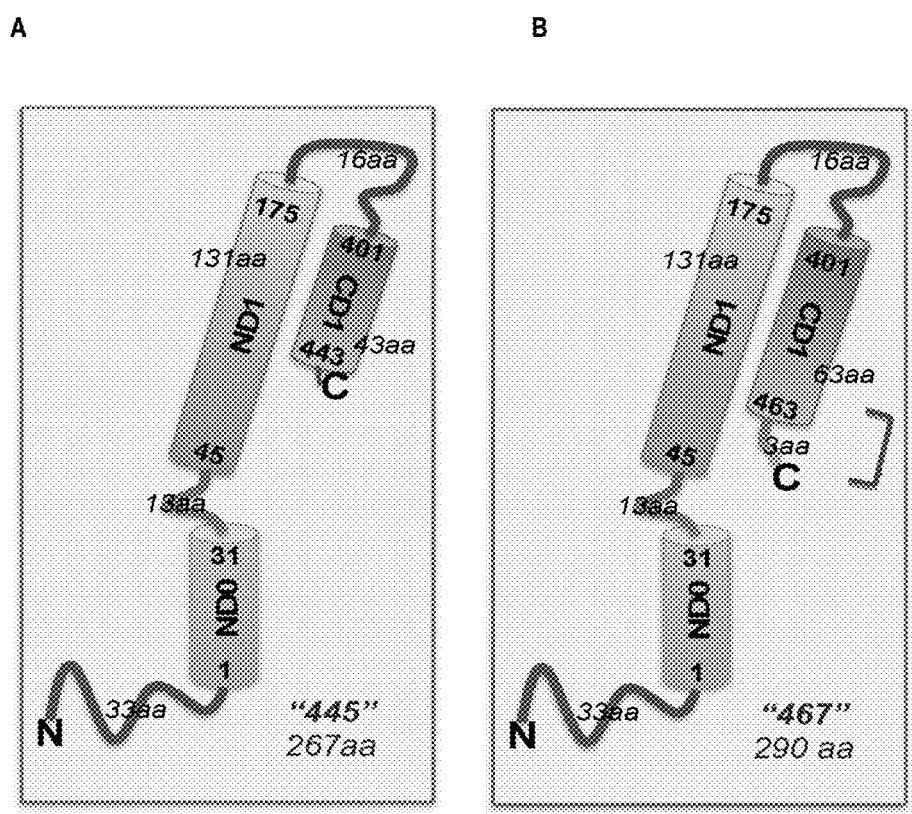

FIG. 12 panels A and B show schematic diagrams of the constructs (A) 445 (SEQ ID NO: 54) and (B) 467 (SEQ ID NO: 62).

Figure 13:
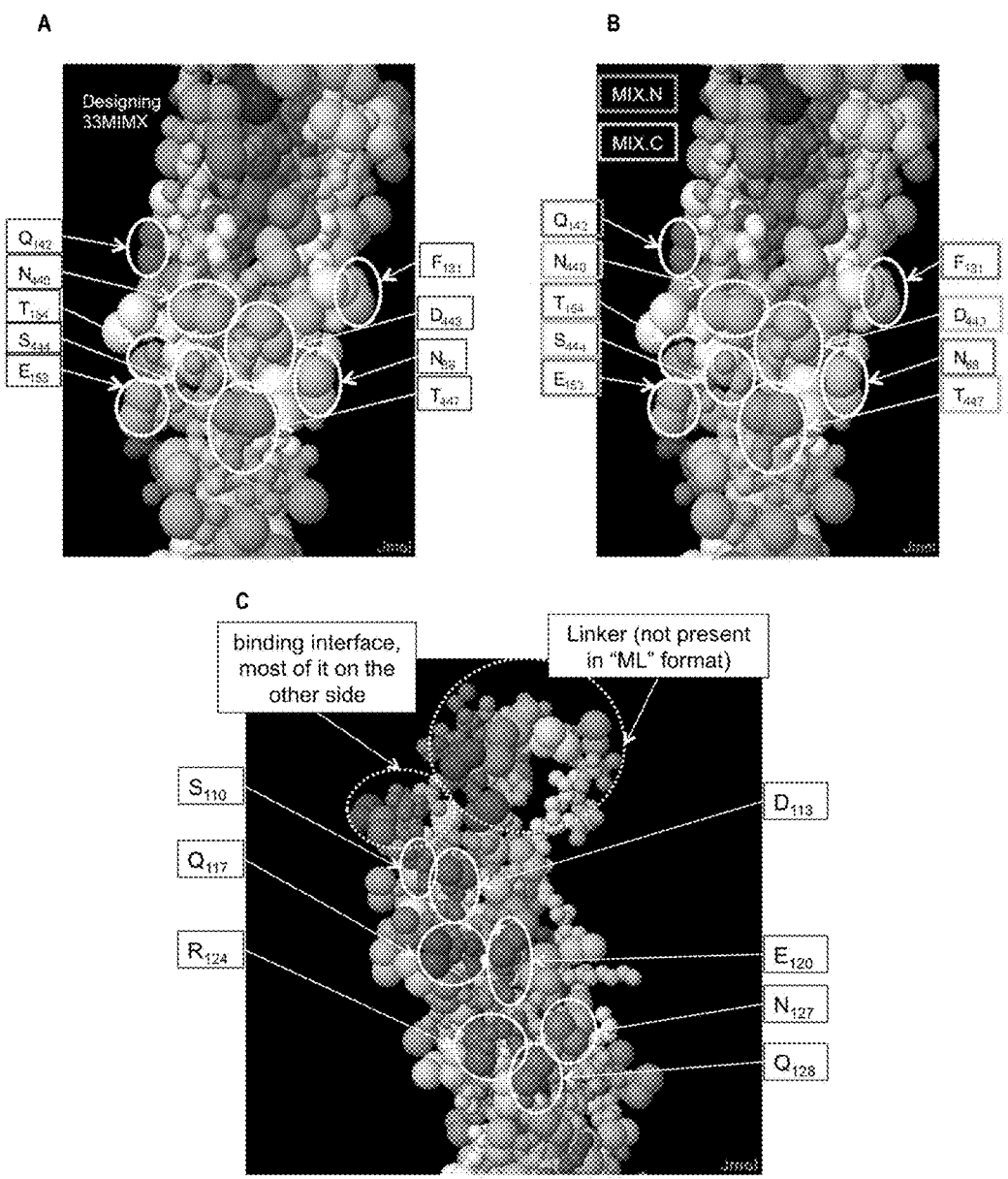

FIG. 13 panels A-C show examples of predicted, without wishing to be bound by theory, structural epitopes used for the design of CBLB502 derivatives.

Figure 14:
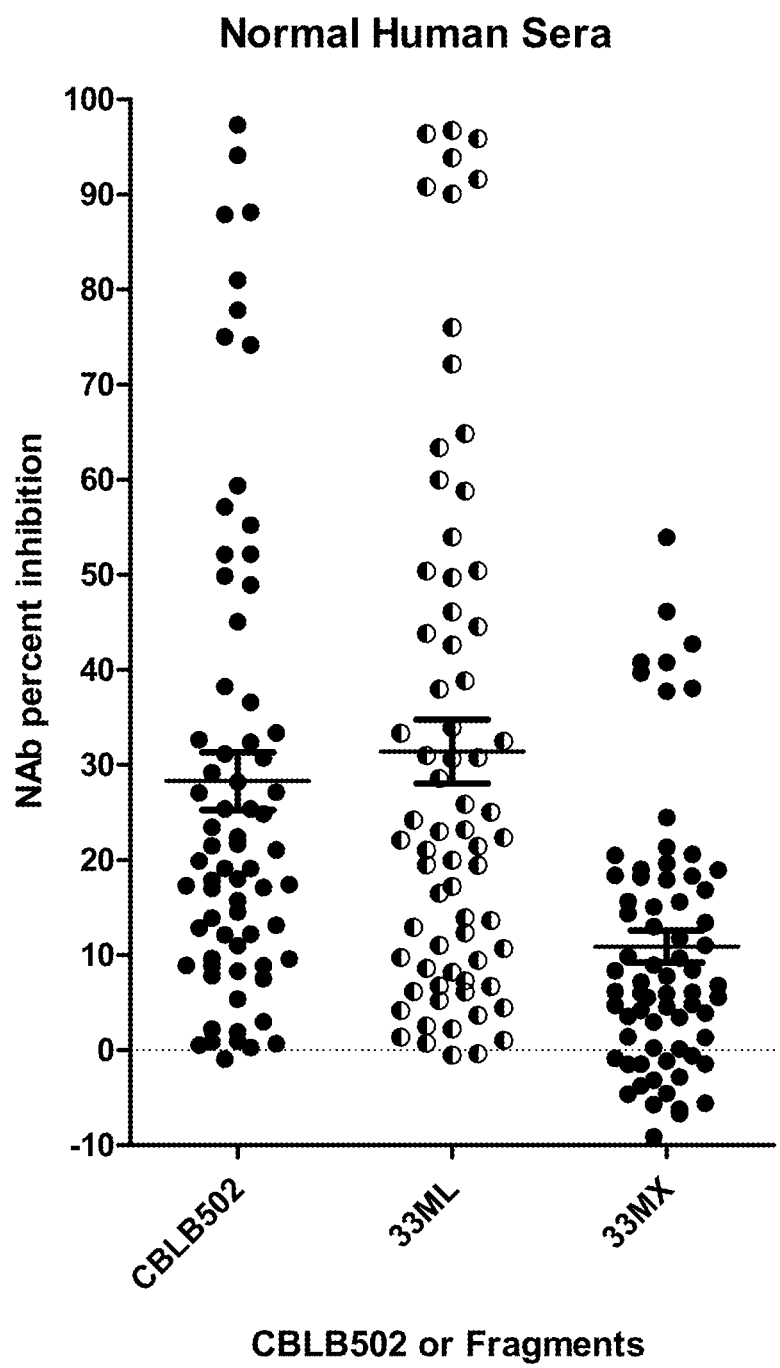

FIG. 14 shows that the construct CBLB502-33MX demonstrates substantial elimination of neutralizing antigenicity. The graph shows a profile of CBLB502-33MX versus CBLB502 and its truncated variant CBLB502-ML over a panel of human sera with the appreciable titer of CBLB502-neutralizing antibodies.

Figure 15:
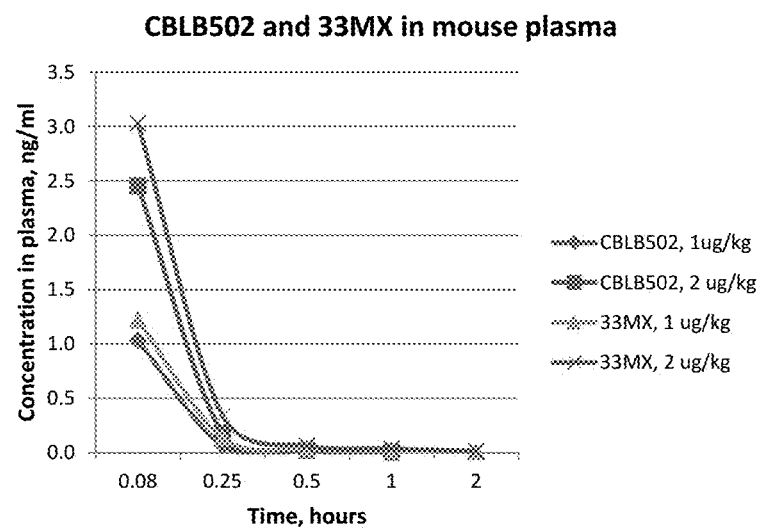

FIG. 15 shows quantification of CBLB502 and CBLB502-33MX in mouse plasma samples. BLQ—below the limit of quantification. Panel A shows raw data while panel B shows a graphical representation of the data in panel A. CBLB502-33MX has very similar PK properties as that of parental CBLB502, i.e. it clears from circulation at approximately the same rate.

Figure 16:
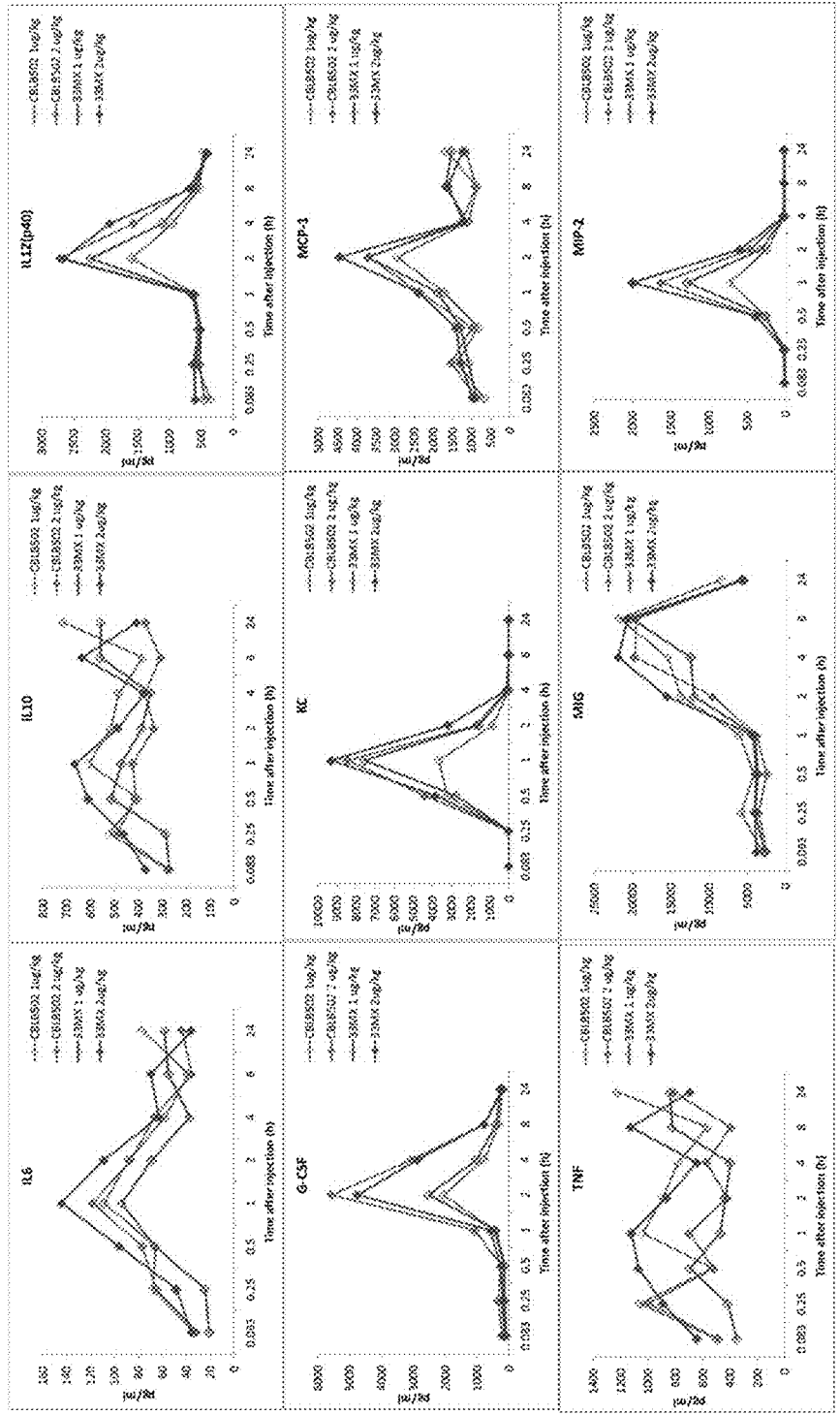

FIG. 16 shows cytokine profiling for the analysis of PD properties of CBLB502-33MX as compared to CBLB502. CBLB502-33MX has a very similar PD profile to the parental CBLB502

Figure 17:
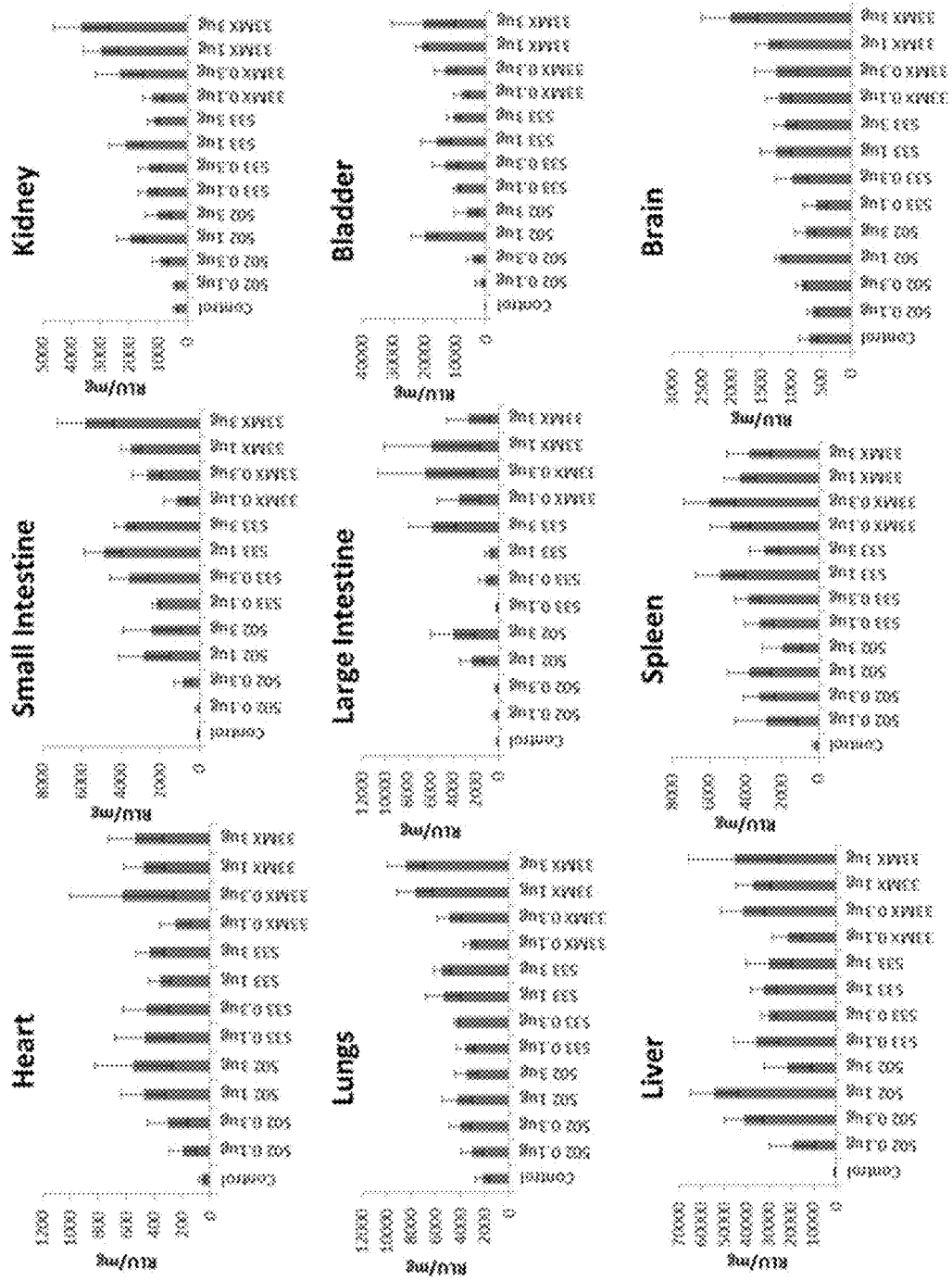

FIG. 17 shows luciferase activity in mouse organs after treatment with CBLB502, CBLB502-S33 and CBLB502-33MX.

Figure 18:
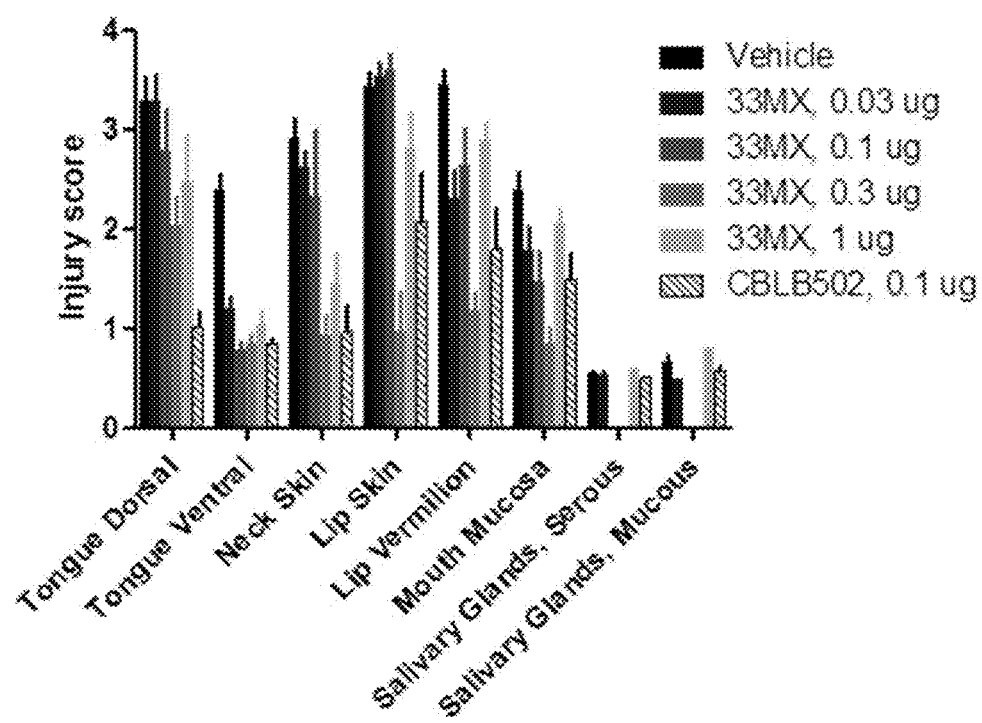

FIG. 18 shows injury scores for a 33MX dose range as compared to a dose of CBLB502

DETAILED DESCRIPTION OF THE INVENTION

The present invention is based, in part, on the discovery of certain mutations of flagellin that improve pharmacologically relevant properties of this biologic and related agents. Such mutations yield various flagellin-related compositions that, by way of non-limiting example, have altered antigenicity and immunogenicity relative to those without the mutations. The flagellin-related compositions retain the ability to active TLR5 signaling at levels the same as, or similar to, that of a full length flagellin-related composition.

Flagellin-Related Compositions

The present invention is based, in part, of the discovery that minimized constructs of flagellin-related compositions can exhibit reduced immunogenicity while still retaining the ability to active TLR5 signaling at levels the same as, or similar to, that of a full length flagellin-related composition. The reduced immunogenicity allows the construct to persist in the host longer than full length flagellin-related compositions. It is possible to eliminate at least half of the endogenous C_D0 segment, leaving only its N-terminal half (470-485) capped by the C-terminal His-tag and still retain most of the molecule's ability to activate TLR5 signaling. The presence of the cap may be essential for activity as the variant 33-485 loses about 90% of signaling activity. These observations taken together suggest that the D_0 domain has only minor (if any) contribution to direct interactions with TLR5, and its role may be limited by maintaining structural integrity of the D1 domain. Conversely, the residual C_D0 segment (470-485) cannot be removed or replaced by the C-terminal half of C_D0 (485-504) or other sequences.

In various embodiments, the present invention provides flagellin-related compositions. In some embodiments, the present invention provides for flagellin-related compositions that have (1) improved pharmacological properties, including reduced antigenicity and immunogenicity, which, for example, allow for use in wide variety of disease states and patient types and/or (2) improved functional properties which, for example, allow for improved medical effects.

The flagellin-related compositions may be a flagellin-related polypeptide. The flagellin-related compositions may be from various sources, including a variety of Gram-positive and Gram-negative bacterial species. In some embodiments, the flagellin-related compositions may have an amino acid sequence that is derived from any of the flagellins from bacterial species that are depicted in FIG. 7 of U.S. Patent Publication No. 2003/0044429, the contents of which are incorporated herein by reference in their entirety. The flagellin-related compositions may have nucleotide sequences related to those encoding the flagellin polypeptides listed in FIG. 7 of U.S. 2003/0044429, which are publicly available at sources including the NCBI Genbank database.

The flagellin-related compositions may be the major component of bacterial flagellum. The flagellin-related compositions may be composed of one, or two, or three, or four, or five, or six, or seven domains or fragments thereof (see, e.g. FIG. 10 of U.S. Pat. No. 8,324,163, the contents of which are incorporated herein by reference in their entirety). The domains may be selected from ND0, ND1, ND2, D3, CD2, CD1, and CD0. Domains 0 (D0), 1 (D1), and 2 (D2) may be discontinuous and may be formed when residues in the amino terminus and carboxy terminus are juxtaposed by the formation of a hairpin structure. The amino and carboxy terminus comprising the D1 and D2 domains may be most conserved, whereas the middle hypervariable domain (D3) may be highly variable. The non-conserved D3 domain may be on the surface of the flagellar filament and may contain the major antigenic epitopes. The potent proinflammatory activity of flagellin may reside in the highly conserved ND1, ND2, CD1, and CD2 regions.

The flagellin-related compositions may be from a species of *Salmonella*, representative examples of which are *S. typhimurium* and *S. dublin* (encoded by GenBank Accession Number M84972). The flagellin related-polypeptide may be a fragment, variant, analog, homolog, or derivative of wild type flagellin (SEQ ID NO: 1), or combination thereof. A fragment, variant, analog, homolog, or derivative of flagellin may be obtained by rational-based design based on the domain structure of flagellin and the conserved structure recognized by TLR5.

The flagellin-related compositions may be related to a flagellin polypeptide from any Gram-positive or Gram-negative bacterial species including, but not limited to, the flagellin polypeptides disclosed in U.S. Pat. Pub. 2003/000044429, the contents of which are incorporated herein, and the flagellin peptides corresponding to the Accession numbers listed in the BLAST results shown in FIG. 7 (panels A-F) of U.S. Patent Pub. 2003/000044429, or variants thereof.

Flagellin and previously described variants suffer from high antigenicity and immunogenicity in large part, without wishing to be bound by theory, because they are intrinsically immunogenic bacterial proteins (e.g. flagellin or "FliC"). A practical limitation in preexisting flagellin constructs is that many subjects have high titers of pre-existing antibodies capable of neutralizing the TLR5-stimulating activity of these constructs. These individuals would be desensitized (or completely resistant) to flagellin-derived treatment, sometimes even in case of single-injections and, without wishing to be bound by theory, more likely upon recurrent treatment. Moreover, the titer of such pre-existing antibodies, even if initially present at lower levels, may be rapidly boosted by a single flagellin-derived injection thereby compromising even a larger group of individuals for the purpose of multi-dose regimen as projected for medical applications. The widespread preexistence of anti-FliC antibodies (including neutralizing Abs) in a population likely reflects humanity's life-long exposure to numerous species of flagellated enterobacteria (e.g. *Salmonella* spp., *E. coli* colonizing (and infecting) the human body. In some embodiments, the presently described flagellin-related compositions comprise alterations of epitopes for various antibodies that neutralize flagellin activity.

In some embodiments, the flagellin-related composition comprises mutations in epitopes recognized by neutralizing anti-CBLB502 antibodies. The flagellin-related composition may comprise one or more mutations in the epitopes recognized by neutralizing anti-CBLB502 antibodies which inhibit or abrogate the ability of the antibodies to neutralize the composition. In yet a further embodiment, the flagellin-related composition comprises a truncation and mutations in one or more epitopes. In a further embodiment, the mutations comprise replacement of the epitope residues with alanine. In a further embodiment, the mutated epitopes comprise one or more of the following residues: E153, S444, T154, N440, Q142, F131, D443, N68, T447, S110, Q117, R124, D113, E120, N127, and Q128.

The flagellin-related compositions may comprise insertions, deletions, transposon insertions, and changes to any one of the D0, D1, D2, and the variable D3 domains. The D3 domain may be substituted in part, or in whole, with a hinge or linker polypeptide that allows the D1 and D2 domains to properly fold such that the variant stimulates TLR5 activity.

In some embodiments, the present invention relates to the development of a minimal functional core of a flagellin, for example, deleting residues relative to the already shortened CBLB502 molecule. In some embodiments, the present invention relates to the development of a flagellin-related composition that has altered amino acid identity relative to wild type, including deletions, additions and substitutions, that provide for improved activity. In some embodiments, the flagellin-related composition is derived from CBLB502 (SEQ ID NO: 2). In some embodiments, the flagellin-related composition comprises a truncation in one or more domains. In a further embodiment, the flagellin-related composition comprises a deletion in a N-terminal domain. In yet a further embodiment, the flagellin-related composition comprises a deletion in the ND0 domain. In yet a further embodiment, the flagellin-related composition comprises a deletion of the entire ND0 domain. In a further embodiment, the flagellin-related composition comprises a deletion in a C-terminal domain. In yet another embodiment, the flagellin-related composition comprises a deletion in the CD0 domain. In yet another embodiment, the flagellin-related composition retains amino acids 470-485 of the CD0 domain. In yet a further embodiment, the minimized flagellin-related composition is CBLB502-S33 (SEQ ID NO: 17).

The flagellin-related compositions may comprise at least 10, 11, 12, or 13 of the 13 conserved amino acids shown in FIG. 1A and FIG. 1B (positions 89, 90, 91, 95, 98, 101, 115, 422, 423, 426, 431, 436 and 452). The flagellin-related compositions may be at least 30-99% identical to amino acids 1-174 and 418-505 of SEQ ID NO: 1.

In some embodiments, the flagellin-related compositions have improved functional and pharmacological properties which, for example, allow for improved medical effects. In some embodiments, the flagellin-related compositions have improved NF-kB activation and radioprotection relative to CBLB502. In some embodiments, the flagellin-related compositions have improved pharmacokinetics leading to a proportionally stronger pharmacodynamic response (as detected by, for example, cytokine assays).

In some embodiments, the flagellin-related compositions have improved pharmacological properties, including reduced antigenicity and immunogenicity, which, for example, allows for use in wide variety of disease states and patient types. A reduced antigenicity and immunogenicity expands the medical applications for which the flagellin-related compositions of the invention can be used including, for example, medical applications requiring recurrent administration. In some embodiments, the decreased antigenicity translates to improved resistance against the neutralizing action of preexisting human antibodies (e.g. anti-flagellin) as well as those induced in response to CBLB502 injection. In further embodiments, the flagellin-related compositions have longer retention times in vivo. A longer retention time may allow the composition to be effective with fewer doses or with doses spaced further apart.

In some embodiments, the flagellin-related composition comprises a tag. In yet a further embodiment, the tag is attached to the N-terminus of the flagellin-related composition. In yet another embodiment, the tag is attached to the C-terminus of the flagellin-related composition.

In some embodiments, the flagellin-related composition comprises a flexible linker. In a further embodiment, the flexible linker comprises SEQ ID NO: 16. In yet a further embodiment, the flexible linker comprises SEQ ID NO: 242.

In some embodiments, the flagellin-related compositions comprise or consist of any of the polypeptides or nucleic acids encoding said polypeptides listed in Table 1. In some embodiments, the flagellin-related composition is encoded by the nucleotide sequences listed in Table 1. In a further embodiment, the flagellin-related composition comprises the polypeptides listed in Table 1. In some embodiments, the flagellin-related compositions comprise or consist of polypeptides encoded by either SEQ ID NOs: 69 or 70. In some embodiments, the flagellin-related compositions comprise or consist of the polypeptides of SEQ ID NO: 71, "CBLB543". In some embodiments, the flagellin-related compositions comprise or consist of polypeptides encoded by either SEQ ID NOs: 149 or 151. In some embodiments, the flagellin-related compositions comprise or consist of the polypeptides of SEQ ID NO: 150, "CBLB533". In some embodiments, the flagellin-related compositions may be at least 30-99% identical to the sequences listed in Table 1, for instance, about 50%, or about 60%, or about 70%, or about 805, or about 90%, or about 95%, or about 97%, or about 98%, or about 99%, or about 100% identical to the sequences listed in Table 1.

TABLE 1

Illustrative Flagellin Compositions

| SEQ ID | Construct Name | DNA/PRT | Sequence | |
|---|---|---|---|---|
| 0001 | Wild type | PRT | Salmonella dublin | MAQVINTNSLSLLTQNNLNKSQSSLSSAIERLSSGLRINSAKDDAAGQAIANRFTSNIKGLTQ ASRNANDGISIAQTTEGALNEINNNLQRVRELSVQATNGTNSDSDLKSIQDEIQQRLEEIDRV SNQTQFNGVKVLSQDNQMKIQVGANDGETITIDLQKIDVKSLGLDGFNVNGPKEATVGDLKSS FKNVTGYDTYAAGADKYRVDINSGAVVTDAAAPDKVYVNAANGQLTTDDAENNTAVDLFKTTK STAGTAEAKAIAGAIKGGKEGDTFDYKGVTFTIDTKTGDDGNGKVSTTINGEKVTLTVADIAT GAADVNAATLQSSKNVYTSVVNGQFTFDDKTKNESAKLSDLEANNAVKGESKITVNGAEYTAN ATGDKITLAGKTMFIDKTASGVSTLINEDAAAAKKSTANPLASIDSALSKVDAVRSSLGAIQN RFDSAITNLGNTVTNLNSARSRIEDADYATEVSNMSKAQILQQAGTSVLAQANQVPQNVLSLL R |
| 0002 | CBLB502 | PRT | Artificial Sequence | MRGSHHHHHHGMASMTGGQQMGRDLYDDDDKDPMAQVINTNSLSLLTQNNLNKSQSSLSSAIE RLSSGLRINSAKDDAAGQAIANRFTSNIKGLTQASRNANDGISIAQTTEGALNEINNNLQRVR ELSVQATNGTNSDSDLKSIQDEIQQRLEEIDRVSNQTQFNGVKVLSQDNQMKIQVGANDGETI TIDLQKIDVKSLGLDGFNVNSPGISGGGGGILDSMGTLINEDAAAAKKSTANPLASIDSALSK VDAVRSSLGAIQNRFDSAITNLGNTVTNLNSARSRIEDADYATEVSNMSKAQILQQAGTSVLA QANQVPQNVLSLLR |
| 0003 | T7 Promoter (forward) | DNA | Artificial Sequence | TAATACGACTCACTATAGGGG |
| 0004 | FliC AA74-80 (forward) | DNA | Artificial Sequence | ATTGCGCAGACCACTGAAGG |
| 0005 | Thrombin cleavage site | PRT | Artificial Sequence | LVPRGS |
| 0006 | Enterokinase cleavage site | | Artificial Sequence | DDDDK |
| 0007 | NS (N-terminal spoke region; Ser32-Ala44) | PRT | Artificial Sequence | SSGLRINSAKDDA |
| 0008 | CS (C-terminal spoke region; Glu464 to Ala469) | PRT | Artificial Sequence | EDADYA |
| 0009 | linker | PRT | Artificial Sequence | AASAGAGQGGGGSG |
| 0010 | linker | PRT | Artificial Sequence | EGKSSGSGSESKST |
| 0011 | linker | PRT | Artificial Sequence | GGGRTSSSAASAGAGQGGGGSG |
| 0012 | linker | PRT | Artificial Sequence | GPSG |

TABLE 1-continued

Illustrative Flagellin Compositions

| SEQ ID | Construct Name | DNA/PRT | Sequence |
|---|---|---|---|
| 0013 | linker | PRT | Artificial Sequence GSAGSAAGSGEF |
| 0014 | linker | PRT | Artificial Sequence GSPG |
| 0015 | linker | PRT | Artificial Sequence KESGSVSSEQLAQFRSLD |
| 0016 | linker | PRT | Artificial Sequence SPGISGGGGILDSMG |
| 0017 | Mutant 33-485 Mutant S33 | PRT | Artificial Sequence MRGSHHHHHHGMASMTGGQQMGRDLYDLVPRGSAKDPSGLRINSAKDDAAGQAIANRFTSNIK GLTQASRNANDGISIAQTTEGALNEINNNLQRVRELSVQATNGTNSDSDLKSIQDEIQQRLEE IDRVSNQTQFNGVKVLSQDNQMKIQVGANDGETITIDLQKIDVKSLGLDGFNVSPGISGGGG GILDSMGTLINEDAAAAKKSTANPLASIDSALSKVDAVRSSLGAIQNRFDSAITNLGNTVTNL NSARSRIEDADYATEVSNMSKAQILQQAGTSVLAQANQVPQNVLSLLR |
| 0018 | Mutant 33-485 Forward Primer CBLB485 | DNA | Artificial Sequence GCAGATTCTGCAGCAGGCTGGTTGATAATCTGGCGCAGGCTAACCAGG |
| 0019 | Mutant 33-485 502 template sequence | DNA | Artificial Sequence TCTAAAGCGCAGATTCTGCAGCAGGCTGGTACTTCCGTTCTGGCGCAGGCTAACCAGGTT |
| 0020 | Mutant 33-485 Reverse Primer CBLB485 | DNA | Artificial Sequence CCTGGTTAGCCTGCGCCAGATTATCAACCAGCCTGCTGCAGAATCTGC |
| 0021 | Mutant 33-485 DNA sequence of 485 Mutant (T7 Promoter to Stop) | DNA | Artificial Sequence TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGATCTGTACGACCTGGTTCCGCGCGGTAGCGCG AAGGATCCGTCTGGTCTGCGTATCAACAGCGCGAAAGACGATGCGGCAGGCCAGGCGATTGCT AACCGCTTCACTTCTAATATCAAAGGTCTGACTCAGGCTTCCCGTAACGCTAACGACGGCATT TCTATTGCGCAGACCACTGAAGGTGCGCTGAATGAAATCAACAACAACCTGCAGCGTGTGCGT GAGTTGTCTGTTCAGGCCACTAACGGGACTAACTCTGATTCCGATCTGAAATCTATCCAGGAT GAAATTCAGCAACGTCTGGAAGAAATCGATCGCGTTTCTAATCAGACTCAATTTAACGGTGTT AAAGTCCTGTCTCAGGACAACCAGATGAAAATCCAGGTTGGTGCTAACGATGGTGAAACCATT ACCATCGATCTGCAAAAAATTGATGTGAAAAGCCTTGGCCTTGATGGGTTCAATGTTAATTCC CCGGGAATTTCCGGTGGTGGTGGTGGAATTCTAGACTCCATGGGTACATTAATCAATGAAGAC GCTGCCGCAGCCAAGAAAGTACCGCTAACCCACTGGCTTCAATTGATTCTGCATTGTCAAAA GTGGACAGTTCGTTCTTCTCTGGGGGCAATTCAAAACCGTTTTGATTCAGCCATTACCAAC CTTGGCAATACGGTAACCAATCTGAACTCCGCGCGTAGCCGTATCGAAGATGCTGACTATGCA ACGGAAGTTTCTAATATGTCTAAAGCGCAGATTCTGCAGCAGGCTGGTTGATAA |
| 0022 | Mutant 33-485 Expressed Mutant 33-485 | PRT | Artificial Sequence MRGSHHHHHHGMASMTGGQQMGRDLYDLVPRGSAKDPSGLRINSAKDDAAGQAIANRFTSNIK GLTQASRNANDGISIAQTTEGALNEINNNLQRVRELSVQATNGTNSDSDLKSIQDEIQQRLEE IDRVSNQTQFNGVKVLSQDNQMKIQVGANDGETITIDLQKIDVKSLGLDGFNVSPGISGGGG GILDSMGTLINEDAAAAKKSTANPLASIDSALSKVDAVRSSLGAIQNRFDSAITNLGNTVTNL NSARSRIEDADYATEVSNMSKAQILQQAG |
| 0023 | Mutant 45CT Mutant 506T | PRT | Artificial Sequence MAQVINTNSLSLLTQNNLNKSQSSLSSAIERLSSGLRINSAKDDAAGQAIANRFTSNIKGLTQ ASRNANDGISIAQTTEGALNEINNNLQRVRELSVQATNGTNSDSDLKSIQDEIQQRLEEIDRV SNQTQFNGVKVLSQDNQMKIQVGANDGETITIDLQKIDVKSLGLDGFNVSPGISGGGGGILD SMGTLINEDAAAAKKSTANPLASIDSALSKVDAVRSSLGAIQNRFDSAITNLGNTVTNLNSAR SRIEDADYATEVSNMSKAQILQQAGTSVLAQANQVPQNVLSLLVPRGSHHHHHHGMASMTGGQ QMGRDLYDDDDKDP |
| 0024 | Mutant 45CT Mutant 506T | DNA | Artificial Sequence ATGGCACAAGTCATTAATACAAACAGCCTGTCGCTGTTGACCCAGAATAACCTGAACAAATCT CAGTCCTCACTGAGTTCCGCTATTGAGCGTCTGTCCTCTGGTCTGCGTATCAACAGCGCGAAA GACGATGCGGCAGGCCAGGCGATTGCTAACCGCTTCACTTCTAATATCAAAGGTCTGACTCAG GCTTCCCGTAACGCTAACGACGGCATTTCTATTGCGCAGACCACTGAAGGTGCGCTGAATGAA ATCAACAACAACCTGCAGCGTGTGCGTGAGTTGTCTGTTCAGGCCACTAACGGGACTAACTCT GATTCCGATCTGAAATCTATCCAGGATGAAATTCAGCAACGTCTGGAAGAAATCGATCGCGTT TCTAATCAGACTCAATTTAACGGTGTTAAAGTCCTGTCTCAGGACAACCAGATGAAAATCCAG GTTGGTGCTAACGATGGTGAAACCATTACCATCGATCTGCAAAAAATTGATGTGAAAAGCCTT GGCCTTGATGGGTTCAATGTTAATTCCCCGGGAATTTCCGGTGGTGGTGGTGGAATTCTAGAC TCCATGGGTACATTAATCAATGAAGACGCTGCCGCAGCCAAGAAAGTACCGCTAACCCACTG GCTTCAATTGATTCTGCATTGTCAAAAGTGGACAGTTCGTTCTTCTCTGGGGGCAATTCAA AACCGTTTTGATTCAGCCATTACCAACCTTGGCAATACGGTAACCAATCTGAACTCCGCGCGT AGCCGTATCGAAGATGCTGACTATGCAACGGAAGTTTCTAATATGTCTAAAGCGCAGATTCTG CAGCAGGCTGGTACTTCCGTTCTGGCGCAGGCTAACCAGGTTCCGCAAAACGTCCTCTCTTTA CTGGTTCCGCGGGTTCTCATCATCATCATCATCATGGTATGGCTAGCATGACTGGTGGACAG CAAATGGGTCGGGATCTGTACGACGATGACGATAAGGATCCGTAAGTCGACAAGCTTGCG |

TABLE 1-continued

Illustrative Flagellin Compositions

| SEQ ID | Construct Name | DNA/PRT | Sequence |
|---|---|---|---|
| 0025 | Mutant 45CT Forward F45CT | DNA | Artificial Sequence<br>CGAAAGACCATATGGCAGGCCAGGCGATTGC |
| 0026 | Mutant 45CT Reverse R45CT | DNA | Artificial Sequence<br>CGCAAGCTTGTCGACTTACGGATCCTTATCGTC |
| 0027 | Mutant 45CT Sequence of 45CT construct | DNA | Artificial Sequence<br>TAATACGACTCACTATAGGGGAATTGTGAGCGGATAACAATTCCCCTCTAGAAATAATTTTGT<br>TTAACTTTAAGAAGGAGATATACATATGGCAGGCCAGGCGATTGCTAACCGCTTCACTTCTAA<br>TATCAAAGGTCTGACTCAGGCTTCCCGTAACGCTAACGACGGCATTTCTATTGCGCAGACCAC<br>TGAAGGTGCGCTGAATGAAATCAACAACAACCTGCAGCGTGTGCGTGAGTTGTCTGTTCAGGC<br>CACTAACGGGACTAACTCTGATTCCGATCTGAAATCTATCCAGGATGAAATTCAGCAACGTCT<br>GGAAGAAATCGATCGCGTTTCTAATCAGACTCAATTTAACGGTGTTAAAGTCCTGTCTCAGGA<br>CAACCAGATGAAAATCCAGGTTGGTGCTAACGATGGTGAAACCATTACCATCGATCTGCAAAA<br>AATTGATGTGAAAAGCCTTGGCCTTGATGGGTTCAATGTTAATTCCCCGGGAATTTCCGGTGG<br>TGGTGGTGGAATTCTAGACTCCATGGGTACATTAATCAATGAAGACGCTGCCGCAGCCAAGAA<br>AAGTACCGCTAACCCACTGGCTTCAATTGATTCTGCATTGTCAAAAGTGGACGCAGTTCGTTC<br>TTCTCTGGGGGCAATTCAAAACCGCTTTGATTCAGCCATTACCAACCTTGGCAATACGGTAAC<br>CAATCTGAACTCCGCGCGTAGCCGTATCGAAGATGCTGACTATGCAACGGAAGTTTCTAATAT<br>GTCTAAAGCGCAGATTCTGCAGCAGGCTGGTACTTCCGTTCTGGCGCAGGCTAACCAGGTTCC<br>GCAAAACGTCCTCTCTTTACTGGTTCCGCGGGGTTCTCATCATCATCATCATGGTATGGC<br>TAGCATGACTGGTGGACAGCAAATGGGTCGGGATCTGTACGACGATGACGATAAGGATCCGTA<br>AGTCGAC |
| 0028 | Mutant 45CT Expressed Mutant 45CT | PRT | Artificial Sequence<br>MAGQAIANRFTSNIKGLTQASRNANDGISIAQTTEGALNEINNNLQRVRELSVQATNGTNSDS<br>DLKSIQDEIQQRLEEIDRVSNQTQFNGVKVLSQDNQMKIQVGANDGETITIDLQKIDVKSLGL<br>DGFNVNSPGISGGGGGILDSMGTLINEDAAAAKKSTANPLASIDSALSKVDAVRSSLGAIQNR<br>FDSAITNLGNTVTNLNSARSRIEDADYATEVSNMSKAQILQQAGTSVLAQANQVPQNVLSLLV<br>PRGSHHHHHHGMASMTGGQQMGRDLYDDDDKDP |
| 0029 | Mutant 33GPS Expressed Mutant 33ML | DNA | Artificial Sequence<br>ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTAACGGGACTAACTCTGATTCCGATCTGAAATCTATCGGACCATCAGGT<br>CAGGATGAAATTCAGCAACGTCTGGAAGAAATCGATCGCGTTTCTAATCAGACTCAATTTAAC<br>GGTGTTAAAGTCCTGTCTCAGGACAACCAGATGAAAATCCAGGTTGGTGCTAACGATGGTGAA<br>ACCATTACCATCGATCTGCAAAAAATTGATGTGAAAAGCCTTGGCCTTGATGGGTTCAATGTT<br>AATTCCCCGGGAAGTACCGCTAACCCACTGGCTTCAATTGATTCTGCATTGTCAAAAGTGGAC<br>GCAGTTCGTTCTTCTCTGGGGGCAATTCAAAACCGCTTTGATTCAGCCATTACCAACCTTGGC<br>AATACGGTAACCAATCTGAACTCCGCGCGTAGCCGTATCGAAGATGCTGACTATGCAACGGAA<br>GTTTCTAATATGTCTAAAGCGCAGATTCTGCAGCAGGCTGGTACTTCCGTTCTGGCGCAGGCT<br>AACCAGGTTCCGCAAAACGTCCTCTCTTTACTGGTTCCGCGGGGTTCTCATCATCATCATCAT<br>CATGGTTAA |
| 0030 | Mutant 33GPS Expressed Mutant 33ML | PRT | Artificial Sequence<br>MSGLRINSAKDDAAGQAIANRFTSNIKGLTQASRNANDGISIAQTTEGALNEINNNLQRVREL<br>SVQATNGTNSDSDLKSIGPSGQDEIQQRLEEIDRVSNQTQFNGVKVLSQDNQMKIQVGANDGE<br>TITIDLQKIDVKSLGLDGFNVNSPGSTANPLASIDSALSKVDAVRSSLGAIQNRFDSAITNLG<br>NTVTNLNSARSRIEDADYATEVSNMSKAQILQQAGTSVLAQANQVPQNVLSLLVPRGSHHHHH<br>HG |
| 0031 | Mutant 33GPS Forward primer FSY3CT | DNA | Artificial Sequence<br>GATATACATATGAGCGGGTTACGGATCAACAG |
| 0032 | Mutant 33GPS Reverse primer RMIMxN | DNA | Artificial Sequence<br>AGATCTCCCGGGGAATTAACATTGAACCC |
| 0033 | Mutant 33GPS DNA sequence of mutant 33GPS | DNA | Artificial Sequence<br>TAATACGACTCACTATAGGGGAATTGTGAGCGGATAACAATTCCCCTCTAGAAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTGGACCATCAGGTGAAATTCAGCAA<br>CGTCTGGAAGAAATCGATCGCGTTTCTAATCAGACTCAATTTAACGGTGTTAAAGTCCTGTCT<br>CAGGACAACCAGATGAAAATCCAGGTTGGTGCTAACGATGGTGAAACCATTACCATCGATCTG<br>CAAAAAATTGATGTGAAAAGCCTTGGCCTTGATGGGTTCAATGTTAATTCCCCGGGAAGTACC<br>GCTAACCCACTGGCTTCAATTGATTCTGCATTGTCAAAAGTGGACGCAGTTCGTTCTTCTCTG<br>GGGGCAATTCAAAACCGCTTTGATTCAGCCATTACCAACCTTGGCAATACGGTAACCAATCTG<br>AACTCCGCGCGTAGCCGTATCGAAGATGCTGACTATGCAACGGAAGTTTCTAATATGTCTAAA<br>GCGCAGATTCTGCAGCAGGCTGGTACTTCCGTTCTGGCGCAGGCTAACCAGGTTCCGCAAAAC<br>GTCCTCTCTTTACTGGTTCCGCGGGGTTCTCATCATCATCATCATCATGGTTAAGTCGAC |
| 0034 | Mutant 33GPS Expressed Mutant 33GPS | PRT | Artificial Sequence<br>MSGLRINSAKDDAAGQAIANRFTSNIKGLTQASRNANDGISIAQTTEGALNEINNNLQRVREL<br>SVQATGPSGEIQQRLEEIDRVSNQTQFNGVKVLSQDNQMKIQVGANDGETITIDLQKIDVKSL<br>GLDGFNVNSPGSTANPLASIDSALSKVDAVRSSLGAIQNRFDSAITNLGNTVTNLNSARSRIE<br>DADYATEVSNMSKAQILQQAGTSVLAQANQVPQNVLSLLVPRGSHHHHHHG |

TABLE 1-continued

Illustrative Flagellin Compositions

| SEQ ID | Construct Name | DNA/PRT | Sequence |
|---|---|---|---|
| 0035 | Mutant 33ML Mutant 33CT (Fixed A) | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGISGGGGGILDSMGTLINEDAAAAKKSTANPLASIDSALSKVD AVRSSLGAIQNRFDSAITNLGNTVTNLNSARSRIEDADYATEVSNMSKAQILQQAGTSVLAQA NQVPQNVLSLLVPRGSHHHHHG |
| 0036 | Mutant 33ML Mutant 33CT (Fixed A) | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA ATTTCCGGTGGTGGTGGTGGAATTCTAGACTCCATGGGTACATTAATCAATGAAGACGCTGCC GCAGCCAAGAAAAGTACCGCTAACCCACTGGCTTCAATTGATTCTGCATTGTCAAAAGTGGAC GCAGTTCGTTCTTCTCTGGGGGCAATTCAAAACCGCTTTGATTCAGCCATTACCAACCTTGGC AATACGGTAACCAATCTGACTCCGCGCGTAGCCGTATCGAAGATGCTGACTATGCAACGGAA GTTTCTAATATGTCTAAAGCGCAGATTCTGCAGCAGGCTGGTACTTCCGTTCTGGCGCAGGCT AACCAGGTTCCGCAAAACGTCCTCTCTTTACTGGTTCCGCGGGGTTCTCATCATCATCATCAT CATGGTTAA |
| 0037 | Mutant 33ML Forward primer F502ML | DNA | Artificial Sequence TCTAGACCCGGGAAGTACCGCTAACCCACTGGCTTCAATTG |
| 0038 | Mutant 33ML Reverse primer R33CT | DNA | Artificial Sequence CCAGTCATGTCGACTTAACCATGATGATGATGATGAG |
| 0039 | Mutant 33ML 502 template sequence | DNA | Artificial Sequence CTCATCATCATCATCATCATGGTTAAGTCGACAAGCTTGCGGCCGCAGAGCTCGC |
| 0040 | Mutant 33ML 33ML construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATGGTAAGTCGAC |
| 0041 | Mutant 33ML Expressed Mutant 33ML | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGACTCCGCGCGTAGCCGTATCGAAGATGCTGACTATGCAACGGAAGTTTCTAATATG TCTAAAGCGCAGATTCTGCAGCAGGCTGGTACTTCCGTTCTGGCGCAGGCTAACCAGGTTCCG CAAAACGTCCTCTCTTTACTGGTTCCGCGGGGTTCTCATCATCATCATCATGGTTAA |
| 0042 | Mutant 33ML Mutant 33ML | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHG |
| 0043 | Mutant 37CT delta ND0 mutant based on CBLB506T | DNA | Artificial Sequence ATGGCACAAGTCATTAATACAAACAGCCTGTCGCTGTTGACCCAGAATAACCTGAACAAATCT CAGTCCTCACTGAGTTCCGCTATTGAGCGTCTGTCCTCTGGTCTGCGTATCAACGGCGCGAAA GACGATGCAGGCCAGGCCATTGCTAACCGCTTCACTTCTAATATCAAAGGTCTGACTCAGGCT GCTTCCCGTAACGCTAACGACGGCATTTCTATTGCGCAGACCACTGAAGGTGCGCTGAATGAA ATCAACAACAACCTGCAGCGTGTGCGTGAGTTGTCTGTTCAGGCCACTAACGGGACTAACTCT GATTCCGATCTGAAATCTATCCAGGATGAAATTCAGCAACGTCTGGAAGAAATCGATCGCGTT TCTAATCAGACTCAATTTAACGGTGTTAAAGTCCTGTCTCAGGACAACCAGATGAAAATCCAG GTTGGTGCTAACGATGGTGAAACCATTACCATCGATCTGCAAAAAATTGATGTGAAAAGCCTT |

TABLE 1-continued

Illustrative Flagellin Compositions

| SEQ ID | Construct Name | DNA/PRT | Sequence |
|---|---|---|---|
| | | | GGCCTTGATGGGTTCAATGTTAATTCCCCGGGAATTTCCGGTGGTGGTGGTGGAATTCTAGAC<br>TCCATGGGTACATTAATCAATGAAGACGCTGCCGCAGCCAAGAAAAGTACCGCTAACCCACTG<br>GCTTCAATTGATTCTGCATTGTCAAAAGTGGACGCAGTTCGTTCTTCTCTGGGGGCAATTCAA<br>AACCGCTTTGATTCAGCCATTACCAACCTTGGCAATACGGTAACCAATCTGAACTCCGCGCGT<br>AGCCGTATCGAAGATGCTGACTATGCAACGGAAGTTTCTAATATGTCTAAAGCGCAGATTCTG<br>CAGCAGGCTGGTACTTCCGTTCTGGCGCAGGCTAACCAGGTTCCGCAAAACGTCCTCTCTTTA<br>CTGGTTCCGCGGGGTTCTCATCATCATCATCATCATGGTATGGCTAGCATGACTGGTGGACAG<br>CAAATGGGTCGGGATCTGTACGACGATGACGATAAGGATCCGTAAGTCGACAAGCTTGCG |
| 0044 | Mutant 37CT delta ND0 mutant based on CBLB506T | PRT | Artificial Sequence | MAQVINTNSLSLLTQNNLNKSQSSLSSAIERLSSGLRINGAKDDAAGQAIANRFTSNIKGLTQ<br>ASRNANDGISIAQTTEGALNEINNNLQRVRELSVQATNGTNSDSDLKSIQDEIQQRLEEIDRV<br>SNQTQFNGVKVLSQDNQMKIQVGANDGETITIDLQKIDVKSLGLDGFNVNSPGISGGGGGILD<br>SMGTLINEDAAAAKKSTANPLASIDSALSKVDAVRSSLGAIQNRFDSAITNLGNTVTNLNSAR<br>SRIEDADYATEVSNMSKAQILQQAGTSVLAQANQVPQNVLSLLVPRGSHHHHHHGMASMTGGQ<br>AMGRDLYDDDDKDP |
| 0045 | Mutant 37CT Forward F37CT | DNA | Artificial Sequence | CTCTGGTCATATGATCAACAGCGCGAAAGACGATGC |
| 0046 | Mutant 37CT Reverse R37CT | DNA | Artificial Sequence | TCTAGAGTCGACTATTAAGCCATACCATGATGATGATGATGAG |
| 0047 | Mutant 37CT 37CT construct | DNA | Artificial Sequence | TAATACGACTCACTATAGGGGAATTGTGAGCGGATAACAATTCCCCTCTAGAAATAATTTTGT<br>TTAACTTTAAGAAGGAGATATACATATGATCAACAGCGCGAAAGACGATGCGGCAGGCCAGGC<br>GATTGCTAACCGCTTCACTTCTAATATCAAAGGTCTGACTCAGGCTTCCCGTAACGCTAACGA<br>CGGCATTTCTATTGCGCAGACCACTGAAGGTGCGCTGAATGAAATCAACAACAACCTGCAGCG<br>TGTGCGTGAGTTGTCTGTTCAGGCCACTAACGGGACTAACTCTGATTCCGATCTGAAATCTAT<br>CCAGGATGAAATTCAGCAACGTCTGGAAGAAATCGATCGCGTTTCTAATCAGACTCAATTTAA<br>CGGTGTTAAAGTCCTGTCTCAGGACAACCAGATGAAAATCCAGGTTGGTGCTAACGATGGTGA<br>AACCATTACCATCGATCTGCAAAAAATTGATGTGAAAAGCCTTGGCCTTGATGGGTTCAATGT<br>TAATTCCCCGGGAATTTCCGGTGGTGGTGGTGGAATTCTAGACTCCATGGGTACATTAATCAA<br>TGAAGACGCTGCCGCAGCCAAGAAAAGTACCGCTAACCCACTGGCTTCAATTGATTCTGCATT<br>GTCAAAAGTGGACGCAGTTCGTTCTTCTCTGGGGCAATTCAAAACCGCTTTGATTCAGCCAT<br>TACCAACCTTGGCAATACGGTAACCAATCTGAACTCCGCGCGTAGCCGTATCGAAGATGCTGA<br>CTATGCAACGGAAGTTTCTAATATGTCTAAAGCGCAGATTCTGCAGCAGGCTGGTACTTCCGT<br>TCTGGCGCAGGCTAACCAGGTTCCGCAAAACGTCCTCTCTTTACTGGTTCCGCGGGGTTCTCA<br>TCATCATCATCATGGTATGGCTTAATAGTCGAC |
| 0048 | Mutant 37CT Mutant 37CT | PRT | Artificial Sequence | MINSAKDDAAGQAIANRFTSNIKGLTQASRNANDGISIAQTTEGALNEINNNLQRVRELSVQA<br>TNGTNSDSDLKSIQDEIQQRLEEIDRVSNQTQFNGVKVLSQDNQMKIQVGANDGETITIDLQK<br>IDVKSLGLDGFNVNSPGISGGGGGILDSMGTLINEDAAAAKKSTANPLASIDSALSKVDAVRS<br>SLGAIQNRFDSAITNLGNTVTNLNSARSRIEDADYATEVSNMSKAQILQQAGTSVLAQANQVP<br>QNVLSLLVPRGSHHHHHHGMA |
| 0049 | Mutant 445 502-SY1 | PRT | Artificial Sequence | MRGSHHHHHHGMASMTGGQQMGRDLYDLVPRGSAKDPMAQVINTNSLSLLTQNNLNKSQSSLS<br>SAIERLSSGLRINSAKDDAAGQAIANRFTSNIKGLTQASRNANDGISIAQTTEGALNEINNNL<br>QRVRELSVQATNGTNSDSDLKSIQDEIQQRLEEIDRVSNQTQFNGVKVLSQDNQMKIQVGAND<br>GETITIDLQKIDVKSLGLDGFNVNSPGISGGGGILDSMGTLINEDAAAAKKSTANPLASIDS<br>ALSKVDAVRSSLGAIQNRFDSAITNLGNTVTNLNSARSRIEDADYATEVSNMSKAQILQQAGT<br>SVLAQANQVPQNVLSLLR |
| 0050 | Mutant 445 502-SY1 | DNA | Artificial Sequence | ATGCGGGGTTCTCATCATCATCATCATCATGGTATGGCTAGCATGACTGGTGGACAGCAAATG<br>GGTCGGGATCTGTACGACCTTGGTTCCGCGCGGTAGCGCGAAGGATCCGATGGCACAAGTCATT<br>AATACAAACAGCCTGTCGCTGTTGACCCAGAATAACCTGAACAAATCTCAGTCCTCACTGAGT<br>TCCGCTATTGAGCGTCTGTCCTCGGTCTGCGTATCAACAGCGCGAAAGACGATGCGGCAGGC<br>CAGGCGATTGCTAACCGCTTCACTTCTAATATCAAAGGTCTGACTCAGGCTTCCCGTAACGCT<br>AACGACGGCATTTCTATTGCGCAGACCACTGAAGGTGCGCTGAATGAAATCAACAACAACCTG<br>CAGCGTGTGCGTGAGTTGTCTGTTCAGGCCACTAACGGGACTAACTCTGATTCCGATCTGAAA<br>TCTATCCAGGATGAAATTCAGCAACGTCTGGAAGAAATCGATCGCGTTTCTAATCAGACTCAA<br>TTTAACGGTGTTAAAGTCCTGTCTCAGGACAACCAGATGAAAATCCAGGTTGGTGCTAACGAT<br>GGTGAAACCATTACCATCGATCTGCAAAAAATTGATGTGAAAAGCCTTGGCCTTGATGGGTTC<br>AATGTTAATTCCCCGGGAATTTCCGGTGGTGGTGGTGGAATTCTAGACTCCATGGGTACATTA<br>ATCAATGAAGACGCTGCCGCAGCCAAGAAAAGTACCGCTAACCCACTGGCTTCAATTGATTCT<br>GCATTGTCAAAAGTGGACGCAGTTCGTTCTTCTCTGGGGCAATTCAAAACCGTTTTGATTCA<br>GCCATTACCAACCTTGGCAATACGGTAACCAATCTGAACTCCGCGCGTAGCCGTATCGAAGAT<br>GCTGACTATGCAACGGAAGTTTCTAATATGTCTAAAGCGCAGATTCTGCAGCAGGCTGGTACT<br>TCCGTTCTGGCGCAGGCTAACCAGGTTCCGCAAAACGTCCTCTCTTTACTGCGTTAA |
| 0051 | Mutant 445 Forward Primer CBLB445 | DNA | Artificial Sequence | GGCAATTCAAAACCGTTTTGATTAAGCCATTACCAACCTTGG |
| 0052 | Mutant 445 Reverse Primer CBLB445 | DNA | Artificial Sequence | CCAAGGTTGGTAATGGCTTAATCAAAACGGTTTTGAATTGCC |

TABLE 1-continued

Illustrative Flagellin Compositions

| SEQ ID | Construct Name | DNA/PRT | Sequence |
|---|---|---|---|
| 0053 | Mutant 445 mutant 445 | DNA | Artificial Sequence TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGGATCTGTACGACCTGGTTCCGCGCGGTAGCGCG AAGGATCCGATGGCACAAGTCATTAATACAAACAGCCTGTCGCTGTTGACCCAGAATAACCTG AACAAATCTCAGTCCTCACTGAGTTCCGCTATTGAGCGTCTGTCCTCTGGTCTGCGTATCAAC AGCGCGAAAGACGATGCGGCAGGCCAGGCGATTGCTAACCGCTTCACTTCTAATATCAAAGGT CTGACTCAGGCTTCCCGTAACGCTAACGACGGCATTTCTATTGCGCAGACCACTGAAGGTGCG CTGAATGAAATCAACAACAACCTGCAGCGTGTGCGTGAGTTGTCTGTTCAGGCCACTAACGGG ACTAACTCTGATTCCGATCTGAAATCTATCCAGGATGAAATTCAGCAACGTCTGGAAGAAATC GATCGCGTTTCTAATCAGACTCAATTTAACGGTGTTAAAGTCCTGTCTCAGGACAACCAGATG AAAATCCAGGTTGGTGCTAACGATGGTGAAACCATTACCATCGATCTGCAAAAATTGATGTG AAAAGCCTTGGCCTTGATGGGTTCAATGTTAATTCCCCGGGAATTTCCGGTGGTGGTGGTGGA ATTCTAGACTCCATGGGTACATTAATCAATGAAGACGCTGCCGCAGCCAAGAAAAGTACCGCT AACCCACTGGCTTCAATTGATTCTGCATTGTCAAAAGTGGACGCAGTTCGTTCTTCTCTGGGG GCAATTCAAAACCGTTTTGATTAA |
| 0054 | Mutant 445 mutant 445 | PRT | Artificial Sequence MRGSHHHHHHGMASMTGGQQMGRDLYDLVPRGSAKDPMAQVINTNSLSLLTQNNLNKSQSSLS SAIERLSSGLRINSAKDDAAGQAIANRFTSNIKGLTQASRNANDGISIAQTTEGALNEINNNL QRVRELSVQATNGTNSDSDLKSIQDEIQQRLEEIDRVSNQTQFNGVKVLSQDNQMKIQVGAND GETITIDLQKIDVKSLGLDGFNVSPGISGGGGGILDSMGTLINEDAAAAKKSTANPLASIDS ALSKVDAVRSSLGAIQNRFD |
| 0055 | Mutant 461 Forward Primer CBLB461 | DNA | Artificial Sequence CAATCTGAACTCCGCGCGTTGACGTATCTAAGATGCTGACTATGC |
| 0056 | Mutant 461 Reverse Primer CBLB461 | DNA | Artificial Sequence GCATAGTCAGCATCTTAGATACGTCAACGCGCGGAGTTCAGATTG |
| 0057 | Mutant 461 Mutant 461 | DNA | Artificial Sequence TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGGATCTGTACGACCTGGTTCCGCGCGGTAGCGCG AAGGATCCGATGGCACAAGTCATTAATACAAACAGCCTGTCGCTGTTGACCCAGAATAACCTG AACAAATCTCAGTCCTCACTGAGTTCCGCTATTGAGCGTCTGTCCTCTGGTCTGCGTATCAAC AGCGCGAAAGACGATGCGGCAGGCCAGGCGATTGCTAACCGCTTCACTTCTAATATCAAAGGT CTGACTCAGGCTTCCCGTAACGCTAACGACGGCATTTCTATTGCGCAGACCACTGAAGGTGCG CTGAATGAAATCAACAACAACCTGCAGCGTGTGCGTGAGTTGTCTGTTCAGGCCACTAACGGG ACTAACTCTGATTCCGATCTGAAATCTATCCAGGATGAAATTCAGCAACGTCTGGAAGAAATC GATCGCGTTTCTAATCAGACTCAATTTAACGGTGTTAAAGTCCTGTCTCAGGACAACCAGATG AAAATCCAGGTTGGTGCTAACGATGGTGAAACCATTACCATCGATCTGCAAAAATTGATGTG AAAAGCCTTGGCCTTGATGGGTTCAATGTTAATTCCCCGGGAATTTCCGGTGGTGGTGGTGGA ATTCTAGACTCCATGGGTACATTAATCAATGAAGACGCTGCCGCAGCCAAGAAAAGTACCGCT AACCCACTGGCTTCAATTGATTCTGCATTGTCAAAAGTGGACGCAGTTCGTTCTTCTCTGGGG GCAATTCAAAACCGTTTTGATTCAGCCATTACCAACCTTGGCAATACGGTAACCAATCTGAAC TCCGCGCGTTGACGTATCTAA |
| 0058 | Mutant 461 Mutant 461 | PRT | Artificial Sequence MRGSHHHHHHGMASMTGGQQMGRDLYDLVPRGSAKDPMAQVINTNSLSLLTQNNLNKSQSSLS SAIERLSSGLRINSAKDDAAGQAIANRFTSNIKGLTQASRNANDGISIAQTTEGALNEINNNL QRVRELSVQATNGTNSDSDLKSIQDEIQQRLEEIDRVSNQTQFNGVKVLSQDNQMKIQVGAND GETITIDLQKIDVKSLGLDGFNVSPGISGGGGGILDSMGTLINEDAAAAKKSTANPLASIDS ALSKVDAVRSSLGAIQNRFDSAITNLGNTVTNLNSAR |
| 0059 | Mutant 467 Forward Primer CBLB467 | DNA | Artificial Sequence CGTAGCCGTATCGAAGATGCTTAATAGGCAACGGAAGTTTCTAATATG |
| 0060 | Mutant 467 Reverse Primer CBLB467 | DNA | Artificial Sequence CATATTAGAAACTTCCGTTGCCTATTAAGCATCTTCGATACGGCTACG |
| 0061 | Mutant 467 Mutant 467 | DNA | Artificial Sequence TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGGATCTGTACGACCTGGTTCCGCGCGGTAGCGCG AAGGATCCGATGGCACAAGTCATTAATACAAACAGCCTGTCGCTGTTGACCCAGAATAACCTG AACAAATCTCAGTCCTCACTGAGTTCCGCTATTGAGCGTCTGTCCTCTGGTCTGCGTATCAAC AGCGCGAAAGACGATGCGGCAGGCCAGGCGATTGCTAACCGCTTCACTTCTAATATCAAAGGT CTGACTCAGGCTTCCCGTAACGCTAACGACGGCATTTCTATTGCGCAGACCACTGAAGGTGCG CTGAATGAAATCAACAACAACCTGCAGCGTGTGCGTGAGTTGTCTGTTCAGGCCACTAACGGG ACTAACTCTGATTCCGATCTGAAATCTATCCAGGATGAAATTCAGCAACGTCTGGAAGAAATC GATCGCGTTTCTAATCAGACTCAATTTAACGGTGTTAAAGTCCTGTCTCAGGACAACCAGATG AAAATCCAGGTTGGTGCTAACGATGGTGAAACCATTACCATCGATCTGCAAAAATTGATGTG AAAAGCCTTGGCCTTGATGGGTTCAATGTTAATTCCCCGGGAATTTCCGGTGGTGGTGGTGGA ATTCTAGACTCCATGGGTACATTAATCAATGAAGACGCTGCCGCAGCCAAGAAAAGTACCGCT |

TABLE 1-continued

Illustrative Flagellin Compositions

| SEQ ID | Construct Name | DNA/PRT | Sequence |
|---|---|---|---|
| | | | AACCCACTGGCTTCAATTGATTCTGCATTGTCAAAAGTGGACGCAGTTCGTTCTTCTCTGGGG<br>GCAATTCAAAACCGTTTTGATTCAGCCATTACCAACCTTGGCAATACGGTAACCAATCTGAAC<br>TCCGCGCGTAGCCGTATCGAAGATGCTTAATAG |
| 0062 | Mutant 467<br>Mutant 467 | PRT | Artificial<br>Sequence | MRGSHHHHHHGMASMTGGQQMGRDLYDLVPRGSAKDPMAQVINTNSLSLLTQNNLNKSQSSLS<br>SAIERLSSGLRINSAKDDAAGQAIANRFTSNIKGLTQASRNANDGISIAQTTEGALNEINNNL<br>QRVRELSVQATNGTNSDSDLKSIQDEIQQRLEEIDRVSNQTQFNGVKVLSQDNQMKIQVGAND<br>GETITIDLQKIDVKSLGLDGFNVNSPGISGGGGGILDSMGTLINEDAAAAKKSTANPLASIDS<br>ALSKVDAVRSSLGAIQNRFDSAITNLGNTVTNLNSARSRIEDA |
| 0063 | Mutant 470CT<br>CBLB502 | DNA | Artificial<br>Sequence | ATGCGGGGTTCTCATCATCATCATCATCATGGTATGGCTAGCATGACTGGTGGACAGCAAATG<br>GGTCGGGATCTGTACGACGATGACGATAAGGATCCGATGGCACAAGTCATTAATACAAACAGC<br>CTGTCGCTGTTGACCCAGAATAACCTGAACAAATCTCAGTCCTCACTGAGTTCCGCTATTGAG<br>CGTCTGTCCTCTGGTCTGCGTATCAACAGCGCGAAAGACGATGCGGCAGGCCAGGCGATTGCT<br>AACCGCTTCACTTCTAATATCAAAGGTCTGACTCAGGCTTCCCGTAACGCTAACGACGGCATT<br>TCTATTGCGCAGACCACTGAAGGTGCGCTGAATGAAATCAACAACAACCTGCAGCGTGTGCGT<br>GAGTTGTCTGTTCAGGCCACTAACGGGACTAACTCTGATTCCGATCTGAAATCTATCCAGGAT<br>GAAATTCAGCAACGTCTGGAAGAAATCGATCGCGTTTCTAATCAGACTCAATTTAACGGTGTT<br>AAAGTCCTGTCTCAGGACAACCAGATGAAAATCCAGGTTGGTGCTAACGATGGTGAAACCATT<br>ACCATCGATCTGCAAAAAATTGATGTGAAAAGCCTTGGCCTTGATGGGTTCAATGTTAATTCC<br>CCGGGAATTTCCGGTGGTGGTGGTGGAATTCTAGACTCCATGGGTACATTAATCAATGAAGAC<br>GCTGCCGCAGCCAAGAAAAGTACCGCTAACCCACTGGCTTCAATTGATTCTGCATTGTCAAAA<br>GTGGACGCAGTTCGTTCTTCTCTGGGGGCAATTCAAAACCGTTTTGATTCAGCCATTACCAAC<br>CTTGGCAATACGGTAACCAATCTGAACTCCGCGCGTAGCCGTATCGAAGATGCTGACTATGCT<br>AACGGAAGTTTCTAATATGTCTAAAGCGCAGATTCTGCAGCAGGCTGGTACTTCCGT<br>CTGGCGCAGGCTAACCAGGTTCCGCAAAACGTCCTCTCTTTACTGCGTTAA |
| 0064 | Mutant 470CT<br>Forward Primer<br>F470CT | DNA | Artificial<br>Sequence | CGATAAGGATCATATGGCACAAGTCATTAATAC |
| 0065 | Mutant 470CT<br>Reverse Primer<br>R470CT | DNA | Artificial<br>Sequence | AGATCTGTCGACTTAACCATGATGATGATGATGATGAGAACCCCGCGGAACCAGTGCATAGTC<br>AGCATCTTCGATACG |
| 0066 | Mutant 470CT<br>Mutant 470CT | DNA | Artificial<br>Sequence | TAATACGACTCACTATAGGGGAATTGTGAGCGGATAACAATTCCCCTCTAGAATAATTTTGTT<br>TAACTTTAAGAAGGAGATATACATATGGCACAAGTCATTAATACAAACAGCCTGTCGCTGTTG<br>ACCCAGAATAACCTGAACAAATCTCAGTCCTCACTGAGTTCCGCTATTGAGCGTCTGTCCTCT<br>GGTCTGCGTATCAACAGCGCGAAAGACGATGCGGCAGGCCAGGCGATTGCTAACCGCTTCACT<br>TCTAATATCAAAGGTCTGACTCAGGCTTCCCGTAACGCTAACGACGGCATTTCTATTGCGCAG<br>ACCACTGAAGGTGCGCTGAATGAAATCAACAACAACCTGCAGCGTGTGCGTGAGTTGTCTGTT<br>CAGGCCACTAACGGGACTAACTCTGATTCCGATCTGAAATCTATCCAGGATGAAATTCAGCAA<br>CGTCTGGAAGAAATCGATCGCGTTTCTAATCAGACTCAATTTAACGGTGTTAAAGTCCTGTCT<br>CAGGACAACCAGATGAAAATCCAGGTTGGTGCTAACGATGGTGAAACCATTACCATCGATCTG<br>CAAAAAATTGATGTGAAAAGCCTTGGCCTTGATGGGTTCAATGTTAATTCCCCGGGAATTTCC<br>GGTGGTGGTGGTGGAATTCTAGACTCCATGGGTACATTAATCAATGAAGACGCTGCCGCAGCC<br>AAGAAAAGTACCGCTAACCCACTGGCTTCAATTGATTCTGCATTGTCAAAAGTGGACGCAGTT<br>CGTTCTTCTCTGGGGGCAATTCAAAACCGTTTTGATTCAGCCATTACCAACCTTGGCAATACG<br>GTAACCAATCTGAACTCCGCGCGTAGCCGTATCGAAGATGCTGACTATGCACTGGTTCCGCGG<br>GGTTCTCATCATCATCATCATCATGGTTAAGTCGAC |
| 0067 | Mutant 470CT<br>Mutant 470CT | PRT | Artificial<br>Sequence | MAQVINTNSLSLLTQNNLNKSQSSLSSAIERLSSGLRINSAKDDAAGQAIANRFTSNIKGLTQ<br>ASRNANDGISIAQTTEGALNEINNNLQRVRELSVQATNGTNSDSDLKSIQDEIQQRLEEIDRV<br>SNQTQFNGVKVLSQDNQMKIQVGANDGETITIDLQKIDVKSLGLDGFNVNSPGISGGGGGILD<br>SMGTLINEDAAAAKKSTANPLASIDSALSKVDAVRSSLGAIQNRFDSAITNLGNTVTNLNSAR<br>SRIEDADYALVPRGSHHHHHHG |
| 0068 | Mutant 485CT<br>Reverse primer<br>R485MC | DNA | Artificial<br>Sequence | AGATCTCCGCGGAACCAGACCAGCCTGCTGCAGAATCTGC |
| 0069 | Mutant 485CT<br>DNA Sequence<br>of 485CT | DNA | Artificial<br>Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTCTGGTTCCG<br>CGGGGTTCTCATCATCATCATCATCATGGTTAAGTCGAC |

TABLE 1-continued

Illustrative Flagellin Compositions

| SEQ ID | Construct Name | DNA/PRT | Sequence |
|---|---|---|---|
| 0070 | Mutant 485CT Mutant 485CT | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCAACGGAAGTTTCTAATATG TCTAAAGCGCAGATTCTGCAGCAGGCTGGTCTGGTTCCGCGGGGTTCTCATCATCATCATCAT CATGGTTAA |
| 0071 | Mutant 485CT Mutant 485CT | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGLVPRGSHHHHHHG |
| 0072 | Mutant 485D DNA template for deletion mutations from Mutant 485CT variant | DNA | Artificial Sequence AACCCACTGGCTTCAATTGATTCTGCATTGTCAAAAGTGGACGCAGTTCGTTCTTCTCTGGGG GCAATTCAAAACCGTTTTGATTCAGCCATTACCGCCCTTGGCAATACGGTAACCAAT |
| 0073 | Mutant 485D PRT sequence for deletion mutations from Mutant 485CT variant | PRT | Artificial Sequence NPLASIDSALSKVDAVRSSLGAIQNRFDSAITALGNTVTN |
| 0074 | Mutant 485D Forward Primer F485D | DNA | Artificial Sequence GTTCGTTCTTCTCTGGGGGCAATTGATTCAGCCATTACCGCCCTTG |
| 0075 | Mutant 485D Reverse Primer R485D | DNA | Artificial Sequence CAAGGGCGGTAATGGCTGAATCAATTGCCCCCAGAGAAGAACGAAC |
| 0076 | Mutant 485D DNA Sequence of 485CT_Delta construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTGATTCAGCCATTACCGCCCTTGGC AATACGGTAACCAATCTGAACTCCGCGCGTAGCCGTATCGAAGATGCTGACTATGCAACGGAA GTTTCTAATATGTCTAAAGCGCAGATTCTGCAGCAGGCTGGTCTGGTTCCGCGGGGTTCTCAT CATCATCATCATCATGGTTAAGTCGAC |
| 0077 | Mutant 485D Mutant 485D (CT_Delta 439-442) | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIDSAITALGNTVTNLNS ARSRIEDADYATEVSNMSKAQILQQAGLVPRGSHHHHHHG |
| 0078 | Mutant CGD1 Mutant SY3CT | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCACTGGTTCCGCGGGGTTCT CATCATCATCATCATCATGGTTAA |
| 0079 | Mutant CGD1 Mutant SY3CT | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYALVPRGSHHHHHHG |

TABLE 1-continued

Illustrative Flagellin Compositions

| SEQ ID | Construct Name | DNA/PRT | Sequence |
|---|---|---|---|
| 0080 | Mutant CGD1 GFPuv4 | DNA | Artificial Sequence ATGAGTAAAGGAGAAGAACTTTTCACTGGAGTTGTCCCAATTCTTGTTGAATTAGATGGTGAT GTTAATGGGCACAAATTTTCTGTCAGTGGAGAGGGTGAAGGTGATGCAACATACGGAAAACTT ACCCTTAAATTTATTTGCACTACTGGAAAACTACCTGTTCCATGGCCAACACTTGTCACTACT CTGACGTATGGTGTTCAATGCTTTTCCCGTTATCCGGATCATATGAAACGGCATGACTTTTTC AAGAGTGCCATGCCCGAAGGTTATGTACAGGAACGCACTATATCTTTCAAAGATGACGGGAAC TACAAGACGCGTGCTGAAGTCAAGTTTGAAGGTGATACCCTTGTTAATCGTATCGAGTTAAAA GGTATTGATTTTAAAGAAGATGGAAACATTCTCGGACACAAACTCGAGTACAACTATAACTCA CACAATGTATACATCACGGCAGACAAACAAAAGAATGGAATCAAAGCTAACTTCAAAATTCGC CACAACATTGAAGATGGATCCGTTCAACTAGCAGACCATTATCAACAAAATACTCCAATTGGC GATGGCCCTGTCCTTTTACCAGACAACCATTACCTGTCGACACAATCTGCCCTTTTGAAAGAT CCCAACGAAAAGCGTGACCACATGGTCCTTCTTGAGTTTGTAACTGCTGCTGGGATTACACAT GGCATGGATGAACTATACAAA |
| 0081 | Mutant CGD1 GFPuv4 | PRT | Artificial Sequence MSKGEELFTGVVPILVELDGDVNGHKFSVSGEGEGDATYGKLTLKFICTTGKLPVPWPTLVTT LTYGVQCFSRYPDHMKRHDFFKSAMPEGYVQERTISFKDDGNYKTRAEVKFEGDTLVNRIELK GIDFKEDGNILGHKLEYNYNSHNVYITADKQKNGIKANFKIRHNIEDGSVQLADHYQQNTPIG DGPVLLPDNHYLSTQSALLKDPNEKRDHMVLLEFVTAAGITHGMDELYK |
| 0082 | Mutant CGD1 GFPuv4 mutation of wt NdeI site | DNA | Artificial Sequence ATGAGTAAAGGAGAAGAACTTTTCACTGGAGTTGTCCCAATTCTTGTTGAATTAGATGGTGAT GTTAATGGGCACAAATTTTCTGTCAGTGGAGAGGGTGAAGGTGATGCAACATACGGAAAACTT ACCCTTAAATTTATTTGCACTACTGGAAAACTACCTGTTCCATGGCCAACACTTGTCACTACT CTGACGTATGGTGTTCAATGCTTTTCCCGTTATCCGGATCATATGAAACGGCATGACTTTTTC AAGAGTGCCATGCCCGAAGGTTATGTACAGGAACGCACTATATCTTTCAAAGATGACGGGAAC TACAAGACGCGTGCTGAAGTCAAGTTTGAAGGTGATACCCTTGTTAATCGTATCGAGTTAAAA GGTATTGATTTTAAAGAAGATGGAAACATTCTCGGACACAAACTCGAGTACAACTATAACTCA CACAATGTATACATCACGGCAGACAAACAAAAGAATGGAATCAAAGCTAACTTCAAAATTCGC CACAACATTGAAGATGGATCCGTTCAACTAGCAGACCATTATCAACAAAATACTCCAATTGGC GATGGCCCTGTCCTTTTACCAGACAACCATTACCTGTCGACACAATCTGCCCTTTTGAAAGAT CCCAACGAAAAGCGTGACCACATGGTCCTTCTTGAGTTTGTAACTGCTGCTGGGATTACACAT GGCATGGATGAACTATACAAATAA |
| 0083 | Mutant CGD1 Forward primer FCGFP | DNA | Artificial Sequence TCTAGACGGCCGATCTCAGGTAAGAATGGAATCAAAGCTAACTTCAAAATTCGC |
| 0084 | Mutant CGD1 PRT altered GFPuv4 sequence | PRT | Artificial Sequence NVYIPISGKNGIKANFKIRH |
| 0085 | Mutant CGD1 Reverse RCGFP | DNA | Artificial Sequence AGATCTCCGCGGTTTGTATAGTTCATCCATGCCATGTGTAATCCC |
| 0086 | Mutant CGD1 DNA Sequence of CGD1 construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTAGCAACAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCACTGGTTCCGCCGATCTCAGGTAAGAATGGAATCAAAGCTAACTTCAAAATTCGCCAC AACATTGAAGATGGATCCGTTCAACTAGCAGACCATTATCAACAAAATACTCCAATTGGCGAT GGCCCTGTCCTTTTACCAGACAACCATTACCTGTCGACACAATCTGCCCTTTTGAAAGATCCC AACGAAAAGCGTGACCACATGGTCCTTCTTGAGTTTGTAACTGCTGCTGGGATTACACATGGC ATGGATGAACTATACAAACCGCGGGGTTCTCATCATCATCATCATCATGGTTAAGTCGAC |
| 0087 | Mutant CGD1 Expressed Mutant CGD1 | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCACTGGTTCCGCCGATCTCA GGTAAGAATGGAATCAAAGCTAACTTCAAAATTCGCCACAACATTGAAGATGGATCCGTTCAA |

TABLE 1-continued

Illustrative Flagellin Compositions

| SEQ ID | Construct Name | DNA/PRT | Sequence |
|---|---|---|---|
| | | | CTAGCAGACCATTATCAACAAAATACTCCAATTGGCGATGGCCCTGTCCTTTTACCAGACAAC CATTACCTGTCGACACAATCTGCCCTTTTGAAAGATCCCAACGAAAAGCGTGACCACATGGTC CTTCTTGAGTTTGTAACTGCTGCTGGGATTACACATGGCATGGATGAACTATACAAACCGCGG GGTTCTCATCATCATCATCATGGTTAA |
| 0088 | Mutant CGD1 Expressed Mutant CGD1 | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYALVPPISGKNGIKANFKIRHNIEDGSVQLADHYQQNTPIGDGPVLLPDN HYLSTQSALLKDPNEKRDHMVLLEFVTAAGITHGMDELYKPRGSHHHHHHG |
| 0089 | Mutant CPM194 Mutant CPM194 | DNA | Artificial Sequence ATGAGTACCGCTAACCCACTGGCTTCAATTGATTCTGCATTGTCAAAAGTGGACGCAGTTCGT TCTTCTCTGGGGGCAATTCAAAACCGCTTTGATTCAGCCATTACCAACCTTGGCAATACGGTA ACCAATCTGAACTCCGCGCGTAGCCGTATCGAAGATGCTGACTATGCATCCCCGGGAAGCGGG TTACGGATCAACAGCGCGAAAGACGATGCGGCAGGCCAGGCGATTGCTAACCGCTTCACTTCT AATATCAAAGGTCTGACTCAGGCTTCCCGTAACGCTAACGACGGCATTTCTATTGCGCAGACC ACTGAAGGTGCGCTGAATGAAATCAACAACAACCTGCAGCGTGTGCGTGAGTTGTCTGTTCAG GCCACTAACGGGACTAACTCTGATTCCGATCTGAAATCTATCCAGGATGAAATTCAGCAACGT CTGGAAGAAATCGATCGCGTTTCTAATCAGACTCAATTTAACGGTGTTAAAGTCCTGTCTCAG GACAACCAGATGAAAATCCAGGTTGGTGCTAACGATGGTCTGGTTCCGCGGGGTTCTCATCAT CATCATCATCATGGTTAA |
| 0090 | Mutant CPM194 Mutant CPM194 | PRT | Artificial Sequence MSTANPLASIDSALSKVDAVRSSLGAIQNRFDSAITNLGNTVTNLNSARSRIEDADYASPGSG LRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGLVPRGSHH HHHG |
| 0091 | Mutant CPM194 Mutant CPM194 | DNA | Artificial Sequence TAATACGACTCACTATAGGGGAATTGTGAGCGGATAACAATTCCCCTCTAGAATAATTTTGTT TAACTTTAAGAAGGAGATATACATATGAGTACCGCTAACCCACTGGCTTCAATTGATTCTGCA TTGTCAAAAGTGGACGCAGTTCGTTCTTCTCTGGGGGCAATTCAAAACCGCTTTGATTCAGCC ATTACCAACCTTGGCAATACGGTAACCAATCTGAACTCCGCGCGTAGCCGTATCGAAGATGCT GACTATGCATCCCCGGGAAGCGGGTTACGGATCAACAGCGCGAAAGACGATGCGGCAGGCCAG GCGATTGCTAACCGCTTCACTTCTAATATCAAAGGTCTGACTCAGGCTTCCCGTAACGCTAAC GACGGCATTTCTATTGCGCAGACCACTGAAGGTGCGCTGAATGAAATCAACAACAACCTGCAG CGTGTGCGTGAGTTGTCTGTTCAGGCCACTAACGGGACTAACTCTGATTCCGATCTGAAATCT ATCCAGGATGAAATTCAGCAACGTCTGGAAGAAATCGATCGCGTTTCTAATCAGACTCAATTT AACGGTGTTAAAGTCCTGTCTCAGGACAACCAGATGAAAATCCAGGTTGGTGCTAACGATGGT CTGGTTCCGCGGGGTTCTCATCATCATCATCATCATGGTTAAGTCGAC |
| 0092 | Mutant CPM194 Forward primer FCD1 | DNA | Artificial Sequence TCTAGACATATGAGTACCGCTAACCCACTGGCTTCAATTG |
| 0093 | Mutant CPM194 Reverse primer RCD1J | DNA | Artificial Sequence GCTTCCCGGGGATGCATAGTCAGCATCTTCGATACGGC |
| 0094 | Mutant CPM194 Forward primer FND1J | DNA | Artificial Sequence GCATCCCCGGGAAGCGGGTTACGGATCAACAGCG |
| 0095 | Mutant CPM194 Reverse primer RND1 | DNA | Artificial Sequence AGATCTCCGCGGAACCAGACCATCGTTAGCACCAACCTGGATTTTCATCT |
| 0096 | Mutant CPM217 Mutant CPM217 | DNA | Artificial Sequence ATGAGTACCGCTAACCCACTGGCTTCAATTGATTCTGCATTGTCAAAAGTGGACGCAGTTCGT TCTTCTCTGGGGGCAATTCAAAACCGCTTTGATTCAGCCATTACCAACCTTGGCAATACGGTA ACCAATCTGAACTCCGCGCGTAGCCGTATCGAAGATGCTGACTATGCAT TABLE 1-continued Illustrative Flagellin Compositions

| SEQ ID | Construct Name | DNA/PRT | Sequence |
|---|---|---|---|
| | | | ATTACCAACCTTGGCAATACGGTAACCAATCTGAACTCCGCGCGTAGCCGTATCGAAGATGCT<br>GACTATGCATCCCCGGGAAGCGGGTTACGGATCAACAGCGCGAAAGACGATGCGGCAGGCCAG<br>GCGATTGCTAACCGCTTCACTTCTAATATCAAAGGTCTGACTCAGGCTTCCCGTAACGCTAAC<br>GACGGCATTTCTATTGCGCAGACCACTGAAGGTGCGCTGAATGAAATCAACAACAACCTGCAG<br>CGTGTGCGTGAGTTGTCTGTTCAGGCCACTAACGGGACTAACTCTGATTCCGATCTGAAATCT<br>ATCCAGGATGAAATTCAGCAACGTCTGGAAGAAATCGATCGCGTTTCTAATCAGACTCAATTT<br>AACGGTGTTAAAGTCCTGTCTCAGGACAACCAGATGAAAATCCAGGTTGGTGCTAACGATGGT<br>GAAACCATTACCATCGATCTGCAAAAAATTGATGTGAAAAGCCTTGGCCTTGATGGGTTCAAT<br>GTTAATCTGGTTCCGCGGGGTTCTCATCATCATCATCATCATGGTTAAGTCGAC |
| 0099 | Mutant CPM217 Reverse primer RCPM217 | DNA | Artificial Sequence AGATCTCCGCGGAACCAGATTAACATTGAACCCATCAAGGCCAAG |
| 0100 | Mutant GD1G Forward Primer FGFP77 | DNA | Artificial Sequence |
| 0101 | Mutant GD1G Reverse Primer RGFP77 | DNA | Artificial Sequence GAAAAAGTCATGCCGTTTCATGTGATCCGGATAACGGG |
| 0102 | Mutant GD1G FGFP54 | DNA | Artificial Sequence CTGTTCCATGGCCAACACTTG |
| 0103 | Mutant GD1G Forward primer FNGFP | DNA | Artificial Sequence TCTAGACATATGAGTAAAGGAGAAGAACTTTTCACTGGAGTTGTCC |
| 0104 | Mutant GD1G altered GFP DNA sequence | DNA | Artificial Sequence GGCCTATGCGGCCGCAGTAAAGGAGAAGAACTTTTCACTGGAGTTGTCCCAATTCTTGTTGAA |
| 0105 | Mutant GD1G Reverse RNGFP | DNA | Artificial Sequence AGATCTATTAATGCGGCCTGATAGGCCTTGTTTGTCTGCCGTGATGTATACATTGTG |
| 0106 | Mutant GD1G altered GFP PRT sequence | PRT | Artificial Sequence SHNVYITADKQGLSGRNM |
| 0107 | Mutant GD1G DNA Sequence of GD1G construct | DNA | Artificial Sequence TAATACGACTCACTATAGGGAATTGTGAG TABLE 1-continued Illustrative Flagellin Compositions

| SEQ ID | Construct Name | DNA/PRT | Sequence |
|---|---|---|---|
| | | | GGTGCGCTGAATGAAATCAACAACAACCTGCAGCGTGTGCGTGAGTTGTCTGTTCAGGCCACT<br>AACGGGACTAACTCTGATTCCGATCTGAAATCTATCCAGGATGAAATTCAGCAACGTCTGGAA<br>GAAATCGATCGCGTTTCTAATCAGACTCAATTTAACGGTGTTAAAGTCCTGTCTCAGGACAAC<br>CAGATGAAAATCCAGGTTGGTGCTAACGATGGTGAAACCATTACCATCGATCTGCAAAAAATT<br>GATGTGAAAAGCCTTGGCCTTGATGGGTTCAATGTTAATTCCCCGGGAAGTACCGCTAACCCA<br>CTGGCTTCAATTGATTCTGCATTGTCAAAAGTGGACGCAGTTCGTTCTTCTCTGGGGGCAATT<br>CAAAACCGTTTGATTCAGCCATTACCAACCTTGGCAATACGGTAACCAATCTGAACTCCGCG<br>CGTAGCCGTATCGAAGATGCTGACTATGCACTGGTTCCGCCGATCTCAGGTAAGAATGGAATC<br>AAAGCTAACTTCAAAATTCGCCACAACATTGAAGATGGATCCGTTCAACTAGCAGACCATTAT<br>CAACAAAATACTCCAATTGGCGATGGCCCTGTCCTTTTACCAGACAACCATTACCTGTCGACA<br>ATCTGCCCTTTTGAAAGATCCCAACGAAAAGCGTGACCACATGGTCCTTCTTGAGTTTGTA<br>ACTGCTGTGGGATTACACATGGCATGGATGAACTATACAAACCGCGGGGTTCTCATCATCAT<br>CATCATCATGGTTAA |
| 0109 | Mutant GD1G Expressed Mutant GD1G | PRT | Artificial Sequence MSKGEELFTGVVPILVELDGDVNGHKFSVSGEGEGDATYGKLTLKFICTTGKLPVPWPTLVTT<br>LTYGVQCFSRYPDHMKRHDFFKSAMPEGYVQERTISFKDDGNYKTRAEVKFEGDTLVNRIELK<br>GIDFKEDGNILGHKLEYNYNSHNVYITADKQGLSGRIMSGLRINSAKDDAAGQAIANRFTSNI<br>KGLTQASRNANDGISIAQTTEGALNEINNNLQRVRELSVQATNGTNSDSDLKSIQDEIQQRLE<br>EIDRVSNQTQFNGVKVLSQDNQMKIQVGANDGETITIDLQKIDVKSLGLDGFNVNSPGSTANP<br>LASIDSALSKVDAVRSSLGAIQNRFDSAITNLGNTVTNLNSARSRIEDADYALVPPISGKNGI<br>KANFKIRHNIEDGSVQLADHYQQNTPIGDGPVLLPDNHYLSTQSALLKDPNEKRDHMVLLEFV<br>TAAGITHGMDELYKPRGSHHHHHG |
| 0110 | Mutant MF227C mutant 470CT template | DNA | Artificial Sequence CTTGGCCTTGATGGGTTCAATGTTAATTCCCCGGGAATTTCCGGTGGTGGTGGTGGAATTACA<br>TTAATCAATGAAGACGCTGCCGCAGCCAAGAAAAGTACCGCTAACCCACTGGCTTCAATTG |
| 0111 | Mutant MF227C mutant 470CT template | PRT | Artificial Sequence LGLDGFNVNSPGISGGGGGITLINEDAAAAKKSTANPLASI |
| 0112 | Mutant MF227C Reverse Primer R2YY | DNA | Artificial Sequence AGATCTCCGCGGAACCAGTAAAGAGAGGACGTTTTGCGGAACCTGGTTTGCATAGTCAGCATC<br>TTCGATACG |
| 0113 | Mutant MF227C DNA sequence of Mutant MF227C | DNA | Artificial Sequence TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGTTTTGATTCAGCCATT<br>ACCAACCTTGGCAATACGGTAACCAATCTGAACTCCGCGCGTAGCCGTATCGAAGATGCTGAC<br>TATGCAAACCAGGTTCCGCAAAACGTCCTCTCTTTACTGGTTCCGCGGGGTTCTCATCATCAT<br>CATCATCATGGTTAAGTCGAC |
| 0114 | Mutant MF227C Mutant MF227C | DNA | Artificial Sequence ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTAACGGGACTAACTCTGATTCCGATCTGAAATCTATCCAGGATGAAATT<br>CAGCAACGTCTGGAAGAAATCGATCGCGTTTCTAATCAGACTCAATTTAACGGTGTTAAAGTC<br>CTGTCTCAGGACAACCAGATGAAAATCCAGGTTGGTGCTAACGATGGTGAAACCATTACCATC<br>GATCTGCAAAAAATTGATGTGAAAAGCCTTGGCCTTGATGGGTTCAATGTTAATTCCCCGGGA<br>AGTACCGCTAACCCACTGGCTTCAATTGATTCTGCATTGTCAAAAGTGGACGCAGTTCGTTCT<br>TCTCTGGGGGCAATTCAAAACCGTTTTGATTCAGCCATTACCAACCTTGGCAATACGGTAACC<br>AATCTGAACTCCGCGCGTAGCCGTATCGAAGATGCTGACTATGCAAACCAGGTTCCGCAAAAC<br>GTCCTCTCTTTACTGGTTCCGCGGGGTTCTCATCATCATCATCATCATGGTTAA |
| 0115 | Mutant MF227C Mutant MF227C | PRT | Artificial Sequence MSGLRINSAKDDAAGQAIANRFTSNIKGLTQASRNANDGISIAQTTEGALNEINNNLQRVREL<br>SVQATNGTNSDSDLKSIQDEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYANQVPQNVLSLLVPRGSHHHHHG |
| 0116 | Mutant MF227N Reverse Primer RMF227N | DNA | Artificial Sequence AGATCTCCCGGGGAACCATCGTTAGCACCAACCTGGATTTTC |
| 0117 | Mutant MF227N DNA sequence of mutant MF227N | DNA | Artificial Sequence TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT |

TABLE 1-continued

Illustrative Flagellin Compositions

| SEQ ID | Construct Name | DNA/PRT | Sequence |
|---|---|---|---|
| | | | CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTTCCCCGGGAAGTACCGCTAACCCACTGGCTTCAATTGATTCTGCATTGTCAAAA GTGGACGCAGTTCGTTCTTCTCTGGGGGCAATTCAAAACCGCTTTGATTCAGCCATTACCAAC CTTGGCAATACGGTAACCAATCTGAACTCCGCGCGTAGCCGTATCGAAGATGCTGACTATGCA ACGGAAGTTTCTAATATGTCTAAAGCGCAGATTCTGCAGCAGGCTGGTACTTCCGTTCTGGCG CAGGCTAACCAGGTTCCGCAAAACGTCCTCTCTTTACTGGTTCCGCGGGGTTCTCATCATCAT CATCATCATGGTTAAGTCGAC |
| 0118 | Mutant MF227N mutant MF227N | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTTCCCCGGGAAGTACC GCTAACCCACTGGCTTCAATTGATTCTGCATTGTCAAAAGTGGACGCAGTTCGTTCTTCTCTG GGGGCAATTCAAAACCGCTTTGATTCAGCCATTACCAACCTTGGCAATACGGTAACCAATCTG AACTCCGCGCGTAGCCGTATCGAAGATGCTGACTATGCAACGGAAGTTTCTAATATGTCTAAA GCGCAGATTCTGCAGCAGGCTGGTACTTCCGTTCTGGCGCAGGCTAACCAGGTTCCGCAAAAC GTCCTCTCTTTACTGGTTCCGCGGGGTTCTCATCATCATCATCATGGTTAA |
| 0119 | Mutant MF227N mutant MF227N | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGSPGST ANPLASIDSALSKVDAVRSSLGAIQNRFDSAITNLGNTVTNLNSARSRIEDADYATEVSNMSK AQILQQAGTSVLAQANQVPQNVLSLLVPRGSHHHHHG |
| 0120 | Mutant MF233 Reverse primer RMF233 | DNA | Artificial Sequence AGATCTCCGCGGAACCAGCAGGTTATTCTGGGTCAACAGCGACAGGCTGTTTGTATTAATGAC TTGTGCATAGTCAGCATCTTCGATACG |
| 0121 | Mutant MF233 DNA Sequence of construct MF233 | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCACAAGTCATTAATACAAACAGCCTGTCGCTGTTGACCCAGAATAACCTGCTGGTTCCG CGGGGTTCTCATCATCATCATCATGGTTAAGTCGAC |
| 0122 | Mutant MF233 MF233 | DNA | Artificial Sequence ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATCGCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCACAAGTCATTAATACAAAC AGCCTGTCGCTGTTGACCCAGAATAACCTGCTGGTTCCGCGGGGTTCTCATCATCATCATCAT CATGGTTAA |
| 0123 | Mutant MF233 MF233 | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVSPGSTANPLASIDSALSKVDAVRSSLGAIQNRFDSAITNLGNTVT NLNSARSRIEDADYAQVINTNSLSLLTQNNLLVPRGSHHHHHG |
| 0124 | Mutant MF471 Forward primer F471-77 | DNA | Artificial Sequence GCTGACTATGCAACGGCAGTTTCTGCTATGTCTGCAGCGCAGATTCTGC |
| 0125 | Mutant MF471 Reverse Primer R471-77 | DNA | Artificial Sequence GCAGAATCTGCGCTGCAGACATAGCAGAAACTGCCGTTGCATAGTCAGC |
| 0126 | Mutant MF471 DNA Sequence of construct MF471 | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT |

TABLE 1-continued

Illustrative Flagellin Compositions

| SEQ ID | Construct Name | DNA/PRT | Sequence |
|---|---|---|---|
| | | | CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGCAGTTTCTGCTATGTCTGCAGCGCAGATTCTGCAGCAGGCTGGTCTGGTTCCG<br>CGGGGTTCTCATCATCATCATCATCATGGTTAAGTCGAC |
| 0127 | Mutant MF471<br>MF471 | DNA | Artificial<br>Sequence<br>ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTAACGGGACTAACTCTGATTCCGATCTGAAATCTATCCAGGATGAAATT<br>CAGCAACGTCTGGAAGAAATCGATCGCGTTTCTAATCAGACTCAATTTAACGGTGTTAAAGTC<br>CTGTCTCAGGACAACCAGATGAAAATCCAGGTTGGTGCTAACGATGGTGAAACCATTACCATC<br>GATCTGCAAAAAATTGATGTGAAAAGCCTTGGCCTTGATGGGTTCAATGTTAATTCCCCGGGA<br>AGTACCGCTAACCCACTGGCTTCAATTGATTCTGCATTGTCAAAAGTGGACGCAGTTCGTTCT<br>TCTCTGGGGGCAATTCAAAACCGCTTTGATTCAGCCATTACCAACCTTGGCAATACGGTAACC<br>AATCTGAACTCCGCGCGTAGCCGTATCGAAGATGCTGACTATGCAACGGCAGTTTCTGCTATG<br>TCTGCAGCGCAGATTCTGCAGCAGGCTGGTCTGGTTCCGCGGGGTTCTCATCATCATCATCAT<br>CATGGTTAA |
| 0128 | Mutant MF471<br>MF471 | PRT | Artificial<br>Sequence<br>MSGLRINSAKDDAAGQAIANRFTSNIKGLTQASRNANDGISIAQTTEGALNEINNNLQRVREL<br>SVQATNGTNSDSDLKSIQDEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATAVSAMSAAQILQQAGLVPRGSHHHHHHG |
| 0129 | Mutant MF479<br>Forward primer<br>F479-83 | DNA | Artificial<br>Sequence<br>GTTTCTAATATGTCTAAAGCGGCGATTCTGGGAGCGGCTGGTCTGGTTCCGCGG |
| 0130 | Mutant MF479<br>Reverse Primer<br>R479-83 | DNA | Artificial<br>Sequence<br>CCGCGGAACCAGACCAGCCGCTCCCAGAATCGCCGCTTTAGACATATTAGAAAC |
| 0131 | Mutant MF479<br>DNA Sequence<br>of construct<br>MF479 | DNA | Artificial<br>Sequence<br>TAATACGACTCACTATAGGGGAATTGTGAGCGGATAACAATTCCCCTCTAGAAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGGCGATTCTGGGAGCGGCTGGTCTGGTTCCG<br>CGGGGTTCTCATCATCATCATCATCATGGTTAAGTCGAC |
| 0132 | Mutant MF479<br>Mutant MF479 | DNA | Artificial<br>Sequence<br>ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTAACGGGACTAACTCTGATTCCGATCTGAAATCTATCCAGGATGAAATT<br>CAGCAACGTCTGGAAGAAATCGATCGCGTTTCTAATCAGACTCAATTTAACGGTGTTAAAGTC<br>CTGTCTCAGGACAACCAGATGAAAATCCAGGTTGGTGCTAACGATGGTGAAACCATTACCATC<br>GATCTGCAAAAAATTGATGTGAAAAGCCTTGGCCTTGATGGGTTCAATGTTAATTCCCCGGGA<br>AGTACCGCTAACCCACTGGCTTCAATTGATTCTGCATTGTCAAAAGTGGACGCAGTTCGTTCT<br>TCTCTGGGGGCAATTCAAAACCGCTTTGATTCAGCCATTACCAACCTTGGCAATACGGTAACC<br>AATCTGAACTCCGCGCGTAGCCGTATCGAAGATGCTGACTATGCAACGGAAGTTTCTAATATG<br>TCTAAAGCGGCGATTCTGGGAGCGGCTGGTCTGGTTCCGCGGGGTTCTCATCATCATCATCAT<br>CATGGTTAA |
| 0133 | Mutant MF479<br>Mutant MF479 | PRT | Artificial<br>Sequence<br>MSGLRINSAKDDAAGQAIANRFTSNIKGLTQASRNANDGISIAQTTEGALNEINNNLQRVREL<br>SVQATNGTNSDSDLKSIQDEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATEVSNMSKAAILGAAGLVPRGSHHHHHHG |
| 0134 | Mutant N45<br>Forward primer<br>N45_F | DNA | Artificial<br>Sequence<br>TCTAGAGGATCCGGCAGGCCAGGCG |
| 0135 | Mutant N45<br>Reverse R502D0 | DNA | Artificial<br>Sequence<br>CGCAAGCTTGTCGACTTAACGC |

TABLE 1-continued

Illustrative Flagellin Compositions

| SEQ ID | Construct Name | DNA/PRT | Sequence | |
|---|---|---|---|---|
| 0136 | Mutant N45 DNA sequence of Mutant N45 | DNA | Artificial Sequence | TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGGATCTGTACGACCTGGTTCCGCGCGGTAGCGCG AAGGATCCGGCAGGCCAGGCGATTGCTAACCGCTTCACTTCTAATATCAAAGGTCTGACTCAG GCTTCCCGTAACGCTAACGACGGCATTTCTATTGCGCAGACCACTGAAGGTGCGCTGAATGAA ATCAACAACAACCTGCAGCGTGTGCGTGAGTTGTCTGTTCAGGCCACTAACGGGACTAACTCT GATTCCGATCTGAAATCTATCCAGGATGAAATTCAGCAACGTCTGGAAGAAATCGATCGCGTT TCTAATCAGACTCAATTTAACGGTGTTAAAGTCCTGTCTCAGGACAACCAGATGAAAATCCAG GTTGGTGCTAACGATGGTGAAACCATTACCATCGATCTGCAAAAAATTGATGTGAAAAGCCTT GGCCTTGATGGGTTCAATGTTAATTCCCCGGGAATTTCCGGTGGTGGTGGTGGAATTCTAGAC TCCATGGGTACATTAATCAATGAAGACGCTGCCGCAGCCAAGAAAAGTACCGCTAACCCACTG GCTTCAATTGATTCTGCATTGTCAAAAGTGGACGCAGTTCGTTCTTCTCTGGGGGCAATTCAA AACCGTTTTGATTCAGCCATTACCAACCTTGGCAATACGGTAACCAATCTGAACTCCGCGCGT AGCCGTATCGAAGATGCTGACTATGCAACGGAAGTTTCTAATATGTCTAAAGCGCAGATTCTG CAGCAGGCTGGTACTTCCGTTCTGGCGCAGGCTAACCAGGTTCCGCAAAACGTCCTCTCTTTA CTGCGTTAAGTCGACAAGCTTGCGG |
| 0137 | Mutant N45 Mutant N45 | PRT | Artificial Sequence | MRGSHHHHHHGMASMTGGQQMGRDLYDLVPRGSAKDPAGQAIANRFTSNIKGLTQASRNANDG ISIAQTTEGALNEINNNLQRVRELSVQATNGTNSDSDLKSIQDEIQQRLEEIDRVSNQTQFNG VKVLSQDNQMKIQVGANDGETITIDLQKIDVKSLGLDGFNVNSPGISGGGGGILDSMGTLINE DAAAAKKSTANPLASIDSALSKVDAVRSSLGAIQNRFDSAITNLGNTVTNLNSARSRIEDADY ATEVSNMSKAQILQQAGTSVLAQANQVPQNVLSLLR |
| 0138 | Mutant NGD1 DNA Sequence of NGD1 construct | DNA | Artificial Sequence | TAATACGACTCACTATAGGGGAATTGTGAGCGGATAACAATTCCCCTCTAGAATAATTTTGTT TAACTTTAAGAAGGAGATATACATATGAGTAAAGGAGAAGAACTTTTCACTGGAGTTGTCCCA ATTCTTGTTGAATTAGATGGTGATGTTAATGGGCACAAATTTTCTGTCAGTGGAGAGGGTGAA GGTGATGCAACATACGGAAAACTTACCCTTAAATTTATTTGCACTACTGGAAAACTACCTGTT CCATGGCCAACACTTGTCACTACTCTGACGTATGGTGTTCAATGCTTTTCCCGTTATCCGGAT CACATGAAACGGCATGACTTTTTCAAGAGTGCCATGCCCGAAGGTTATGTACAGGAACGCACT ATATCTTTCAAAGATGACGGGAACTACAAGACGCGTGCTGAAGTCAAGTTTGAAGGTGATACC CTTGTTAATCGTATCGAGTTAAAAGGTATTGATTTTAAAGAAGATGGAAACATTCTCGGACAC AAACTCGAGTACAACTATAACTCACACAATGTATACATCACGGCAGACAAACAAGGCCTATCA GGCCGCATTATGAGCGGGTTACGGATCAACAGCGCGAAAGACGATGCGGCAGGCCAGGCGATT GCTAACCGCTTCACTTCTAATATCAAAGGTCTGACTCAGGCTTCCCGTAACGCTAACGACGGC ATTTCTATTGCGCAGACCACTGAAGGTGCGCTGAATGAAATCAACAACAACCTGCAGCGTGTG CGTGAGTTGTCTGTTCAGGCCACTAACGGGACTAACTCTGATTCCGATCTGAAATCTATCCAG GATGAAATTCAGCAACGTCTGGAAGAAATCGATCGCGTTTCTAATCAGACTCAATTTAACGGT GTTAAAGTCCTGTCTCAGGACAACCAGATGAAAATCCAGGTTGGTGCTAACGATGGTGAAACC ATTACCATCGATCTGCAAAAAATTGATGTGAAAAGCCTTGGCCTTGATGGGTTCAATGTTAAT TCCCCGGGAAGTACCGCTAACCCACTGGCTTCAATTGATTCTGCATTGTCAAAAGTGGACGCA GTTCGTTCTTCTCTGGGGGCAATTCAAAACCGCTTTGATTCAGCCATTACCAACCTTGGCAAT ACGGTAACCAATCTGAACTCCGCGCGTAGCCGTATCGAAGATGCTGACTATGCACTGGTTCCG CGGGGTTCTCATCATCATCATCATCATGGTTAAGTCGAC |
| 0139 | Mutant NGD1 Expressed Mutant SY3-GFP | DNA | Artificial Sequence | ATGAGTAAAGGAGAAGAACTTTTCACTGGAGTTGTCCCAATTCTTGTTGAATTAGATGGTGAT GTTAATGGGCACAAATTTTCTGTCAGTGGAGAGGGTGAAGGTGATGCAACATACGGAAAACTT ACCCTTAAATTTATTTGCACTACTGGAAAACTACCTGTTCCATGGCCAACACTTGTCACTACT CTGACGTATGGTGTTCAATGCTTTTCCCGTTATCCGGATCACATGAAACGGCATGACTTTTTC AAGAGTGCCATGCCCGAAGGTTATGTACAGGAACGCACTATATCTTTCAAAGATGACGGGAAC TACAAGACGCGTGCTGAAGTCAAGTTTGAAGGTGATACCCTTGTTAATCGTATCGAGTTAAAA GGTATTGATTTTAAAGAAGATGGAAACATTCTCGGACACAAACTCGAGTACAACTATAACTCA CACAATGTATACATCACGGCAGACAAACAAGGCCTATCAGGCCGCATTATGAGCGGGTTACGG ATCAACAGCGCGAAAGACGATGCGGCAGGCCAGGCGATTGCTAACCGCTTCACTTCTAATATC AAAGGTCTGACTCAGGCTTCCCGTAACGCTAACGACGGCATTTCTATTGCGCAGACCACTGAA GGTGCGCTGAATGAAATCAACAACAACCTGCAGCGTGTGCGTGAGTTGTCTGTTCAGGCCACT AACGGGACTAACTCTGATTCCGATCTGAAATCTATCCAGGATGAAATTCAGCAACGTCTGGAA GAAATCGATCGCGTTTCTAATCAGACTCAATTTAACGGTGTTAAAGTCCTGTCTCAGGACAAC CAGATGAAAATCCAGGTTGGTGCTAACGATGGTGAAACCATTACCATCGATCTGCAAAAAATT GATGTGAAAAGCCTTGGCCTTGATGGGTTCAATGTTAATTCCCCGGGAAGTACCGCTAACCCA CTGGCTTCAATTGATTCTGCATTGTCAAAAGTGGACGCAGTTCGTTCTTCTCTGGGGGCAATT CAAAACCGCTTTGATTCAGCCATTACCAACCTTGGCAATACGGTAACCAATCTGAACTCCGCG CGTAGCCGTATCGAAGATGCTGACTATGCACTGGTTCCGCGGGGTTCTCATCATCATCATCAT CATGGTTAA |
| 0140 | Mutant NGD1 Expressed Mutant SY3-GFP/Mutant NGD1 | PRT | Artificial Sequence | MSKGEELFTGVVPILVELDGDVNGHKFSVSGEGEGDATYGKLTLKFICTTGKLPVPWPTLVTT LTYGVQCFSRYPDHMKRHDFFKSAMPEGYVQERTISFKDDGNYKTRAEVKFEGDTLVNRIELK GIDFKEDGNILGHKLEYNYNSHNVYITADKQGLSGRIMSGLRINSAKDDAAGQAIANRFTSNI KGLTQASRNANDGISIAQTTEGALNEINNNLQRVRELSVQATNGTNSDSDLKSIQDEIQQRLE EIDRVSNQTQFNGVKVLSQDNQMKIQVGANDGETITIDLQKIDVKSLGLDGFNVNSPGSTANP LASIDSALSKVDAVRSSLGAIQNRFDSAITNLGNTVTNLNSARSRIEDADYALVPRGSHHHH HG |
| 0141 | Mutant S33 Forward F502_S33 | DNA | Artificial Sequence | TCTAGAGGATCCGTCTGGTCTGCGTATCAACAGCGC |

TABLE 1-continued

Illustrative Flagellin Compositions

| SEQ ID | Construct Name | DNA/PRT | Sequence | |
|---|---|---|---|---|
| 0142 | Mutant S33 DNA sequence of Mutant S33 | DNA | Artificial Sequence | TAATACGACTCACTATAGGGGAATTGTGAGCGGATAACAATTCCCCTCTAGAATAATTTTGTT<br>TAACTTTAAGAAGGAGATATACATATGCGGGGTTCTCATCATCATCATCATCATGGTATGGCT<br>AGCATGACTGGTGGACAGCAAATGGGTCGGGATCTGTACGACCTGGTTCCGCGCGGTAGCGCG<br>AAGGATCCGTCTGGTCTGCGTATCAACAGCGCGAAAGACGATGCGGCAGGCCAGGCGATTGCT<br>AACCGCTTCACTTCTAATATCAAAGGTCTGACTCAGGCTTCCCGTAACGCTAACGACGGCATT<br>TCTATTGCGCAGACCACTGAAGGTGCGCTGAATGAAATCAACAACAACCTGCAGCGTGTGCGT<br>GAGTTGTCTGTTCAGGCCACTAACGGGACTAACTCTGATTCCGATCTGAAATCTATCCAGGAT<br>GAAATTCAGCAACGTCTGGAAGAAATCGATCGCGTTTCTAATCAGACTCAATTTAACGGTGTT<br>AAAGTCCTGTCTCAGGACAACCAGATGAAAATCCAGGTTGGTGCTAACGATGGTGAAACCATT<br>ACCATCGATCTGCAAAAAATTGATGTGAAAAGCCTTGGCCTTGATGGGTTCAATGTTAATTCC<br>CCGGGAATTTCCGGTGGTGGTGGTGGAATTCTAGACTCCATGGGTACATTAATCAATGAAGAC<br>GCTGCCGCAGCCAAGAAAGTACCGCTAACCCACTGGCTTCAATTGATTCTGCATTGTCAAAA<br>GTGGACGCAGTTCGTTCTTCTCTGGGGGCAATTCAAAACCGTTTTGATTCAGCCATTACCAAC<br>CTTGGCAATACGGTAACCAATCTGAACTCCGCGCGTAGCCGTATCGAAGATGCTGACTATGCA<br>ACGGAAGTTTCTAATATGTCTAAAGCGCAGATTCTGCAGCAGGCTGGTACTTCCGTTCTGGCG<br>CAGGCTAACCAGGTTCCGCAAAACGTCCTCTCTTTACTGCGTTAAGTCGAC |
| 0143 | Mutant S33 Mutant S33 | DNA | Artificial Sequence | ATGCGGGGTTCTCATCATCATCATCATCATGGTATGGCTAGCATGACTGGTGGACAGCAAATG<br>GGTCGGGATCTGTACGACCTGGTTCCGCGCGGTAGCGCGAAGGATCCGTCTGGTCTGCGTATC<br>AACAGCGCGAAAGACGATGCGGCAGGCCAGGCGATTGCTAACCGCTTCACTTCTAATATCAAA<br>GGTCTGACTCAGGCTTCCCGTAACGCTAACGACGGCATTTCTATTGCGCAGACCACTGAAGGT<br>GCGCTGAATGAAATCAACAACAACCTGCAGCGTGTGCGTGAGTTGTCTGTTCAGGCCACTAAC<br>GGGACTAACTCTGATTCCGATCTGAAATCTATCCAGGATGAAATTCAGCAACGTCTGGAAGAA<br>ATCGATCGCGTTTCTAATCAGACTCAATTTAACGGTGTTAAAGTCCTGTCTCAGGACAACCAG<br>ATGAAAATCCAGGTTGGTGCTAACGATGGTGAAACCATTACCATCGATCTGCAAAAAATTGAT<br>GTGAAAAGCCTTGGCCTTGATGGGTTCAATGTTAATTCCCCGGGAATTTCCGGTGGTGGTGGT<br>GGAATTCTAGACTCCATGGGTACATTAATCAATGAAGACGCTGCCGCAGCCAAGAAAGTACC<br>GCTAACCCACTGGCTTCAATTGATTCTGCATTGTCAAAAGTGGACGCAGTTCGTTCTTCTCTG<br>GGGGCAATTCAAAACCGTTTTGATTCAGCCATTACCAACCTTGGCAATACGGTAACCAATCTG<br>AACTCCGCGCGTAGCCGTATCGAAGATGCTGACTATGCAACGGAAGTTTCTAATATGTCTAAA<br>GCGCAGATTCTGCAGCAGGCTGGTACTTCCGTTCTGGCGCAGGCTAACCAGGTTCCGCAAAAC<br>GTCCTCTCTTTACTGCGTTAA |
| 0144 | Mutant S33 Mutant S33 | PRT | Artificial Sequence | MRGSHHHHHHGMASMTGGQQMGRDLYDLVPRGSAKDPSGLRINSAKDDAAGQAIANRFTSNIK<br>GLTQASRNANDGISIAQTTEGALNEINNNLQRVRELSVQATNGTNSDSDLKSIQDEIQQRLEE<br>IDRVSNQTQFNGVKVLSQDNQMKIQVGANDGETITIDLQKIDVKSLGLDGFNVNSPGISGGGG<br>GILDSMGTLINEDAAAKKSTANPLASIDSALSKVDAVRSSLGAIQNRFDSAITNLGNTVTNL<br>NSARSRIEDADYATEVSNMSKAQILQQAGTSVLAQANQVPQNVLSLLR |
| 0145 | Mutant SY3CT Reverse primer RSY3CT | DNA | Artificial Sequence | AGATCTCCGCGGAACCAGTGCATAGTCAGCATCTTCGATACGGC |
| 0146 | Mutant SY3CT DNA Sequence of SY3CT construct | DNA | Artificial Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGAGCTGACT<br>TATGCACTGGTTCCGCGGGGTTCTCATCATCATCATCATCATGGTTAAGTCGAC |
| 0147 | Mutant SY3CT Expressed Mutant SY3CT | DNA | Artificial Sequence | ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTAACGGGACTAACTCTGATTCCGATCTGAAATCTATCCAGGATGAAATT<br>CAGCAACGTCTGGAAGAAATCGATCGCGTTTCTAATCAGACTCAATTTAACGGTGTTAAAGTC<br>CTGTCTCAGGACAACCAGATGAAAATCCAGGTTGGTGCTAACGATGGTGAAACCATTACCATC<br>GATCTGCAAAAAATTGATGTGAAAAGCCTTGGCCTTGATGGGTTCAATGTTAATTCCCCGGGA<br>AGTACCGCTAACCCACTGGCTTCAATTGATTCTGCATTGTCAAAAGTGGACGCAGTTCGTTCT<br>TCTCTGGGGGCAATTCAAAACCGCTTTGATTCAGCCATTACCAACCTTGGCAATACGGTAACC<br>AATCTGAACTCCGCGCGTAGCCGTATCGAAGATGCTGACTATGCACTGGTTCCGCGGGGTTCT<br>CATCATCATCATCATCATGGTTAA |
| 0148 | Mutant SY3CT Expressed Mutant SY3CT | PRT | Artificial Sequence | MSGLRINSAKDDAAGQAIANRFTSNIKGLTQASRNANDGISIAQTTEGALNEINNNLQRVREL<br>SVQATNGTNSDSDLKSIQDEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYALVPRGSHHHHHHG |

TABLE 1-continued

Illustrative Flagellin Compositions

| SEQ ID | Construct Name | DNA/ PRT | Sequence | |
|---|---|---|---|---|
| 0149 | Mutant 33MX Mutant 33MX | DNA | Artificial Sequence | ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTGCAGACGGCATTTCTATT GCGCAGACCACTGAAGGTGCGCTGAATGAAATCAACAACAACCTGCAGCGTGTGCGTGAGTTG TCTGTTCAGGCCACTGCCGGGGCTAACGCTGATGCCGCTCTGAAAGCTATCCAGGCTGAAATT CAGCAACGTCTGGAAGAAATCGATCGCGTTTCTCAGCAGACTCAAGCTGCCGCTGTTAAAGTC CTGTCTCAGGACAACGCAATGGCAATCCAGGTTGGTGCTAACGATGGTGCCGCTATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCAACGGAAGTTTCTCAAATG TCTAAAGCGCAGATTCTGCAGCAGGCTGGTACTTCCGTTCTGGCGCAGGCTAACCAGGTTCCG CAAAACGTCCTCTCTTTACTGGTTCCGCGGGTTCTCATCATCATCATCATGGTTAA |
| 0150 | Mutant 33MX Mutant 33MX | PRT | Artificial Sequence | MSGLRINSAKDDAAGQAIANRFTSNIKGLTQASRNAADGISIAQTTEGALNEINNNLQRVREL SVQATAGANADAALKAIQAEIQQRLEEIDRVSQQTQAAAVKVLSQDNAMAIQVGANDGAAITI DLQKIDVKSLGLDGFNVNSPGSTANPLASIDSALSKVDAVRSSLGAIQNRFDSAITNLGNTVT NLNSARSRIEDADYATEVSQMSKAQILQQAGTSVLAQANQVPQNVLSLLVPRGSHHHHHG |
| 0151 | Mutant 33MX DNA sequence of 33MX | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTGCAGACGGCATTTCTATTGCGCAGACCACTGAAGGTGCGCTGAATGAAATCAACAAC AACCTGCAGCGTGTGCGTGAGTTGTCTGTTCAGGCCACTGCCGGGGCTAACGCTGATGCCGCT CTGAAAGCTATCCAGGCTGAAATTCAGCAACGTCTGGAAGAAATCGATCGCGTTTCTCAGCAG ACTCAAGCTGCCGCTGTTAAAGTCCTGTCTCAGGACAACGCAATGGCAATCCAGGTTGGTGCT AACGATGGTGCCGCTATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTCAAATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGTTCTCAT CATCATCATCATCATGGTTAAGTCGAC |
| 0152 | Mutant 48514X DNA Sequence of 485MX construct | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTGCAGACGGCATTTCTATTGCGCAGACCACTGAAGGTGCGCTGAATGAAATCAACAAC AACCTGCAGCGTGTGCGTGAGTTGTCTGTTCAGGCCACTGCCGGGGCTAACGCTGATGCCGCT CTGAAAGCTATCCAGGCTGAAATTCAGCAACGTCTGGAAGAAATCGATCGCGTTTCTCAGCAG ACTCAAGCTGCCGCTGTTAAAGTCCTGTCTCAGGACAACGCAATGGCAATCCAGGTTGGTGCT AACGATGGTGCCGCTATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTCAAATGTCTAAAGCGCAGATTCTGCAGCAGGCTGGTCTGGTTCCG CGGGGTTCTCATCATCATCATCATGGTTAAGTCGAC |
| 0153 | Mutant 48514X 485MX construct | DNA | Artificial Sequence | ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTGCAGACGGCATTTCTATT GCGCAGACCACTGAAGGTGCGCTGAATGAAATCAACAACAACCTGCAGCGTGTGCGTGAGTTG TCTGTTCAGGCCACTGCCGGGGCTAACGCTGATGCCGCTCTGAAAGCTATCCAGGCTGAAATT CAGCAACGTCTGGAAGAAATCGATCGCGTTTCTCAGCAGACTCAAGCTGCCGCTGTTAAAGTC CTGTCTCAGGACAACGCAATGGCAATCCAGGTTGGTGCTAACGATGGTGCCGCTATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT TCTCTGGGGGCAATTCAAAACCGCTTTGATTCAGCCATTACCAACCTTGGCAATACGGTAACC AATCTGAACTCCGCGCGTAGCCGTATCGAAGATGCTGACTATGCAACGGAAGTTTCTCAAATG TCTAAAGCGCAGATTCTGCAGCAGGCTGGTCTGGTTCCGCGGGGTTCTCATCATCATCATCAT CATGGTTAA |
| 0154 | Mutant 48514X 485MX construct | PRT | Artificial Sequence | MSGLRINSAKDDAAGQAIANRFTSNIKGLTQASRNAADGISIAQTTEGALNEINNNLQRVREL SVQATAGANADAALKAIQAEIQQRLEEIDRVSQQTQAAAVKVLSQDNAMAIQVGANDGAAITI DLQKIDVKSLGLDGFNVNSPGSTANPLASIDSALSKVDAVRSSLGAIQNRFDSAITNLGNTVT NLNSARSRIEDADYATEVSQMSKAQILQQAGLVPRGSHHHHHG |
| 0155 | Mutant MIM4 CBLB502 variant | DNA | Artificial Sequence | ATGCGGGGTTCTCATCATCATCATCATCATGGTATGGCTAGCATGACTGGTGGACAGCA TABLE 1-continued Illustrative Flagellin Compositions

| SEQ ID | Construct Name | DNA/PRT | Sequence |
|---|---|---|---|
| | | | CCGGGAATTTCCGGTGGTGGTGGTGGAATTCTAGACTCCATGGGTACATTAATCAATGAAGAC<br>GCTGCCGCAGCCAAGAAAAGTACCGCTAACCCACTGGCTTCAATTGATTCTGCATTGTCAAAA<br>GTGGACGCAGTTCGTTCTTCTCTGGGGGCAATTCAAAACCGTTTTGATTCAGCCATTACCAAC<br>CTTGGCAATACGGTAACCAATCTGAACTCCGCGCGTAGCGCTATCGAAGATGCTGACTATGCA<br>ACGGAAGTTTCTCAAATGTCTAAAGCGCAGATTCTGCAGCAGGCTGGTACTTCCGTTCTGGCG<br>CAGGCTAACCAGGTTCCGCAAAACGTCCTCTCTTTACTGCGTTAA |
| 0156 | Mutant MIM4 Primers design (for deletion aa Gln439; Asn440; Arg441; Phe442): | DNA Artificial Sequence | AACCCACTGGCTTCAATTGATTCTGCATTGTCAAAAGTGGACGCAGTTCGTTCTTCTCTGGGG<br>GCAATTCAAAACCGTTTTGATTCAGCCATTACCGCCCTTGGCGCTACGGTAACCGCTCTGGCC<br>TCCGCGCGTAGCGCTATCGAAGATGCTGACTATGCAACGGAAGTTTCTCAAATG |
| 0157 | Mutant MIM4 Primers design (for deletion aa Gln439; Asn440; Arg441; Phe442): | PRT Artificial Sequence | NPLASIDSALSKVDAVRSSLGAIQNRFDSAITALGATVTALASARSAIEDADYATEVSNM |
| 0158 | Mutant MIM4 Forward Primer MIM4 | DNA Artificial Sequence | GCAGTTCGTTCTTCTCTGGGGGCAATTGATTCAGCCATTACCGCCCTTGG |
| 0159 | Mutant MIM4 Reverse Primer MIM4 | DNA Artificial Sequence | CCAAGGGCGGTAATGGCTGAATCAATTGCCCCCAGAGAAGAACGAACTGC |
| 0160 | Mutant MIM4 MIM4 | DNA Artificial Sequence | TAATACGACTCACTATAGGGGAATTGTGAGCGGATAACAATTCCCCTCTAGAAATAATTTTGT<br>TTAACTTTAAGAAGGAGATATACATATGCGGGGTTCTCATCATCATCATCATCATGGTATGGC<br>TAGCATGACTGGTGGACAGCAAATGGGTCGGGATCTGTACGACGATGACGATAAGGATCCGAT<br>GGCACAAGTCATTAATACAAACAGCCTGTCGCTGTTGACCCAGAATAACCTGAACAAATCTCA<br>GTCCTCACTGAGTTCCGCTATTGAGCGTCTGTCCTCTGGTCTGCGTATCAACAGCGCGAAAGA<br>CGATGCGGCAGGCCAGGCGATTGCTAACCGCTTCACTTCTAATATCAAAGGTCTGACTCAGGC<br>TTCCCGTAACGCTAACGACGGCATTTCTATTGCGCAGACCACTGAAGGTGCGCTGAATGAAAT<br>CAACAACAACCTGCAGCGTGTGCGTGAGTTGTCTGTTCAGGCCACTAACGGGACTAACTCTGA<br>TTCCGATCTGAAATCTATCCAGGATGAAATTCAGCAACGTCTGGAAGAAATCGATCGCGTTTC<br>TAATCAGACTCAATTTAACGGTGTTAAAGTCCTGTCTCAGGACAACCAGATGAAAATCCAGGT<br>TGGTGCTAACGATGGTGAAACCATTACCATCGATCTGCAAAAAATTGATGTGAAAAGCCTTGG<br>CCTTGATGGGTTCAATGTTAATTCCCCGGGAATTTCCGGTGGTGGTGGTGGAATTCTAGACTC<br>CATGGGTACATTAATCAATGAAGACGCTGCCGCAGCCAAGAAAAGTACCGCTAACCCACTGGC<br>TTCAATTGATTCTGCATTGTCAAAAGTGGACGCAGTTCGTTCTTCTCTGGGGGCAATTGATTC<br>AGCCATTACCGCCCTTGGCGCTACGGTAACCGCTCTGGCCTCCGCGGGTAGCCGTATCGAAGA<br>TGCTGACTATGCAACGGAAGTTTCTAATATGTCTAAAGCGCAGATTCTGCAGCAGGCTGGTAC<br>TTCCGTTCTGGCGCAGGCTAACCAGGTTCCGCAAAACGTCCTCTCTTTACTGCGTTAA |
| 0161 | Mutant MIM4 MIM4 | PRT Artificial Sequence | MRGSHHHHHHGMASMTGGQQMGRDLYDDDDKDPMAQVINTNSLSLLTQNNLNKSQSSLSSAIE<br>RLSSGLRINSAKDDAAGQAIANRFTSNIKGLTQASRNANDGISIAQTTEGALNEINNNLQRVR<br>ELSVQATNGTNSDSDLKSIQDEIQQRLEEIDRVSNQTQFNGVKVLSQDNQMKIQVGANDGETI<br>TIDLQKIDVKSLGLDGFNVNSPGISGGGGGILDSMGTLINEDAAAAKKSTANPLASIDSALSK<br>VDAVRSSLGAIDSAITALGATVTALASAASRIEDADYATEVSNMSKAQILQQAGTSVLAQANQ<br>VPQNVLSLLR |
| 0162 | Mutant MIM5 Primers design (mutations Gln439Ala; Asn440Lys; Arg441Ala): | DNA Artificial Sequence | AACCCACTGGCTTCAATTGATTCTGCATTGTCAAAAGTGGACGCAGTTCGTTCTTCTCTGGGG<br>GCAATTGCAAAGGCTTTTGATTCAGCCATTACCGCCCTTGGCGCTACGGTAACCGCTCTGGCC<br>TCCGCGCGTAGCGCTATCGAAGATGCTGACTATGCAACGGAAGTTTCTCAAATG |
| 0163 | Mutant MIM5 Primers design (mutations Gln439Ala; Asn440Lys; Arg441Ala): | PRT Artificial Sequence | NPLASIDSALSKVDAVRSSLGAIAKAFDSAITALGATVTALASARSAIEDADYATEVSNM |
| 0164 | Mutant MIM5 Forward Primer MIM5 | DNA Artificial Sequence | CGTTCTTCTCTGGGGGCAATTGCAAAGGCTTTTGATTCAGCCATTACCGC |

TABLE 1-continued

Illustrative Flagellin Compositions

| SEQ ID | Construct Name | DNA/PRT | Sequence |
|---|---|---|---|
| 0165 | Mutant MIM5 Reverse Primer MIM5 | DNA | Artificial Sequence GCGGTAATGGCTGAATCAAAAGCCTTTGCAATTGCCCCCAGAGAAGAACG |
| 0166 | Mutant MIM5 MIM5 | DNA | Artificial Sequence TAATACGACTCACTATAGGGGAATTGTGAGCGGATAACAATTCCCCTCTAGAAATAATTTTGT TTAACTTTAAGAAGGAGATATACATATGCGGGGTTCTCATCATCATCATCATCATGGTATGGC TAGCATGACTGGTGGACAGCAAATGGGTCGGGATCTGTACGACGATGACGATAAGGATCCGAT GGCACAAGTCATTAATACAAACAGCCTGTCGCTGTTGACCCAGAATAACCTGAACAAATCTCA GTCCTCACTGAGTTCCGCTATTGAGCGTCTGTCCTCTGGTCTGCGTATCAACAGCGCGAAAGA CGATGCGGCAGGCCAGGCCGATTGCTAACCGCTTCACTTCTAATATCAAAGGTCTGACTCAGGC TTCCCGTAACGCTAACGACGGCATTTCTATTGCGCAGACCACTGAAGGTGCGCTGAATGAAAT CAACAACAACCTGCAGCGTGTGCGTGAGTTGTCTGTTCAGGCCACTAACGGGACTAACTCTGA TTCCGATCTGAAATCTATCCAGGATGAAATTCAGCAACGTCTGGAAGAAATCGATCGCGTTTC TAATCAGACTCAATTTAACGGTGTTAAAGTCCTGTCTCAGGACAACCAGATGAAAATCCAGGT TGGTGCTAACGATGGTGAAACCATTACCATCGATCTGCAAAAAATTGATGTGAAAAGCCTTGG CCTTGATGGGTTCAATGTTAATTCCCCGGGAATTTCCGGTGGTGGTGGTGGAATTCTAGACTC CATGGGTACATTAATCAATGAAGACGCTGCCGCAGCCAAGAAAAGTACCGCTAACCCACTGGC TTCAATTGATTCTGCATTGTCAAAAGTGGACGCAGTTCGTTCTTCTCTGGGGGCAATTGCAAA GGCTTTTGATTCAGCCATTACCGCCCTTGGCGCTACGGTAACCGCTCTGGCCTCCGCGGCTAG CCGTATCGAAGATGCTGACTATGCAACGGAAGTTTCTAATATGTCTAAAGCGCAGATTCTGCA GCAGGCTGGTACTTCCGTTCTGGCGCAGGCTAACCAGGTTCCGCAAAACGTCCTCTCTTTACT GCGTTAA |
| 0167 | Mutant MIM5 MIM5 | PRT | Artificial Sequence MRGSHHHHHHGMASMTGGQQMGRDLYDDDDKDPMAQVINTNSLSLLTQNNLNKSQSSLSSAIE RLSSGLRINSAKDDAAGQAIANRFTSNIKGLTQASRNANDGISIAQTTEGALNEINNNLQRVR ELSVQATNGTNSDSDLKSIQDEIQQRLEEIDRVSNQTQFNGVKVLSQDNQMKIQVGANDGETI TIDLQKIDVKSLGLDGFNVNSPGISGGGGGILDSMGTLINEDAAAAKKSTANPLASIDSALSK VDAVRSSLGAIAKAFDSAITALGATVTALASAASRIEDADYATEVSNMSKAQILQQAGTSVLA QANQVPQNVLSLLR |
| 0168 | Mutant MIMX Mutant 33MIMX | DNA | Artificial Sequence ATGCGGGGTTCTCATCATCATCATCATCATGGTATGGCTAGCATGACTGGTGGACAGCAAATG GGTCGGGATCTGTACGACCTGGTTCCGCGCGGTAGCGCGAAGGATCCGTCTGGTCTGCGTATC AACAGCGCGAAAGACGATGCGGCAGGCCAGGCCGATTGCTAACCGCTTCACTTCTAATATCAAA GGTCTGACTCAGGCTTCCCGTAACGCTGCAGACGGCATTTCTATTGCGCAGACCACTGAAGGT GCGCTGAATGAAATCAACAACAACCTGCAGCGTGTGCGTGAGTTGTCTGTTCAGGCCACTAAC GGGACTAACTCTGATTCCGATCTGAAATCTATCCAGGATGAAATTCAGCAACGTCTGGAAGAA ATCGATCGCGTTTCTAATCAGACTCAAGCTAACGGTGTTAAAGTCCTGTCTCAGGACAACGCA ATGAAAATCCAGGTTGGTGCTAACGATGGTGCCGCTATTACCATCGATCTGCAAAAAATTGAT GTGAAAAGCCTTGGCCTTGATGGGTTCAATGTTAATTCCCCGGGAATTTCCGGTGGTGGTGGT GGAATTCTAGACTCCATGGGTACATTAATCAATGAAGACGCTGCCGCAGCCAAGAAAAGTACC GCTAACCCACTGGCTTCAATTGATTCTGCATTGTCAAAAGTGGACGCAGTTCGTTCTTCTCTG GGGGCAATTCAAGCTCGTTTTGCCGCGGCCATTGCTAACCTTGGCAATACGGTAACCAATCTG AACTCCGCGCGTAGCCGTATCGAAGATGCTGACTATGCAACGGAAGTTTCTAATATGTCTAAA GCGCAGATTCTGCAGCAGGCTGGTACTTCCGTTCTGGCGCAGGCTAACCAGGTTCCGCAAAAC GTCCTCTCTTTACTGCGTTAA |
| 0169 | Mutant MIMX MIMx | PRT | Artificial Sequence MRGSHHHHHHGMASMTGGQQMGRDLYDLVPRGSAKDPSGLRINSAKDDAAGQAIANRFTSNIK GLTQASRNAADGISIAQTTEGALNEINNNLQRVRELSVQATNGTNSDSDLKSIQDEIQQRLEE IDRVSNQTQANGVKVLSQDNAMKIQVGANDGAAITIDLQKIDVKSLGLDGFNVNSPGISGGGG GILDSMGTLINEDAAAAKKSTANPLASIDSALSKVDAVRSSLGAIQARFAAAIANLGNTVTNL NSARSRIEDADYATEVSNMSKAQILQQAGTSVLAQANQVPQNVLSLLR |
| 0170 | Mutant MIMX DNA sequence of 33MIMx | DNA | Artificial Sequence TAATACGACTCACTATAGGGGAATTGTGAGCGGATAACAATTCCCCTCTAGAATAATTTTGTT TAACTTTAAGAAGGAGATATACATATGCGGGGTTCTCATCATCATCATCATCATGGTATGGCT AGCATGACTGGTGGACAGCAAATGGGTCGGGATCTGTACGACCTGGTTCCGCGCGGTAGCGCG AAGGATCCGTCTGGTCTGCGTATCAACAGCGCGAAAGACGATGCGGCAGGCCAGGCCGATTGCT AACCGCTTCACTTCTAATATCAAAGGTCTGACTCAGGCTTCCCGTAACGCTGCAGACGGCATT TCTATTGCGCAGACCACTGAAGGTGCGCTGAATGAAATCAACAACAACCTGCAGCGTGTGCGT GAGTTGTCTGTTCAGGCCACTAACGGGACTAACTCTGATTCCGATCTGAAATCTATCCAGGAT GAAATTCAGCAACGTCTGGAAGAAATCGATCGCGTTTCTAATCAGACTCAAGCTAACGGTGTT AAAGTCCTGTCTCAGGACAACGCAATGAAAATCCAGGTTGGTGCTAACGATGGTGCCGCTATT ACCATCGATCTGCAAAAAATTGATGTGAAAAGCCTTGGCCTTGATGGGTTCAATGTTAATTCC CCGGGAATTTCCGGTGGTGGTGGTGGAATTCTAGACTCCATGGGTACATTAATCAATGAAGAC GCTGCCGCAGCCAAGAAAAGTACCGCTAACCCACTGGCTTCAATTGATTCTGCATTGTCAAAA GTGGACGCAGTTCGTTCTTCTCTGGGGGCAATTCAAGCTCGTTTTGCCGCGGCCATTGCTAAC CTTGGCAATACGGTAACCAATCTGAACTCCGCGCGTAGCCGTATCGAAGATGCTGACTATGCA ACGGAAGTTTCTAATATGTCTAAAGCGCAGATTCTGCAGCAGGCTGGTACTTCCGTTCTGGCG CAGGCTAACCAGGTTCCGCAAAACGTCCTCTCTTTACTGCGTTAAGTCGAC |
| 0171 | Mutant MIXC Reverse primer RMIXC | DNA | Artificial Sequence AGATCTGTCGACTTAACCATGATGATGATGATGATGAGAACCCCGCGGAACCAGTAAAGAGAG GACGTTTTGCGGAACC |

TABLE 1-continued

Illustrative Flagellin Compositions

| SEQ ID | Construct Name | DNA/PRT | Sequence |
|---|---|---|---|
| 0172 | Mutant MIXC DNA sequence of MIXC | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAGCTCGTTTTGCCGCGGCCATT GCTAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0173 | Mutant MIXC MIXC | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQARFAAAIANLGNTVT NLNSARSRIEDADYATEVSNMSKAQILQQAGTSVLAQANQVPQNVLSLLVPRGSHHHHHHG |
| 0174 | Mutant MIXN Forward primer FMIMxN | DNA | Artificial Sequence AGATCTCATATGAGCGGGTTACGGATCAACAGCGCGAAAGACGATGC |
| 0175 | Mutant MIXN DNA sequence of MIX.N | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTGCAGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAAGCTAACGGTGTTAAAGTCCTGTCTCAGGACAACGCAATGAAAATCCAGGTTGGTGCT AACGATGGTGCCGCTATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0176 | Mutant MIXN Expressed Mutant MIX.N | PRT | Artificial Sequence MSGLRINSAKDDAAGQAIANRFTSNIKGLTQASRNAADGISIAQTTEGALNEINNNLQRVREL SVQATNGTNSDSDLKSIQDEIQQRLEEIDRVSNQTQFNGVKVLSQDNAMKIQVGANDGAAITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |
| 0177 | Mutants MIMI; MIM2 and MIM3 502 Mutants MIM1; MIM2 and MIM3 C-terminal part of CBLB502 | DNA | Artificial Sequence AACCCACTGGCTTCAATTGATTCTGCATTGTCAAAAGTGGACGCAGTTCGTTCTTCTCTGGGG GCAATTCAAAACCGTTTTGATTCAGCCATTACCAACCTTGGCAATACGGTAACCAATCTGAAC TCCGCGCGTAGCCGTATCGAAGATGCTGACTATGCAACGGAAGTTTCTCAAATGTCTAAAGCG CAGATTCTGCAGCAGGCTGGTACTTCCGTTCTGGCGCAGGCTAACCAGGTTCCGCAAAACGTC CTCTCTTTACTGCGTTAA |
| 0178 | Mutants MIMI; MIM2 and MIM3 Primers design (mutant MIM1) | DNA | Artificial Sequence ATTACCAACCTTGGCAATACGGTAACCAATCTGAACTCCGCGCGTAGCCGTATCGAAGAT |
| 0179 | Mutants MIMI; MIM2 and MIM3 Primers design (mutant MIM1) | PRT | Artificial Sequence ITNLGNTVTNLNSARSRIED |
| 0180 | Mutants MIMI; MIM2 and MIM3 Forward Primer 455-57 | DNA | Artificial Sequence CCTTGGCAATACGGTAACCGCTCTGGCCTCCGCGCGTAGCCGTATC |
| 0181 | Mutants MIMI; MIM2 and MIM3 Reverse Primer 455-57 | DNA | Artificial Sequence GATACGGCTACGCGCGGAGGCCAGAGCGGTTACCGTATTGCCAAGG |

TABLE 1-continued

Illustrative Flagellin Compositions

| SEQ ID | Construct Name | DNA/PRT | Sequence |
|---|---|---|---|
| 0182 | Mutants MIM1; MIM2 and MIM3 Primers design (mutant MIM2_MIM1 plus R460A) | DNA | Artificial Sequence ACGGTAACCGCTCTGGCCTCCGCGCGTAGCCGTATCGAAGATGCTGACTATGCAACGGAA |
| 0183 | Mutants MIM1; MIM2 and MIM3 Primers design (mutant MIM2_MIM1 plus R460A) | PRT | Artificial Sequence TVTALASARSRIEDADYATE |
| 0184 | Mutants MIM1; MIM2 and MIM3 Forward Primer 460 | DNA | Artificial Sequence GCTCTGGCCTCCGCGGCTAGCCGTATCGAAGATG |
| 0185 | Mutants MIM1; MIM2 and MIM3 Reverse Primer 460 | DNA | Artificial Sequence CATCTTCGATACGGCTAGCCGCGGAGGCCAGAGC |
| 0186 | Mutants MIM1; MIM2 and MIM3 Primers design (mutant MIM3_MIM2 plus N448A; N451A) | DNA | Artificial Sequence CAAAACCGTTTTGATTCAGCCATTACCAACCTTGGCAATACGGTAACCGCTCTGGCCTCC |
| 0187 | Mutants MIM1; MIM2 and MIM3 Primers design (mutant MIM3_MIM2 plus N448A; N451A) | PRT | Artificial Sequence QNRFDSAITNLGNTVTALAS |
| 0188 | Mutants MIM1; MIM2 and MIM3 Forward Primer 448-51 | DNA | Artificial Sequence GTTTTGATTCAGCCATTACCGCCCTTGGCGCTACGGTAACCGCTCTGG |
| 0189 | Mutants MIM1; MIM2 and MIM3 Reverse Primer 448-51 | DNA | Artificial Sequence CCAGAGCGGTTACCGTAGCGCCAAGGGCGGTAATGGCTGAATCAAAAC |
| 0190 | Mutant ME42 Forward Primer ME42 | DNA | Artificial Sequence CAACAGCGCGAAAGCCGATGCGGGAGGCCAGGCGATTGC |
| 0191 | Mutant ME42 Reverse Primer ME42 | DNA | Artificial Sequence GCAATCGCCTGGCCTCCCGCATCGGCTTTCGCGCTGTTG |
| 0192 | Mutant ME42 Sequence of ME42 construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGCCGATGCG GGAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0193 | Mutant ME42 Mutant ME42 | PRT | Artificial Sequence MSGLRINSAKADAGGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |

TABLE 1-continued

Illustrative Flagellin Compositions

| SEQ ID | Construct Name | DNA/PRT | Sequence | |
|---|---|---|---|---|
| 0194 | Mutant ME110 Forward Primer ME100 | DNA | Artificial Sequence | GTCTGTTCAGGCCACTGCCGGGGCTAACTCTGATTCCGATCTG |
| 0195 | Mutant ME110 Reverse Primer ME100 | DNA | Artificial Sequence | CAGATCGGAATCAGAGTTAGCCCCGGCAGTGGCCTGAACAGAC |
| 0196 | Mutant ME110 Sequence of ME100 construct | DNA | Artificial Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTGCCGGGGCTAACTCTGATTCCGAT<br>CTGAAATCTATCCAGGATGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTACTTCCGTT<br>CTGGCGCAGGCTAACCAGGTTCCGCAAAACGTCCTCTCTTTACTGGTTCCGCGGGGTTCTCAT<br>CATCATCATCATCATGGTTAAGTCGAC |
| 0197 | Mutant ME110 Mutant ME110 | PRT | Artificial Sequence | MSGLRINSAKDDAAGQAIANRFTSNIKGLTQASRNANDGISIAQTTEGALNEINNNLQRVREL<br>SVQATAGANSDSDLKSIQDEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATEVSNMSKAQILQQAGTSVLAQANQVPQNVLSLLVPRGSHHHHHHG |
| 0198 | Mutant ME100/110 Forward Primer ME110 | DNA | Artificial Sequence | CTGATTCCGATCTGAAAGCTATCCAGGCTGAAATTCAGCAACGTC |
| 0199 | Mutant ME100/110 Reverse Primer ME110 | DNA | Artificial Sequence | GACGTTGCTGAATTTCAGCCTGGATAGCTTTCAGATCGGAATCAG |
| 0200 | Mutant ME100/110 Sequence of ME100/110 construct | DNA | Artificial Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTGCCGGGGCTAACTCTGATTCCGAT<br>CTGAAAGCTATCCAGGCTGAAATTCAGCAACGTCTGGAAGAAATCGATCGCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTACTTCCGTT<br>CTGGCGCAGGCTAACCAGGTTCCGCAAAACGTCCTCTCTTTACTGGTTCCGCGGGGTTCTCAT<br>CATCATCATCATCATGGTTAAGTCGAC |
| 0201 | Mutant ME104N Intermediate Mutant ME100/110 | DNA | Artificial Sequence | ATGAGCGGGTTACGGATCAACAGCGCGAAAGACGATGCGGCAGGCCAGGCGATTGCTAACCGC<br>TTCACTTCTAATATCAAAGGTCTGACTCAGGCTTCCCGTAACGCTAACGACGGCATTTCTATT<br>GCGCAGACCACTGAAGGTGCGCTGAATGAAATCAACAACAACCTGCAGCGTGTGCGTGAGTTG<br>TCTGTTCAGGCCACTGCCGGGGCTAACTCTGATTCCGATCTGAAAGCTATCCAGGCTGAAATT<br>CAGCAACGTCTGGAAGAAATCGATCGCGTTTCTAATCAGACTCAATTTAACGGTGTTAAAGTC<br>CTGTCTCAGGACAACCAGATGAAAATCCAGGTTGGTGCTAACGATGGTGAAACCATTACCATC<br>GATCTGCAAAAAATTGATGTGAAAAGCCTTGGCCTTGATGGGTTCAATGTTAATTCCCCGGGA<br>AGTACCGCTAACCCACTGGCTTCAATTGATTCTGCATTGTCAAAAGTGGACGCAGTTCGTTCT<br>TCTCTGGGGGCAATTCAAAACCGCTTTGATTCAGCCATTACCAACCTTGGCAATACGGTAACC<br>AATCTGAACTCCGCGCGTAGCCGTATCGAAGATGCTGACTATGCAACGGAAGTTTCTAATATG<br>TCTAAAGCGCAGATTCTGCAGCAGGCTGGTACTTCCGTTCTGGCGCAGGCTAACCAGGTTCCG<br>CAAAACGTCCTCTCTTTACTGGTTCCGCGGGGTTCTCATCATCATCATCATCATGGTTAA |
| 0202 | Mutant ME100/110 Mutant ME110/110 | PRT | Artificial Sequence | MSGLRINSAKDDAAGQAIANRFTSNIKGLTQASRNANDGISIAQTTEGALNEINNNLQRVREL<br>SVQATAGANSDSDLKAIQAEIQQRLEEIDRVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATEVSNMSKAQILQQAGTSVLAQANQVPQNVLSLLVPRGSHHHHHHG |
| 0203 | Mutant ME104 Forward Primer ME104 | DNA | Artificial Sequence | GCCACTAACGGGACTAACGCTGATGCCGCTCTGAAATCTATCCAG |

TABLE 1-continued

Illustrative Flagellin Compositions

| SEQ ID | Construct Name | DNA/PRT | Sequence | |
|---|---|---|---|---|
| 0204 | Mutant ME104 Reverse Primer ME104 | DNA | Artificial Sequence | CTGGATAGATTTCAGAGCGGCATCAGCGTTAGTCCCGTTAGTGGC |
| 0205 | Mutant ME104 Sequence of ME104 construct | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACGCTGATGCCGCT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0206 | Mutant ME104 Mutant ME104 | PRT | Artificial Sequence | MSGLRINSAKDDAAGQAIANRFTSNIKGLTQASRNANDGISIAQTTEGALNEINNNLQRVREL SVQATNGTNADAALKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |
| 0207 | Mutant ME104N Primer FME104New | DNA | Artificial Sequence | GCCACTGCCGGGGCTAACGCTGATGCCGCTCTGAAAGCTATCCAG |
| 0208 | Mutant ME104N Primer RME104New | DNA | Artificial Sequence | CTGGATAGCTTTCAGAGCGGCATCAGCGTTAGCCCCGGCAGTGGC |
| 0209 | Mutant ME104N Sequence of construct ME104New | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTGCCGGGGCTAACGCTGATGCCGCT CTGAAAGCTATCCAGGCTGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0210 | Mutant ME104N Mutant ME104N | PRT | Artificial Sequence | MSGLRINSAKDDAAGQAIANRFTSNIKGLTQASRNANDGISIAQTTEGALNEINNNLQRVREL SVQATAGANADAALKAIQAEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |
| 0211 | Mutant ME110 Sequence of ME110 construct | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAAGCTATCCAGGCTGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0212 | Mutant ME110 Mutant ME110 | PRT | Artificial Sequence | MSGLRINSAKDDAAGQAIANRFTSNIKGLTQASRNANDGISIAQTTEGALNEINNNLQRVREL SVQATNGTNSDSDLKAIQAEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |

TABLE 1-continued

Illustrative Flagellin Compositions

| SEQ ID | Construct Name | DNA/PRT | Sequence | |
|---|---|---|---|---|
| 0213 | Mutant ME117 Forward Primer ME117 | DNA | Artificial Sequence | CTATCCAGGATGAAATTCAGGCACGTCTGGCAGAAATCGATCGCG |
| 0214 | Mutant ME117 Reverse Primer ME117 | DNA | Artificial Sequence | CGCGATCGATTTCTGCCAGACGTGCCTGAATTTCATCCTGGATAG |
| 0215 | Mutant ME117 Sequence of 33ML construct (should this say ME117?) | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGGCACGTCTGGCAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0216 | Mutant ME117 Mutant ME117 | PRT | Artificial Sequence | MSGLRINSAKDDAAGQAIANRFTSNIKGLTQASRNANDGISIAQTTEGALNEINNNLQRVREL SVQATNGTNSDSDLKSIQDEIQARLAEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |
| 0217 | Mutant ME124 Forward Primer ME104 | DNA | Artificial Sequence | GGAAGAAATCGATGCCGTTTCTGCTGCGACTCAATTTAACGGTGTTAAAGTCCTGTCTC |
| 0218 | Mutant ME124 Reverse Primer ME104 | DNA | Artificial Sequence | GAGACAGGACTTTAACACCGTTAAATTGAGTCGCAGCAGAAACGGCATCGATTTCTTCC |
| 0219 | Mutan ME124 Sequence of ME124 construct | DNA | Artificial Sequence | TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATGCCGTTTCTGCTGCG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0220 | Mutant ME124 Mutant ME124 | PRT | Artificial Sequence | MSGLRINSAKDDAAGQAIANRFTSNIKGLTQASRNANDGISIAQTTEGALNEINNNLQRVREL SVQATNGTNSDSDLKSIQDEIQQRLEEIDAVSAATQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHHG |
| 0221 | Mutant ME124P Forward Primer ME124P | DNA | Artificial Sequence | CAGCAACGTCTGGAAGAAATCGATGCCGTTTCTAATCAGACTCAATTTAACGG |
| 0222 | Mutant ME124P Reverse Primer ME124P | DNA | Artificial Sequence | CCGTTAAATTGAGTCTGATTAGAAACGGCATCGATTTCTTCCAGACGTTGCTG |
| 0223 | Mutant ME124 Expressed Mutant ME124P | DNA | Artificial Sequence | ATGAGCGGGTTACGGATCAACAGCGCGAAAGACGATGCGGCAGGCCAGGCGATTGCTAACCGC TTCACTTCTAATATCAAAGGTCTGACTCAGGCTTCCCGTAACGCTAACGACGGCATTTCTATT GCGCAGACCACTGAAGGTGCGCTGAATGAAATCAACAACAACCTGCAGCGTGTGCGTGAGTTG TCTGTTCAGGCCACTAACGGGACTAACTCTGATTCCGATCTGAAATCTATCCAGGATGAAATT CAGCAACGTCTGGAAGAAATCGATGCCGTTTCTAATCAGACTCAATTTAACGGTGTTAAAGTC CTGTCTCAGGACAACCAGATGAAAATCCAGGTTGGTGCTAACGATGGTGAAACCATTACCATC GATCTGCAAAAAATTGATGTGAAAAGCCTTGGCCTTGATGGGTTCAATGTTAATTCCCCGGGA AGTACCGCTAACCCACTGGCTTCAATTGATTCTGCATTGTCAAAAGTGGACGCAGTTCGTTCT |

TABLE 1-continued

Illustrative Flagellin Compositions

| SEQ ID | Construct Name | DNA/PRT | Sequence |
|---|---|---|---|
| | | | TCTCTGGGGGCAATTCAAAACCGCTTTGATTCAGCCATTACCAACCTTGGCAATACGGTAACC<br>AATCTGAACTCCGCGCGTAGCCGTATCGAAGATGCTGACTATGCAACGGAAGTTTCTAATATG<br>TCTAAAGCGCAGATTCTGCAGCAGGCTGGTACTTCCGTTCTGGCGCAGGCTAACCAGGTTCCG<br>CAAAACGTCCTCTCTTTACTGGTTCCGCGGGGTTCTCATCATCATCATCATGGTTAA |
| 0224 | Mutant ME124P<br>ME124P | DNA | Artificial<br>Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATGCCGTTTCTAATCAG<br>ACTCAATTTAACGGTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTACTTCCGTT<br>CTGGCGCAGGCTAACCAGGTTCCGCAAAACGTCCTCTCTTTACTGGTTCCGCGGGGTTCTCAT<br>CATCATCATCATGGTTAAGTCGAC |
| 0225 | Mutant ME124P<br>ME124P | PRT | Artificial<br>Sequence | MSGLRINSAKDDAAGQAIANRFTSNIKGLTQASRNANDGISIAQTTEGALNEINNNLQRVREL<br>SVQATNGTNSDSDLKSIQDEIQQRLEEIDAVSNQTQFNGVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATEVSNMSKAQILQQAGTSVLAQANQVPQNVSLLVPRGSHHHHHG |
| 0226 | Mutant ME132<br>Forward Primer<br>ME132 | DNA | Artificial<br>Sequence | CGTTTCTAATCAGACTCAATTTGCCGCTGTTAAAGTCCTGTCTCAGGACAACC |
| 0227 | Mutant ME132<br>Reverse Primer<br>ME132 | DNA | Artificial<br>Sequence | GGTTGTCCTGAGACAGGACTTTAACAGCGGCAAATTGAGTCTGATTAGAAACG |
| 0228 | Mutant ME132<br>Sequence of<br>ME132<br>construct | DNA | Artificial<br>Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATGCGTTTCTAATCAG<br>ACTCAATTTGCCGCTGTTAAAGTCCTGTCTCAGGACAACCAGATGAAAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTACTTCCGTT<br>CTGGCGCAGGCTAACCAGGTTCCGCAAAACGTCCTCTCTTTACTGGTTCCGCGGGGTTCTCAT<br>CATCATCATCATGGTTAAGTCGAC |
| 0229 | Mutant ME132<br>Mutant ME117<br>(ME132?) | PRT | Artificial<br>Sequence | MSGLRINSAKDDAAGQAIANRFTSNIKGLTQASRNANDGISIAQTTEGALNEINNNLQRVREL<br>SVQATNGTNSDSDLKSIQDEIQQRLEEIDRVSNQTQFAAVKVLSQDNQMKIQVGANDGETITI<br>DLQKIDVKSLGLDGFNVNSPGSTANPLASIDSALSKVDAVRSSLGAIQNRFDSAITNLGNTVT<br>NLNSARSRIEDADYATEVSNMSKAQILQQAGTSVLAQANQVPQNVSLLVPRGSHHHHHG |
| 0230 | Mutant ME142<br>Forward Primer<br>ME142 | DNA | Artificial<br>Sequence | GTTAAAGTCCTGTCTCAGGACAACGCGATGGCAATCCAGGTTGGTGCTAACG |
| 0231 | Mutant ME142<br>Reverse Primer<br>ME142 | DNA | Artificial<br>Sequence | CGTTAGCACCAACCTGGATTGCCATCGCGTTGTCCTGAGACAGGACTTTAAC |
| 0232 | Mutant ME142<br>Sequence of<br>ME142<br>construct | DNA | Artificial<br>Sequence | TAATACGACTCACTATAGGGGAATTGTGAGCGGATAACAATTCCCCTCTAGAATAATTTTGTT<br>TAACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCGT<br>AACGCTAACGACGGCATTTCTATTGCGCAGACCACTGAAGGTGCGCTGAATGAAATCAACAAC<br>AACCTGCAGCGTGTGCGTGAGTTGTCTGTTCAGGCCACTAACGGGACTAACTCTGATTCCGAT<br>CTGAAATCTATCCAGGATGAAATTCAGCAACGTCTGGAAGAAATCGATGCGTTTCTAATCAG<br>ACTCAATTTAACGGTGTTAAAGTCCTGTCTCAGGACAACGCGATGGCAATCCAGGTTGGTGCT<br>AACGATGGTGAAACCATTACCATCGATCTGCAAAAAATTGATGTGAAAAGCCTTGGCCTTGAT<br>GGGTTCAATGTTAATTCCCCGGGAAGTACCGCTAACCCACTGGCTTCAATTGATTCTGCATTG<br>TCAAAAGTGGACGCAGTTCGTTCTTCTCTGGGGGCAATTCAAAACCGCTTTGATTCAGCCATT<br>ACCAACCTTGGCAATACGGTAACCAATCTGAACTCCGCGCGTAGCCGTATCGAAGATGCTGAC<br>TATGCAACGGAAGTTTCTAATATGTCTAAAGCGCAGATTCTGCAGCAGGCTGGTACTTCCGTT<br>CTGGCGCAGGCTAACCAGGTTCCGCAAAACGTCCTCTCTTTACTGGTTCCGCGGGGTTCTCAT<br>CATCATCATCATGGTTAAGTCGAC |

TABLE 1-continued

Illustrative Flagellin Compositions

| SEQ ID | Construct Name | DNA/PRT | Sequence |
|---|---|---|---|
| 0233 | Mutant ME142 Mutant ME142 | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNAMAIQVGANDGETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHG |
| 0234 | Mutant ME150 Forward Primer ME150 | DNA | Artificial Sequence GATGAAAATCCAGGTTGGTGCTAGCGCTGCTGAAACCATTACCATCGATCTGC |
| 0235 | Mutant ME150 Reverse Primer ME150 | DNA | Artificial Sequence GCAGATCGATGGTAATGGTTTCAGCAGCGCTAGCACCAACCTGGATTTTCATC |
| 0236 | Mutant ME150 Sequence of ME150 construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AGCGCTGCTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC TATGCAACGGAAGTTTCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0237 | Mutant ME150 Mutant ME150 | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGASAAETITI DLQKIDVKSLGLDGFNVNSPGSTANPLASIDSALSKVDAVRSSLGAIQNRFDSAITNLGNTVT NLNSARSRIEDADYATEVSNMSKAQILQQAGTSVLAQANQVPQNVLSLLVPRGSHHHHHG |
| 0238 | Mutant ME468 Forward Primer ME468 | DNA | Artificial Sequence GCCGTATCGAAGATGCTGACGCTGGAGCGGAAGTTGCTAATATGTCTAAAGCGCAG |
| 0239 | Mutant ME468 Reverse Primer ME468 | DNA | Artificial Sequence CTGCGCTTTAGACATATTAGCAACTTCCGCTCCAGCGTCAGCATCTTCGATACGGC |
| 0240 | Mutant ME468 Sequence of ME468 construct | DNA | Artificial Sequence TAATACGACTCACTATAGGGGAATTGTGAGCGGATAACAATTCCCCTCTAGAATAATTTTGTT TAACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCGT AACGCTAACGACGGCATTTCTATTGCGCAGACCACTGAAGGTGCGCTGAATGAAATCAACAAC AACCTGCAGCGTGTGCGTGAGTTGTCTGTTCAGGCCACTAACGGGACTAACTCTGATTCCGAT CTGAAATCTATCCAGGATGAAATTCAGCAACGTCTGGAAGAAATCGATCGCGTTTCTAATCAG ACTCAATTTAACGGTGTTAAAGTCCTGTCTCAGGACAACCAGATGAAAATCCAGGTTGGTGCT AACGATGGTGAAACCATTACCATCGATCTGCAAAAAATTGATGTGAAAAGCCTTGGCCTTGAT GGGTTCAATGTTAATTCCCCGGGAAGTACCGCTAACCCACTGGCTTCAATTGATTCTGCATTG TCAAAAGTGGACGCAGTTCGTTCTTCTCTGGGGGCAATTCAAAACCGCTTTGATTCAGCCATT ACCAACCTTGGCAATACGGTAACCAATCTGAACTCCGCGCGTAGCCGTATCGAAGATGCTGAC GCTGGAGCGGAAGTTGCTAATATGTCTAAAGCGCAGATTCTGCAGCAGGCTGGTACTTCCGTT CTGGCGCAGGCTAACCAGGTTCCGCAAAACGTCCTCTCTTTACTGGTTCCGCGGGGTTCTCAT CATCATCATCATCATGGTTAAGTCGAC |
| 0241 | Mutant ME468 Mutant ME468 | PRT | Artificial Sequence MSGLRINSAKDDAAGQAIANRFTSNIKGLTQASRNANDGISIAQTTEGALNEINNNLQRVREL SVQATNGTNSDSDLKSIQDEIQQRLEEIDRVSNQTQFNGVKVLSQDNQMKIQVGANDGETITI DLQKIDVKSLGLDGFNVNSPGSTANPLASIDSALSKVDAVRSSLGAIQNRFDSAITNLGNTVT NLNSARSRIEDADAGAEVANMSKAQILQQAGTSVLAQANQVPQNVLSLLVPRGSHHHHHG |
| 0242 | Linker | PRT | Artificial Sequence SPG |

Uses of Flagellin-Related Compositions

In some embodiments, the flagellin-related compositions may stimulate Toll-like receptor activity (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13). The TLR family is composed of at least 10 members and is essential for innate immune defense against pathogens. The innate immune system recognizes conserved pathogen-associated molecular patterns (PAMPs). TLR may recognize a conserved structure that is particular to bacterial flagellin which may be composed of a large group of residues that are somewhat permissive to variation in amino acid content. Smith et al., Nat. Immunol. 4:1247-53 (2003) have identified 13 conserved amino acids in flagellin that are part of the conserved structure recognized by TLR5. The 13 conserved amino acids of flagellin that may be important for TLR5 activity are shown in FIGS. 1A and 1B.

In some embodiments, the flagellin-related composition activates TLR5 signaling. In some embodiments, the flagellin-related composition activates TLR5 at the same levels, or levels similar to, CBLB502. Activation of TLR5 induces expression of the nuclear factor NF-κB, which in turn activates numerous inflammatory-related cytokines. In further embodiments, the flagellin-related compositions induce expression of proinflammatory cytokines. In further embodiments, the flagellin-related compositions induce expression of anti-inflammatory molecules. In another embodiment, the flagellin-related compositions induce expression of anti-apoptotic molecules. In yet a further embodiment, the flagellin-related compositions induce expression of anti-bacterial molecules. The targets of NF-κB, include, but are not limited to, IL-β, TNF-α, IL-6, IL-8, IL-18, G-CSF, TNFSF13B, keratinocyte chemoattractant (KC), BLIMP1/PRDM1, CCL5, CCL15, CCL17, CCL19, CCL20, CCL22, CCL23, CXCL1, CCL28, CXCL11, CXCL10, CXCL3, CXCL1, GRO-beta, GRO-gamma, CXCL1, ICOS, IFNG, IL-1A, IL-1B, URN, IL-2, IL-9, IL-10, IL-11, IL-12, IL-12B, IL-12A, IL-13, IL-15, IL-17, IL-23A, IL-27, EBI3, IFNB1, CXCL5, KC, liGp1, CXCL5, CXCL6, LTA, LTB, CCL2, CXCL9, MCP-1/JE, CCL3, CCL4, CXCL3, CCL20, CXCL10, CXCL5, CCL5, CCL1, TNFbeta, TNFSF10, TFF3, TNFSF15, CD86, complement component 8a, CCL27, defensin-β3, MIG, MIP-2, and/or NOD2/CARD15.

In some embodiments, activating TLR5 signaling may regulate CD4+ T-cell immune function by increasing the generation of regulatory T-cells ($T_{regs}$), decreasing LPS-induced ERK1/2 activation, and/or activating Natural Killer (NK) T-cells.

Diseases and Methods of Treatment/Prevention

In various embodiments, the flagellin-related compositions (and/or additional agents) and methods described herein are applicable to variety of disease states. In one aspect, the invention provides a method of stimulating TLR5 signaling comprising administering a flagellin-related composition of the invention to a subject in need thereof. Activating TLR5 signaling may have broad therapeutic applications, including, but not limited to treating cancer, protecting from radiation-induced or reperfusion-induced damage, acting as adjuvant in vaccines, or protecting cells from cytotoxic compounds.

In some embodiments, the flagellin-related compositions of the invention, or fragments thereof may be provided as adjuvants to viral vaccines. In one embodiment, the flagellin-related compositions or fragments thereof may be administered in conjunction with an influenza vaccine or antigen to elicit a greater host immune response to the influenza antigens. In yet a further embodiment, the flagellin-related compositions of the invention, or fragments thereof may be provided as adjuvants to vaccines against parasites. In one embodiment, the flagellin-related compositions or fragments thereof may be administered in conjunction with an *Plasmodium* vaccine or antigen to elicit a greater host immune response to the *Plasmodium* antigen.

In some embodiments, the flagellin-related compositions of the invention may be administered to protect cells from toxic conditions. In some embodiments, the flagellin-related compositions may prevent liver cells from Fas-mediated injury. The flagellin-related compositions of the invention may cause a decrease in liver enzymes in the peripheral blood and caspase activation.

Cancers

In various embodiments, the present invention pertains to cancers and/or tumors; for example, the treatment or prevention of cancers and/or tumors. As used herein, "cancer" or "tumor" refers to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g. virus infected cells). A subject that has a cancer or a tumor is a subject having objectively measurable cancer cells present in the subject's body. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death.

The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis.

The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from, for example, melanoma, colon, breast, or prostate, and thus may be made up of cells that were originally skin, colon, breast, or prostate, respectively. The cancer may also be a hematological malignancy, which may be lymphoma. The cancer may invade a tissue such as liver, lung, bladder, or intestinal. The invaded tissue may express a TLR, while the cancer may or may not express a TLR.

Also provided herein is a method of reducing cancer recurrence, comprising administering to a mammal in need thereof a flagellin-related composition of the invention. The cancer may be or may have been present in a tissue that either does or does not express TLR, such as TLR5. The method may also prevent cancer recurrence. The cancer may be an oncological disease. The cancer may be a dormant tumor, which may result from the metastasis of a cancer. The dormant tumor may also be left over from surgical removal of a tumor. The cancer recurrence may be tumor regrowth, a lung metastasis, or a liver metastasis.

Representative cancers and/or tumors of the present invention may or may not express TLR5, and may include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The flagellin-related compositions (and/or additional agents) and methods described herein are applicable metastatic diseases, including cancers and/or tumors. "Metastasis" refers to the spread of cancer from a primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases may be detected through the sole or combined use of magnetic resonance imaging (MRI) scans, computed tomography (CT) scans, blood and platelet counts, liver function studies, chest X-rays and bone scans in addition to the monitoring of specific symptoms.

In some embodiments, the invention relates to a method of treating a mammal suffering from a constitutively active NF-κB cancer comprising administering to the mammal a composition comprising a therapeutically effective amount of an agent that induces NF-κB activity, including the flagellin-related compositions (and/or additional agents) described herein. The agent that induces NF-κB activity may be administered in combination with a cancer treatment.

In some embodiments, the present invention includes methods for treatment of side effects from cancer treatment comprising administering the flagellin-related composition (and/or additional agents) described herein. In some embodiments, the side effects from cancer treatment include alopecia, myelosuppression, renal toxicity, weight loss; pain, nausea, vomiting, diarrhea, constipation, anemia, malnutrition, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

In some embodiments, the present invention relates to a method of treating a mammal suffering from damage to normal tissue attributable to treatment of cancer, including but not limited to a constitutively active NF-κB cancer, comprising administering to the mammal a composition comprising a therapeutically effective amount of the flagellin-related composition (and/or additional agents) described herein.

Aging and Stress

In some embodiments, the present invention includes methods for modulation of cell aging comprising administering the flagellin-related composition (and/or additional agents) described herein.

In some embodiments, the present invention includes methods for treatment of stress comprising administering the flagellin-related composition (and/or additional agents) described herein. This invention also relates to a method of treating a subject suffering from damage to normal tissue attributable to stress, comprising administering to the mammal a composition comprising a therapeutically effective amount of a flagellin-related composition (and/or additional agents). The stress may be attributable to any source including, but not limited to, radiation, wounding, poisoning, infection, and temperature shock.

In some embodiments, the flagellin-related composition (and/or additional agents) may be administered at any point prior to exposure to the stress including, but not limited to, about 48 hr, about 46 hr, about 44 hr, about 42 hr, about 40 hr, about 38 hr, about 36 hr, about 34 hr, about 32 hr, about 30 hr, about 28 hr, about 26 hr, about 24 hr, about 22 hr, about 20 hr, about 18 hr, about 16 hr, about 14 hr, about 12 hr, about 10 hr, about 8 hr, about 6 hr, about 4 hr, about 3 hr, about 2 hr, or about 1 hr prior to exposure. In some embodiments, the flagellin-related composition may be administered at any point after exposure to the stress including, but not limited to, about 1 hr, about 2 hr, about 3 hr, about 4 hr, about 6 hr, about 8 hr, about 10 hr, about 12 hr, about 14 hr, about 16 hr, about 18 hr, about 20 hr, about 22 hr, about 24 hr, about 26 hr, about 28 hr, about 30 hr, about 32 hr, about 34 hr, about 36 hr, about 38 hr, about 40 hr, about 42 hr, about 44 hr, about 46 hr, or about 48 hr after exposure.

Mitigation and Prevention of Radiation Damage

In still other embodiments, the present invention relates to treatment of radiation related diseases or damage. In specific embodiments, the present invention relates to mitigation of or prevention and/or protection from radiation related diseases.

In one embodiment, the present invention relates to the protection of cells from the effects of exposure to radiation. In some embodiments, the present invention pertains to a method of protecting a subject from radiation comprising administering a flagellin-related composition (and/or additional agents) described herein. In some embodiments, the radiation is ionizing radiation. In some embodiments, the ionizing radiation is sufficient to cause gastrointestinal syndrome or hematopoietic syndrome. In some embodiments, the flagellin-related composition (and/or additional agents) described herein is administered in combination with a radioprotectant e.g. an antioxidant (e.g. amifostine and vitamin E), a cytokine (e.g. a stem cell factor), etc. In some embodiments, the flagellin-related composition (and/or additional agents) described herein is administered prior to, together with, or after radiation. In some embodiments, the flagellin-related composition (and/or additional agents) described herein is administered in combination with a growth factor (e.g. keratinocyte growth factor), a steroid (e.g. 5-androstenediol), ammonium trichloro(dioxoethylene-O,O')tellurate, thyroid protecting agents (e.g. Potassium iodide (KI)), anti-nausea agents, anti-diarrhea agents, analgesics, anxiolytics, sedatives, cytokine therapy, antibiotics, antifungal agents, and/or antiviral agents.

In some embodiments, the present invention pertains to a method of treating and/or mitigating apoptosis-mediated tissue damage in a subject, comprising administering to a subject in need thereof a composition comprising a flagellin-related composition (and/or additional agents) described herein. In some embodiments the apoptosis is attributable to cellular stress. In some embodiments, the flagellin-related composition (and/or additional agents) described herein is administered prior to, together with, or after the tissue damage. In some embodiments, the cellular stress is radiation. In some embodiments, the flagellin-related composition (and/or additional agents) is administered in combination with a radioprotectant (e.g. an antioxidant (e.g. amifostine and vitamin E), a cytokine (e.g. a stem cell factor), etc.

Injury and death of normal cells from ionizing radiation is a combination of a direct radiation-induced damage to the exposed cells and an active genetically programmed cell reaction to radiation-induced stress resulting in a suicidal death or apoptosis. Apoptosis plays a key role in massive cell loss occurring in several radiosensitive organs (e.g., hematopoietic and immune systems, epithelium of digestive tract, etc.), the failure of which determines general radiosensitivity of the organism. In some embodiments, administration of the flagellin-related compositions of the invention to a subject in need thereof suppresses apoptosis in cells. In some embodiments, the flagellin-related compositions of the invention are administered to a subject undergoing cancer radiotherapy treatment to protect healthy cells from the damaging effects of the radiation treatment.

Exposure to ionizing radiation (IR) may be short- or long-term, and/or it may be applied as a single or multiple doses and/or it may be applied to the whole body or locally. The present invention, in some embodiments, pertains to nuclear accidents or military attacks, which may involve exposure to a single high dose of whole body irradiation (sometimes followed by a long-term poisoning with radioactive isotopes). The same is true (with strict control of the applied dose), for example, for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation. Poisoning or treatment with radioactive isotopes results in a long-term local exposure to radiation of targeted organs (e.g., thyroid gland in the case of inhalation of $^{125}$I).

Further, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as, several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached.

Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

Acute pathological outcome of gamma irradiation leading to death is different for different doses and may be determined by the failure of certain organs that define the threshold of organism's sensitivity to each particular dose. Thus, lethality at lower doses occurs, for example, from bone marrow aplasia, while moderate doses kill faster, for example, by inducing a gastrointestinal (GI) syndrome. Very high doses of radiation can cause almost instant death eliciting neuronal degeneration.

Organisms that survive a period of acute toxicity of radiation can suffer from long-term remote consequences that include radiation-induced carcinogenesis and fibrosis developing in exposed organs (e.g., kidney, liver or lungs) in the months and years after irradiation.

Cellular DNA is a major target of IR that causes a variety of types of DNA damage (genotoxic stress) by direct and indirect (e.g. free radical-based) mechanisms. All organisms maintain DNA repair system capable of effective recovery of radiation-damaged DNA; errors in DNA repair process may lead to mutations.

In some embodiments, the radiation exposure experienced by the subject is a consequence of cancer radiotherapy treatment. Tumors are generally more sensitive to gamma radiation and can be treated with multiple local doses that cause relatively low damage to normal tissue. Nevertheless, in some instances, damage of normal tissues is a limiting factor in application of gamma radiation for cancer treatment. The use of gamma-irradiation during cancer therapy by conventional, three-dimensional conformal or even more focused BeamCath delivery has also dose-limiting toxicities caused by cumulative effect of irradiation and inducing the damage of the stem cells of rapidly renewing normal tissues, such as bone marrow and gastrointestinal (GI) tract. Administration of the flagellin-related compositions of the invention may protect the patient's healthy cells from radiation damage without affecting the radiosensitivity of the tumor cells.

In some embodiments, the subject has been exposed to lethal doses of radiation. At high doses, radiation-induced lethality is associated with so-called hematopoietic and gastrointestinal radiation syndromes. Hematopoietic syndrome is characterized by loss of hematopoietic cells and their progenitors making it impossible to regenerate blood and lymphoid system. Death usually occurs as a consequence of infection (result of immunosuppression), hemorrhage and/or anemia. GI syndrome is caused by massive cell death in the intestinal epithelium, predominantly in the small intestine, followed by disintegration of intestinal wall and death from bacteriemia and sepsis. Hematopoietic syndrome usually prevails at the lower doses of radiation and leads to the more delayed death than GI syndrome.

In the past, radioprotectants were typically antioxidants-both synthetic and natural. More recently, cytokines and growth factors have been added to the list of radioprotectants; the mechanism of their radioprotection is considered to be a result of facilitating the effects on regeneration of sensitive tissues. There is no clear functional distinction between both groups of radioprotectants, however, since some cytokines induce the expression of the cellular antioxidant proteins, such as manganese superoxide dismutase (MnSOD) and metallothionein.

The measure of protection for a particular agent may be expressed by dose modification factor (DMF or DRF). DMF is determined by irradiating the radioprotector treated subject and untreated control subjects with a range of radiation doses and then comparing the survival or some other endpoints. DMF is commonly calculated for 30-day survival (LD50/30 drug-treated divided by LD50/30 vehicle-treated) and quantifies the protection of the hematopoietic system. In order to estimate gastrointestinal system protection, LD50 and DMF are calculated for 6- or 7-day survival.

The flagellin-related compositions described herein possess strong pro-survival activity at the cellular level and on the organism as a whole. In response to super-lethal doses of radiation, the flagellin-related compositions described herein may inhibit both gastrointestinal and hematopoietic syndromes, which are major causes of death from acute radiation exposure. As a result of these properties, the flagellin-related compositions described herein may be used to treat the effects of natural radiation events and nuclear accidents. Moreover, the flagellin-related compositions described herein can be used in combination with other radioprotectants, thereby, dramatically increasing the scale of protection from ionizing radiation.

As opposed to conventional radioprotective agents (e.g., scavengers of free radicals), anti-apoptotic agents may not reduce primary radiation-mediated damage but may act against secondary events involving active cell reaction on primary damage, therefore complementing the existing lines of defense. Pifithrin-alpha, a pharmacological inhibitor of p53 (a key mediator of radiation response in mammalian cells), is an example of this new class of radioprotectants. However, the activity of p53 inhibitors is limited to protection of the hematopoietic system and has no protective effect in digestive tract (gastrointestinal syndrome), therefore reducing therapeutic value of these compounds.

The flagellin-related compositions described herein may be used as a radioprotective agent to extend the range of tolerable radiation doses by increasing radioresistance of humans beyond the levels achievable by currently available measures (shielding and application of existing bioprotective agents) and drastically increase the chances of crew survival in case of nuclear accidents or large-scale solar particle events, for example.

The flagellin-related compositions described herein are also useful for treating irreplaceable cell loss caused by low-dose irradiation, for example, in the central nervous system and reproductive organs. The flagellin-related compositions described herein may also be used during cancer chemotherapy to treat the side effects associated with chemotherapy, including alopecia, myelosuppression, renal toxicity, weight loss, pain, nausea, vomiting, diarrhea, constipation, anemia, malnutrition, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

In one embodiment, a mammal is treated for exposure to radiation, comprising administering to the mammal a composition comprising a therapeutically effective amount of a flagellin-related composition. The flagellin-related composition may be administered in combination with one or more radioprotectants. The one or more radioprotectants may be any agent that treats the effects of radiation exposure including, but not limited to, antioxidants, free radical scavengers and cytokines.

The flagellin-related compositions described herein may inhibit radiation-induced programmed cell death in response to damage in DNA and other cellular structures. In some embodiments, the flagellin-related compositions described herein may not deal with damage at the cellular and may not prevent mutations. Free radicals and reactive oxygen species (ROS) are the major cause of mutations and other intracellular damage. Antioxidants and free radical scavengers are effective at preventing damage by free radicals. The combination of a flagellin-related composition and an antioxidant or free radical scavenger may result in less extensive injury, higher survival, and improved health for mammals exposed to radiation. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

The flagellin-related compositions described herein may also be administered in combination with a number of cytokines and growth factors that confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (all mentioned cytokines), and prevention of their apoptosis (SCF). The treatment allows accumulation of leukocytes and their precursors prior to irradiation thus enabling quicker reconstitution of the immune system after irradiation. SCF efficiently rescues lethally irradiated mice with DMF in range 1.3-1.35 and is also effective against gastrointestinal syndrome. Flt-3 ligand also provides strong protection in mice and rabbits.

Several factors, while not cytokines by nature, stimulate the proliferation of the immunocytes and may be used in combination with the flagellin-related compositions described herein. For example, 5-AED (5-androstenediol) is a steroid that stimulates the expression of cytokines and increases resistance to bacterial and viral infections. Synthetic compounds, such as ammonium tri-chloro(dioxoethylene-O,O'—) tellurate (AS-101), may also be used to induce secretion of numerous cytokines and for combination with the flagellin-related compositions described herein.

Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

The flagellin-related compositions described herein may offer protection against both gastrointestinal (GI) and hematopoietic syndromes. Such compositions may be used in combination with one or more inhibitors of GI syndrome (including, but are not limited to, cytokines such as SCF and KGF).

The flagellin-related composition may be administered at any point prior to exposure to radiation including, but not limited to, about 48 hr, about 46 hr, about 44 hr, about 42 hr, about 40 hr, about 38 hr, about 36 hr, about 34 hr, about 32 hr, about 30 hr, about 28 hr, about 26 hr, about 24 hr, about 22 hr, about 20 hr, about 18 hr, about 16 hr, about 14 hr, about 12 hr, about 10 hr, about 8 hr, about 6 hr, about 4 hr, about 3 hr, about 2 hr, or about 1 hr prior to exposure. The flagellin-related composition may be administered at any point after exposure to radiation including, but not limited to, about 1 hr, about 2 hr, about 3 hr, about 4 hr, about 6 hr, about 8 hr, about 10 hr, about 12 hr, about 14 hr, about 16 hr, about 18 hr, about 20 hr, about 22 hr, about 24 hr, about 26 hr, about 28 hr, about 30 hr, about 32 hr, about 34 hr, about 36 hr, about 38 hr, about 40 hr, about 42 hr, about 44 hr, about 46 hr, or about 48 hr after exposure to radiation.

In various embodiments, the present methods and compositions provide treatment or prevention of radiation-related disorders, such as ARS. In various embodiments, the treatments described herein reduce morbidity or mortality of an exposed population of human patients or accelerates recovery from symptoms of ARS. ARS often presents as a sequence of phased symptoms, which may vary with individual radiation sensitivity, type of radiation, and the radiation dose absorbed. Generally, without wishing to be bound by theory, the extent of symptoms will heighten and the duration of each phase will shorten with increasing radiation dose. ARS can be divided into three phases: prodromal phase (a.k.a. N-V-D stage), latent period and manifest illness. In various embodiments, the flagellin-related compositions (and/or additional agents), as described herein, may be administered to a human patient in any one of these three stages (i.e. the flagellin-related compositions (and/or additional agents) may be administered to a human patient in the prodromal phase, the flagellin-related compositions (and/or additional agents) may be administered to a human patient in latent period, or the flagellin-related compositions (and/or additional agents) may be administered to a human patient in manifest illness stage).

In the prodromal phase there is often a relatively rapid onset of nausea, vomiting, and malaise. Use of antiemetics, (e.g. oral prophylactic antiemetics) such as granisetron (KYTRIL), ondansetron (ZOFRAN), and 5-HT3 blockers with or without dexamethasone, may be indicated in situations where high-dose radiological exposure has occurred, is likely, or is unavoidable. Accordingly, in various embodiments, the flagellin-related compositions (and/or additional agents) may be administered to a human patient in receiving an anti-emetic agent or CBLB502 may be administered to a human patient in combination with an anti-emetic agent. For example, the flagellin-related compositions (and/or additional agents) may also be added to the following antiemetic regimens: Ondansetron: initially 0.15 mg/kg IV; a continuous IV dose option consists of 8 mg followed by 1 mg/h for the next 24 hours. Oral dose is 8 mg every 8 hours as needed or Granisetron (oral dosage form): dose is usually 1 mg initially, then repeated 12 hours after the first dose. Alternatively, 2 mg may be taken as one dose. IV dose is based on body weight; typically 10 µg/kg (4.5 µg/lb) of body weight.

In the latent period, a human patient may be relatively symptom free. The length of this phase varies with the dose. The latent phase is longest preceding the bone-marrow depression of the hematopoietic syndrome and may vary between about 2 and 6 weeks. The latent period is somewhat shorter prior to the gastrointestinal syndrome, lasting from a few days to a week. It is shortest of all preceding the neurovascular syndrome, lasting only a matter of hours. These times are variable and may be modified by the presence of other disease or injury. Manifest illness presents with the clinical symptoms associated with the major organ system injured (marrow, intestinal, neurovascular).

In some embodiments, the present invention relates to the mitigation of, or protection of cells from, the effects of exposure to radiation. In some embodiments, the present invention pertains to a method of mitigating and/or protecting a human patient from radiation comprising administering the flagellin-related compositions (and/or additional agents). In some embodiments, the radiation is ionizing radiation. In some embodiments, the ionizing radiation is sufficient to cause gastrointestinal syndrome or hematopoietic syndrome.

In some embodiments, the ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage.

Hematopoietic syndrome (a.k.a. bone marrow syndrome) is characterized by loss of hematopoietic cells and their progenitors making it impossible to regenerate blood and lymphoid system. This syndrome is often marked by a drop in the number of blood cells, i.e., aplastic anemia. This may result in infections (e.g. opportunistic infections) due to a low amount of white blood cells, bleeding due to a lack of platelets, and anemia due to few red blood cells in the circulation. These changes can be detected by blood tests after receiving a whole-body acute dose. Conventional trauma and burns resulting from a bomb blast are complicated by the poor wound healing caused by hematopoietic syndrome, increasing mortality. Death may occur as a consequence of infection (result of immunosuppression), hemorrhage and/or anemia. Hematopoietic syndrome usually prevails at the lower doses of radiation and leads to the more delayed death than GI syndrome.

Gastrointestinal syndrome is caused by massive cell death in the intestinal epithelium, predominantly in the small intestine, followed by disintegration of intestinal wall and death from bacteriemia and sepsis. Symptoms of this form of radiation injury include nausea, vomiting, loss of appetite, loss of absorptive capacity, hemorrhage in denuded areas, and abdominal pain. Illustrative systemic effects of gastrointestinal syndrome include malnutrition, dehydration, renal failure, anemia, sepsis, etc. Without treatment (including, for example, bone marrow transplant), death is common (e.g. via infection from intestinal bacteria). In some embodiments, the flagellin-related compositions (and/or additional agents), may be used in combination with bone marrow transplant. In some embodiments, the flagellin-related compositions (and/or additional agents), may be used in combination with one or more inhibitors of GI syndrome and/or any of the additional agents described herein.

Neurovascular syndrome presents with neurological symptoms such as dizziness, headache, or decreased level of consciousness, occurring within minutes to a few hours, and with an absence of vomiting. Additional symptoms include extreme nervousness and confusion; severe nausea, vomiting, and watery diarrhea; loss of consciousness; and burning sensations of the skin. Neurovascular syndrome is commonly fatal.

In some embodiments, the present invention provides a method for reducing the risk of death following exposure to irradiation comprising administering an effective amount of the flagellin-related compositions (and/or additional agents) In some embodiments, the radiation is potentially lethal, and, optionally, occurs as the result of a radiation disaster. In various embodiments, the flagellin-related compositions (and/or additional agents) is administered within about 25 hours following radiation exposure. In some embodiments, the present invention provides a method for reducing the risk of death following exposure to potentially lethal irradiation occurring as the result of a radiation disaster, comprising administering the flagellin-related compositions (and/or additional agents) within about 25 hours following radiation exposure.

In various embodiments, the flagellin-related compositions (and/or additional agents) are administered to a patient who has been exposed to a high dose of radiation, namely a whole body dose. In various embodiments, the high dose of radiation may not be uniform. In various embodiments, the ARS is a result of a high dose of radiation. In various embodiments, the high dose of radiation is about 2.0 Gy, or about 2.5 Gy, or about 3.0 Gy, or about 3.5 Gy, or about 4.0 Gy, or about 4.5 Gy, or about 5 Gy, or about 10 Gy, or about 15 Gy, or about 20 Gy, or about 25 Gy, or about 30 Gy. In various embodiments, the high dose of radiation is about 5 to about 30 Gy, or about 10 to 25 Gy, or about 15 to 20 Gy. In some embodiments, the high dose of radiation is assessed by one or more of physical dosimetry and/or biological dosimetry (e.g. multiparameter dose assessments), cytogenics (e.g. chromosomal analysis for, for example, blood samples (including, by way of non-limiting example, dicentric analysis). In various embodiments, whole-body radiation doses can be divided into sublethal (<2 Gy), potentially lethal (2-10 Gy), and supralethal (>10 Gy).

Reperfusion Injuries

In some embodiments, the present invention pertains to a method of treating the effects of reperfusion on a subject's tissue comprising administering the flagellin-related compositions (and/or additional agents) described herein. The flagellin-related compositions (and/or additional agents) described herein may be administered in combination with an antioxidant, such as, for example, amifostine and vitamin E.

Reperfusion may be caused by an injury, which may be ischemia or hypoxia. The ischemia may result from a condition such as, for example, tachycardia, infarction, hypotension, embolism, thromboemoblism (blood clot), sickle cell disease, localized pressure to extremities to the body, and tumors. The hypoxia may be selected from hypoxemic hypoxia (carbon monoxide poisoning; sleep apnea, chronic obstructive pulmonary disease, respiratory arrest; shunts), anemic hypoxia ($O_2$ content low), hypoxemic hypoxia, and histotoxic hypoxia. The localized pressure may be due to a tourniquet.

The flagellin-related compositions (and/or additional agents) described herein may be administered prior to, together with, or after the influx of oxygen. The tissue may be for example, the GI tract, lung, kidney, liver, cardiovascular system, blood vessel endothelium, central nervous system, peripheral nervous system, muscle, bone, and hair follicle.

Reperfusion may damage a body component when blood supply returns to the body component after the injury. The effects of reperfusion may be more damaging to the body component than the injury itself. There are several mechanism and mediators of reperfusion including, for example, oxygen free radicals, intracellular calcium overload, and endothelial dysfunction. Excessive quantities of reactive oxygen species, when reintroduced into a previously injured body component, undergo a sequential reduction leading to the formation of oxygen free radicals. Potent oxidant radicals, such as superoxide anion, hydroxyl radical, and peroxynitrite may be produced within the first few minutes of reflow to the body component and may play a crucial role in the development of reperfusion injury. Oxygen free radicals also can be generated from sources other than reduction of molecular oxygen. These sources include enzymes, such as, for example, xanthine oxidase, cytochrome oxidase, and cyclooxygenase, and the oxidation of catecholamines.

Reperfusion is also a potent stimulus for neutrophil activation and accumulation, which in turn serve as potent stimuli for reactive oxygen species production. Specifically, the main products of the neutrophil respiratory burst are strong oxidizing agents including hydrogen peroxide, free oxygen radicals and hypochlorite. Neutrophils are the most abundant type of phagocyte, normally representing 50 to 60% of the total circulating leukocytes, and are usually the first cells to arrive at the site of injured body component. Oxygen-derived free radicals produce damage by reacting with polyunsaturated fatty acids, resulting in the formation of lipid peroxides and hydroperoxides that damage the body component and impair the function of membrane-bound enzyme systems. Free radicals stimulate the endothelial release of platelet activating factor and chemokines such as neutrophil activator factor, chemokine (C—X—C motif) ligand 1, and chemokine (C—X—C motif) ligand 1 which attracts more neutrophils and amplifies the production of oxidant radicals and the degree of reperfusion injury. Reactive oxygen species also quench nitric oxide, exaggerating endothelial injury and tissue cell dysfunction. In addition to an increased production, there is also a relative deficiency in endogenous oxidant scavenging enzymes, which further exaggerates free radical-mediated cardiac dysfunction.

Reperfusion may further result in marked endothelial cell dysfunction. Endothelial dysfunction facilitates the expression of a prothrombotic phenotype characterized by platelet and neutrophil activation, important mediators of reperfusion. Once neutrophils make contact with the dysfunctional endothelium, they are activated, and in a series of well-defined steps (rolling, firm adherence, and transmigration) they migrate into areas of tissue injury through endothelial cell junctions as part of the innate immune response.

Changes in intracellular calcium homeostasis play an important role in the development of reperfusion. Reperfusion may be associated with an increase in intracellular calcium; this effect may be related to increased sarcolemmal calcium entry through L-type calcium channels or may be secondary to alterations in sarcoplasmic reticulum calcium cycling. In addition to intracellular calcium overload, alterations in myofilament sensitivity to calcium have been implicated in reperfusion. Activation of calcium-dependent proteases (calpain I) with resultant myofibril proteolysis has been suggested to underscore reperfusion injury, as has proteolysis of troponin.

Reperfusion of tissue cells subjected to an injury had an altered cellular metabolism, which in turn may contribute to delayed functional recovery. For example, an injury may induce anaerobic metabolism in the cell with a net production of lactate. Lactate release persists during reperfusion, suggesting a delayed recovery of normal aerobic metabolism. Likewise, the activity of mitochondrial pyruvate dehydrogenase (PDH) may be inhibited up to 40% after an injury and may remain depressed for up to 30 minutes after reperfusion.

Each of these events during reperfusion can lead to stress to the tissue cells and programmed cell death (apoptosis) and necrosis of the tissue cells. Apoptosis normally functions to "clean" tissues from wounded and genetically damaged cells, while cytokines serve to mobilize the defense system of the organism against the pathogen. However, under conditions of severe injury both stress response mechanisms can by themselves act as causes of death.

In various embodiments, the effects of reperfusion may be caused by an injury to the body. The injury may be due to ischemia, hypoxia, an infarction, or an embolism. Treatment of the injury may lead to reperfusion and further damage to the body component.

Ischemia may be an absolute or relative shortage of blood supply to a body component. Relative shortage may be a mismatch, however small, of blood supplied (oxygen delivery) to a body component versus blood required to a body component for the adequate oxygenation. Ischemia may also be an inadequate flow of blood to a part of the body due to a constriction or blockage of blood vessels supplying it and may affect any body component in the body. Insufficient blood supply causes body components to become hypoxic, or, if no oxygen is supplied at all, anoxic. This may cause necrosis. The mechanisms of ischemia may vary greatly. For example, ischemia to any body component may be due to tachycardia (abnormally rapid beating of the heart), atherosclerosis (lipid-laden plaque obstructing the lumen of arteries), hypotension (low blood pressure in septic shock, heart failure), thromboembolisms (blood clots), outside compression of blood vessels (tumor), embolisms (foreign bodies in the circulation, e.g., amniotic fluid embolism), sickle cell disease (abnormally shaped hemoglobin), infarctions, induced g-forces which restrict the blood flow and force the blood to extremities of the body, localized extreme cold due to frostbite, ice, improper cold compression therapy, and any other force that restricts blood flow to the extremities such as a tourniquet. Force to restrict blood flow to extremities may be required due to severe lacerations, incisions, puncture such as a knifing, crushing injuries due to blunt force trauma, and ballistic trauma due to gunshot or shrapnel wounds. Ischemia may be a feature of heart diseases, ischemic colitis, transient ischemia attacks, cerebrovascular accidents, acute renal injury, ruptured arteriovenous malformations, and peripheral artery occlusive disease.

Hypoxia may be a deprivation of adequate supply of oxygen. Hypoxia may be pathological condition in which the body as a whole (generalized hypoxia) or region of the body (tissue hypoxia) is deprived of adequate oxygen supply. A variation in levels of arterial oxygen may be due to a mismatch between supply and demand of oxygen by body components. A complete deprivation of oxygen supply is anoxia. Hypoxia may be hypoxemic hypoxia, anemic hypoxia, hypoxemic hypoxia, histotoxic hypoxia, histotoxic hypoxia, and ischemic hypoxia.

Hypoxemic hypoxia may be an inadequate supply of oxygen to the body as a whole caused by low partial pressure of oxygen in arterial blood. Hypoxemic hypoxia may be due to low partial pressure of atmospheric oxygen such as at high altitudes, replacement of oxygen in breathing mix of a modified atmosphere such as a sewer, replacement of oxygen intentionally as in recreational use of nitrous oxide, a decrease in oxygen saturation of the blood due to sleep apnea, or hypopnea, inadequate pulmonary ventilation such as chronic obstructive pulmonary disease or respiratory arrest, anatomical or mechanical shunts in the pulmonary circulation or a right to left shunt in the heart and lung. Shunts may cause collapsed alveoli that are still perfused or a block in ventilation to an area of the lung. Shunts may present blood meant for the pulmonary system to not be ventilated and prevent gas exchange because the blood vessels empty into the left ventricle and the bronchial circulation, which supplies the bronchi with oxygen.

Anemia hypoxia may be the total oxygen content is reduced but the arterial oxygen pressure is normal. Hypoxemic hypoxia may be when blood fails to deliver oxygen to target body components. Hypoxemic hypoxia may be caused by carbon monoxide poisoning which inhibits the ability of hemoglobin to release the oxygen bound to it, or methaemoglobinaemia, an abnormal hemoglobin that accumulates in the blood. Histotoxic hypoxia may be due to being unable to effectively use oxygen due to disabled oxidative phosphorylation enzymes.

Infarction is a type of pathological condition that can cause ischemia. Infarction may be a macroscopic area of necrotic tissue caused the loss of an adequate blood supply due to an occlusion. The infarction may be a white infarction composed of platelets and causes necrosis in organ tissues such as heart, spleen, and kidneys. The infarction may be a red infarction composed of red blood cells and fibrin strands in organ tissues of the lung. Disease associated with infarction may include myocardial infarction, pulmonary embolism, cerebrovascular accident (stroke), acute renal failure, peripheral artery occlusive disease (example being gangrene), antiphospholipid syndrome, sepsis, giant cell arthritis, hernia, and volvulus.

Embolism is a type of pathological condition that can cause ischemia. Embolism may be an object that migrates from one part of the body and causes an occlusion or blockage of a blood vessel in another part of the body. An embolism may be thromboembolism, fat embolism, air embolism, septic embolism, tissue embolism, foreign body embolism, amniotic fluid embolism. Thromboembolism may be a blood clot that is completely or partially detached from the site of thrombosis. Fat embolism may be endogenous fat tissues that escape into the blood circulation. The fracture of bones is one example of a leakage of fat tissue into the ruptured vessels and arteries. Air embolism may be a rupture of alveoli and inhaled air that leaks into the blood vessels. The puncture of the subclavian vein or intravenous therapy are examples of leakage of air into the blood vessels. A gas embolism may be gasses such as nitrogen and helium because insoluble and forming small bubbles in the blood.

Pharmaceutically Acceptable Salts and Excipients

The flagellin-related compositions (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any flagellin-related compositions (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

Formulations, Administration, Dosing, and Treatment Regimens

The present invention includes the described flagellin-related compositions (and/or additional agents) in various formulations. Any flagellin-related composition (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the flagellin-related compositions (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the flagellin-related compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In one embodiment, any flagellin-related composition (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and depends in-part upon the site of the medical condition. In most instances, administration results in the release of any agent described herein into the bloodstream.

Any flagellin-related composition (and/or additional agents) described herein can be administered orally. Such flagellin-related compositions (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment.

In one embodiment, any flagellin-related composition (and/or additional agents) described herein is formulated in accordance with routine procedures as a composition adapted for oral administration to humans. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any flagellin-related composition (and/or additional agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of any flagellin-related composition (and/or additional agents) described herein as well as the dosing schedule can depend on various parameters, including, but not limited to, the disease being treated, the subject's general health, and the administering physician's discretion. Any agent described herein, can be administered prior to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks before), concurrently with, or subsequent to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks after) the administration of an additional therapeutic agent, to a subject in need thereof. In various embodiments any agent described herein is administered about 1 minute apart, about 10 minutes apart, about 30 minutes apart, less than about 1 hour apart, about 1 hour apart, about 1 hour to about 2 hours apart, about 2 hours to about 3 hours apart, about 3 hours to about 4 hours apart, about 4 hours to about 5 hours apart, about 5 hours to about 6 hours apart, about 6 hours to about 7 hours apart, about 7 hours to about 8 hours apart, about 8 hours to about 9 hours apart, about 9 hours to about 10 hours apart, about 10 hours to about 11 hours apart, about 11 hours to about 12 hours apart, no more than about 24 hours apart or no more than 48 hours apart.

The amount of any flagellin-related composition (and/or additional agents) described herein that is admixed with the carrier materials to produce a single dosage can vary depending upon the subject being treated and the particular mode of administration. In vitro or in vivo assays can be employed to help identify optimal dosage ranges.

In general, the doses that are useful are known to those in the art. For example, doses may be determined with reference *Physicians' Desk Reference,* 66th Edition, PDR Network; 2012 Edition (Dec. 27, 2011), the contents of which are incorporated by reference in its entirety.

The dosage of any flagellin-related composition (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

Generally, when orally administered to a mammal, the dosage of any flagellin-related composition (and/or additional agents) described herein may be about 0.001 mg/kg/day to about 100 mg/kg/day, about 0.01 mg/kg/day to about 50 mg/kg/day, or about 0.1 mg/kg/day to about 10 mg/kg/day. When orally administered to a human, the dosage of any agent described herein is normally about 0.001 mg to about 1000 mg per day, about 1 mg to about 600 mg per day, or about 5 mg to about 30 mg per day.

For administration of any flagellin-related composition (and/or additional agents) described herein by parenteral injection, the dosage is normally about 0.1 mg to about 250 mg per day, about 1 mg to about 20 mg per day, or about 3 mg to about 5 mg per day. Injections may be given up to four times daily. Generally, when orally or parenterally administered, the dosage of any agent described herein is normally about 0.1 mg to about 1500 mg per day, or about 0.5 mg to about 10 mg per day, or about 0.5 mg to about 5 mg per day. A dosage of up to about 3000 mg per day can be administered.

In another embodiment, delivery can be in a vesicle, in particular a liposome (see Langer, 1990, *Science* 249:1527-1533; Treat et al., in *Liposomes in the Therapy of Infectious Disease and Cancer,* Lopez-Berestein and Fidler (eds.), Liss, New York, pp. 353-365 (1989).

Any flagellin-related composition (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123;

4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any flagellin-related composition (and/or additional agents) described herein can, independently, be one to four times daily or one to four times per month or one to six times per year or once every two, three, four or five years. Administration can be for the duration of about one day or about one month, about two months, about three months, about six months, about one year, about two years, about three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing any flagellin-related composition (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any flagellin-related composition (and/or additional agents) described herein can be administered in a single daily dose, or the total daily dosage can be administered in divided doses of two, three or four times daily. Furthermore, any flagellin-related composition (and/or additional agents) described herein can be administered continuously rather than intermittently throughout the dosage regimen.

Combination Therapies and Conjugation

In some embodiments, the invention provides for flagellin-related compositions and methods that further comprise administering an additional agent to a subject. In some embodiments, the invention pertains to co-administration and/or co-formulation. Any of the compositions described herein may be co-formulated and/or co-administered.

In some embodiments, any flagellin-related composition described herein acts synergistically when co-administered with another agent and is administered at doses that are lower than the doses commonly employed when such agents are used as monotherapy. In various embodiments, any agent referenced herein may be used in combination with any of the flagellin-related compositions described herein.

In some embodiments, the present invention pertains to chemotherapeutic agents as additional agents.

Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal1 and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid;

aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, the flagellin-related compositions (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

In still other embodiments, the flagellin-related compositions (and/or additional agents) described herein further comprise a cytotoxic agent, comprising, in exemplary embodiments, a toxin, a chemotherapeutic agent, a radioisotope, and an agent that causes apoptosis or cell death. Such agents may be conjugated to a composition described herein.

The flagellin-related compositions (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Exemplary detectable moieties further include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine-125, Carbon-14, Sulfur-35, Tritium and Phosphorus-32.

In various embodiments, the additional agents of the present invention include one or more of blood products, colony stimulating factors, cytokines and/or growth factors, antibiotics, diluting and/or blocking agents, mobilizing or chelating agents, stem cell transplants, antioxidants or free radicals, and radioprotectants.

In some embodiments, the blood product is one or more of hematopoietic growth factors, such as filgrastim (e.g. NEUPOGEN), a granulocyte colony-stimulating factor (G-CSF), which may be optionally pegylated (e.g. NEULASTA); sargramostim (LEUKINE); and a granulocyte-macrophage colony-stimulating factor (GM-CSF) and a KSF.

In some embodiments, the additional agent is one or more cytokines and/or growth factors that may confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (e.g. via all mentioned cytokines), and prevention of their apoptosis (e.g. via SCF). The treatment allows accumulation of leukocytes and their precursors prior to irradiation thus enabling quicker reconstitution of the immune system after irradiation. SCF efficiently rescues lethally irradiated mice with a dose modifying factor (DMF) in range 1.3-1.35 and is also effective against gastrointestinal syndrome. Flt-3 ligand also provides strong protection in mice and rabbits.

Several factors, while not cytokines by nature, stimulate the proliferation of the immunocytes and may be used in combination with the flagellin-related compositions at the doses and regimens described herein. For example, 5-AED (5-androstenediol) is a steroid that stimulates the expression of cytokines and increases resistance to bacterial and viral infections. Synthetic compounds, such as ammonium trichloro(dioxoethylene-O,O'—) tellurate (AS-101), may also be used to induce secretion of numerous cytokines and for combination with the flagellin-related compositions. Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

In certain embodiments, the flagellin-related compositions may be added to a regimen of cytokines (e.g. for FILGRASTIM (G-CSF) 2.5-5 µg/kg/d QD s.c. (100-200 µg/m$^2$/d); for SARGRAMOSTIM (GM-CSF) 5-10 µg/kg/d QD s.c. (200-400 µg/m$^2$/d); and/or for PEGFILGRASTIM (pegG-CSF) 6 mg once s.c.).

In some embodiments, the antibiotic is one or more of an anti-bacterial (anti-gram positive and anti-gram negative agents), and/or anti-fungal, and/or anti-viral agent. By way of non-limiting example, in some embodiments, the antibiotic may be a quinolone, e.g. ciprofloxacin, levofloxacin, a third- or fourth-generation cephalosporin with pseudomonal coverage: e.g., cefepime, ceftazidime, or an aminoglycoside: e.g. gentamicin, amikacin, penicillin or amoxicillin, acyclovir, vanomycin. In various embodiments, the antibiotic targets *Pseudomonas aeruginosa*.

In some embodiments, the additional agent is a diluting and/or blocking agents. For example, stable iodide compounds may be used (e.g. liquid (ThyroShield) and the tablet (Iosat) KI (NUKEPILLS), Rad Block, I.A.A.A.M., No-Rad, Life Extension (LEF), KI4U, NukeProtect, ProKI)). A 130 mg dose of daily of oral potassium iodide (KI) may be used in conjunction with the flagellin-related compositions.

In some embodiments, the additional agent is a mobilizing or chelating agent. Illustrative mobilizing agents include propylthiouracil and methimazole, with may reduce the thyroid's retention of radioactive compounds. Further the flagellin-related compositions can be used alongside increasing oral fluids to a human patient to promote excretion. Illustrative chelating agents are water soluble and excreted in urine. Illustrative chelating agents include DTPA and EDTA. Dimercaprol forms stable chelates with mercury, lead, arsenic, gold, bismuth, chromium, and nickel and therefore may be considered for the treatment of internal contamination with the radioisotopes of these elements. Penicillamine chelates copper, iron, mercury, lead, gold, and possibly other heavy metals.

In some embodiments, the additional agent is a stem cell transplant (e.g. bone marrow transplant, PBSCT, MSCT). In some embodiments the stem cell transplant is Remestemcel-L (Osiris) of CLT-008 (Cellerant).

In some embodiments, the additional agent is an antioxidant or free radical. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

In some embodiments, the additional agent may be a radioprotectant e.g. an antioxidant (e.g. amifostine and vitamin E, gamma tocotrienol (a vitamin-E moiety), and genistein (a soy byproduct)), a cytokine (e.g. a stem cell factor), a growth factor (e.g. keratinocyte growth factor), a steroid (e.g. 5-androstenediol), ammonium trichloro(dioxoethylene-O,O')tellurate, thyroid protecting agents (e.g. Potassium iodide (KI) or potassium iodate ($KIO_3$) (e.g. liquid (ThyroShield) and the tablet (Iosat) KI (NUKEPILLS), Rad Block, I.A.A.A.M., No-Rad, Life Extension (LEF), KI4U, NukeProtect, ProKI)), anti-nausea agents, anti-diarrhea agents, antiemetics ((e.g. oral prophylactic antiemetics) such as granisetron (KYTRIL), ondansetron (ZOFRAN), and 5-HT3 blockers with or without dexamethasone), analgesics, anxiolytics, sedatives, cytokine therapy, and antibiotics.

Gastric lavage and emetics, which can be used as additional agents, can be used to empty the stomach promptly and completely after the ingestion of poisonous materials. Purgatives, laxatives, and enemas, which also can be used as additional agents, can reduce the residence time of radioactive materials in the colon. Further additional agents include ion exchange resins which may limit gastrointestinal uptake of ingested or inhaled radionuclides, ferric ferrocyanide (Prussian blue) and alginates, which have been used in humans to accelerate fecal excretion of cesium-137.

In still other embodiments, the additional agent may be an agent used to treat radiation-related disorders, such as, for example, 5-AED (Humanetics), Ex-RAD (Onconova), Beclometasone Dipropionate (Soligenix), detoxified endotoxin, EA-230 (Exponential Biotherapies), ON-01210.Na (Onconova), Sothrombomodulin alfa (PAION), Remestemcel-L (Osiris), BIO-100, BIO-200, BIO-300, BIO-400, BIO- 500 (Humanetics), CLT-008 (Cellerant), EDL-2000 (Rx-Bio), Homspera (ImmuneRegen), MnDTEIP (Aeolus Pharmaceuticals), RLIP-76 (Terapio), and RX-100 and RX 101 (RxBio).

Further, in some embodiments, the flagellin-related compositions (and/or additional agents) can be used in combination with shielding; reduction of radiation exposure time; and use of agents to reduce body exposure (e.g. uses of gloves, face mask, hood, protective clothing (e.g. anticontamination suits such as TYVEK ANTI-C SUITS or MOPP-4)).

Viral Vectors Encoding Therapeutic Agents and Cells Expressing Same

In various embodiments, the flagellin-related compositions (and/or additional agents) of the present invention is expressed by viral vectors and transformed cells. For example, the viral vectors and transformed human cells described herein may express the present compositions. In an embodiment, the viral vector or human cells expressing the therapeutic agent are capable of expressing the agent proximal to a tumor. The cells can be modified in vivo, or alternatively cells modified ex vivo can be administered to a patient by a variety of methods, such as by injection.

In one embodiment, the cell is a tumor cell. For ex vivo transformation, such tumor cells can be irradiated to eliminate the ability of the cell to replicate, as known in the art, while maintaining the transient expression of the therapeutic agent after administration. For in vivo transformation, non-integrative expression vectors may be preferred.

In certain embodiments, the tumor cell is autologous or endogenous. In the former instance, the tumor cell is taken from a patient, transfected or transduced with a construct encoding the therapeutic agent and re-introduced to the patient, for example after irradiation. In the latter instance, the tumor cell is transformed in vivo by local administration of an appropriate construct as described herein.

In an alternative embodiment, the modified tumor cell is allogeneic. The allogeneic tumor cell thus can be maintained in a cell line. In this instance, the tumor cell can be selected from the cell line, irradiated, and introduced to the patent.

Modified human cells capable of producing the flagellin-related compositions (and/or additional agents) can be made by transfecting or transducing the cells with an expression vector encoding the therapeutic agent. Expression vectors for the expression of the flagellin-related compositions (and/or additional agents), or a combination of therapeutic agents can be made by methods well known in the art.

In various embodiments, the flagellin-related compositions (and/or additional agents) can be administered to a patient in the form of one or more nucleic acid construct.

In one embodiment, the construct comprises a retroviral vector. Retroviral vectors are capable of permanently integrating DNA encoding flagellin-related compositions (and/or additional agents) into the cell genome. Thus, in the case of ex vivo manipulation of autologous or allogeneic cells, stable cell lines that constitutively produce the flagellin-related compositions (and/or additional agents) can be prepared. In an embodiment, the cells are irradiated prior to administration to a patient. The irradiated cells produce the flagellin-related compositions (and/or additional agents) for a limited period of time.

In one embodiment, the expression construct comprises an SFV vector, which demonstrates high levels of transient expression in mammalian cells. The SFV vector is described, for example, in Lundstrom, Expert Opin. Biol. Ther. 3:771-777 (2003), incorporated herein by reference in its entirety. Thus, in the case of in vivo manipulation of endogenous cells in a patient, transient expression of high levels of the flagellin-related compositions (and/or additional agents) can be accomplished.

Systems capable of expressing recombinant protein in vivo are known in the art. By way of example, the system can use the 2A mediated antibody expression system disclosed in Fang et al., Nature Biotech. 23(5): 584-590 (2005) and U.S. Patent Publication No. 2005/0003506, the disclosures of which are expressly incorporated by reference herein in their entirety. Other systems known in the art are contemplated, and can also be adapted to produce the flagellin-related compositions (and/or additional agents) in vivo as described herein.

In various embodiments, administration of the flagellin-related composition (and/or additional agents) expressing cells disclosed herein or the agents of the invention disclosed herein can be combined with administration of cytokines that stimulate antigen-presenting cells such as granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interferon, etc., or cellular vaccines capable of expressing such cytokines. In some embodiments, the flagellin-related composition (and/or additional agents) expressing cells are further modified to express such cytokines. Additional proteins and/or cytokines known to enhance T cell proliferation and secretion, such as IL-1, IL-2, B7, anti-CD3 and anti-CD28 can be employed simultaneously or sequentially with the flagellin-related compositions (and/or additional agents) of the invention to augment the immune response, and/or stimulate co-stimulatory pathways and/or induce activation/proliferation of effector T cells.

Vectors and Methods of Transformation

Expression vectors encoding the flagellin-related compositions (and/or additional agents) may be viral or non-viral. Viral vectors are preferred for use in vivo. Expression vectors of the invention comprise a nucleic acid encoding the flagellin-related compositions (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid.

An expression control region of an expression vector of the invention is capable of expressing operably linked encoding nucleic acid in a human cell. In an embodiment, the cell is a tumor cell. In another embodiment, the cell is a non-tumor cell.

In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present invention contemplates the use of inducible promoters capable of effecting high level of expression transiently in response to a cue. When in the proximity of a tumor cell, a cell transformed with an expression vector for the flagellin-related compositions (and/or additional agents) comprising such an expression control sequence is induced to transiently produce a high level of the agent by exposing the transformed cell to an appropriate cue. Exemplary inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a B7-H4 ligand coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also preferred for in vivo transduction. In some situations it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of MV (Kootstra et al., Ann. Rev. Pharm. Toxicol., 43:413-439, 2003).

Viral Vectors

In one aspect, the invention provides expression vectors for the expression of the flagellin-related compositions (and/or additional agents) that are viral vectors. Many viral vectors useful for gene therapy are known (see, e.g., Lundstrom, Trends Biotechnol., 21: 1 17, 122, 2003.

Exemplary viral vectors include those selected from Antiviruses (LV), retroviruses (RV), adenoviruses (AV), adeno-associated viruses (MV), and α viruses, though other viral vectors may also be used. For in vivo uses, viral vectors that do not integrate into the host genome are preferred, such as α viruses and adenoviruses, with α viruses being especially preferred. Exemplary types of α viruses include Sindbis virus, Venezuelan equine encephalitis (VEE) virus, and Semliki Forest virus (SFV), with SFV being especially preferred. For in vitro uses, viral vectors that integrate into the host genome are preferred, such as retroviruses, AAV, and Antiviruses.

In an embodiment, the viral vector provides for transient high level expression in a transduced human cell.

In one embodiment, the viral vector does not provide for integration of the flagellin-related composition (and/or additional agents) encoding nucleic acid into the genome of a transduced human cell.

In another embodiment, the viral vector provides for integration of the flagellin-related compositions (and/or additional agents) encoding nucleic acid into the genome of a transduced human cell.

In one embodiment, the invention provides methods of transducing a human cell in vivo, comprising contacting a solid tumor in vivo with a viral vector of the invention.

In another embodiment, the invention provides methods of transducing a human cell ex vivo, comprising contacting a human cell ex vivo with the viral vector of the invention. In one embodiment, the human cell is a tumor cell. In one embodiment, the human cell is allogeneic. In one embodiment, the tumor cell is derived from the patient. In one embodiment, the human cell is a non-tumor cell, such as, e.g., an antigen presenting cell (APC), or a T cell.

Virus particle coats may be modified to alter specificity and improve cell/tissue targeting, as is well known in the art. Viral vectors may also be delivered in other vehicles, for example, liposomes. Liposomes may also have targeting moieties attached to their surface to improve cell/tissue targeting.

In some embodiments, the present invention provides human cells expressing the therapeutic agent of the invention. In various embodiments, the human cells express the agent proximal to a tumor cell of, for example, a patient.

Diagnostic and Predictive Methods

In some aspects, the invention provides a method for identifying a subject who may respond to treatment with a TLR5 agonist. In some embodiments, the present invention provides a method of determining if a patient's tumor expresses TLR5.

TLR5 expression may be a predictive marker for determining the grade and/or progression of a patient's tumor or dysplasia. In some embodiments, the flagellin-related compositions (and/or additional agents) described herein are useful in determining a tumor grade and/or stage of a particular cancer.

Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade may vary with each type of cancer and are known in the art.

Histologic grade, also called differentiation, refers to how much the tumor cells resemble normal cells of the same tissue type. Nuclear grade refers to the size and shape of the nucleus in tumor cells and the percentage of tumor cells that are dividing.

Based on the microscopic appearance of cancer cells, pathologists commonly describe tumor grade by four degrees of severity: Grades 1, 2, 3, and 4. The cells of Grade 1 tumors resemble normal cells, and tend to grow and multiply slowly. Grade 1 tumors are generally considered the least aggressive in behavior. Conversely, the cells of Grade 3 or Grade 4 tumors do not look like normal cells of the same type. Grade 3 and 4 tumors tend to grow rapidly and spread faster than tumors with a lower grade. The American Joint Committee on Cancer recommends the following guidelines for grading tumors: GX-grade cannot be assessed (Undetermined grade); G1—well-differentiated (Low grade); G2—moderately differentiated (Intermediate grade); G3—poorly differentiated (High grade); and G4—undifferentiated (High grade).

Grading systems are different for each type of cancer. For example, pathologists use the Gleason system to describe the degree of differentiation of prostate cancer cells. The Gleason system uses scores ranging from Grade 2 to Grade 10. Lower Gleason scores describe well-differentiated, less aggressive tumors. Higher scores describe poorly differentiated, more aggressive tumors. Other grading systems include, for example, the Bloom-Richardson system for breast cancer and the Fuhrman system for kidney cancer.

Cancer survival rates or survival statistics may refer to the percentage of people who survive a certain type of cancer for a specific amount of time. Cancer statistics often use an overall five-year survival rate. For example the overall five-year survival rate for bladder cancer is 80 percent, i.e. 80 of every 100 of people diagnosed with bladder cancer were living five years after diagnosis and 20 out of every 100 died within five years of a bladder cancer diagnosis. Other types of survival rates may be used, for example: disease-free survival rate (number of people with cancer who achieve remission) and progression-free survival rate. (number of people who still have cancer, but their disease is not progressing).

In some embodiments, the flagellin-related compositions (and/or additional agents) described herein are useful in establishing a tumor grade for the purposes of diagnosis or prognosis of a particular cancer, including prognosing the survival rate, disease-free survival rate and/or progression-free survival rate prior to, during and/or after administration of a flagellin-related composition (and/or additional agents) disclosed herein and/or prior to, during and/or after administration of an anti-cancer agent or therapy.

In some embodiments, the flagellin-related compositions (and/or additional agents) described herein are used as part of a method of scoring tumor grades to assist in the selection and/or predict the outcome of treatment. For example, the flagellin-related compositions (and/or additional agents) described herein may be used to diagnose or identify the cancer from a patient as stage I (e.g. not locally advanced) predicting the need for less aggressive treatment. Alternatively, the therapeutic agent described herein may be used to diagnose or identify the cancer from a patient as stage II or III, (e.g. the cancer may be locally advanced) predicting the need for more aggressive treatment. Similarly, the flagellin-related compositions (and/or additional agents) described herein may be used to diagnose or identify the cancer from a patient as stage IV, or is metastatic, predicting the need for very aggressive treatment.

In some embodiments, the cancer is non-resectable. A non-resectable cancer is a malignancy which cannot be surgically removed, due either to the number of metastatic foci, or because it is in a surgical danger zone. In some embodiments, the therapeutic agent described herein is used as part of a method of treating tumors to assist in selecting the nature and/or timing/administration of treatment including, for example, administering anti-cancer agents which reduce tumor volume, prior to chemotherapeutic and/or radiation treatment, and/or increase or decrease the dose of chemotherapy or radiation administered to a patient.

In some embodiments, the cancer is multidrug resistant. For example, the patient may have undergone one or more cycles of chemotherapy, without substantial response. Alternatively or in addition, the tumor has one or more markers of multidrug resistance. Thus, as used herein, the term multidrug resistant means a cancer exhibiting non-responsiveness to at least one cycle of combination chemotherapy, or alternatively, has scored (diagnostically) as resistant to at least two of (including comparable agent to) docetaxel, paclitaxel, doxorubicin, epirubicin, carboplatin, cisplatin, vinblastine, vincristine, oxaliplatin, carmustine, fluorouracil, gemcitabine, cyclophosphamide, ifosfamide, topotecan, erlotinib, etoposide, and mitomycin. In some embodiments, the therapeutic agents described herein are useful in establishing whether the tumor is responsive to one or more chemotherapeutics, radiation therapy and/or other anti-cancer therapy.

In other embodiments, the cancer is a recurrence following conventional chemotherapy of an initial cancer. Often, recurrent cancer has developed drug resistance, and thus is particularly difficult to treat and often comes with a poor prognosis for survival.

In some embodiments, the flagellin-related compositions (and/or additional agents) described herein are used as part of a method of tumor evaluation which takes the place of a performance status. Performance status can be quantified using any system and methods for scoring a patient's performance status which are known in the art. The measure is often used to determine whether a patient can receive chemotherapy, dose adjustment, and/or to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry.

Higher performance status (e.g., at least about 80%, or at least about 70% using the Karnofsky scoring system) may indicate treatment to prevent progression of the disease state, and enhance the patient's ability to accept chemotherapy and/or radiation treatment. For example, when the therapeutic agent described herein indicates higher performance status, the patient is ambulatory and capable of self care. In other embodiments, when the therapeutic agent described herein indicates a low performance status (e.g., less than about 50%, less than about 30%, or less than about 20% using the Karnofsky scoring system), the patient is largely confined to bed or chair and is disabled even for self-care.

The Karnofsky score runs from 100 to 0, where 100 is "perfect" health and 0 is death. The score may be employed at intervals of 10, where: about 100% is normal, no complaints, no signs of disease; about 90% is capable of normal activity, few symptoms or signs of disease, about 80% is normal activity with some difficulty, some symptoms or signs; about 70% is caring for self, not capable of normal activity or work; about 60% is requiring some help, can take care of most personal requirements; about 50% requires help often, requires frequent medical care; about 40% is disabled, requires special care and help; about 30% is severely disabled, hospital admission indicated but no risk of death; about 20% is very ill, urgently requiring admission, requires supportive measures or treatment; and about 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than about 50% of waking hours; 3, capable of only limited self-care, confined to bed or chair more than about 50% of waking hours; 4, completely disabled, cannot carry on any self-care, totally confined to bed or chair; 5, dead.

In some embodiments, histological samples of tumors are graded using the therapeutic agent described herein according to Elston & Ellis, Histopathology, 1991, 19:403-10, which is hereby incorporated by reference in its entirety. In some embodiments, the therapeutic agent described herein is useful in establishing a tumor grade for the purposes of diagnosis or prognosis of a particular cancer.

In some embodiments, the flagellin-related compositions (and/or additional agents) described herein are useful for evaluating a subject and/or a specimen from a subject (e.g. a cancer patient). In some embodiments, evaluation is one or more of diagnosis, prognosis, and/or response to treatment.

Diagnosis refers to the process of attempting to determine or identify a possible disease or disorder, such as, for example, cancer. Prognosis refers to the predicting of a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and probability of recurrence.

In various embodiments, the diagnostic and predictive methods described herein comprise evaluating a presence, absence, or level of a protein. In another embodiment, the methods described herein comprise evaluating a presence, absence, or level of expression of a nucleic acid. The compositions described herein may be used for these measurements. For example, in some embodiments, the methods described herein comprise contacting a specimen of the tumor or cells cultured from the tumor with a therapeutic agent as described herein.

In some embodiments, the present invention includes the measurement of a tumor specimen, including biopsy or surgical specimen samples. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen. In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained. In some embodiments, the tumor specimen may be a biopsy sample, such as cultured cells. These cells may be processed using the usual cell culture techniques that are known in the art. These cells may be circulating tumor cells. In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue. In certain embodiments, the tumor specimen contains less than about 100 mg of tissue, or in certain embodiments, contains about 50 mg of tissue or less. The tumor specimen (or biopsy) may contain from about 20 mg to about 50 mgs of tissue, such as about 35 mg of tissue. The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In some embodiments, the diagnostic and predictive methods and/or evaluation may direct treatment (including treatment with the therapeutic agents described herein). In one embodiment, the evaluation may direct the use or withholding of adjuvant therapy after resection. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the therapeutic agents described herein are used as an adjuvant therapy in the treatment of a cancer. In some embodiments, the therapeutic agents described herein are used as the sole adjuvant therapy in the treatment of a cancer. In some embodiments, the therapeutic agents described herein are withheld as an adjuvant therapy in the treatment of a cancer. For example, if a patient is unlikely to respond to a therapeutic agent described herein or will have a minimal response, treatment may not be administered in the interest of quality of life and to avoid unnecessary toxicity from ineffective chemotherapies. In such cases, palliative care may be used.

In some embodiments the therapeutic agents described herein are administered as a neoadjuvant therapy prior to resection. In certain embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means a therapeutic agent described herein is administered to cancer patients prior to surgery. Types of cancers for which neoadjuvant chemotherapy is commonly considered include, for example, breast, colorectal, ovarian, cervical, bladder, and lung. In some embodiments, the therapeutic agents described herein are used as a neoadjuvant therapy in the treatment of a cancer. In some embodiments, the use is prior to resection. In some embodiments, the therapeutic agents described herein are withheld as a neoadjuvant therapy in the treatment of a cancer. For example, if a patient is unlikely to respond to a therapeutic agent described herein or will have a minimal response, treatment may not be administered in the interest of quality of life and to avoid unnecessary toxicity from ineffective chemotherapies. In such cases, palliative care may be used.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. flagellin-related compositions (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

In certain embodiments, a pharmacologically effective amount that will treat cancer will modulate the symptoms typically by at least about 10%, at least about 20%, at least about 30%, at least about 40%, or at least about 50%. In exemplary embodiments, such modulations will result in, for example, statistically significant and quantifiable changes in the numbers of cancerous cells.

This invention is further illustrated by the following non-limiting examples.

EXAMPLES

Figure 2:
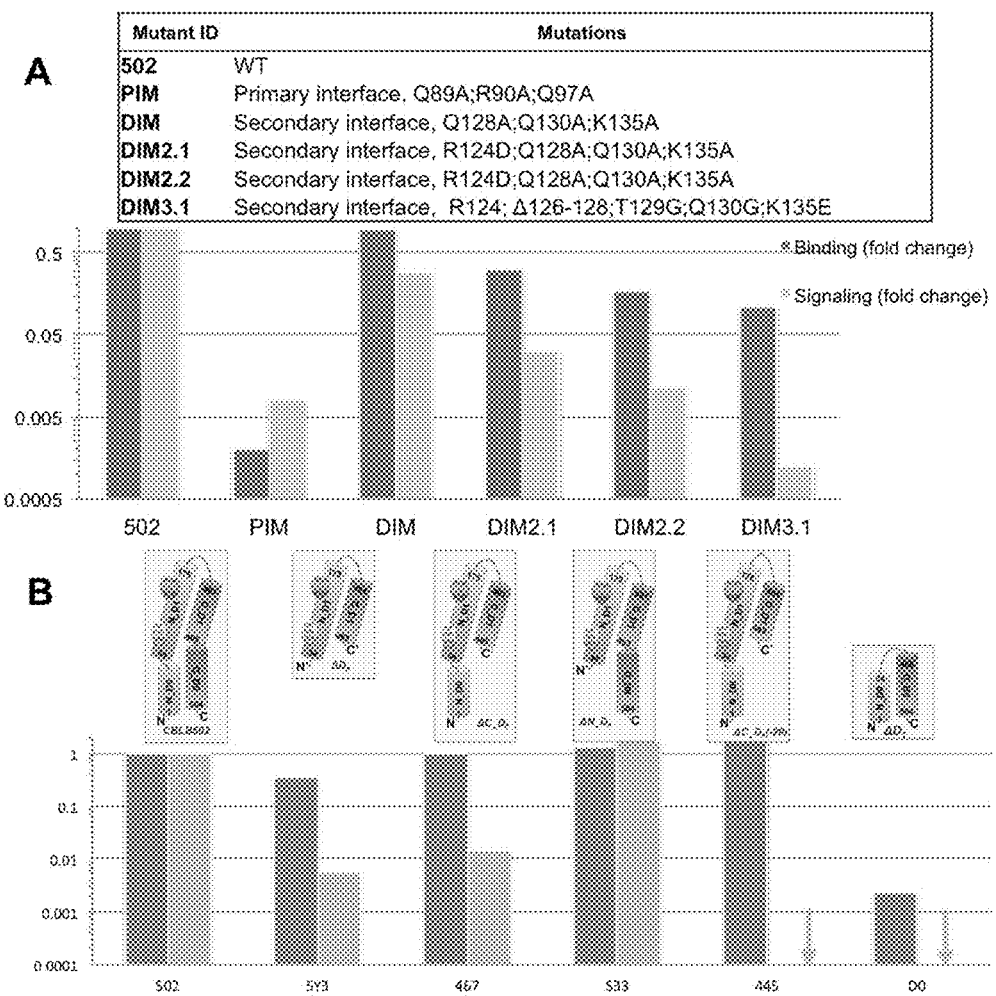
FIG. 2 shows early structure-activity relationship analysis (SAR) data reflecting the contribution of individual segments and entire domains of CBLB502 to the efficiency of binding and signaling. Relative binding and signaling affinities were obtained using FP biochemical assay and cell-based reporter assay respectively and normalized to CBLB502. Analyses were performed for a series of mutations within predicted primary and secondary dimerization interfaces (A) as well as for a deletion of larger segments or entire domains D0 or D1 (B) as diagrammatically shown above the graph.
Figure 3:
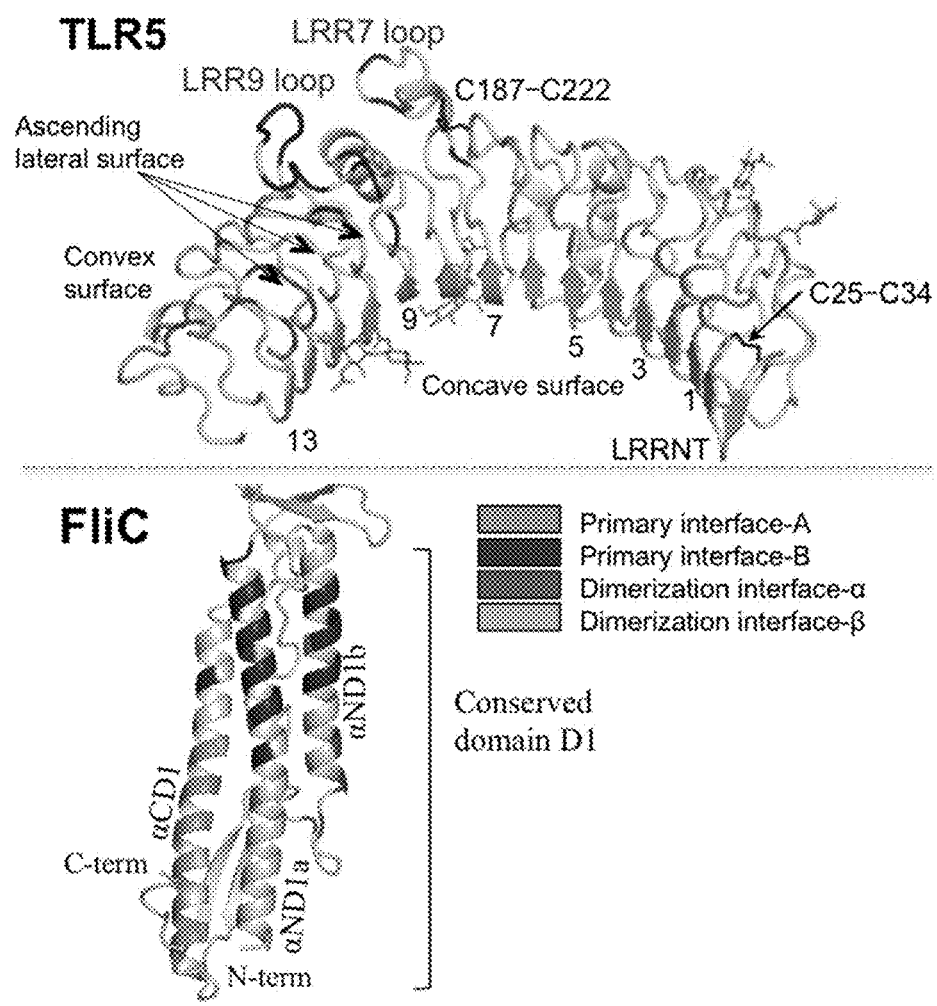
FIG. 3 shows the structural regions involved in interactions between TLR5 ectodomain and CBLB502 (FliC) domain D1. Note a contribution of loops LRR 7 and 9 (characteristic of TLR5 family) to high-affinity primary interactions.

Example 1: Engineering of Flagellin-Related Compositions with Improved Efficacy Relative to CBLB502 a. Structure-Activity Relationship Analysis (SAR):

The results of analysis, which included a combination of site-directed mutagenesis and deletions are illustrated in FIG. 2. Resulting variants of CBLB502 were expressed in *E. coli*, purified and characterized by: (i) relative binding affinity in cell-free system by competition-based fluorescent polarization (FP) assay with recombinant purified fragment of TLR5 ectodomain of fish origin and (ii) relative signaling efficiency by cell-based luciferase reporter assay using wild-type CBLB502 as a reference (as described in Yoon et al. (2012)). This analysis confirmed the role of amino acid segments and certain residues of domain D1 in the formation of primary and secondary interfaces predicted from 3D structure (FIG. 3). It also revealed the importance of domain D0 for signaling (but not primary binding) although the actual role of this domain remained unknown. This analysis also revealed that only the C-terminal segment of D0 (C_D0) is essential, while the N-terminal segment can be eliminated without loss of signaling activity (as in, for example, the deletion variant S33 (SEQ ID NO: 17)).

In vivo testing of the signaling activity of the mutants in primary and secondary interface as well as the delta-D0 deletion variant of CBLB502 revealed a correlation with the in vitro signaling data. This was established by injection of varying doses of respective mutants (recombinant purified and detoxed proteins) into NF-kB-luciferase reporter mice and measurement of luciferase activity in various organs (See FIG. 4, panels A-E).

Briefly, NF-kB luciferase reporter mice were injected s.c with CBLB502 mutants (three mice per group) as indicated. The relative amounts of injection used were based on their signaling efficacy in cell based NF-kB reporter assays. Organs were collected 3 hours post injection and snap frozen in dry ice. Tissue homogenates were prepared by pulverization of organs followed by lysis using RIPA buffer supplemented with protease inhibitors. For luciferase assays, 20 ul of each lysate was mixed with 30 ul of luciferin reagent (Bright-Glo luciferase assay system, Promega Inc.) and luciferase activity was quantified using a luminometer. Luciferase activity was normalized based on protein concentration measured using Bradford assay. The results demonstrate that while the response in the liver observed for the S33 mutant was moderately increased about 3-fold, this mutant showed a much stronger enhancement (>10-fold at the same dose of 0.3 μg) was observed in the bladder and large intestine.

During additional systematic SAR, a large number of truncated variants were generated and characterized primarily for signaling activity (using luciferase-based or a standard CBLB502 bioactivity assay using LacZ reporter system). These deletions (partially illustrated by diagrams in FIG. 5) allowed us to refine the boundaries of the minimal essential core and address a potential relevance of the length (from 33 aa to 12 aa) and position of the tag (N-terminal vs. C-terminal) as well as test the possibility to minimize a linker region (as in the construct "33ML" (SEQ ID NO: 35)).

A list of CBLB502 variants comprising an extensive SAR analysis is provided in Table 2. Among the most important observations, without wishing to be bound by theory, is the principle possibility to eliminate at least one half of the indigenous C_D0 segment, leaving only its N-terminal half (470-485) capped by the C-terminal His-tag (the presence of the cap is essential for activity as the variant 33-485 loses about 90% of signaling activity, see Table 2). These observations taken together suggest, without wishing to be bound by theory, that the D0 domain has only minor (if any) contribution to direct interactions with TLR5, and its role may be limited to maintaining structural integrity of D1 domain. On the other hand, the residual C_D0 segment (470-485) cannot be removed or replaced by the C-terminal half of C_D0 (485-504) or other sequences (e.g. fragment of GFP as in CGD1 or the N-D0 segment as in a new construct MF233 (SEQ ID NO: 123), see below Table 2). At the same time, some of the polar residues could be replaced by alanine in this segment without appreciable loss of activity (see Table 2).

TABLE 2

CBLB502 deletion/fusion variants

| | CBLB502 variant ID | Brief description | Length (aa) | Modular composition (design) | Objectives | Conclusions | Relative EC50 vs 502 Binding (FP) | Relative EC50 vs 502 Signaling (Luc) | Relative EC50 vs 502 Signaling (LacZ) |
|---|---|---|---|---|---|---|---|---|---|
| | 502 | Starting point-original construct | 329 | 6xH-EK-Tag (33 aa~"N-Tag-HEK") - ND0_ND1" (1-175) - Linker16 - CD1_CD0* (401-504). [*aa 32-44: N-terminal spoke region (NS); aa 464-469: C-terminal spoke region (CS)] | | | 1.0 | 1.0 | 1.0 |
| | SY3 | Delta D0; described before | 262 | 6xH-Thrombin-Tag (37 aa ; "N-Tag-HT") - ND1 (Start@ aa 33) - Linker16 - CD1 (Term@ aa 466) | | | 2.9 | 185 | 309 |
| 1 | 445 | Delta CD0; Truncated CD1 | 272 | N-Tag-HT - ND0_ND1 - Linker16 - CD1 (Term@ aa 443) | Importance of C-terminal fragment of D0 domain (CD0) and 26 | Deletion of CD0 fragment alone has significant effect - | 0.4 | 141000 | 691 |
| 2 | 461 | Delta CD0; Truncated CD1 | 289 | N-Tag-HT - ND0 - ND1 - Linker16 - CD1 (Term@ aa 460) | C-terminal aa of D1 fragment (CD1) in signaling? | approximately 50-100 times lower activity. Additional | ND | 97 | 105 |
| 3 | 467 | Delta CD0 | 295 | N-Tag-HT - ND0 - ND1 - Linker16 - CD1 (Term@ aa 466) | | truncation of 26 C-terminal aa of CD fragmentleads to | 1.0 | 71 | 57 |
| 4 | 470 CT | Delta CD0; Minimal C-Tag | 274 | ND0 - ND1 - Linker16 - CD1 (Term@ aa 469) - Thrombin-6xH-Tag (13 aa ; C-Tag) | | nearly loss of activity (at least 700 times) | ND | 44 | 38 |
| 5 | S33 | Delta ND0, N-terminal tag | 300 | N-Tag-HT - ND1 (Start@ aa 33) - Linker16 - CD1 - CD0 | [Variant CBLB502-S33 was characterized in vivo] | [Vriant S33 showed improved PK and higher in vivo activity | 0.8 | 1.4 | ND |
| 6 | 33 CT | Delta ND0; C-terminal tag | 275 | ND1 (Start@ aa 33) - Linker16 - CD1 - CD0 - C-Tag | Contribution of N-terminal fragment of D0 domain (ND0) and N-terminal | by PD, Luc-mice and in radioprotection.] | ND | 2.3 | ND |
| 7 | 37 CT | Delta ND0 | 273 | ND1 (Start@ aa 37) - Linker16 - CD1 - CD0 - C-Tag | spoke region (NS; aa 32-44) to signaling? | Deletion of ND0 fragment and truncation of NS has little effect | ND | 3.2 | ND |
| 8 | N45 | Delta ND0 | 288 | N-Tag-HT - ND1 (Start@ aa 45) - Linker16 - CD1 - CD0 | | on activity (1.5-3.5 times decrease), regardless of position | ND | 3.6 | ND |
| 9 | 45 CT | Delta ND0 | 285 | ND1 (Start@ aa 45) - Linker16 - CD1 - CD0 - "Long" C-Tag (34 aa ) | | of the tag. | ND | 3.5 | ND |
| 10 | 33-485 | Delta ND0; Truncated CD0 | 281 | N-Tag-HT - ND1 (Start@ aa 33) - Linker16 - CD1 - CD0 (Term@ aa 485) | Minimal essential fragment of CD0? | Truncation of 20 C-terminal aa of CD0 leads to 11×-lower activity | ND | 11 | ND |
| 11 | 33 ML | Delta ND0; Minimized Linker; Truncated CD1 | 250 | ND1 (Start@ aa 33) - Linker3 - CD1 (Starts@ aa 413) - CD0 - C-Tag | Test structure-based hypothesis - minimize the Linkerand have start of CD1 at aa 412 (401 in CBLB502). Confirmed | | ND | 1.5 | 1.3 |
| 12 | MF227C | 33 ML based; Deletion within CD0 | 227 | ND1 (Start@ aa 33) - Linker3 - CD1 - CD0 (deleted aa 470-792) - C-Tag | Continue testing further minimiation in 33 ML background. | The N-terminal part of CD0 is essential (5× loss) | ND | ND | 5.5 |
| 13 | MF227N | 33 ML based; Truncated ND1 | 227 | ND1 ( aa 33-152) - Linker3 - CD1 - CD0 - C-Tag | | C-terminal part of ND1 (aa 153-175, connector) is indispensable. | ND | ND | 159 |
| 14 | 485 CT | 33 ML based; Truncated CD0 | 233 | ND1 - Linker3 - CD1 - CD0 (Term@ aa 485) - C-Tag | | Partial CD0 (aa 470-485) + C-terminal "cap" (Thrombin/6xHis Tag) retains full activity (in contrust with 11× loss in 33-485 with N-tag | ND | ND | 1.2 |
| 15 | 485 D | 485 CT based; Q439::F442 deletion | 229 | ND1 - Linker3 - CD1 - CD0 (Term@ aa 485) - C-Tag Q439::F442 deletion | | Detrimental (44× loss) - defines boundaries | ND | ND | 44 |

TABLE 2-continued

CBLB502 deletion/fusion variants

| | CBLB502 variant ID | Brief description | Length (aa) | Modular composition (design) | Objectives | Conclusions | Relative EC50 vs 502 Binding (FP) | Signaling (Luc) | Signaling (LacZ) |
|---|---|---|---|---|---|---|---|---|---|
| 16 | SY3CT | Delta D0; minimal linker; C-terminal tag | 217 | ND1 - Linker3 - CD1 - C-Tag | Hypothesis: C-terminl capping of D1 domain with C-tag may yield the shortest active variant. | Only partially true: This variant is >20× more active then N-terminal tag version (SY3). Still it is worse than 502 by 16×. | ND | ND | 16 |
| 17 | NGD1 | Fusion: N-terminal GFP fragment (1-157) - D1 | 380 | GPF ( aa 1-157) - Linker7 - ND1 - Linker3 - CD1 - C-Tag | Hypothesis: (1) capping (N-terminal and C-terminal separate, or together) and make active. We used N-terminal and C-terminal fragments of GFP for capping. (2) Fusion of N- and C-terminal fragments of GFP to D1 domain instead of D0 (GD1G Mutant) may stabilize D1 domain, and allow us to monitor its stabilized conformation through reconstitution of GFP fluorescence* | (1) N-terminal GFP-cap is not helpful; C-terminal brings activity to ⅛ of 502; (2) GFP fusion was fluorescent but not active | ND | ND | 58 |
| 18 | CGD1 | Fusion: D1 - C-terminal GFP fragment (158-238) | 303 | ND1 - Linker3 - CD1 - Linker7' - GFP ( aa 158-238) - C-Tag | | | ND | ND | 8 |
| 19 | GD1G | Fusion: N-GFP (1-157) - D1 - C-GFP (158-238) | 466 | GFP ( aa 1-157) - Linker7 - ND1 - Linker3 - CD1 - Linker7' - GFP ( aa 158-238) - C-Tag | | | ND | ND | 259 |
| 20 | CPM194 | Circular Permutant: CD1 (413-469) // ND1 (33-152) | 194 | CD1 - Linker3 - ND1 (Term@ aa 152) - C-Tag | Exploring alternative approach in stabilizing D1 using circular permutation technique. | So far, unsuccessful. One protein not folded. The other is folded but inactive | ND | ND | N/A |
| 21 | CPM217 | Circular Permutant: CD1 (413-469) // ND1 (33-175) | 217 | CD1 - Linker3 - ND1 (Term@ aa 175) - C-Tag | | | ND | ND | 1112 |

Ghosh, I., Hamilton, A.D. & Regan, L. Antiparallel leucine zipper-directed protein reassembly: application to the green fluorescent protein. J. Am. Chem. Soc. 122, 5658-5659 (2000).
Jeong, J. et al. Monitoring of conformational change in maltose binding protein using split green fluorescent protein. Biochem. Biophys. Res. Commun. 339, 647-651. (2006).
Latz E, Verma A, Visintin A, Gong M, Sirois CM, et al. (2007) Ligand-induced conformational changes allosterically activated Toll-like receptor 9. Nature. Immunology 8: 772-779.

In summary, the variant CBLB502-485CT ("CBLB533" (SEQ ID NO: 71)) represents the result of ultimate minimization of CBLB502 without loss of signaling activity (at least in vitro). This variant (233 aa long) is 30% shorter than CBLB502 (329 aa). (See FIG. 5).

In vivo characterization was accomplished for the key intermediate in minimization—CBLB502-S33 (SEQ ID NO: 17) with deleted N_D0 segment and the original 33aa N-terminal tag (FIG. 5). The respective recombinant purified protein displayed nearly full signaling activity in vitro (Table 2). Remarkably, the first results of in vivo testing in NF-kB-Luc-reporter mice performed side-by-side with CBLB502 revealed a substantially higher potency of CBLB502-S33 in vivo (FIG. 6) based on Xenogen imaging. A more quantitative analysis of luciferase activity in individual organs showed that while the response in the liver was moderately increased, about 3-fold, a much stronger enhancement (>10-fold, at the same dose 0.3 μg) was observed in bladder and large intestine (FIG. 7).

Importantly, the enhanced response was also observed at the level of radioprotection potency (FIG. 8).

This observation suggests, without wishing to be bound by theory, that a minimized variant of CBLB502 can be efficiently used for anti-acute radiation syndrome (ARS) indications at lower doses. This enhanced potency may also be manifested in radiomitigation mode (post-exposure administration). This expectation is substantiated by the observed stronger cytokine response (FIG. 9) including the key cytokines (G-CSF and IL-6) selected as CBLB502 PD-biomarkers and proven to be mechanistically essential for its radiomitigation activity (Burdelya et al. 2008).

An apparent rationale for the correlated enhancement of CBLB502-S33 in vivo activity at the level of NF-kB signaling, radioprotection and cytokine production (PD) is a substantially improved PK (FIG. 10). The enhanced persistence of CBLB502-S33 in plasma might reflect higher stability to proteolysis or, more likely, less efficient "trapping" in certain organs/tissues (e.g. in the liver) and slower clearance from circulation thus increasing exposure of other tissues. The latter interpretation provides additional evidence of the contribution of such tissues (e.g. peripheral blood cells) to the MOA of the drug.

By way of non-limiting summary, characterization of CBLB502-S33 showed that the SAR analysis and iterative minimization deliver biologically active protein variants with improved pharmacological properties. This information was used to design, engineer and characterize the ultimate design for CBLB533.

The SAR results suggest the ultimate design of CBLB533 based on the variant CBLB502-485CT (with or without additional mutations). This protein can be produced in sufficient amount and characterized in vivo similar to the analysis performed for the intermediate lead candidate CBLB502-S33 additionally expanded by testing of radiomitigation properties. Importantly, they provided an optimal scaffold for designing the de-immunized Nextgen drug candidate CBLB543.

Example 2: Engineering of Flagellin-Related Compositions with Reduced Antigenicity Relative to CBLB502

Anti-CBLB502 antibodies (preexisting or/and boosted by CBLB502 treatment) showing neutralizing activity in vitro should also neutralize its NF-kB signaling (and therefore therapeutic) activity. This was confirmed by the direct experiment in mice (FIG. 11). Indeed, the injection of CBLB502 neutralizing human sera or monoclonal antibodies in NF-kB luciferase mice completely abrogates the luciferase activity in organ (live) lysates.

In this experiment, five groups of NF-kB reporter mice (3 per group) were injected intravenously with (1) PBS (2) non neutralizing serum, (3) neutralizing serum (day 15 bleed) (4) mAb 7C (5) mAb 11D and animals were bled after 45 minutes. The monoclonal antibodies were used at the dose of 100 μg per mouse. CBLB502 (1 μg) was injected subcutaneously to all mice one hour after the initial injection of antibodies. Animals were imaged three hours after CBLB502 injection and liver was collected for preparation of lysates. The results from this study are shown in Table 3.

The specific activity of luciferase was measured per the following protocol. A Bio-pulverizer was used to crush the liver samples on the dry ice. 750 μl of 1× Reporter Lysis Buffer (Promega cat #E397A)+1× protease inhibitor cocktail (PIC, sigma P8340) was added and the homogenized mixture was centrifuged at 13,000 rpm at 4° C. for 30 minutes. The supernatant was collected into a clean eppendorf tube and the protein concentration of the supernatant was measured. 20 μl of supernatant and 20 μl of luciferase buffer (Promega E2620) were added. Everything was normalized to the lowest protein sample and added accordingly, and the volume of the supernatant was adjusted using the Lysis buffer with PIC. The luciferase activity was measured on a luminoplate reader.

TABLE 3

In vivo neutralization of CBLB502 by injection of antisera and antibodies (neutralizing and not neutralizing) in reporter mice.
Anti-CBLB502 antibody assay results

| Sample # | Sample ID | Study group | NAb % inhibition | Anti-CBLB502 titer |
| --- | --- | --- | --- | --- |
| 1 | #1-1 | PBS | −1.08 | 0 |
| 2 | #1-2 | PBS | −4.68 | 0 |
| 3 | #1-3 | PBS | 0.51 | 0 |
| 4 | #2-1 | Non-neutralizing human serum | 1.77 | 0 |
| 5 | #2-2 | Non-neutralizing human serum | −5.38 | 0 |
| 6 | #2-3 | Non-neutralizing human serum | 0.15 | 0 |
| 7 | #3-1 | Neutralizing human serum | 77.37 | 19462 |
| 8 | #3-2 | Neutralizing human serum | 86.04 | 20879 |
| 9 | #3-3 | Neutralizing human serum | 83.52 | 17000 |
| 10 | #4-1 | Non-neutralizing MAb 7C | 5.18 | 791 |
| 11 | #4-2 | Non-neutralizing MAb 7C | 1.21 | 487 |
| 12 | #4-3 | Non-neutralizing MAb 7C | 2.63 | 858 |
| 13 | #5-1 | Neutralizing MAb 11D | 44.81 | 114496 |

TABLE 3-continued

In vivo neutralization of CBLB502 by injection of antisera and
antibodies (neutralizing and not neutralizing) in reporter mice.
Anti-CBLB502 antibody assay results

| Sample # | Sample ID | Study group | NAb % inhibition | Anti-CBLB502 titer |
|---|---|---|---|---|
| 14 | #5-2 | Neutralizing MAb 11D | 49.41 | 87249 |
| 15 | #5-3 | Neutralizing MAb 11D | 54.48 | 109475 |

*Human sera were diluted 10-fold with PBS for injections
**Both MAbs, 7C and 11D, were at 2 mg/ml in PBS for injections
*Mouse serum samples were collected 1 hr after Ab injections A brief summary of is provided below (and illustrated in Tables 4, and 5 and FIG. 12**).

TABLE 4

CBLB502 epitope mapping and de-immunization

| Protein | Scaffold | Mutations | Length (aa) | Signaling EC50 Normalized by CBLB502 | Neutralization by antibodies (IC50 improvement vs. 502) | | | | | | | | | Note |
|---|---|---|---|---|---|---|---|---|---|---|---|---|---|---|
| | | | | | mAB4D11 | mAB11D04 | NSP79 | NSP85 | NSP99 | NSP61 | NSP103 | P12 | P14 | |
| MIM1 | 502 based | N455A; N457A | 329 | 0.9 | No improvement in neutralization with any of the antibodies | | | | | | | | | 1 |
| MIM2 | 502 based | N455A; N457A; R460A | 329 | 1.2 | | | | | | | | | | |
| MIM3 | 502 based | N448A; N451A; N455A, N457A; R460A | 329 | 4.6 | | | | | | | | | | |
| MIM4 | 502 based | Q439::F442 deletion; N448A; N451A; N455A, N457A; R460A | 329 | 37 | | | | | | | | | | |
| MIM5 | 502 based | Q439A; N440K; R441A; N448A; N451A; N455A, N457A; R460A | 329 | 54 | | | | | | | | | | |
| 33MIMX | S33 based | N68A; F131A; Q142A; E153A; T154A; N440A; D443A; S444A; T447A | 300 | 1.3 | ~10× | 4-5× | No improvement | | | 2× | 1× | ~3× | ~2× | 2 |
| MIXN | 33 ML based | N68A; F131A; Q142A; E153A; T154A | 250 | 1.5 | ~10× | ~10× | | | | | | 4-5× | 4-5× | 3 |
| MIXC | 33 ML based | N440A; D443A; S444A; T447A | 250 | 1.5 | ~10× | ~10× | | | | | | | worse | |
| ME42 | 33 ML based | D42A; A45G | 250 | 1.3 | 4× | 5× | | | | 2× | 2× | 1× | 1× | 4 |
| ME100 | 33 ML based | N100A; T102A | 250 | 0.6 | >5× | >10× | | | | 3× | 2× | 1× | 2× | |

TABLE 4-continued

CBLB502 epitope mapping and de-immunization

| Protein | Scaffold | Mutations | Length (aa) | Signaling EC50 Normalized by CBLB502 | Neutralization by antibodies (IC50 improvement vs. 502) ||||||| | | |
|---|---|---|---|---|---|---|---|---|---|---|---|---|---|---|
| | | | | | mAB4D11 | mAB11D04 | NSP79 | NSP85 | NSP99 | NSP61 | NSP103 | P12 | P14 | Note |
| ME104 | 33 ML based | S104A; S106A; D107A | 250 | 1.0 | >5× | >10× | | | | >5× | >5× | 1× | 2× | |
| ME110 | 33 ML based | S110A; D113A | 250 | 0.7 | >5× | >10× | | | | 3× | 2× | 1× 1× | 2× 2× | |
| ME117 | 33 ML based | Q117A; E120A | 250 | 0.8 | 5× | >10× | | | | 2× | 2× | 1× | 1× | |
| ME124P | 33 ML based | R124A | 250 | * | | | | | | | | | | |
| ME124 | 33 ML based | R124A; N127A; Q128A | 250 | 0.9 | 3× | 6× | | | | 2× | 1× | 3× | 1× | |
| ME132 | 33 ML based | N132A; G133A | 250 | 0.94 | >5× | >10× | | | | 4× | >5× | 2× | 3× | |
| ME142 | 33 ML based | Q142A; K144A | 250 | 0.3 | >5× | >10× | | | | 3× | >5× | 2× | 2× | |
| ME150 | 33 ML based | N150S; D151A; G152A | 250 | 0.5 | >5× | >10× | | | | 3× | 2× | 1× | 2× | |
| ME468 | 33 ML based | Y468A; A469G; T470A; S473A | 250 | 0.7 | >5× | >10× | | | | 2× | 2× | 4× | 1× | |
| ME100/110 | 33 ML based | N100A; T102A; S110A; D113A | 250 | * | | | | | | | | | | |
| ME104N | 33 ML based | N100A; T102A; S104A; S106A; D107A; S110A; D113A | 250 | 0.9 | 1× | 2× | | | | 2× | 2× | 1× | 1× | |
| 33GPS | 33 ML based | Deletion N100::D113. Replaced with Linker "GPSG" | 240 | * | | | | | | | | | | |
| 33MX | 33 ML based | N68A; F131A; Q142A; E153; T154A; S104A; S106A; D107A; S110A; D113A; N132A; G133A; K144A; N127Q; N474Q | 250 | 1.3 | >4× | >4× | >2× | >2× | | | | 6× | 7× | 5 |

TABLE 5

Antigenicity of CBLB502 deletion variants by antibody titration (ELISA) with? multiple human antisera

| | Titers | | | | | | | | | | | |
|---|---|---|---|---|---|---|---|---|---|---|---|---|
| | Plate 1 Pt. serum #004 Day 15, CBLB502 | Plate 2 Pt. serum #006 Day 15, CBLB502 | Plate 3 Pt. serum #009 Day 15, CBLB502 | Plate 4 Pt. serum #010 Day 15, CBLB502 | Plate 5 Pt. serum #012 Day 15, CBLB502 | Plate 6 Pt. serum #008 No CBLB502 | Plate 7 Pt. serum #013 No CBLB502 | Plate 8 Mab 7C No effect | Plate 9 Mab 11D Neutral-izing | Plate 10 Mab 12D No effect | Plate 11 Goat PAb CBLB502 assays | Plate 12 Rabbit PAb CBLB502 assays |
| Deletion SY3 | 429687 | 319746 | 117275 | 261211 | 543635 | 3331 | 7023 | 1392 | 39297 | 11433 | 33248 | 41555 |
| Deletion 467 | 414991 | 319843 | 160498 | 276131 | 626631 | 2413 | 8462 | 1619 | 39722 | 10233 | 35372 | 40853 |
| Deletion S33 | 429436 | 322443 | 199057 | 264892 | 649834 | 9846 | 9490 | 1596 | 42485 | 11725 | 38755 | 39092 |
| Deletion 445 | 67857 | 152052 | 21824 | 57521 | 150700 | 978 | 914 | 1470 | 8609 | 1577 | 40988 | 19077 |
| CBLB502 Ref, Std | 519509 | 357298 | 296948 | 337398 | 761754 | 12082 | 23459 | 1547 | 52663 | 15364 | 59596 | 46738 |
| | Titer % of CBLB502 reference standard | | | | | | | | | | | |
| | Plate 1 Pt. serum #004 Day 15, CBLB502 | Plate 2 Pt. serum #006 Day 15, CBLB502 | Plate 3 Pt. serum #009 Day 15, CBLB502 | Plate 4 Pt. serum #010 Day 15, CBLB502 | Plate 5 Pt. serum #012 Day 15, CBLB502 | Plate 6 Pt. serum #008 No CBLB502 | Plate 7 Pt. serum #013 No CBLB502 | Plate 8 Mab 7C No effect | Plate 9 Mab 11D Neutral-izing | Plate 10 Mab 12D No effect | Plate 11 Goat PAb CBLB502 assays | Plate 12 Rabbit PAb CBLB502 assays |
| Deletion SY3 | 83 | 89 | 39 | 77 | 71 | 28 | 30 | 90 | 75 | 74 | 56 | 89 |
| Deletion 467 | 80 | 90 | 54 | 82 | 82 | 20 | 36 | 105 | 75 | 67 | 59 | 87 |
| Deletion S33 | 83 | 90 | 67 | 79 | 85 | 81 | 40 | 103 | 81 | 76 | 65 | 84 |
| Deletion 445 | 13 | 43 | 7 | 17 | 20 | 8 | 4 | 95 | 16 | 10 | 69 | 41 |
| CBLB502 Ref, Std | 100 | 100 | 100 | 100 | 100 | 100 | 100 | 100 | 100 | 100 | 100 | 100 |

The initial studies were based on the computational prediction of linear epitopes, a comparative analysis of antigenicity (assessed by ELISA with a series of human serum samples) for a series of truncated variants, and the observation that the deletion variant 445 (see Table 2 for composition) significantly lost antigenicity pointing to the existence of the major epitope within a rather short amino acid segment (440-470). However the analysis of antigenicity in a number of mutants generated based on this premise did not confirm these predictions (see FIG. 12).

Based on these observations, in the following work, the approach was adjusted to the use of predicted structural (potentially noncontiguous) epitopes (FIG. 13), testing intermediate mutants for "neutralizing antigenicity" assessed by the extent of inhibition by neutralizing Abs in signaling assay. We progressed from using a full-size CBLB502 scaffold to the first truncated lead CBLB502-S33 (see Table 2 for composition), and its further modification S33MX (SEQ ID NO: 150).

In the first series of designed mutants, substantial progress was attained in decreasing sensitivity to neutralizing monoclonal antibodies and neutralizing antisera raised against CBLB502. An improvement was observed on a series of human normal sera containing an appreciable un-induced titer of neutralizing antibodies.

To address this problem, an additional series of mutant were designed and characterized.

As a result of such iterations, the majority of neutralizing epitopes were mapped and eliminated without loss of signaling activity (see Table 4).

To engineer the first generation of fully active "deimmunized" CBLB502 lead candidate (CBLB543), the following was undertaken.

Epitope mapping data obtained as described above (See Table 5) provided foundation for the ultimate design of the de-immunized CBLB543 lead candidate (CBLB502-S33MX (SEQ ID NO: 150)). This protein was engineered and characterized by signaling activity (unchanged) and neutralizing antigenicity. As illustrated in FIG. 14 (for individual data, see Table 4), in this protein the neutralizing antigenicity was substantially reduced compared to CBLB502. The additional comparison with CBLB502-S33ML (SEQ ID NO: 35), a truncated scaffold used for lead engineering shows this effect is due to a combination of mutations, and not reduced size.

Example 3: Potency and Pharmacological Properties of De-Immunized Variants (CBLB502-33MX and CBLB502-S33)

Studies were undertaken to evaluate the PK/PD properties of selected flagellin-related compositions Specifically, the PK/PD properties of the partially deimmunized protein CBLB502-33MX were compared with those of CBLB502. Accordingly, this study established the functional and pharmacological characteristics of the engineered new variant CBLB502-33MX with substantially reduced "neutralizing antigenicity" and thus resistant to neutralization by human neutralizing antibodies in the in vitro signaling assay.

In-life phase of PK/PD study: 320 C57Bl6 mice were used for the experiment in groups of 10 mice. CBLB502 (1 and 2 µg/kg) and 33MX (1 and 2 µg/kg) were injected intravenously. The animals were sacrificed after 5 min, 15 min, 30 min, 1 hour, 2 hours, 4 hours, 8 hours and 24 hours after treatment, and plasma samples were collected.

PK measurements: the concentration of CBLB502 and 33MX in the plasma samples was measured according to the standard ELISA-based protocol using CBLB502 and 33MX calibration curves.

The results of PK measurements are illustrated in FIG. 15. FIG. 15, panels A and B show quantification of CBLB502 and 33MX in mouse plasma samples. (BLQ—below the limit of quantification.). Therefore, CBLB502-33MX has very similar PK properties to that of parental CBLB502, i.e. it clears from circulation at approximately the same rate. Accordingly, PK features of CBLB502 are not abrogated by the mutations that were engineered to de-immunize the construct (e.g. in the context of CBLB502-33MX).

The same 320 plasma samples were used for cytokine profiling for the analysis of PD properties of 33MX as compared to CBLB502. The data (FIG. 16) shows that CBLB502-33MX has a very similar PD profile to the parental CBLB502. Accordingly, PD features of CBLB502 also are not abrogated by the mutations that were engineered to de-immunize the construct (e.g. in the context of CBLB502-33MX).

In vivo signaling of the parental CBLB502 was compared to an intermediate variant CBLB502-S33 (minimized, prior to deimmunization) and CBLB502-33MX, the final product of Stage I deimmunization. A NF-kB-luciferase reporter assay in mice was used and mice were injected with the one of the following proteins: CBLB502 (at doses of 0.1 µg, 0.3 µg, 1 µg and 3 µg); CBLB502-S33 (at doses of 0.1 µg, 0.3 µg, 1 µg and 3 µg); and CBLB502-33MX (at doses of 0.1 µg, 0.3 µg, 1 µg and 3 µg). 3 hours after treatment the mice were sacrificed and the following organs were harvested and frozen at −80° C.: liver, bladder, small and large intestine, heart, spleen, lungs, brain and kidney. Luciferase activity in organ lysates was measured using Bright-Glo Luciferase Assay solution (Promega) and presented as specific luciferase activity (RLU/mg of protein+/−SEM).

The results of experiment shown in FIG. 17 demonstrate that NF-KB activating ability of de-immunized candidate 33MX is similar to S33 and CBLB502 and in some organs (for example, large intestine and lungs) even exceeds activity of these proteins in some organs.

Therefore, among others, this Example shows that that de-immunized variant CBLB502-33MX fully retained or exceeded in some parameters the biological activity and pharmacological characteristics of the original CBLB502.

Example 4: In Vivo Efficacy of 33MX in a Murine Model of Local Head-And-Neck Irradiation The in vivo effects of 33MX in the context of irradiation were evaluated at a variety of doses as compared to CBLB502. Treatment was injected 1 h after each irradiation preventing damage and accelerating tissue recovery following fractionated H&N irradiation.

Six groups by 8 mice were evaluated and are listed in the order that the data is presented in FIG. 18 (in series for 8 tissue types, the bars identified from left to right for each tissue type): Group 1 (vehicle): 6 Gy×5 times with 24 h interval (30 Gy total), inject PBS-Tween 1 h after each IR, Group 6 (33MX, 0.03 µg): 6 Gy×5 times with 24 h interval (30 Gy total), inject 0.03 µg 33MX 1 h after each 111, Group 5 (33MX, 0.1 µg): 6 Gy×5 times with 24 h interval (30 Gy total), inject 0.1 µg 33MX 1 h after each IR, Group 4 (33MX, 0.3 µg): 6 Gy×5 times with 24 h interval (30 Gy total), inject 0.3 µg 33MX 1 h after each IR, Group 3 (33MX, 1 µg): 6 Gy×5 times with 24 h interval (30 Gy total), inject 1 µg 33MX 1 h after each IR, and Group 2 (CBLB502, 0.1 µg): 6 Gy×5 times with 24 h interval (30 Gy total), to inject 0.1 µg CBLB502 1 h after each IR (this dose was determined to be particularly efficacious in a separate study).

All mice were taken for histopathological analysis of mouse epithelia, tongue, upper esophagus, salivary glands and skin on day 10 after the first IR (day 0).

The results of the study are presented in FIG. 18. Injury scores are based on histological evaluation of the tissue sections. The scores values scale: 0 for no injury and 4 for the highest injury.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

1. Yoon S I, Kurnasov O, Natarajan V, Hong M, Gudkov A V, Osterman A L, Wilson I A., 2012. Structural Basis of TLR5-Flagellin Recognition and Signaling. Science 335: 859-864 (PMID: 22344444)
2. Smith K D, Andersen-Nissen E, Hayashi F, Strobe K, Bergman M A, Barrett S L, Cookson B T, Aderem A. 2003. Toll-like receptor 5 recognizes a conserved site on flagellin required for protofilament formation and bacterial motility. Nat Immunol. 4:1247-53 (PMID: 14625549)
3. Mizel, S. B., A. P. West, R. R. Hantgan. 2003. Identification of a sequence in human Toll-like receptor 5 required for the binding of Gram-negative flagellin. J. Biol. Chem. 278:23624-23629 (PMID: 12711596)
4. Murthy, K. G., Deb, A., Goonesekera, S., Szabo, C. & Salzman, A. L. (2004) J. Biol. Chem. 279:5667-5675 (PMID: 14634022)
5. Andersen-Nissen E., Smith K. D., Strobe K. L., Barrett S. L., Cookson B. T., Logan S. M., Aderem A. (2005)

Evasion of Toll-like receptor 5 by flagellated bacteria. Proc. Natl. Acad. Sci. U.S.A. 102: 9247-9252 (PMID: 15956202)
6. Andersen-Nissen E, Smith K D, Bonneau R, Strong R K, Aderem A. 2007. A conserved surface on Toll-like receptor 5 recognizes bacterial flagellin. J Exp Med. 204:393-403 (PMID: 17283206)
7. Burdelya L G, Krivokrysenko V I, Tallant T C, Strom E, Gleiberman A S, Gupta D, Kurnasov O V, Fort F L, Osterman A L, Didonato J A, Feinstein E, Gudkov A V., 2008. An agonist of Toll-like receptor 5 has radioprotective activity in mouse and primate models. Science 320: 226-230 (PMID: 18403709).
8. Huleatt J W, Nakaar V, Desai P, Huang Y, Hewitt D, Jacobs A, Tang J, McDonald W, Song L, Evans R K et al. 2008. Potent immunogenicity and efficacy of a universal influenza vaccine candidate comprising a recombinant fusion protein linking influenza M2e to the TRL5 ligand flagellin. Vaccine. 26:201-214.

What is claimed is:

1. A composition comprising a polypeptide having an amino acid sequence having about 95% sequence identity to SEQ ID NO: 17, SEQ ID NO: 71, or SEQ ID NO: 150.

2. The composition of claim 1, wherein the composition has reduced antigenicity and immunogenicity as compared to the polypeptide having the amino acid sequence that is SEQ ID NO: 2.

3. The composition of claim 1, wherein the composition demonstrates improved pharmacokinetics as compared to the polypeptide having the amino acid sequence that is SEQ ID NO: 2.

4. The composition of claim 1, wherein the composition demonstrates increased in vivo retention as compared to the polypeptide having the amino acid sequence that is SEQ ID NO: 2.

5. The composition of claim 1, wherein the composition activates TLR5 signaling at a level the same as, or similar to, that of the polypeptide having the amino acid sequence that is SEQ ID NO: 2.

6. The composition of claim 1, further comprising a N-terminal tag.

7. The composition of claim 1, further comprising a C-terminal tag.

8. The composition of claim 1, wherein the composition induces NF-κB mediated expression of one or more of the cytokines selected from IL-6, IL-12, keratinocyte chemoattractant (KC), IL-10, G-CSF, MCP-1, TNF-α, MIG, and MIP-2.

9. A pharmaceutical composition comprising the composition of claim 1 and a pharmaceutically acceptable carrier.

10. A method of stimulating TLR5 signaling comprising administering to a subject in need thereof a composition comprising a polypeptide having an amino acid sequence having about 95% sequence identity to SEQ ID NO: 17, SEQ ID NO: 71, or SEQ ID NO: 150.

11. The method of claim 10, wherein the subject suffers from radiation-induced cellular damage.

12. The method of claim 11, wherein the subject has been subjected to a lethal dose of radiation.

13. The method of claim 11, wherein the subject is undergoing radiation treatment.

14. The method of claim 11, wherein the composition is administered prior to exposure to radiation.

15. The method of claim 11, wherein the composition is administered during exposure to radiation.

16. The method of claim 11, wherein the composition is administered after exposure to radiation.

17. The method of claim 10, wherein the composition has reduced antigenicity and immunogenicity as compared to the polypeptide having the amino acid sequence that is SEQ ID NO: 2.

18. The composition of claim 1, the composition comprising a polypeptide having an amino acid sequence having about 98% sequence identity to SEQ ID NO: 17, SEQ ID NO: 71, or SEQ ID NO: 150.

19. The composition of claim 1, the composition comprising a polypeptide having an amino acid sequence that is SEQ ID NO: 17, SEQ ID NO: 71, or SEQ ID NO: 150.

20. A pharmaceutical composition, the pharmaceutical composition comprising a polypeptide having the amino acid sequence that is SEQ ID NO: 150 and a pharmaceutically acceptable carrier.

* * * * *